(12) United States Patent
Griswold-Prenner et al.

(10) Patent No.: US 9,567,395 B2
(45) Date of Patent: Feb. 14, 2017

(54) METHODS OF TREATING A TAUOPATHY

(71) Applicant: iPierian, Inc., South San Francisco, CA (US)

(72) Inventors: Irene Griswold-Prenner, Jackson, WY (US); Nancy E. Stagliano, South San Francisco, CA (US); Vu Cao Dang, South San Francisco, CA (US)

(73) Assignee: IPIERIAN, INC., South San Francisco, CA (US)

( * ) Notice: Subject to any disclaimer, the term of this patent is extended or adjusted under 35 U.S.C. 154(b) by 0 days.

(21) Appl. No.: 14/421,073

(22) PCT Filed: Aug. 15, 2013

(86) PCT No.: PCT/US2013/055203
§ 371 (c)(1),
(2) Date: Feb. 11, 2015

(87) PCT Pub. No.: WO2014/028777
PCT Pub. Date: Feb. 20, 2014

(65) Prior Publication Data
US 2015/0239963 A1  Aug. 27, 2015

Related U.S. Application Data

(60) Provisional application No. 61/754,085, filed on Jan. 18, 2013, provisional application No. 61/833,355, filed on Jun. 10, 2013, provisional application No. 61/813,797, filed on Apr. 19, 2013, provisional application No. 61/781,823, filed on Mar. 14, 2013, provisional application No. 61/683,902, filed on Aug. 16, 2012.

(51) Int. Cl.
| | |
|---|---|
| *C07K 16/18* | (2006.01) |
| *A61K 39/395* | (2006.01) |
| *C07K 16/46* | (2006.01) |
| *G01N 33/68* | (2006.01) |
| *A61K 39/00* | (2006.01) |

(52) U.S. Cl.
CPC .......... *C07K 16/18* (2013.01); *A61K 39/3955* (2013.01); *C07K 16/461* (2013.01); *G01N 33/6896* (2013.01); *A61K 2039/505* (2013.01); *C07K 2317/24* (2013.01); *C07K 2317/34* (2013.01); *C07K 2317/76* (2013.01); *C07K 2317/92* (2013.01); *G01N 2333/4709* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,492,812 A | 2/1996 | Vooheis |
| 5,535,663 A | 7/1996 | Yamashita et al. |
| 5,600,392 A | 2/1997 | Sakamoto et al. |
| 5,666,808 A | 9/1997 | Yamashita et al. |
| 5,733,734 A | 3/1998 | Trojanowski et al. |
| 5,811,310 A | 9/1998 | Ghanbari et al. |
| 5,843,779 A | 12/1998 | Vandermeeren et al. |
| 5,861,257 A | 1/1999 | Vandermeeren et al. |
| 6,008,024 A | 12/1999 | Vandermeeren et al. |
| 6,010,913 A | 1/2000 | Vandermeeren et al. |
| 6,121,003 A | 9/2000 | Vanmechelen et al. |
| 6,232,437 B1 | 5/2001 | Vandermeeren et al. |
| 6,238,892 B1 | 5/2001 | Mercken et al. |
| 6,500,674 B1 | 12/2002 | Vandermeeren et al. |
| 6,680,173 B2 | 1/2004 | Vanmechelen et al. |
| 6,900,293 B2 | 5/2005 | Mercken et al. |
| 7,387,879 B2 | 6/2008 | Vanmechelen et al. |
| 7,427,392 B1 | 9/2008 | Seubert et al. |
| 7,446,180 B2 | 11/2008 | Novak |
| 7,466,180 B2 | 12/2008 | Slawecki |
| 8,012,936 B2 | 9/2011 | Sigurdsson et al. |
| 8,163,873 B2 | 4/2012 | Mercken et al. |
| 8,409,584 B2 | 4/2013 | Wisniewski et al. |
| 8,926,974 B2 | 1/2015 | Griswold-Prenner et al. |
| 8,980,270 B2 | 3/2015 | Griswold-Prenner et al. |
| 8,980,271 B2 | 3/2015 | Griswold-Prenner et al. |
| 9,051,367 B2 | 6/2015 | Griswold-Prenner et al. |
| 2001/0018191 A1 | 8/2001 | Mercken et al. |
| 2002/0001857 A1 | 1/2002 | Vandermeeren et al. |
| 2002/0019016 A1 | 2/2002 | Vanmechelen et al. |
| 2003/0138972 A1 | 7/2003 | Vandermeeren et al. |
| 2003/0143760 A1 | 7/2003 | Vandermeeren et al. |
| 2003/0147811 A1 | 8/2003 | Wisniewski et al. |

(Continued)

FOREIGN PATENT DOCUMENTS

| | | |
|---|---|---|
| WO | 96/20218 A1 | 7/1996 |
| WO | 98/22120 A1 | 5/1998 |

(Continued)

OTHER PUBLICATIONS

Gomèz-Ramos et al., FEBS Letters, 2006; 580: 4842-4850.*
Odetti et al., Journal of Neuropathology and Experimental Neurology, 2000; 59: 393-397.*
Bright, J. et al., "Human secreted tau increases amyloid-beta production," Neurobiology of Aging, vol. 36: 693-709 (2015).
European Search Report, EP Application No. 13830020.7, dated May 9, 2016, 9 pages.
International Preliminary Report on Patentability, PCT/US2014/041553, Dec. 15, 2015, 7 pages.

(Continued)

*Primary Examiner* — Christina Borgeest
(74) *Attorney, Agent, or Firm* — Nelson Mullins Riley & Scarborough LLP; Jane E. Remillard, Esq.; Jill Gorny Sloper, Esq.

(57) ABSTRACT

The present disclosure provides methods of treating a tauopathy, involving administering an anti-Tau antibody. The present disclosure also provides anti-Tau antibodies, and formulations comprising same, for use in the methods.

16 Claims, 65 Drawing Sheets

(56) References Cited

U.S. PATENT DOCUMENTS

| | | |
|---|---|---|
| 2003/0194742 A1 | 10/2003 | Vanmechelen et al. |
| 2004/0014142 A1 | 1/2004 | VanMechelen et al. |
| 2004/0038430 A1 | 2/2004 | Vandermeeren et al. |
| 2004/0072261 A1 | 4/2004 | Kostanjevecki et al. |
| 2004/0091942 A1 | 5/2004 | Vanmechelen et al. |
| 2004/0110250 A1 | 6/2004 | Wischik et al. |
| 2004/0265919 A1 | 12/2004 | Vanderstichele et al. |
| 2005/0014821 A1 | 1/2005 | Tsai et al. |
| 2005/0181460 A1 | 8/2005 | Ohno et al. |
| 2005/0191685 A1 | 9/2005 | Vanmechelen et al. |
| 2005/0196844 A1 | 9/2005 | Lee |
| 2005/0221391 A1 | 10/2005 | Davies |
| 2005/0255113 A1 | 11/2005 | Huston et al. |
| 2005/0260697 A1 | 11/2005 | Wang et al. |
| 2005/0261475 A1 | 11/2005 | Tseng et al. |
| 2006/0008853 A1 | 1/2006 | Mercken et al. |
| 2006/0122122 A1 | 6/2006 | Kobayashi et al. |
| 2006/0167227 A1 | 7/2006 | Kontsekova |
| 2007/0218491 A1 | 9/2007 | Vasan et al. |
| 2008/0050383 A1 | 2/2008 | Sigurdsson et al. |
| 2008/0057593 A1 | 3/2008 | Vanderstichele et al. |
| 2008/0213834 A1 | 9/2008 | Reed et al. |
| 2008/0220449 A1 | 9/2008 | Vasan et al. |
| 2008/0261889 A1 | 10/2008 | Vanmechelen et al. |
| 2009/0137051 A1 | 5/2009 | Mercken et al. |
| 2009/0317805 A1 | 12/2009 | Wang et al. |
| 2010/0055722 A1 | 3/2010 | Nayak et al. |
| 2010/0063250 A1 | 3/2010 | Kontsekova |
| 2010/0284909 A1 | 11/2010 | Wisniewski et al. |
| 2010/0297108 A1 | 11/2010 | Henco et al. |
| 2010/0316564 A1 | 12/2010 | Sigurdsson |
| 2010/0323343 A1 | 12/2010 | Egan et al. |
| 2011/0027817 A1 | 2/2011 | Arancio et al. |
| 2011/0143380 A1 | 6/2011 | Holtzman et al. |
| 2011/0143443 A9 | 6/2011 | Mercken et al. |
| 2011/0177109 A1 | 7/2011 | Smith, III et al. |
| 2011/0201098 A1 | 8/2011 | Laureyn et al. |
| 2011/0250237 A1 | 10/2011 | O'Hagan et al. |
| 2011/0312059 A1 | 12/2011 | Moe et al. |
| 2011/0318358 A1 | 12/2011 | Sigurdsson et al. |
| 2012/0029169 A1 | 2/2012 | Moe et al. |
| 2012/0087861 A1 | 4/2012 | Nitsch et al. |
| 2012/0142602 A1 | 6/2012 | Brady et al. |
| 2012/0183599 A1 | 7/2012 | Pfeifer et al. |
| 2012/0244146 A1 | 9/2012 | Chain |
| 2012/0244174 A1 | 9/2012 | Chain |
| 2012/0276009 A1 | 11/2012 | Pfeifer et al. |
| 2013/0028914 A1 | 1/2013 | Kayed |
| 2013/0156783 A1 | 6/2013 | Wisniewski et al. |
| 2013/0266514 A1 | 10/2013 | Nitsch et al. |
| 2013/0266585 A1 | 10/2013 | Nitsch et al. |
| 2013/0266586 A1 | 10/2013 | Nitsch et al. |
| 2013/0287838 A1 | 10/2013 | Hickman et al. |
| 2013/0288280 A1 | 10/2013 | Ladenson et al. |
| 2013/0295021 A1 | 11/2013 | Chen et al. |
| 2013/0310541 A1 | 11/2013 | Bohrmann et al. |
| 2014/0056901 A1 | 2/2014 | Agadjanyan et al. |
| 2014/0086921 A1 | 3/2014 | Griswold-Prenner et al. |
| 2014/0099303 A1 | 4/2014 | Griswold-Prenner et al. |
| 2014/0099304 A1 | 4/2014 | Griswold-Prenner et al. |
| 2014/0234214 A1 | 8/2014 | Griswold-Prenner et al. |
| 2014/0294831 A1 | 10/2014 | Griswold-Prenner et al. |
| 2015/0232544 A1 | 8/2015 | Griswold-Prenner et al. |
| 2016/0122421 A1 | 5/2016 | Griswold-Prenner et al. |

FOREIGN PATENT DOCUMENTS

| | | |
|---|---|---|
| WO | 02/45743 A2 | 6/2002 |
| WO | 03/014960 A2 | 2/2003 |
| WO | 2004/007547 A2 | 1/2004 |
| WO | 2005/010044 A2 | 2/2005 |
| WO | 2005/120166 A2 | 12/2005 |
| WO | 2011/013034 A1 | 2/2011 |
| WO | 2011/026031 A1 | 3/2011 |
| WO | 2011/056300 A1 | 5/2011 |
| WO | 2012/045882 A2 | 4/2012 |
| WO | 2012/049570 A1 | 4/2012 |
| WO | 2012/054008 A2 | 4/2012 |
| WO | 2012/106363 A2 | 8/2012 |
| WO | 2013/007839 A1 | 1/2013 |
| WO | 2013/041962 A1 | 3/2013 |
| WO | 2013/044147 A1 | 3/2013 |
| WO | 2013/050567 A1 | 4/2013 |
| WO | 2013/063086 A1 | 5/2013 |
| WO | 2013/096380 A2 | 6/2013 |
| WO | 2013/151762 A1 | 10/2013 |
| WO | 2014/008404 A1 | 1/2014 |
| WO | 2014/028777 A2 | 2/2014 |
| WO | 2014/031694 A2 | 2/2014 |
| WO | 2014/200921 A1 | 12/2014 |
| WO | 2015/081085 A2 | 6/2015 |

OTHER PUBLICATIONS

Arnesen, Thomas, "Towards a Functional Understanding of Protein N-Terminal Acetylation," PLoS Biology, vol. 9 (5):e1001074, doi: 10 .1371/journal.pbio.1 001 074, 5 pages (2011).

Asuni, Ayodeji A. et al., "Immunotherapy Targeting Pathological Tau Conformers in a Tangle Mouse Model Reduces Brain Pathology with Associated Functional Improvements," The Journal of Neuroscience, vol. 27(34):9115-9129 (2007).

Bartos, Ales et al., "Patients with Alzheimer disease have elevated intrathecal synthesis of antibodies against tau protein and heavy neurofilament," Journal of Neuroimmunology, vol. 252:100-105 (2012).

Bi, Mian et al., "Tau-Targeted Immunization Impedes Progression of Neurofibrillary Histopathology in Aged P301L Tau Transgenic Mice," PLoS ONE, vol. 6(12):e26860, doi: 10.1371/journal.pone. 0026860, 7 pages (2011).

Binder, Lester I. et al., "Tau, tangles, and Alzheimer's disease," Biochimica et Biophysica Acta, vol. 1739:216-223 (2005).

Borroni, B. et al., "Pattern of Tau forms in CSF is altered in progressive supranuclear palsy," Neurobiology of Aging, vol. 30:34-40 (2009).

Boutajangout, Allal et al., "Passive immunization targeting pathological phospho-tau protein in a mouse model reduces functional decline and clears tau aggregates from the brain," Journal of Neurochemistry, vol. 118:658-667 (2011).

Braak, Heiko et al., "Staging of Alzheimer's Disease-Related Neurofibrillary Changes," Neurobiology of Aging, vol. 16 (3):271-284 (1995).

Brunden, Kurt R. et al., "Advances in Tau-focused drug discovery for Alzheimer's disease and related tauopathies," Nat. Rev. Drug Discov., vol. 8(10):783-793 (2009).

Carmel, Gilles et al., The Structural Basis of Monoclonal Antibody Alz50's Selectivity for Alzheimer's Disease Pathology, vol. 271(51):32789-32795 (1996).

Chai, Xiyun et al., "Passive Immunization with Anti-Tau Antibodies in Two Transgenic Models, Reduction of Tau Pathology and Delay of Disease Progression," The Journal of Biological Chemistry, vol. 286(39):34457-34467 (2011).

Chow, K. Martin et al., "Aminopeptidases do not directly degrade tau protein," Molecular Neurodegeneration, vol. 5:48, doi: 10.1186/1750-1326-5-48, 10 pages (2010).

De Meyer, Geert et al., "Diagnosis-Independent Alzheimer Disease Biomarker Signature in Cognitively Normal Elderly People," Arch. Neurol., vol. 67(8):949-956 (2010).

De Strooper, Bart, "Proteases and Proteolysis in Alzheimer Disease: A Multifactorial View on the Disease Process," Physiol. Rev., vol. 90:465-494 (2010).

Demeule, Michel et al., "Identification and Design of Peptides as a New Drug Delivery System for the Brain," The Journal of Pharmacology and Experimental Therapeutics, vol. 324(3):1064-1072 (2008).

Fagan, Anne M. et al., "Cerebrospinal Fluid biomarkers of Alzheimer's disease," Biomark. Med., vol. 4(1):51-63 (2010).

Garcia-Sierra, Francisco et al., "Conformational changes and truncation of tau protein during tangle evolution in Alzheimer's disease," Journal of Alzheimer's Disease, vol. 5:65-77 (2003).

(56) References Cited

OTHER PUBLICATIONS

GenBank Accession No. CAI54295, "kappa light chain variable region, partial [Mus musculus]," 2 pages Apr. 15, 2005.
GenBank Accession No. NP_058525, "microtubule-associated protein tau isoform 4 [*Homo sapiens*]," 22 pages, May 5, 2014.
Ghoshal, Nupur et al., "Tau Conformational Changes Correspond to Impairments of Episodic Memory in Mild Cognitive Impairment and Alzheimer's Disease," Experimental Neurology, vol. 177:475-493 (2002).
Ghoshal, Nupur et al., "Tau-66: evidence for a novel tau conformation in Alzheimer's disease," Journal of Neurochemistry, vol. 77:1372-1385 (2001).
Griswold-Prenner, I. et al., "Effects of a Tau therapeutic antibody of the ISF/CSF levels of secreted Tau in the P301L mouse model," Neuroscience, Nanosymposium, Poster No. 598.07, 2 pages (2013).
Gu, Jiaping et al., "Two Novel Tau Antibodies Targeting the 396/404 Region Are Primarily Taken Up by Neurons and Reduce Tau Protein Pathology," The Journal of Biological Chemistry, vol. 288(46):33081-33095 (2013).
Guillozet-Bongaarts, Angela L. et al., "Tau truncation during neurofibrillary tangle evolution in Alzheimer's disease," Neurobiology of Aging, vol. 26:1015-1022 (2005).
Higuchi, Makoto et al., "Tau Protein and Tauopathy," Neuropsychopharmacology—5th Generation of Progress, Williams, & Wilkins, Philadelphia, Chapter 94, pp. 1339-1354 (2002).
Horowitz, Peleg M. et al., "Early N-Terminal Changes and Caspase-6 Cleavage of Tau in Alzheimer's Disease," The Journal of Neuroscience, vol. 24(36):7895-7902 (2004).
Hu, William T. et al., "Biomarker Discovery for Alzheimer's Disease, Frontotemporal Lobar Degeneration, and Parkinson's Disease," Acta Neuropathol., vol. 120(3):385-399 (2010).
International Preliminary Report on Patentability for Application No. PCT/US2013/055203, 9 pages, dated Sep. 30, 2014.
International Search Report and Written Opinion for Application No. PCT/US2014/041553, 14 pages, dated Sep. 2, 2014.
International Search Report and Written Opinion, PCT/US2013/055203, 18 pages, dated Mar. 18, 2014.
Ishiguro, Koichi et al., "Phosphorylated tau in human cerebrospinal fluid is a diagnostic marker for Alzheimer's disease," Neuroscience Letters, vol. 270:91-94 (1999).
Israel, Mason A. et al., "Probing sporadic and familial Alzheimer's disease using induced pluripotent stem cells," Nature, vol. 482(7384):216-220 (2012).
Jicha, Gregory A. et al., "Sequence Requirements for Formation of Conformational Variants of Tau Similar to Those Found in Alzheimer's Disease," Journal of Neuroscience Research, vol. 56:713-723 (1999).
Johnson, Gail V.W. et al., "The tau Protein in Human Cerebrospinal Fluid in Alzheimer's Disease Consists of Proteolytically Derived Fragments," Journal of Neurochemistry, vol. 68:430-433 (1997).
Kanaan, Nicholas M. et al., "Pathogenic Forms of Tau Inhibit Kinesin-Dependent Axonal Transport through a Mechanism Involving Activation of Axonal Phosphotransferases," The Journal of Neuroscience, vol. 31(27):9858-9868 (2011).
Kanaan, Nicholas M. et al., "Phosphorylation in the amino terminus of tau prevents inhibition of anterograde axonal transport," Neurobiol. Aging, vol. 33(4):826.e15-826.e30 (2012).
Kfoury, Najla et al., "Trans-cellular Propagation of Tau Aggregation by Fibrillar Species," The Journal of Biological Chemistry, vol. 287(23):19440-19451 (2012).
Kim, WonHee et al., "Secretion of human tau fragments resembling CDF-tau Alzheimer's disease is modulated by the presence of the exon 2 insert," FEBS Letters, vol. 584:3085-3088 (2010).
Ksiezak-Reding, H. et al., "Mapping of the Alz 50 Epitope in Microtubule-Associated Proteins Tau," Journal of Neuroscience Research, vol. 25:412-419 (1990).
Lewis, Jada et al., "Neurofibrillary tangles, amyotrophy and progressive motor disturbance in mice expressing mutant (P301L) tau protein," Nature Genetics, vol. 25:402-405 (2000).
Lin, Wen-Lang et al., "Filamentous Tau in Oligodendrocytes and Astrocytes of Transgenic Mice Expressing the Human Tau Isoform with the P301L Mutation," American Journal of Pathology, vol. 162(1):213-218 (2003).
Liu, Li et al., "Trans-Synaptic Spread of Tau Pathology In Vivo," PLoS ONE, vol. 7(2):e31302, doi: 10.1371/journal.pone.0031302, 9 pages (2012).
Meredith, Jere E. Jr. et al., "Characterization of Novel CSF Tau and ptau Biomarkers for Alzheimer's Disease," PLoS ONE, vol. 8(10):e76523, doi: 1031371/journal.pone.0076523, 14 pages (2013).
Meredith, Jere et al., "Novel Tau Fragments are Present in Human CSF," Alzheimer's Association International Conference, p. P276, Poster Presentation No. P2-039, 2 pages (2012).
Min, Sang-Won et al., "Acetylation of Tau Inhibits Its Degradation and Contributes to Tauopathy," Neuron., vol. 67 (6):953-966 (2010).
Plouffe, Vanessa et al., "Hyperphosphorylation and Cleavage of D421 Enhance Tau Secretion," PLoS ONE, vol. 7(5):e36873, doi: 1031371/journal.pone.0036873, 13 pages (2012).
Rafii, Michael S. et al., "Recent developments in Alzheimer's disease therapeutics," BMC Medicine, vol. 7(7), doi: 103.1186/1741-7015-7-7, 4 pages (2009).
Saman, Sudad et al., "Exosome-associated Tau Is Secreted in Tauopathy Models and Is Selectively Phosphorylated in Cerebrospinal Fluid in Early Alzheimer Disease," The Journal of Biological Chemistry, vol. 287(6):3842-3849 (2012).
Second Written Opinion for Application No. PCT/US2013/055203, 9 pages, dated Jul. 28, 2014.
Sigurdsson, Einar M., "Immunotherapy Targeting Pathological Tau Protein in Alzheimer's Disease and Related Tauopathies," J. Alzheimer's Dis., vol. 15(2):157-168 (2008).
U.S. Appl. No. 14/705,615, filed Jun. 7, 2016.
U.S. Appl. No. 14/705,615, filed May 24, 2016.
U.S. Appl. No. 14/896,611, filed Dec. 7, 2015, Irene Griswold-Prenner.
U.S. Appl. No. 14/705,615, filed Feb. 8, 2016.
U.S. Appl. No. 14/705,615, filed Sep. 29, 2015.
U.S. Appl. No. 14/705,615, filed Jul. 9, 2015.
U.S. Appl. No. 14/154,954, filed Jan. 14, 2014, Irene Griswold-Prenner.
U.S. Appl. No. 14/281,319, filed May 19, 2014, Irene Griswold-Prenner.
U.S. Appl. No. 14/481,544, filed Sep. 9, 2014, Irene Griswold-Prenner.
U.S. Appl. No. 14/092,539, filed Nov. 27, 2013, Irene Griswold-Prenner.
U.S. Appl. No. 14/104,717, filed Dec. 12, 2013, Irene Griswold-Prenner.
U.S. Appl. No. 14/104,706, filed Dec. 12, 2013, Irene Griswold-Prenner.
U.S. Appl. No. 14/154,954, filed Nov. 13, 2014.
U.S. Appl. No. 14/154,954, filed Jun. 20, 2014.
U.S. Appl. No. 14/281,319, filed Dec. 11, 2014.
U.S. Appl. No. 14/281,319, filed Nov. 4, 2014.
U.S. Appl. No. 14/281,319, filed Jul. 15, 2014.
U.S. Appl. No. 14/481,544, filed Dec. 23, 2014.
U.S. Appl. No. 14/092,539, filed Aug. 26, 2014.
U.S. Appl. No. 14/092,539, filed Apr. 30, 2014.
U.S. Appl. No. 14/092,539, filed Jan. 17, 2014.
U.S. Appl. No. 14/104,717, filed Apr. 21, 2014.
U.S. Appl. No. 14/104,717, filed Feb. 26, 2014.
U.S. Appl. No. 14/104,706, filed Apr. 25, 2014.
U.S. Appl. No. 14/104,706, filed Feb. 28, 2014.
Sigurdsson, Einar M., "Tau-Focused Immunotherapy for Alzheimer's Disease and Related Tauopathies," Curr. Alzheimer Res., vol. 6(5):446-450 (2009).
Terwel, Dick et al., "Changed Conformation of Mutant Tau-P301L Underlies the Moribund Tauopathy, Absent in Progressive, Nonlethal Axonopathy of Tau-4R/2N Transgenic Mice," The Journal of Biological Chemistry, vol. 280 (5):3963-3973 (2005).

(56) References Cited

OTHER PUBLICATIONS

Troquier, Laetitia et al., "Targeting Phospho-Ser422 by Active Tau Immunotherapy in the THY-Tau22 Mouse Model: A Suitable Therapeutic Approach," Current Alzheimer Research, vol. 9:397-405 (2012).

Vigo-Pelfrey, C. et al., "Elevation of microtubule-associated protein tau in the cerebrospinal fluid of patients with Alzheimer's disease," Neurology, vol. 45:788-793 (1995).

Ward, Sarah M. et al., "Tau oligomers and tau toxicity in neurodegenerative disease," Biochem. Soc. Trans, vol. 40:667-671 (2012).

Waxman, Elisa A. et al., "Induction of intracellular tau aggregation is promoted by a-synuclein seeds, and provides novel insights into the hyperphosphorylation of tau," J. Neurosci., vol. 31(21):7604-7618 (2011).

Whiteman, Ineka T. et al., "Rapid Changes in Phosph-MAP/Tau Epitopes during Neuronal Stress: Cofilin-Actin Rods Primarily Recruit Microtubule Binding Domain Epitopes," PLoS ONE, vol. 6(6):e20878, doi: 1031371/journal.pone.0020878, 12 pages (2011).

Yamamori, Hidenaga et al., "Tau in cerebrospinal fluid: a sensitive sandwich enzyme-linked immunosorbent assay using tyramide signal amplification," Neurosci. Lett., vol. 418(2):186-189 (2007).

Yanamandra, Kiran et al., "Anti-Tau Antibodies that Block Tau Aggregate Seeding In Vitro Markedly Decrease Pathology and Improve Cognition In Vivo," Neuron, vol. 80:402-414 (2013).

Yoshiyama, Yasumasa et al., "Therapeutic strategies for tau mediated neurodegeneration," J. Neurol. Neurosurg. Psychiatry, vol. 84:784-795 (2013).

U.S. Appl. No. 14/705,615, filed May 6, 2015, Irene Griswold-Penner.

U.S. Appl. No. 14/481,544, Irene Griswold-Penner, filed Sep. 9, 2014, Date Mailed Apr. 13, 2015.

\* cited by examiner

Hybridoma IPN001 Heavy Chain Sequences

```
        E   V   Q   L   V   E   S       G   E   D       L   V   K   P   G   G   S       L   K   L
  1   GAGGTGCAGT TGGTGGAGTC TGGGGAAGAC TTAGTGAAGC CTGGAGGGTC CCTGAAACTC
  2
        S   C   V   A   S   G   F       A   F   S       S   Y   G   M   S       W   V   R   Q   T
 61   TCCTGTGTCG CTTCTGGATT CGCTTTCAGT AGCTATGGCA TGTCTTGGGT TCGCCAGACT

P   D   M   R   L   E   W       V   A       T   I   S   S   S   G   S   R       T   Y   F
121   CCAGACATGA GGCTGGAGTG GGTCGCAACA ATTAGTAGCA GTGGTAGTCG CACCTACTTT

P   D   S   V   K   G       R   L   T   I   S   R   D   N   D   K   N       I   L   Y
181   CCAGACAGTG TGAAGGGGCG ACTCACCATC TCCAGAGACA ATGACAAGAA CATCCTATAC

L   Q   M   S   L   R       S   E   D       T   A   M   Y   Y   C   T   I       T   W
241   CTACAAATGA GCAGTCTGAG GTCTGAGGAC ACAGCCATGT ACTATTGTAC GATTACCTGG

D   G   A   M   D   Y       W   G   R   G       I   S   V   T   V   S   S       (SEQ ID NO:14)
301   GACGGTGCTA TGGACTACTG GGGTCGTGGA ATATCAGTCA CCGTCTCCTC A         (SEQ ID NO:18)
```

CDR definitions and protein sequence numbering according to Kabat numbering system.
CDRs, and nucleotide sequences encoding the CDRs, are in bold text and underlined.

FIG. 1A

Hybridoma IPN001 Light Chain Sequences

```
          D   V   L   M   T   Q   T   P   L   S   L   A   V   N   L   G   D   Q   A   S
  1   GATGTTTTGA TGACCCAAAC TCCGCTCTCC CTGGCAGTCA ATCTTGGAGA TCAAGCCTCC

L   S   C   R   S   S   Q   T   I   L   H   S   N   G   N   T   Y   L   E   W
 61   CTCTCTTGCA GATCGAGTCA GACTATTTTA CATAGTAATG GAAATACCTA TTTAGAATGG

Y   L   Q   K   P   G   Q   S   P   R   L   L   I   Y   K   V   S   K   R   F
121   TATTTGCAGA AACCAGGCCA GTCTCCAAGA CTCCTGATCT ACAAAGTTTC TAAACGATTT

S   G   V   P   D   R   F   S   G   S   G   S   G   T   D   F   T   L   K   I
181   TCTGGGGTCC CAGACAGGTT CAGTGGCAGT GGATCAGGGA CAGATTTCAC ACTCAAGATC

S   R   V   E   A   D   D   L   G   I   Y   Y   C   F   Q   G   S   L   V   P
241   AGCAGAGTGG AGGCTGACGA TCTGGGAATT TATTACTGCT TTCAAGGTTC ACTTGTTCCT

W   A   F   G   G   G   T   K   L   E   I   K          (SEQ ID NO:13)
301   TGGGCGTTCG GTGGAGGCAC CAAGCTGGAA ATCAAA     (SEQ ID NO:17)
```

CDR definitions and protein sequence numbering according to Kabat numbering system. CDRs, and nucleotide sequences encoding the CDRs, are in bold text and underlined.

FIG. 1B

Hybridoma IPN002 Heavy Chain Sequences

```
1     E  V  H  L  V  E  S     G  G  A     L  V  K  P  G  G  S     L  K  L
      GAGGTTCATC TGGTGGAGTC TGGGGGAGCC TTAGTGAAGC CTGGAGGGTC CCTGAAACTC

61    S  C  A  A  S  G  F     S  F  S     Q  F  S     K  Y  G  M  S     W  V  R  Q  T
      TCCTGTGCAG CCTCTGGATT CAGTTTCAGT AAATATGGCA TGTCTTGGGT TCGCCAGACT

121   P  D  K  R  L  E  W     V  A  T     I  S  S  G  S  R     T  Y  Y
      CCAGACAAGA GGCTGGAGTG GGTCGCAACC ATTAGTAGTA GTGGGAGTCG CACCTACTAT

181   P  D  S  V  K  G     Q  F  T  I     S  R  D  N  A  K  N     T  L  Y
      CCAGACAGTG TGAAGGGCCA ATTCACCATC TCCAGAGACA ATGCCAAGAA CACCCTGTAC

241   L  Q  M  S  L  K     S  E  D     T  A  M  Y  Y  C  S     I  S  W
      CTGCAAATGA GCAGTCTGAA GTCTGAGGAC ACAGCCATGT ATTACTGTTC AATTAGCTGG

301   D  G  A  M  D  Y     W  G  Q  G     T  S  V  T  V  S  S       (SEQ ID NO:16)
      GACGGTGCTA TGGACTACTG GGGTCAAGGG ACCTCAGTCA CCGTCTCCTC A    (SEQ ID NO:20)
```

CDR definitions and protein sequence numbering according to Kabat numbering system.
CDRs, and nucleotide sequences encoding the CDRs, are in bold text and underlined.

FIG. 2A

Hybridoma IPN002 Light Chain Sequences

```
       D   V   L   M   T   Q   T   P   L   S   L   P   V   S   L   G   D   Q   A   S
  1    GATGTTTTGA TGACCCAAAC TCCACTCTCC CTGCCCTGTCA GTCTTGGAGA TCAAGCCTCC

I   S   C   K   S   S   Q   S   I   V   H   S   N   G   N   T   Y   L   E   W
 61    ATCTCTTGCA AATCTAGTCA GAGCATTGTA CATAGTAATG GAAACACCTA TTTAGAATGG

Y   L   Q   K   P   G   Q   S   P   K   L   L   V   Y   K   V   S   N   R   F
121    TACCTGCAGA AACCAGGCCA GTCTCCAAAG CTCCTGGTCT ACAAAGTTTC CAATCGATTT

S   G   V   P   D   R   F   S   G   S   G   S   G   T   D   F   T   L   K   I
181    TCTGGGGTCC CAGACAGGTT CAGTGGCAGT GGATCAGGGA CAGATTTCAC ACTCAAGATC

S   R   V   E   A   E   D   L   G   T   Y   Y   C   F   Q   G   S   L   V   P
241    AGCAGAGTGG AGGCTGAGGA TCTGGGAACT TATTACTGCT TTCAAGGTTC ACTTGTTCCT

W   A   F   G   G   G   T   K   L   E   I   K           (SEQ ID NO:15)
301    TGGGCGTTCG GTGGAGGCAC CAAGCTGGAA ATCAAA     (SEQ ID NO:19)
```

CDR definitions and protein sequence numbering according to Kabat numbering system. CDRs, and nucleotide sequences encoding the CDRs, are in bold text and underlined.

FIG. 2B

Human tau isoforms

| | | |
|---|---|---|
| isoform 2 | MAEPRQEFEVMEDHAGTYGLGDRKDQGGYTMHQDQEGDTDAGLKESPLQTPTEDGSEEPG | 60 |
| isoform 3 | MAEPRQEFEVMEDHAGTYGLGDRKDQGGYTMHQDQEGDTDAGLK----------------- | 44 |
| isoform 4 | MAEPRQEFEVMEDHAGTYGLGDRKDQGGYTMHQDQEGDTDAGLK----------------- | 44 |
| isoform 5 | MAEPRQEFEVMEDHAGTYGLGDRKDQGGYTMHQDQEGDTDAGLKESPLQTPTEDGSEEPG | 60 |
| isoform 6 | MAEPRQEFEVMEDHAGTYGLGDRKDQGGYTMHQDQEGDTDAGLKESPLQTPTEDGSEEPG | 60 |
| isoform 1 | MAEPRQEFEVMEDHAGTYGLGDRKDQGGYTMHQDQEGDTDAGLKESPLQTPTEDGSEEPG | 60 |
| fetal | MAEPRQEFEVMEDHAGTYGLGDRKDQGGYTMHQDQEGDTDAGLK----------------- | |
| | ******************************************                 | |

| | | |
|---|---|---|
| isoform 2 | SETSDAKSTPTAEDVTAPLVDEGAPGKQAAAQPHTEIPEGTTAEEAGIGDTPSLEDEAAG | 120 |
| isoform 3 | -----------------------------------------AEEAGIGDTPSLEDEAAG | 62 |
| isoform 4 | -----------------------------------------AEEAGIGDTPSLEDEAAG | 62 |
| isoform 5 | SETSDAKSTP-------------------------TAEAEEAGIGDTPSLEDEAAG | 91 |
| isoform 6 | SETSDAKSTPTAEDVTAPLVDEGAPGKQAAAQPHTEIPEGTTAEEAGIGDTPSLEDEAAG | 120 |
| isoform 1 | SETSDAKSTPTAEDVTAPLVDEGAPGKQAAAQPHTEIPEGTTAEEAGIGDTPSLEDEAAG | 120 |
| fetal | -----------------------------------------AEEAGIGDTPSLEDEAAG | |
| | ******************                      | |

| | | |
|---|---|---|
| isoform 2 | HVTQ-------------------------------------------------------- | 124 |
| isoform 3 | HVTQ-------------------------------------------------------- | 66 |
| isoform 4 | HVTQ-------------------------------------------------------- | 66 |
| isoform 5 | HVTQ-------------------------------------------------------- | 95 |
| isoform 6 | HVTQEPESGKVVQEGFLREPGPPGLSHQLMSGMPGAPLLPEGPREATRQPSGTGPEDTEG | 180 |
| isoform 1 | HVTQEPESGKVVQEGFLREPGPPGLSHQLMSGMPGAPLLPEGPREATRQPSGTGPEDTEG | 180 |
| fetal | HVTQ-------------------------------------------------------- | |
| | ****                                                        | |

FIG. 6A

```
isoform 2    ------------------------------------------------------------
isoform 3    ------------------------------------------------------------
isoform 4    ------------------------------------------------------------
isoform 5    ------------------------------------------------------------
isoform 6    GRHAPELLKHQLLGDLHQEGPPLKGAGGKERPGSKEEVDEDRDVDESSPQDSPPSKASPA  240
isoform 1    GRHAPELLKHQLLGDLHQEGPPLKGAGGKERPGSKEEVDEDRDVDESSPQDSPPSKASPA  240
fetal        ------------------------------------------------------------ isoform 2    ------------------------------------------------------------
isoform 3    ------------------------------------------------------------
isoform 4    ------------------------------------------------------------
isoform 5    ------------------------------------------------------------
isoform 6    QDGRPPQTAAREATSIPGFPAEGAIPLPVDFLSKVSTEIPASEPDGPSVGRAKGQDAPLE  300
isoform 1    QDGRPPQTAAREATSIPGFPAEGAIPLPVDFLSKVSTEIPASEPDGPSVGRAKGQDAPLE  300
fetal        ------------------------------------------------------------ isoform 2    ------------------------------------------------------------
isoform 3    ------------------------------------------------------------
isoform 4    ------------------------------------------------------------
isoform 5    ------------------------------------------------------------
isoform 6    FTFHVEITPNVQKEQAHSEEHLGRAAFPGAPGEGPEARGPSLGEDTKEADLPEPSEKQPA  360
isoform 1    FTFHVEITPNVQKEQAHSEEHLGRAAFPGAPGEGPEARGPSLGEDTKEADLPEPSEKQPA  360
fetal        ------------------------------------------------------------ isoform 2    ---------------ARMVSKSKDGTGSDDKKAK------------------------  143
isoform 3    ---------------ARMVSKSKDGTGSDDKKAK--------------------------   85
isoform 4    ---------------ARMVSKSKDGTGSDDKKAK--------------------------   85
isoform 5    ---------------ARMVSKSKDGTGSDDKKAK--------------------------  114
isoform 6    ---------------ARMVSKSKDGTGSDDKKAK--------------------------  420
isoform 1    AAPRGKPVSRVPQLKARMVSKSKDGTGSDDKKAKTSTRSSAKTLKNRPCLSPKHPTPGSS  420
fetal        AAPRGKPVSRVPQLKARMVSKSKDGTGSDDKKAKTSTRSSAKTLKNRPCLSPKHPTPGSS  420
                            ******************
```

FIG. 6B

```
isoform 2   ------------------------------------------------------------GADGKTKIATPRGAAPPGQK  163
isoform 3   ------------------------------------------------------------GADGKTKIATPRGAAPPGQK  105
isoform 4   ------------------------------------------------------------GADGKTKIATPRGAAPPGQK  105
isoform 5   ------------------------------------------------------------GADGKTKIATPRGAAPPGQK  134
isoform 6   DPLIQPSSPAVCPEPPSSPKHVSSVTSRTGSSGAKEMKLKGADGKTKIATPRGAAPPGQK  480
isoform 1   DPLIQPSSPAVCPEPPSSPKHVSSVTSRTGSSGAKEMKLKGADGKTKIATPRGAAPPGQK  480
fetal       ------------------------------------------------------------GADGKTKIATPRGAAPPGQK
                                                                        ******************* isoform 2   GQANATRIPAKTPPAPKTPPSS---------------------------------GEPPKSGDRSGYSSPGSPGT  205
isoform 3   GQANATRIPAKTPPAPKTPPSS---------------------------------GEPPKSGDRSGYSSPGSPGT  147
isoform 4   GQANATRIPAKTPPAPKTPPSS---------------------------------GEPPKSGDRSGYSSPGSPGT  147
isoform 5   GQANATRIPAKTPPAPKTPPSS---------------------------------GEPPKSGDRSGYSSPGSPGT  176
isoform 6   GQANATRIPAKTPPAPKTPPSSATKQVQRRPPPAGPRSERGEPPKSGDRSGYSSPGSPGT  540
isoform 1   GQANATRIPAKTPPAPKTPPSS---------------------------------GEPPKSGDRSGYSSPGSPGT  522
fetal       GQANATRIPAKTPPAPKTPPSS---------------------------------GEPPKSGDRSGYSSPGSPGT
            ********************                                 ****************** isoform 2   PGSRSRTPSLPTPPTREPKKVAVVRTPPKSPSSAKSRLQTAPVPMPDLKNVKSKIGSTEN  265
isoform 3   PGSRSRTPSLPTPPTREPKKVAVVRTPPKSPSSAKSRLQTAPVPMPDLKNVKSKIGSTEN  207
isoform 4   PGSRSRTPSLPTPPTREPKKVAVVRTPPKSPSSAKSRLQTAPVPMPDLKNVKSKIGSTEN  207
isoform 5   PGSRSRTPSLPTPPTREPKKVAVVRTPPKSPSSAKSRLQTAPVPMPDLKNVKSKIGSTEN  236
isoform 6   PGSRSRTPSLPTPPTREPKKVAVVRTPPKSPSSAKSRLQTAPVPMPDLKNVKSKIGSTEN  600
isoform 1   PGSRSRTPSLPTPPTREPKKVAVVRTPPKSPSSAKSRLQTAPVPMPDLKNVKSKIGSTEN  582
fetal       PGSRSRTPSLPTPPTREPKKVAVVRTPPKSPSSAKSRLQTAPVPMPDLKNVKSKIGSTEN
            ***********************************************************
```

FIG. 6C

| isoform 2 | LKHQPGGGKVQIINKKLDLSNVQSKCGSKDNIKHVPGGGSVQIVYKPVDLSKVTSKCGSL | 325 |
| isoform 3 | LKHQPGGGKVQIINKKLDLSNVQSKCGSKDNIKHVPGGGSVQIVYKPVDLSKVTSKCGSL | 267 |
| isoform 4 | LKHQPGGGK--------------------------------VQIVYKPVDLSKVTSKCGSL | 236 |
| isoform 5 | LKHQPGGGKVQIINKKLDLSNVQSKCGSKDNIKHVPGGGSVQIVYKPVDLSKVTSKCGSL | 296 |
| isoform 6 | LKHQPGGGKVQIINKKLDLSNVQSKCGSKDNIKHVPGGGSVQIVYKPVDLSKVTSKCGSL | 660 |
| isoform 1 | LKHQPGGGKVQIINKKLDLSNVQSKCGSKDNIKHVPGGGSVQIVYKPVDLSKVTSKCGSL | 642 |
| fetal     | LKHQPGGGK--------------------------------VQIVYKPVDLSKVTSKCGSL |     |
|           | *********                               ******************* |     |

| isoform 2 | GNIHHKPGGGQVEVKSEKLDFKDRVQSKIGSLDNITHVPGGGNKKIETHKLTFRENAKAK | 385 |
| isoform 3 | GNIHHKPGGGQVEVKSEKLDFKDRVQSKIGSLDNITHVPGGGNKKIETHKLTFRENAKAK | 327 |
| isoform 4 | GNIHHKPGGGQVEVKSEKLDFKDRVQSKIGSLDNITHVPGGGNKKIETHKLTFRENAKAK | 296 |
| isoform 5 | GNIHHKPGGGQVEVKSEKLDFKDRVQSKIGSLDNITHVPGGGNKKIETHKLTFRENAKAK | 356 |
| isoform 6 | GNIHHKPGGGQVEVKSEKLDFKDRVQSKIGSLDNITHVPGGGNKKIETHKLTFRENAKAK | 720 |
| isoform 1 | GNIHHKPGGGQVEVKSEKLDFKDRVQSKIGSLDNITHVPGGGNKKIETHKLTFRENAKAK | 702 |
| fetal     | ************************************************************ |     |

| isoform 2 | TDHGAEIVYKSPVVSGDTSPRHLSNVSSTGSIDMVDSPQLATLADEVSASLAKQGL | 441 | (SEQ ID NO:21) |
| isoform 3 | TDHGAEIVYKSPVVSGDTSPRHLSNVSSTGSIDMVDSPQLATLADEVSASLAKQGL | 383 | (SEQ ID NO:22) |
| isoform 4 | TDHGAEIVYKSPVVSGDTSPRHLSNVSSTGSIDMVDSPQLATLADEVSASLAKQGL | 352 | (SEQ ID NO:23) |
| isoform 5 | TDHGAEIVYKSPVVSGDTSPRHLSNVSSTGSIDMVDSPQLATLADEVSASLAKQGL | 412 | (SEQ ID NO:24) |
| isoform 6 | TDHGAEIVYKSPVVSGDTSPRHLSNVSSTGSIDMVDSPQLATLADEVSASLAKQGL | 776 | (SEQ ID NO:25) |
| isoform 1 | TDHGAEIVYKSPVVSGDTSPRHLSNVSSTGSIDMVDSPQLATLADEVSASLAKQGL | 758 | (SEQ ID NO:26) |
| fetal     | TDHGAEIVYKSPVVSGDTSPRHLSNVSSTGSIDMVDSPQLATLADEVSASLAKQGL | (SEQ ID NO:27) | |

FIG. 6D

IPN002 VH Variant 1

```
         10        20        30        40        50        60        70        80        90       100
GAGGTTCATCTGGTGGAGTCTGGGGGAGGCTTAGTGAAGCCTGGAGGGTCCCTGAGACTCTCCTGTGCAGCCTCTGGATTCAGTTTCAGTAAATATGGCA
 E  V  H  L  V  E  S  G  G  A  L  V  K  P  G  G  S  L  R  L  S  C  A  A  S  G  F  S  F  S  K  Y  G
                           10                          20                          30

110       120       130       140       150       160       170       180       190       200
TGTCTCTTGGGTTCGCCAGGCTCCAGGGAAGGGCCCTGGAGTGGGTCGCAACCATTAGTAGTAGTGGAGTCGCACTACTATCCAGACAGTGTGAAGGGCAG
 M  S  W  V  R  Q  A  P  G  K  G  L  E  W  V  A  T  I  S  S  S  G  S  R  T  Y  Y  P  D  S  V  K  G  R
                40                             50 52 A                     60
                                                    B  C 210       220       230       240       250       260       270       280       290       300
ATTCACCATCTCCAGAGACAATGCCAAGAACACCCTGTACCTGCAAATGAGCAGTCTGAAGTCTGAGGACACAGCCATGTATTACTGTTCAATTAGCTGG
 F  T  I  S  R  D  N  A  K  N  T  L  Y  L  Q  M  S  S  L  K  S  E  D  T  A  M  Y  Y  C  S  I  S  W
                    70                          80 82 A                     90
                                                       B  C 310       320       330       340       350
GACGGGTGCTATGGACTACTGGGGTCAAGGGACCTCAGTCACCGTCTCCTCA (SEQ ID NO:28)
 D  G  A  M  D  Y  W  G  Q  G  T  S  V  T  V  S  S    (SEQ ID NO:36)
                   100                        110  113
```

CDR definitions and protein sequence numbering according to Kabat. CDR nucleotide and amino acid sequences are underlined.

FIG. 9

IPN002 VH Variant 2

```
         10        20        30        40        50        60        70        80        90       100
GAGGTTCATCTGGTGGAGTCTGGGGGAGCCTTAGTGAAGCCTGGAGGGTCCCTGAGACTCTCCTGTGCAGCCTCTGGATTCAGTTTCAGTAAATATGGCA
 E  V  H  L  V  E  S  G  G  A  L  V  K  P  G  G  S  L  R  L  S  C  A  A  S  G  F  S  F  S  K  Y  G
                               10                        20                        30

110       120       130       140       150       160       170       180       190       200
TGTCTCTTGGGTTCGCCAGGCCCCAGGCCAAGGGCCTGGAGTGGGTCGCCAACCATTAGTAGTAGTGGGAGTCGCACCTACTATCCAGACAGTGTGAAGGGCAG
 M  S  W  V  R  Q  A  P  G  K  G  L  E  W  V  A  T  I  S  S  G  S  R  T  Y  Y  P  D  S  V  K  G  R
                     40                               50 52 A                     60
                                                           A  B  C 210       220       230       240       250       260       270       280       290       300
ATTCACCATCTCCAGAGACAATGCCAAGAACACCCTGTACCTGCAAATGAACAGTCTGAGAGCCGAGGACACAGCCATGTATTACTGTTCAATTAGCTGG
 F  T  I  S  R  D  N  A  K  N  T  L  Y  L  Q  M  N  S  L  R  A  E  D  T  A  M  Y  Y  C  S  I  S  W
               70                        80  82 A                    90
                                              A  B  C 310       320       330       340       350
GACGGGTGCTATGGACTACTGGGGTCAAGGAACCACCGTCACCGTCTCCTCA (SEQ ID NO:29)
 D  G  A  M  D  Y  W  G  Q  G  T  T  V  T  V  S  S    (SEQ ID NO:37)
      100                      110              113
```

CDR definitions and protein sequence numbering according to Kabat. CDR nucleotide and amino acid sequences are underlined.

FIG. 10

IPN002 VH Variant 3

```
         10         20         30         40         50         60         70         80         90        100
GAGGTTCAGCTGGTGGAGTCTGGGGGAGGCTTAGTGAAGCCTGGGGGGTCCCTGAGACTCTCCTGTGCAGCCTCTGGATTCAGTTTCAGTAAATATGGCA
 E  V  Q  L  V  E  S  G  G  G  L  V  K  P  G  G  S  L  R  L  S  C  A  A  S  G  F  S  F  S  K  Y  G
                            10                          20                          30

110        120        130        140        150        160        170        180        190        200
TGTCTTGGGTTCGCCAGGCCCCAGGCAAGGGCCTGGAGTGGGTCGCAACCATTAGTAGTGGGAGTCGCACCTACTATCCAGACAGTGTGAAGGGCAG
 M  S  W  V  R  Q  A  P  G  K  G  L  E  W  V  A  T  I  S  S  G  S  R  T  Y  Y  P  D  S  V  K  G  R
                40                          50  52 A                        60

210        220        230        240        250        260        270        280        290        300
ATTCACCATCTCCAGAGACAATGCCAAGAACACCCTGTACCTGCAAATGAACAGTCTGAGAGCCGAGGACACAGCCATGTATTACTGTTCAATTAGCTGG
 F  T  I  S  R  D  N  A  K  N  T  L  Y  L  Q  M  N  S  L  R  A  E  D  T  A  M  Y  Y  C  S  I  S  W
                70                  82 A B C        80                           90

310        320        330        340        350
GACGGTGCTATGGACTACTGGGGTCAAGGAACCACCGTCACCGTCTCCTCA (SEQ ID NO:30)
 D  G  A  M  D  Y  W  G  Q  G  T  T  V  T  V  S  S     (SEQ ID NO:38)
      100                       110          113
```

CDR definitions and protein sequence numbering according to Kabat. CDR nucleotide and amino acid sequences are underlined.

FIG. 11

IPN002 VH Variant 4

```
         10         20         30         40         50         60         70         80         90        100
GAGGTTCAGCTGGTGGAGTCTGGGGGAGGCTTAGTGAAGCCTGGAGGGTCCCTGAGACTCTCCTGTGCAGCCTCTGGATTCAGTTTCAGTAAATATGGCA
 E  V  Q  L  V  E  S  G  G  A  L  V  K  P  G  G  S  L  R  L  S  C  A  A  S  G  F  S  F  S  K  Y  G
                                                    10                            20                  30

110        120        130        140        150        160        170        180        190        200
TGTCTTGGGTTCGCCAGGCCCCAGGGAAGGGCCTGGAGTGGGTCGCAACCATTAGTAGTAGTGGAGTGGGAGTCGCACCTACTATCCAGACACAGTGTGAAGGGCAG
 M  S  W  V  R  Q  A  P  G  K  G  L  E  W  V  A  T  I  S  S  S  G  S  R  T  Y  Y  P  D  S  V  K  G  R
                          40                         50 52 A                       60

210        220        230        240        250        260        270        280        290        300
ATTCACCATCTCCAGAGACAATGCCAAGAACACCCTGTACCTGCAAATGAACAGTCTGAGAGCCGAGGACACAGCCATGTATTACTGTGCCATTAGCTGG
 F  T  I  S  R  D  N  A  K  N  T  L  Y  L  Q  M  N  S  L  R  A  E  D  T  A  M  Y  Y  C  A  I  S  W
                  70                         80 82 A B C                           90

310        320        330        340        350
GACGGTGCTATGGACTACTGGGGTCAAGGGACCACCGTCTCCTCA  (SEQ ID NO:31)
 D  G  A  M  D  Y  W  G  Q  G  T  T  V  S  S     (SEQ ID NO:39)
         100                     110         113
```

CDR definitions and protein sequence numbering according to Kabat. CDR nucleotide and amino acid sequences are underlined.

FIG. 12

IPN002 Vk Variant 1

```
         10         20         30         40         50         60         70         80         90        100
GATGTTTTGATGACCCAAAGCCCACTCTCCCTGCCTGTCAGTCTTGGACAGCCCGCCTCCATCTCTTGCAAATCTAGTCAGAGCATTGTACATAGTAATG
 D  V  L  M  T  Q  S  P  L  S  L  P  V  T  L  G  Q  P  A  S  I  S  C  K  S  S  Q  S  I  V  H  S  N
                                       10                        20                       27 A B C D E 110        120        130        140        150        160        170        180        190        200
GAAACACCTATTTAGAATGGTACCTGCAGAAACCAGGCCAGTCTCCACAGCTCCTGATCTACAAAGTTTCCAATCGATTTTCTGGGGTCCCAGACAGATT
 G  N  T  Y  L  E  W  Y  L  Q  K  P  G  Q  S  P  Q  L  L  V  Y  K  V  S  N  R  F  S  G  V  P  D  R  F
    30                       40                                     50                        60

210        220        230        240        250        260        270        280        290        300
CAGTGGCAGTGGATCAGGGACAGATTTCACACTCAAGATCAGCAGAGTGGAGGCTGAGGATGTGGGAACTTATTACTGCTTTCAAGGCTCACTTGTTCCT
 S  G  S  G  S  G  T  D  F  T  L  K  I  S  R  V  E  A  E  D  V  G  T  Y  Y  C  F  Q  G  S  L  V  P
              70                                      80                                    90

310        320
TGGGGCGTTCGGTGGAGGCACCAAGGTGGAAATCAAA        (SEQ ID NO:32)
 W  A  F  G  G  G  T  K  V  E  I  K            (SEQ ID NO:40)
           100                   106 A
```

FIG. 13

CDR definitions and protein sequence numbering according to Kabat. CDR nucleotide and amino acid sequences are underlined.

IPN002 Vk Variant 2

```
         10         20         30         40         50         60         70         80         90        100
GATGTTGTGATGACCCAAAGCCCACTCTCCCTGCCTGTCACCCTTGGACAGCCCGCCTCCATCTCTTGCAAATCTAGTCAGAGCATTGTACATAGTAATG
 D  V  V  M  T  Q  S  P  L  S  L  P  V  T  L  G  Q  P  A  S  I  S  C  K  S  S  Q  S  I  V  H  S  N
                      10                      20                                  27 A B C D E 110        120        130        140        150        160        170        180        190        200
GAAACACCTATTTAGAATGGTACCTGCAGAAACCAGGCCAGTCTCCACAGCTCCTGGTCTACAAAGTTTCCAATCGATTTTCTGGGGTCCCAGACAGATT
 G  N  T  Y  L  E  W  Y  L  Q  K  P  G  Q  S  P  Q  L  L  V  Y  K  V  S  N  R  F  S  G  V  P  D  R  F
 30                         40                                      50                          60

210        220        230        240        250        260        270        280        290        300
CAGTGGCAGTGGATCAGGGACAGATTTCACACTCAAGATCAGCAGAGTGGAGGCTGAGGATGTGGGAACTTATTACTGCTTTCAAGGCTCACTTGTTCCT
 S  G  S  G  S  G  T  D  F  T  L  K  I  S  R  V  E  A  E  D  V  G  T  Y  Y  C  F  Q  G  S  L  V  P
                     70                             80                              90

310        320
TGGGGCGTTCGGTGGAGGCACCAAGGTGGAAATCAAA    (SEQ ID NO:33)
 W  A  F  G  G  G  T  K  V  E  I  K      (SEQ ID NO:41)
            100            106 A
```

CDR definitions and protein sequence numbering according to Kabat. CDR nucleotide and amino acid sequences are underlined.

FIG. 14

IPN002 Vk Variant 3

```
         10         20         30         40         50         60         70         80         90        100
GATGTTGTGATGACCCAAACTCCACTCTCCCTGCCTGTCACCCTTGGACAGCCGGCCTCCATCTCTTGCAAATCTAGTCAGAGCATTGTACATAGTAATG
 D  V  V  M  T  Q  T  P  L  S  L  P  V  T  L  G  Q  P  A  S  I  S  C  K  S  S  Q  S  I  V  H  S  N
                   10                      20                                    27 A  B  C  D  E 110        120        130        140        150        160        170        180        190        200
GAAACACCTATTTAGAATGTACCTGCAGAAACCAGGCCAGTCTCCACAGCTCCTGGTCTCACAAAGTTTCCAATCGATTTTCTGGGGTCCCAGACAGATT
 G  N  T  Y  L  E  W  Y  L  Q  K  P  G  Q  S  P  Q  L  L  V  Y  K  V  S  N  R  F  S  G  V  P  D  R  F
 30                         40                                              50                        60

210        220        230        240        250        260        270        280        290        300
CAGTGGCAGTGGATCAGGGACAGATTTCACACTCAAGATCAGCAGAGTGGAGGCTGAGGATGTGGGAGTGTATTACTGCTTTCAAGGCTCACTTGTTCCT
 S  G  S  G  S  G  T  D  F  T  L  K  I  S  R  V  E  A  E  D  V  G  V  Y  Y  C  F  Q  G  S  L  V  P
                   70                                    80                               90

310        320
TGGGGCGTTCGGTGGAGGCACCAAGGTGGAAATCAAA    (SEQ ID NO:34)
 W  A  F  G  G  G  T  K  V  E  I  K       (SEQ ID NO:42)
         100                  106 A
```

CDR definitions and protein sequence numbering according to Kabat. CDR nucleotide and amino acid sequences are underlined.

FIG. 15

IPN002 Vk Variant 4

```
         10         20         30         40         50         60         70         80         90        100
GATGTTGTGATGACCCAAAGCCCACTCTCCCTGCCTGTCACCCTTGGACAGCCGGCCTCCATCTCTTGCAAATCTAGTCAGAGCATTGTACATAGTAATG
 D  V  V  M  T  Q  S  P  L  S  L  P  V  T  L  G  Q  P  A  S  I  S  C  K  S  S  Q  S  I  V  H  S  N
                             10                          20                    27 A B C D E 110        120        130        140        150        160        170        180        190        200
GAAACACCTATTTAGAATGTACTTGGTACCTGCAGAAACCAGGCCAGTCTCCACAGCTCCTGATCTACAAAGTTTCCAATCGATTTTCTGGGGTCCCAGACAGATT
 G  N  T  Y  L  E  W  Y  L  Q  K  P  G  Q  S  P  Q  L  L  I  Y  K  V  S  N  R  F  S  G  V  P  D  R  F
    30                          40                          50                          60

210        220        230        240        250        260        270        280        290        300
CAGTGGCAGTGGATCAGGGACAGATTTCACACTCAAGATCAGCAGAGTGGAGGCTGAGGATGTGGGAGTGTATTACTGCTTTCAAGGCTCACTTGTTCCT
 S  G  S  G  S  G  T  D  F  T  L  K  I  S  R  V  E  A  E  D  V  G  V  Y  Y  C  F  Q  G  S  L  V  P
                   70                          80                          90

310        320
TGGGGCGTTCGGTGGAGGCACCAAGGTGGAAATCAAA (SEQ ID NO:35)
 W  A  F  G  G  G  T  K  V  E  I  K      (SEQ ID NO:43)
       100                   106 A
```

CDR definitions and protein sequence numbering according to Kabat. CDR nucleotide and amino acid sequences are underlined.

FIG. 16

Table 4: Binding of IPN002 variants to Tau proteins

| Antibody | $K_D$ values (M) | | | | | |
|---|---|---|---|---|---|---|
| | rTau383 | eTau 1a | eTau 1b | eTau 2 | eTau 4 | eTau 4 |
| VH1/Vk1 | 1.83E-10 | 2.94E-10 | 7.37E-10 | 4.65E-10 | 3.58E-10 | 5.77E-10 |
| VH1/Vk2 | 1.21E-10 | 2.12E-10 | 5.58E-10 | 3.61E-10 | 3.21E-10 | 6.33E-10 |
| VH1/Vk3 | 1.75E-10 | 2.91E-10 | 5.90E-10 | 4.44E-10 | 4.78E-10 | 7.61E-10 |
| VH1/Vk4 | 2.86E-10 | 2.52E-10 | 5.97E-10 | 4.27E-10 | 2.69E-10 | 8.69E-10 |
| VH2/Vk1 | 2.42E-10 | 2.81E-10 | 2.15E-10 | 2.25E-10 | 3.69E-10 | 3.21E-10 |
| VH2/Vk2 | 1.99E-10 | 3.27E-10 | 2.29E-10 | 2.83E-10 | 2.94E-10 | 3.94E-10 |
| VH2/Vk3 | 2.23E-10 | 3.27E-10 | 2.87E-10 | 2.61E-10 | 2.19E-10 | 4.11E-10 |
| VH2/Vk4 | 2.48E-10 | 3.43E-10 | 5.20E-10 | 3.54E-10 | 4.18E-10 | 6.71E-10 |
| VH3/Vk1 | 2.36E-10 | 2.41E-10 | 5.29E-10 | 7.05E-10 | 4.54E-10 | 9.21E-10 |
| VH3/Vk2 | 2.58E-10 | 2.82E-10 | 6.14E-10 | 4.08E-10 | 5.89E-10 | 7.01E-10 |
| VH3/Vk3 | 2.24E-10 | 2.20E-10 | 6.89E-10 | 4.71E-10 | 4.69E-10 | 6.65E-10 |
| VH3/Vk4 | 2.55E-10 | 2.16E-10 | 3.82E-10 | 4.47E-10 | 3.81E-10 | 5.86E-10 |
| VH4/Vk1 | 1.87E-10 | 1.98E-10 | 3.59E-10 | 4.05E-10 | 2.80E-10 | 4.98E-10 |
| VH4/Vk2 | 1.60E-10 | 1.91E-10 | 4.83E-10 | 4.51E-10 | 2.91E-10 | 4.67E-10 |
| VH4/Vk3 | 2.76E-10 | 1.78E-10 | 3.13E-10 | 4.73E-10 | 6.36E-10 | 6.29E-10 |
| VH4/Vk4 | 3.79E-10 | 3.25E-10 | 5.35E-10 | 5.64E-10 | 4.62E-10 | 1.03E-09 |

FIG. 17

Table 5: Binding of humanized IPN002 variants to Tau383

| Antibody | $K_D$ (M) | $k_{on}$ (1/Ms) | $k_{dis}$ (1/s) |
|---|---|---|---|
| VH1/VK1 | 4.26E-11 | 2.06E+05 | 8.75E-06 |
| VH1/VK2 | 4.46E-10 | 1.96E+05 | 8.74E-05 |
| VH1/VK3 | 1.28E-09 | 1.82E+05 | 2.33E-04 |
| VH1/VK4 | 5.71E-10 | 1.67E+05 | 9.52E-05 |
| VH2/VK1 | 4.67E-10 | 2.14E+05 | 1.00E-05 |
| VH2/VK2 | 2.32E-10 | 2.05E+05 | 4.75E-05 |
| VH2/VK3 | 1.73E-09 | 1.34E+05 | 2.32E-04 |
| VH2/VK4 | 1.66E-09 | 1.42E+05 | 2.36E-04 |
| VH3/VK1 | 1.99E-09 | 1.29E+05 | 2.57E-04 |
| VH3/VK2 | 5.77E-10 | 1.85E+05 | 1.07E-04 |
| VH3/VK3 | 1.69E-10 | 1.87E+05 | 3.15E-05 |
| VH3/VK4 | 4.75E-10 | 2.11E+05 | 1.00E-04 |
| VH4/VK1 | 2.12E-09 | 1.40E+05 | 2.97E-04 |
| VH4/VK2 | 1.88E-09 | 1.63E+05 | 3.07E-04 |
| VH4/VK3 | 5.71E-10 | 1.64E+05 | 9.39E-05 |
| VH4/VK4 | 8.12E-10 | 1.56E+05 | 1.26E-04 |
| IPN002 | 2.06E-10 | 2.33E+05 | 4.78E-05 |

FIG. 18

```
fetal    MAEPRQEFEVMEDHAGTYGLGDRKDQGGYTMHQDEGDTDAGLKAEEAGIGDTPSLEDEA
#2        AEPRQEFEVMEDHAGTYGLGDRKDQGGYTMHQDEGDTDAGLKAEEAGIGDTPSLEDEA
#3        AEPRQEFEVMEDHAGTYGLGDRKDQGGYTMHQDEGDTDAGLKAEEAGIGDTPSLEDEA
#4        AEPRQEFEVMEDHAGTYGLGDRKDQGGYTMHQDEGDTDAGLKAEEAGIGDTPSLEDEA
eTau 2-172 AEPRQEFEVMEDHAGTYGLGDRKDQGGYTMHQDEGDTDAGLKAEEAGIGDTPSLEDEA
eTau 2-176 AEPRQEFEVMEDHAGTYGLGDRKDQGGYTMHQDEGDTDAGLKAEEAGIGDTPSLEDEA fetal    AGHVTQARMVSKSKDGTGSDDKKAKGADGKTKIATPRGAAPPGQKGQANATRIPAKTPPA
2       AGHVTQARMVSKSKDGTGSDDKKAKGADGKTKIATPRGAAPPGQKGQANATRIPAKTPPA
#3       AGHVTQARMVSKSKDGTGSDDKKAKGADGKTKIATPRGAAPPGQKGQANATRIPAKTPPA
#4       AGHVTQAR (68) (SEQ ID NO:48)
eTau 2-172 AGHVTQARMVSKSKDGTGSDDKKAKGADGKTKIATPRGAAPPGQKGQANATRIPAKTPPA
eTau 2-176 AGHVTQARMVSKSKDGTGSDDKKAKGADGKTKIATPRGAAPPGQKGQANATRIPAKTPPA fetal    PKTPPSSGEPPKSGDRSGYSSPGSPGTPGSRSRTPSLPTPPTREPKKVAVVRTPPKSPSSA
2       PKTPPSSGEPPKSGDRSGYSSPGSPGTPGSRSRTPSLPTPPTREPKKVAVVRTPPKSPGSR (151) (SEQ ID NO:46)
#3       PK (122) (SEQ ID NO:47)
eTau 2-172 PKTPPSSGEPPKSGDRSGYSSPGSPGTPGSRSRTPSLPTPPTREPKKVAVVR    (SEQ ID NO:44)
eTau 2-176 PKTPPSSGEPPKSGDRSGYSSPGSPGTPGSRSRTPSLPTPPTREPKKVAVVRTPPK (SEQ ID NO:45)

fetal    KSRLQTAPVPMPDLKNVKSKIGSTENLKHQPGGGKVQIVYKPVDLSKVTSKCGSLGNIHHK
fetal    PGGGQVEVKSEKLDFKDRVQSKIGSLDNITHVPGGGNKKIETHKLTFRENAKAKTDHGAEI
fetal    VYKSPVVSGDTSPRHLSNVSSTGSIDMVDSPQLATLADEVSASLAKQGL (SEQ ID NO:27)
```

FIG. 20

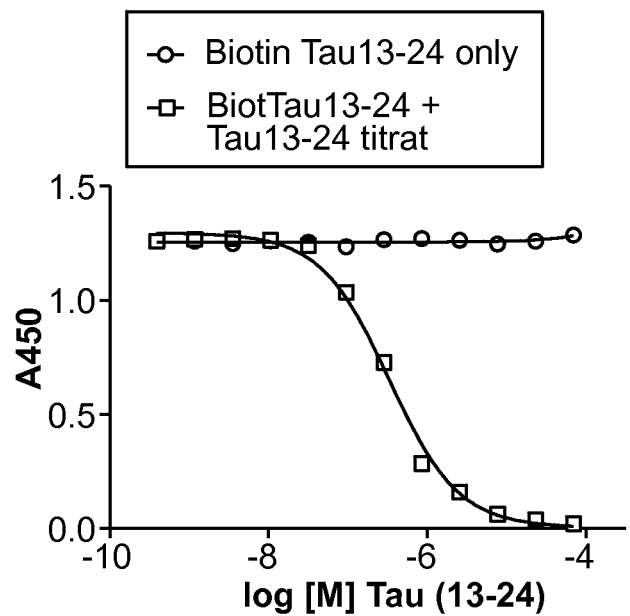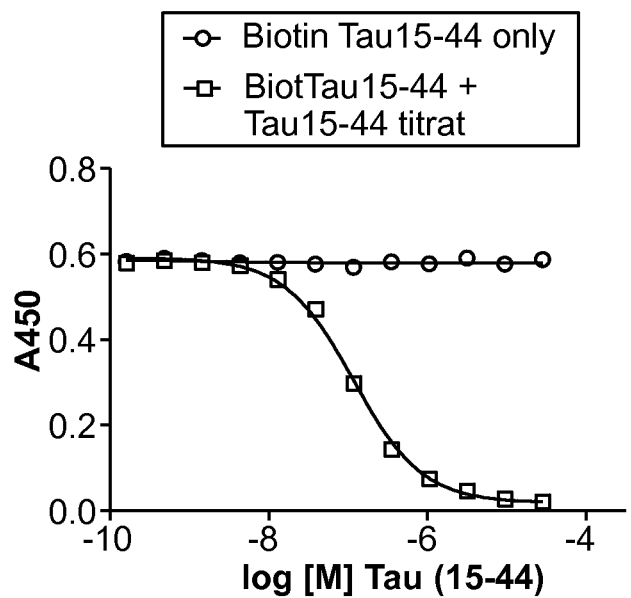
FIG. 30

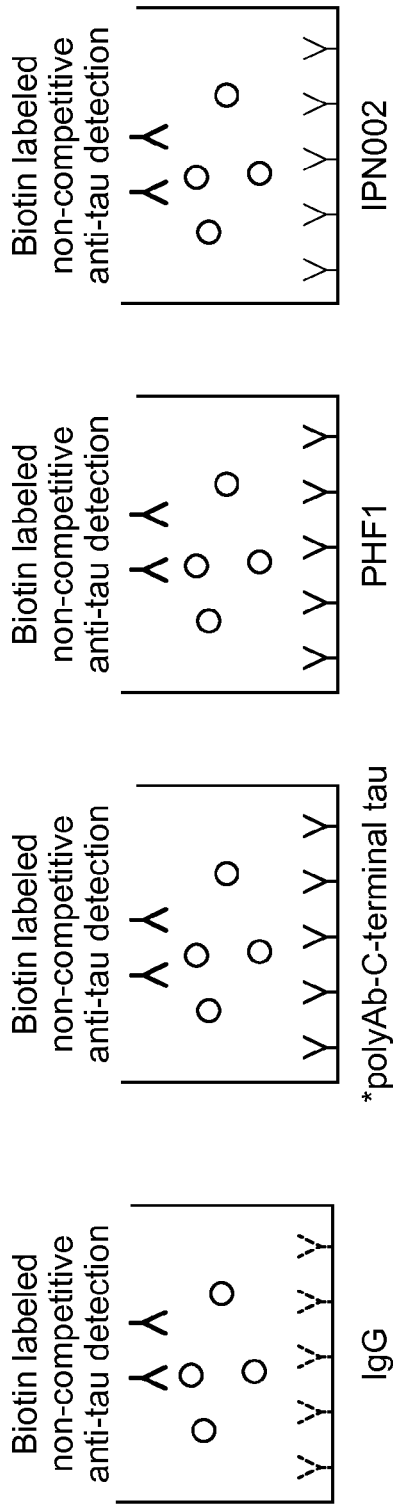
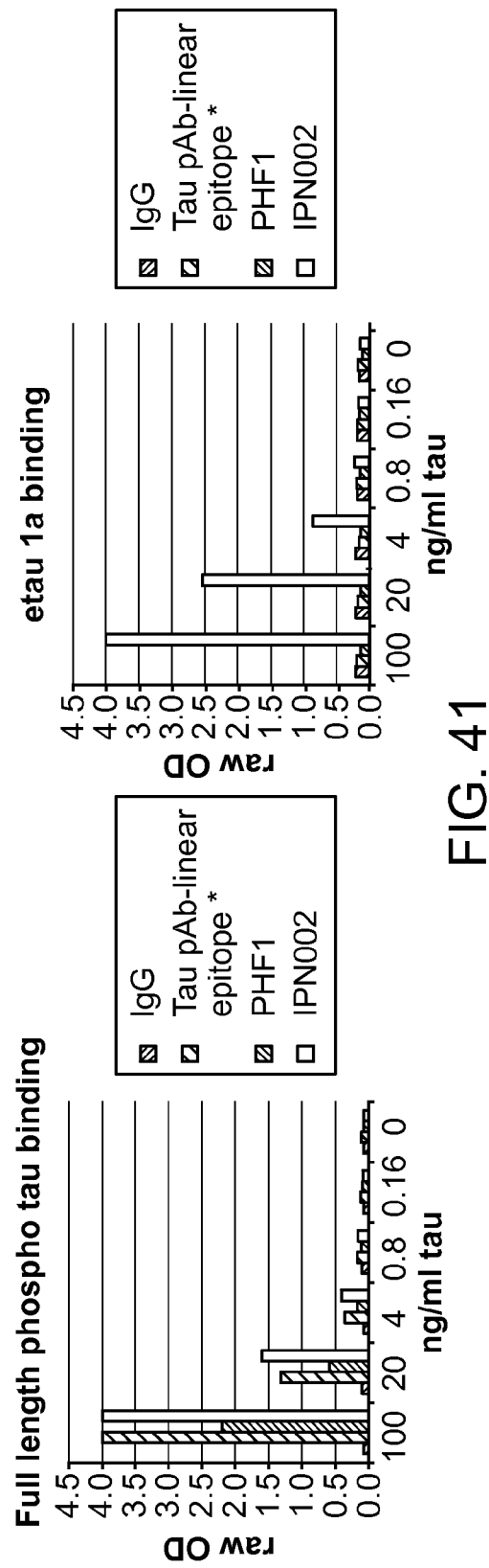
FIG. 41

SEQUENCE LISTING

```
<160> NUMBER OF SEQ ID NOS: 86

<210> SEQ ID NO 1
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 1

Arg Ser Ser Gln Thr Ile Leu His Ser Asn Gly Asn Thr Tyr Leu Glu
1               5                   10                  15
```

<210> SEQ ID NO 2
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 2

Lys Val Ser Lys Arg Phe Ser
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 3

Phe Gln Gly Ser Leu Val Pro Trp Ala
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 4

Ser Tyr Gly Met Ser
1               5

<210> SEQ ID NO 5
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 5

Thr Ile Ser Ser Ser Gly Ser Arg Thr Tyr Phe Pro Asp Ser Val Lys
1               5                   10                  15

Gly

<210> SEQ ID NO 6
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 6

Thr Trp Asp Gly Ala Met Asp Tyr
1               5

<210> SEQ ID NO 7
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 7

Lys Ser Ser Gln Ser Ile Val His Ser Asn Gly Asn Thr Tyr Leu Glu

```
<210> SEQ ID NO 8
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 8

Lys Val Ser Asn Arg Phe Ser
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 9

Phe Gln Gly Ser Leu Val Pro Trp Ala
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 10

Lys Tyr Gly Met Ser
1               5

<210> SEQ ID NO 11
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 11

Thr Ile Ser Ser Ser Gly Ser Arg Thr Tyr Tyr Pro Asp Ser Val Lys
1               5                   10                  15

Gly

<210> SEQ ID NO 12
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 12

Ser Trp Asp Gly Ala Met Asp Tyr
1               5

<210> SEQ ID NO 13
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 13
```

Asp Val Leu Met Thr Gln Thr Pro Leu Ser Leu Ala Val Asn Leu Gly
1               5                   10                  15

Asp Gln Ala Ser Leu Ser Cys Arg Ser Ser Gln Thr Ile Leu His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Ile Tyr Tyr Cys Phe Gln Gly
                85                  90                  95

Ser Leu Val Pro Trp Ala Phe Gly Gly Gly Thr Lys Leu Glu Ile Lys
            100                 105                 110

<210> SEQ ID NO 14
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 14

Glu Val Gln Leu Val Glu Ser Gly Glu Asp Leu Val Lys Pro Gly Gly
1               5                   10                  15

Ser Leu Lys Leu Ser Cys Val Ala Ser Gly Phe Ala Phe Ser Ser Tyr
            20                  25                  30

Gly Met Ser Trp Val Arg Gln Thr Pro Asp Met Arg Leu Glu Trp Val
        35                  40                  45

Ala Thr Ile Ser Ser Gly Ser Arg Thr Tyr Phe Pro Asp Ser Val
    50                  55                  60

Lys Gly Arg Leu Thr Ile Ser Arg Asp Asn Lys Asn Ile Leu Tyr
65                  70                  75                  80

Leu Gln Met Ser Ser Leu Arg Ser Glu Asp Thr Ala Met Tyr Tyr Cys
                85                  90                  95

Thr Ile Thr Trp Asp Gly Ala Met Asp Tyr Trp Gly Arg Gly Ile Ser
            100                 105                 110

Val Thr Val Ser Ser
        115

<210> SEQ ID NO 15
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 15

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Val Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Thr Tyr Tyr Cys Phe Gln Gly
            85                  90                  95

Ser Leu Val Pro Trp Ala Phe Gly Gly Thr Lys Leu Glu Ile Lys
            100                 105                 110

<210> SEQ ID NO 16
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 16

Glu Val His Leu Val Glu Ser Gly Gly Ala Leu Val Lys Pro Gly Gly
1               5                   10                  15

Ser Leu Lys Leu Ser Cys Ala Ala Ser Gly Phe Ser Phe Ser Lys Tyr
            20                  25                  30

Gly Met Ser Trp Val Arg Gln Thr Pro Asp Lys Arg Leu Glu Trp Val
            35                  40                  45

Ala Thr Ile Ser Ser Ser Gly Ser Arg Thr Tyr Tyr Pro Asp Ser Val
            50                  55                  60

Lys Gly Gln Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ser Ile Ser Trp Asp Gly Ala Met Asp Tyr Trp Gly Gln Gly Thr Ser
            100                 105                 110

Val Thr Val Ser Ser
        115

<210> SEQ ID NO 17
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 17
gatgttttga tgacccaaac tccgctctcc ctggcagtca atcttggaga tcaagcctcc      60
ctctcttgca gatcgagtca gactatttta catagtaatg aaataccta tttagaatgg     120 tatttgcaga aaccaggcca gtctccaaga ctcctgatct acaaagtttc taaacgattt     180
tctggggtcc cagacaggtt cagtggcagt ggatcaggga cagatttcac actcaagatc     240
agcagagtgg aggctgacga tctgggaatt tattactgct ttcaaggttc acttgttcct     300
tgggcgttcg gtggaggcac caagctggaa atcaaa                              336

<210> SEQ ID NO 18
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 18
gaggtgcagt tggtggagtc tggggaagac ttagtgaagc ctggagggtc cctgaaactc      60
tcctgtgtcg cttctggatt cgctttcagt agctatggca tgtcttgggt tcgccagact     120
ccagacatga ggctggagtg ggtcgcaaca attagtagca gtggtagtcg cacctacttt     180

```
ccagacagtg tgaagggcg actcaccatc tccagagaca atgacaagaa catcctatac    240
ctacaaatga gcagtctgag gtctgaggac acagccatgt actattgtac gattacctgg    300
gacggtgcta tggactactg gggtcgtgga atatcagtca ccgtctcctc a             351
```

<210> SEQ ID NO 19
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 19

```
gatgttttga tgacccaaac tccactctcc ctgcctgtca gtcttggaga tcaagcctcc    60
atctcttgca aatctagtca gagcattgta catagtaatg aaacacccta tttagaatgg   120
tacctgcaga accaggcca gtctccaaag ctcctggtct acaaagtttc caatcgattt    180
tctggggtcc cagacaggtt cagtggcagt ggatcaggga cagatttcac actcaagatc   240
agcagagtgg aggctgagga tctgggaact tattactgct ttcaaggttc acttgttcct   300
tgggcgttcg gtggaggcac caagctggaa atcaaa                              336
```

<210> SEQ ID NO 20
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 20

```
gaggttcatc tggtggagtc tgggggagcc ttagtgaagc ctggagggtc cctgaaactc    60
tcctgtgcag cctctggatt cagtttcagt aaatatggca tgtcttgggt tcgccagact   120
ccagacaaga ggctggagtg ggtcgcaacc attagtagta gtgggagtcg cacctactat   180
ccagacagtg tgaagggcca attcaccatc tccagagaca tgccaagaa caccctgtac    240 ctgcaaatga gcagtctgaa gtctgaggac acagccatgt attactgttc aattagctgg   300
gacggtgcta tggactactg gggtcaaggg acctcagtca ccgtctcctc a             351
```

<210> SEQ ID NO 21
<211> LENGTH: 441
<212> TYPE: PRT
<213> ORGANISM: Artificial sequence
<220> FEATURE:
<223> OTHER INFORMATION: Synthetic amino acid sequence

<400> SEQUENCE: 21

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
```

```
            100                 105                 110
Ser Leu Glu Asp Glu Ala Ala Gly His Val Thr Gln Ala Arg Met Val
            115                 120                 125
Ser Lys Ser Lys Asp Gly Thr Gly Ser Asp Lys Lys Ala Lys Gly
            130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
            195                 200                 205
Arg Ser Arg Thr Pro Ser Leu Pro Thr Pro Pro Thr Arg Glu Pro Lys
            210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
            260                 265                 270
Gly Lys Val Gln Ile Ile Asn Lys Lys Leu Asp Leu Ser Asn Val Gln
            275                 280                 285
Ser Lys Cys Gly Ser Lys Asp Asn Ile Lys His Val Pro Gly Gly Gly
            290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
            355                 360                 365
Lys Lys Ile Glu Thr His Lys Leu Thr Phe Arg Glu Asn Ala Lys Ala
            370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
            435                 440

<210> SEQ ID NO 22
<211> LENGTH: 383
<212> TYPE: PRT
<213> ORGANISM: Artificial sequence
<220> FEATURE:
<223> OTHER INFORMATION: Synthetic amino acid sequence

<400> SEQUENCE: 22

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
```

```
            20                  25                  30
Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 23
<211> LENGTH: 352
<212> TYPE: PRT
<213> ORGANISM: Artificial sequence
<220> FEATURE:
<223> OTHER INFORMATION: Synthetic amino acid sequence

<400> SEQUENCE: 23

Met Ala Glu Pro Arg Gln Glu Phe Glu Val Met Glu Asp His Ala Gly
```

```
              1               5                  10                 15
            Thr Tyr Gly Leu Gly Asp Arg Lys Asp Gln Gly Gly Tyr Thr Met His
                            20                  25                 30
            Gln Asp Gln Glu Gly Asp Thr Asp Ala Gly Leu Lys Ala Glu Glu Ala
                            35                  40                 45
            Gly Ile Gly Asp Thr Pro Ser Leu Glu Asp Glu Ala Ala Gly His Val
                    50                  55                 60
            Thr Gln Ala Arg Met Val Ser Lys Ser Lys Asp Gly Thr Gly Ser Asp
            65                  70                  75                 80
            Asp Lys Lys Ala Lys Gly Ala Asp Gly Lys Thr Lys Ile Ala Thr Pro
                                85                  90                 95
            Arg Gly Ala Ala Pro Pro Gly Gln Lys Gly Gln Ala Asn Ala Thr Arg
                            100                 105                110
            Ile Pro Ala Lys Thr Pro Ala Pro Lys Thr Pro Pro Ser Ser Gly
                            115                 120                125
            Glu Pro Pro Lys Ser Gly Asp Arg Ser Gly Tyr Ser Ser Pro Gly Ser
                            130                 135                140
            Pro Gly Thr Pro Gly Ser Arg Ser Arg Thr Pro Ser Leu Pro Thr Pro
            145                 150                 155                160
            Pro Thr Arg Glu Pro Lys Lys Val Ala Val Val Arg Thr Pro Pro Lys
                                165                 170                175
            Ser Pro Ser Ser Ala Lys Ser Arg Leu Gln Thr Ala Pro Val Pro Met
                            180                 185                190
            Pro Asp Leu Lys Asn Val Lys Ser Lys Ile Gly Ser Thr Glu Asn Leu
                            195                 200                205
            Lys His Gln Pro Gly Gly Gly Lys Val Gln Ile Val Tyr Lys Pro Val
                    210                 215                 220
            Asp Leu Ser Lys Val Thr Ser Lys Cys Gly Ser Leu Gly Asn Ile His
            225                 230                 235                240
            His Lys Pro Gly Gly Gly Gln Val Glu Val Lys Ser Glu Lys Leu Asp
                                245                 250                255
            Phe Lys Asp Arg Val Gln Ser Lys Ile Gly Ser Leu Asp Asn Ile Thr
                            260                 265                270
            His Val Pro Gly Gly Gly Asn Lys Lys Ile Glu Thr His Lys Leu Thr
                            275                 280                285
            Phe Arg Glu Asn Ala Lys Ala Lys Thr Asp His Gly Ala Glu Ile Val
                            290                 295                300
            Tyr Lys Ser Pro Val Val Ser Gly Asp Thr Ser Pro Arg His Leu Ser
            305                 310                 315                320
            Asn Val Ser Ser Thr Gly Ser Ile Asp Met Val Asp Ser Pro Gln Leu
                            325                 330                335
            Ala Thr Leu Ala Asp Glu Val Ser Ala Ser Leu Ala Lys Gln Gly Leu
                            340                 345                350

<210> SEQ ID NO 24
<211> LENGTH: 412
<212> TYPE: PRT
<213> ORGANISM: Artificial sequence
<220> FEATURE:
<223> OTHER INFORMATION: Synthetic amino acid sequence

<400> SEQUENCE: 24

Met Ala Glu Pro Arg Gln Glu Phe Glu Val Met Glu Asp His Ala Gly
1               5                   10                 15

Thr Tyr Gly Leu Gly Asp Arg Lys Asp Gln Gly Gly Tyr Thr Met His
```

```
                    20                  25                  30
Gln Asp Gln Glu Gly Asp Thr Asp Ala Gly Leu Lys Glu Ser Pro Leu
                35                  40                  45
Gln Thr Pro Thr Glu Asp Gly Ser Glu Glu Pro Gly Ser Glu Thr Ser
            50                  55                  60
Asp Ala Lys Ser Thr Pro Thr Ala Glu Ala Glu Ala Gly Ile Gly
65                  70                  75                  80
Asp Thr Pro Ser Leu Glu Asp Glu Ala Ala Gly His Val Thr Gln Ala
                85                  90                  95
Arg Met Val Ser Lys Ser Lys Asp Gly Thr Gly Ser Asp Asp Lys Lys
            100                 105                 110
Ala Lys Gly Ala Asp Gly Lys Thr Lys Ile Ala Thr Pro Arg Gly Ala
        115                 120                 125
Ala Pro Pro Gly Gln Lys Gly Gln Ala Asn Ala Thr Arg Ile Pro Ala
        130                 135                 140
Lys Thr Pro Pro Ala Pro Lys Thr Pro Pro Ser Ser Gly Glu Pro Pro
145                 150                 155                 160
Lys Ser Gly Asp Arg Ser Gly Tyr Ser Ser Pro Gly Ser Pro Gly Thr
                165                 170                 175
Pro Gly Ser Arg Ser Arg Thr Pro Ser Leu Pro Thr Pro Pro Thr Arg
            180                 185                 190
Glu Pro Lys Lys Val Ala Val Val Arg Thr Pro Lys Ser Pro Ser
        195                 200                 205
Ser Ala Lys Ser Arg Leu Gln Thr Ala Pro Val Pro Met Pro Asp Leu
        210                 215                 220
Lys Asn Val Lys Ser Lys Ile Gly Ser Thr Glu Asn Leu Lys His Gln
225                 230                 235                 240
Pro Gly Gly Gly Lys Val Gln Ile Ile Asn Lys Lys Leu Asp Leu Ser
                245                 250                 255
Asn Val Gln Ser Lys Cys Gly Ser Lys Asp Asn Ile Lys His Val Pro
            260                 265                 270
Gly Gly Gly Ser Val Gln Ile Val Tyr Lys Pro Val Asp Leu Ser Lys
        275                 280                 285
Val Thr Ser Lys Cys Gly Ser Leu Gly Asn Ile His His Lys Pro Gly
        290                 295                 300
Gly Gly Gln Val Glu Val Lys Ser Glu Lys Leu Asp Phe Lys Asp Arg
305                 310                 315                 320
Val Gln Ser Lys Ile Gly Ser Leu Asp Asn Ile Thr His Val Pro Gly
                325                 330                 335
Gly Gly Asn Lys Lys Ile Glu Thr His Lys Leu Thr Phe Arg Glu Asn
            340                 345                 350
Ala Lys Ala Lys Thr Asp His Gly Ala Glu Ile Val Tyr Lys Ser Pro
        355                 360                 365
Val Val Ser Gly Asp Thr Ser Pro Arg His Leu Ser Asn Val Ser Ser
        370                 375                 380
Thr Gly Ser Ile Asp Met Val Asp Ser Pro Gln Leu Ala Thr Leu Ala
385                 390                 395                 400
Asp Glu Val Ser Ala Ser Leu Ala Lys Gln Gly Leu
                405                 410

<210> SEQ ID NO 25
<211> LENGTH: 776
<212> TYPE: PRT
<213> ORGANISM: Artificial sequence
```

<220> FEATURE:
<223> OTHER INFORMATION: Synthetic amino acid sequence

<400> SEQUENCE: 25

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
385                 390                 395                 400
```

```
Ala Lys Thr Leu Lys Asn Arg Pro Cys Leu Ser Pro Lys His Pro Thr
            405                 410                 415

Pro Gly Ser Ser Asp Pro Leu Ile Gln Pro Ser Ser Pro Ala Val Cys
        420                 425                 430

Pro Glu Pro Ser Ser Pro Lys His Val Ser Ser Val Thr Ser Arg
    435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Pro Lys Ser Gly Asp
        515                 520                 525

Arg Ser Gly Tyr Ser Ser Pro Gly Ser Pro Gly Thr Pro Gly Ser Arg
        530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
                580                 585                 590

Ser Lys Ile Gly Ser Thr Glu Asn Leu Lys His Gln Pro Gly Gly Gly
            595                 600                 605

Lys Val Gln Ile Ile Asn Lys Lys Leu Asp Leu Ser Asn Val Gln Ser
        610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
                660                 665                 670

Glu Val Lys Ser Glu Lys Leu Asp Phe Lys Asp Arg Val Gln Ser Lys
            675                 680                 685

Ile Gly Ser Leu Asp Asn Ile Thr His Val Pro Gly Gly Gly Asn Lys
        690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
        755                 760                 765

Ala Ser Leu Ala Lys Gln Gly Leu
    770                 775

<210> SEQ ID NO 26
<211> LENGTH: 758
<212> TYPE: PRT
<213> ORGANISM: Artificial sequence
<220> FEATURE:
```

<223> OTHER INFORMATION: Synthetic amino acid sequence

<400> SEQUENCE: 26

```
Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Glu Pro Glu Ser
        115                 120                 125
Gly Lys Val Val Gln Glu Gly Phe Leu Arg Glu Pro Gly Pro Pro Gly
    130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
            180                 185                 190
Leu Gly Asp Leu His Gln Glu Gly Pro Pro Leu Lys Gly Ala Gly Gly
        195                 200                 205
Lys Glu Arg Pro Gly Ser Lys Glu Glu Val Asp Glu Asp Arg Asp Val
    210                 215                 220
Asp Glu Ser Ser Pro Gln Asp Ser Pro Ser Lys Ala Ser Pro Ala
225                 230                 235                 240
Gln Asp Gly Arg Pro Pro Gln Thr Ala Ala Arg Glu Ala Thr Ser Ile
                245                 250                 255
Pro Gly Phe Pro Ala Glu Gly Ala Ile Pro Leu Pro Val Asp Phe Leu
            260                 265                 270
Ser Lys Val Ser Thr Glu Ile Pro Ala Ser Glu Pro Asp Gly Pro Ser
        275                 280                 285
Val Gly Arg Ala Lys Gly Gln Asp Ala Pro Leu Glu Phe Thr Phe His
    290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                325                 330                 335
Ala Arg Gly Pro Ser Leu Gly Glu Asp Thr Lys Glu Ala Asp Leu Pro
            340                 345                 350
Glu Pro Ser Glu Lys Gln Pro Ala Ala Ala Pro Arg Gly Lys Pro Val
        355                 360                 365
Ser Arg Val Pro Gln Leu Lys Ala Arg Met Val Ser Lys Ser Lys Asp
    370                 375                 380
Gly Thr Gly Ser Asp Asp Lys Lys Ala Lys Thr Ser Thr Arg Ser Ser
385                 390                 395                 400
```

```
Ala Lys Thr Leu Lys Asn Arg Pro Cys Leu Ser Lys His Pro Thr
                405                 410                 415

Pro Gly Ser Ser Asp Pro Leu Ile Gln Pro Ser Ser Pro Ala Val Cys
        420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
        450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 27
<211> LENGTH: 352
<212> TYPE: PRT
<213> ORGANISM: Artificial sequence
<220> FEATURE:
<223> OTHER INFORMATION: Synthetic amino acid sequence

<400> SEQUENCE: 27
```

```
Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Ala Glu Glu Ala
        35                  40                  45
Gly Ile Gly Asp Thr Pro Ser Leu Glu Asp Glu Ala Ala Gly His Val
    50                  55                  60
Thr Gln Ala Arg Met Val Ser Lys Ser Lys Asp Gly Thr Gly Ser Asp
65                  70                  75                  80
Asp Lys Lys Ala Lys Gly Ala Asp Gly Lys Thr Lys Ile Ala Thr Pro
                85                  90                  95
Arg Gly Ala Ala Pro Pro Gly Gln Lys Gly Gln Ala Asn Ala Thr Arg
            100                 105                 110
Ile Pro Ala Lys Thr Pro Pro Ala Pro Lys Thr Pro Ser Ser Gly
        115                 120                 125
Glu Pro Pro Lys Ser Gly Asp Arg Ser Gly Tyr Ser Ser Pro Gly Ser
    130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Arg Thr Pro Pro Lys
                165                 170                 175
Ser Pro Ser Ser Ala Lys Ser Arg Leu Gln Thr Ala Pro Val Pro Met
            180                 185                 190
Pro Asp Leu Lys Asn Val Lys Ser Lys Ile Gly Ser Thr Glu Asn Leu
        195                 200                 205
Lys His Gln Pro Gly Gly Gly Lys Val Gln Ile Val Tyr Lys Pro Val
    210                 215                 220
Asp Leu Ser Lys Val Thr Ser Lys Cys Gly Ser Leu Gly Asn Ile His
225                 230                 235                 240
His Lys Pro Gly Gly Gly Gln Val Glu Val Lys Ser Glu Lys Leu Asp
                245                 250                 255
Phe Lys Asp Arg Val Gln Ser Lys Ile Gly Ser Leu Asp Asn Ile Thr
            260                 265                 270
His Val Pro Gly Gly Gly Asn Lys Lys Ile Glu Thr His Lys Leu Thr
        275                 280                 285
Phe Arg Glu Asn Ala Lys Ala Lys Thr Asp His Gly Ala Glu Ile Val
    290                 295                 300
Tyr Lys Ser Pro Val Val Ser Gly Asp Thr Ser Pro Arg His Leu Ser
305                 310                 315                 320
Asn Val Ser Ser Thr Gly Ser Ile Asp Met Val Asp Ser Pro Gln Leu
                325                 330                 335
Ala Thr Leu Ala Asp Glu Val Ser Ala Ser Leu Ala Lys Gln Gly Leu
            340                 345                 350
```

<210> SEQ ID NO 28
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 28
gaggttcatc tggtggagtc tgggggagcc ttagtgaagc tggagggtc cctgagactc       60 tcctgtgcag cctctggatt cagtttcagt aaatatggca tgtcttgggt tcgccaggcc      120

```
ccaggcaagg gcctggagtg ggtcgcaacc attagtagta gtgggagtcg cacctactat    180
ccagacagtg tgaagggcag attcaccatc tccagagaca atgccaagaa caccctgtac    240
ctgcaaatga gcagtctgaa gtctgaggac acagccatgt attactgttc aattagctgg    300
gacggtgcta tggactactg gggtcaaggg acctcagtca ccgtctcctc a             351
```

<210> SEQ ID NO 29
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 29

```
gaggttcatc tggtggagtc tgggggagcc ttagtgaagc ctggagggtc cctgagactc    60
tcctgtgcag cctctggatt cagtttcagt aaatatggca tgtcttgggt tcgccaggcc    120
ccaggcaagg gcctggagtg ggtcgcaacc attagtagta gtgggagtcg cacctactat    180
ccagacagtg tgaagggcag attcaccatc tccagagaca atgccaagaa caccctgtac    240
ctgcaaatga acagtctgag agccgaggac acagccatgt attactgttc aattagctgg    300
gacggtgcta tggactactg gggtcaaggg accaccgtca ccgtctcctc a             351
```

<210> SEQ ID NO 30
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 30

```
gaggttcagc tggtggagtc tgggggagcc ttagtgaagc ctggagggtc cctgagactc    60
tcctgtgcag cctctggatt cagtttcagt aaatatggca tgtcttgggt tcgccaggcc    120
ccaggcaagg gcctggagtg ggtcgcaacc attagtagta gtgggagtcg cacctactat    180
ccagacagtg tgaagggcag attcaccatc tccagagaca atgccaagaa caccctgtac    240
ctgcaaatga acagtctgag agccgaggac acagccatgt attactgttc aattagctgg    300
gacggtgcta tggactactg gggtcaaggg accaccgtca ccgtctcctc a             351
```

<210> SEQ ID NO 31
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 31

```
gaggttcagc tggtggagtc tgggggagcc ttagtgaagc ctggagggtc cctgagactc    60
tcctgtgcag cctctggatt cagtttcagt aaatatggca tgtcttgggt tcgccaggcc    120
ccaggcaagg gcctggagtg ggtcgcaacc attagtagta gtgggagtcg cacctactat    180
ccagacagtg tgaagggcag attcaccatc tccagagaca atgccaagaa caccctgtac    240
ctgcaaatga acagtctgag agccgaggac acagccatgt attactgtgc cattagctgg    300
gacggtgcta tggactactg gggtcaaggg accaccgtca ccgtctcctc a             351
```

<210> SEQ ID NO 32
<211> LENGTH: 336
<212> TYPE: DNA

<213> ORGANISM: Artificial sequence
<220> FEATURE:
<223> OTHER INFORMATION: Synthetic nucleic acid sequence

<400> SEQUENCE: 32

| | | |
|---|---|---|
| gatgttttga tgacccaaag cccactctcc ctgcctgtca cccttggaca gcccgcctcc | 60 |
| atctcttgca aatctagtca gagcattgta catagtaatg gaaacaccta tttagaatgg | 120 |
| tacctgcaga aaccaggcca gtctccacag ctcctggtct acaaagtttc caatcgattt | 180 |
| tctggggtcc cagacagatt cagtggcagt ggatcaggga cagatttcac actcaagatc | 240 |
| agcagagtgg aggctgagga tgtgggaact tattactgct ttcaaggctc acttgttcct | 300 |
| tgggcgttcg gtggaggcac caaggtggaa atcaaa | 336 |

<210> SEQ ID NO 33
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 33

| | | |
|---|---|---|
| gatgttgtga tgacccaaag cccactctcc ctgcctgtca cccttggaca gcccgcctcc | 60 |
| atctcttgca aatctagtca gagcattgta catagtaatg gaaacaccta tttagaatgg | 120 |
| tacctgcaga aaccaggcca gtctccacag ctcctggtct acaaagtttc caatcgattt | 180 |
| tctggggtcc cagacagatt cagtggcagt ggatcaggga cagatttcac actcaagatc | 240 |
| agcagagtgg aggctgagga tgtgggaact tattactgct ttcaaggctc acttgttcct | 300 |
| tgggcgttcg gtggaggcac caaggtggaa atcaaa | 336 |

<210> SEQ ID NO 34
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 34

| | | |
|---|---|---|
| gatgttgtga tgacccaaag cccactctcc ctgcctgtca cccttggaca gcccgcctcc | 60 |
| atctcttgca aatctagtca gagcattgta catagtaatg gaaacaccta tttagaatgg | 120 |
| tacctgcaga aaccaggcca gtctccacag ctcctggtct acaaagtttc caatcgattt | 180 |
| tctggggtcc cagacagatt cagtggcagt ggatcaggga cagatttcac actcaagatc | 240 |
| agcagagtgg aggctgagga tgtgggagtg tattactgct ttcaaggctc acttgttcct | 300 |
| tgggcgttcg gtggaggcac caaggtggaa atcaaa | 336 |

<210> SEQ ID NO 35
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 35

| | | |
|---|---|---|
| gatgttgtga tgacccaaag cccactctcc ctgcctgtca cccttggaca gcccgcctcc | 60 |
| atctcttgca aatctagtca gagcattgta catagtaatg gaaacaccta tttagaatgg | 120 |
| tacctgcaga aaccaggcca gtctccacag ctcctgatct acaaagtttc caatcgattt | 180 |
| tctggggtcc cagacagatt cagtggcagt ggatcaggga cagatttcac actcaagatc | 240 |

-continued

```
agcagagtgg aggctgagga tgtgggagtg tattactgct ttcaaggctc acttgttcct    300
tgggcgttcg gtggaggcac caaggtggaa atcaaa                              336
```

<210> SEQ ID NO 36
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 36

```
Glu Val His Leu Val Glu Ser Gly Gly Ala Leu Val Lys Pro Gly Gly
1               5                   10                  15

Ser Leu Arg Leu Ser Cys Ala Ala Ser Gly Phe Ser Phe Ser Lys Tyr
            20                  25                  30

Gly Met Ser Trp Val Arg Gln Ala Pro Gly Lys Gly Leu Glu Trp Val
        35                  40                  45

Ala Thr Ile Ser Ser Ser Gly Ser Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Ile Ser Trp Asp Gly Ala Met Asp Tyr Trp Gly Gln Gly Thr Ser
            100                 105                 110

Val Thr Val Ser Ser
        115
```

<210> SEQ ID NO 37
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 37

```
Glu Val His Leu Val Glu Ser Gly Gly Ala Leu Val Lys Pro Gly Gly
1               5                   10                  15

Ser Leu Arg Leu Ser Cys Ala Ala Ser Gly Phe Ser Phe Ser Lys Tyr
            20                  25                  30

Gly Met Ser Trp Val Arg Gln Ala Pro Gly Lys Gly Leu Glu Trp Val
        35                  40                  45

Ala Thr Ile Ser Ser Ser Gly Ser Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ser Ile Ser Trp Asp Gly Ala Met Asp Tyr Trp Gly Gln Gly Thr Thr
            100                 105                 110

Val Thr Val Ser Ser
        115
```

<210> SEQ ID NO 38
<211> LENGTH: 117
<212> TYPE: PRT
<213> ORGANISM: Artificial sequence
<220> FEATURE:

<223> OTHER INFORMATION: Synthetic amino acid sequence

<400> SEQUENCE: 38

```
Glu Val Gln Leu Val Glu Ser Gly Gly Ala Leu Val Lys Pro Gly Gly
1               5                   10                  15
Ser Leu Arg Leu Ser Cys Ala Ala Ser Gly Phe Ser Phe Ser Lys Tyr
            20                  25                  30
Gly Met Ser Trp Val Arg Gln Ala Pro Gly Lys Gly Leu Glu Trp Val
        35                  40                  45
Ala Thr Ile Ser Ser Ser Gly Ser Arg Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Met Tyr Tyr Cys
                85                  90                  95
Ser Ile Ser Trp Asp Gly Ala Met Asp Tyr Trp Gly Gln Gly Thr Thr
            100                 105                 110
Val Thr Val Ser Ser
        115
```

<210> SEQ ID NO 39
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 39

```
Glu Val Gln Leu Val Glu Ser Gly Gly Ala Leu Val Lys Pro Gly Gly
1               5                   10                  15
Ser Leu Arg Leu Ser Cys Ala Ala Ser Gly Phe Ser Phe Ser Lys Tyr
            20                  25                  30
Gly Met Ser Trp Val Arg Gln Ala Pro Gly Lys Gly Leu Glu Trp Val
        35                  40                  45
Ala Thr Ile Ser Ser Ser Gly Ser Arg Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Met Tyr Tyr Cys
                85                  90                  95
Ala Ile Ser Trp Asp Gly Ala Met Asp Tyr Trp Gly Gln Gly Thr Thr
            100                 105                 110
Val Thr Val Ser Ser
        115
```

<210> SEQ ID NO 40
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 40

```
Asp Val Leu Met Thr Gln Ser Pro Leu Ser Leu Pro Val Thr Leu Gly
1               5                   10                  15
Gln Pro Ala Ser Ile Ser Cys Lys Ser Ser Gln Ser Ile Val His Ser
            20                  25                  30
Asn Gly Asn Thr Tyr Leu Glu Trp Tyr Leu Gln Lys Pro Gly Gln Ser
```

```
                35                  40                  45
Pro Gln Leu Leu Val Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Thr Tyr Tyr Cys Phe Gln Gly
                85                  90                  95
Ser Leu Val Pro Trp Ala Phe Gly Gly Gly Thr Lys Val Glu Ile Lys
                100                 105                 110

<210> SEQ ID NO 41
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 41

Asp Val Val Met Thr Gln Ser Pro Leu Ser Leu Pro Val Thr Leu Gly
1               5                   10                  15
Gln Pro Ala Ser Ile Ser Cys Lys Ser Ser Gln Ser Ile Val His Ser
                20                  25                  30
Asn Gly Asn Thr Tyr Leu Glu Trp Tyr Leu Gln Lys Pro Gly Gln Ser
            35                  40                  45
Pro Gln Leu Leu Val Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Thr Tyr Tyr Cys Phe Gln Gly
                85                  90                  95
Ser Leu Val Pro Trp Ala Phe Gly Gly Gly Thr Lys Val Glu Ile Lys
                100                 105                 110

<210> SEQ ID NO 42
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 42

Asp Val Val Met Thr Gln Ser Pro Leu Ser Leu Pro Val Thr Leu Gly
1               5                   10                  15
Gln Pro Ala Ser Ile Ser Cys Lys Ser Ser Gln Ser Ile Val His Ser
                20                  25                  30
Asn Gly Asn Thr Tyr Leu Glu Trp Tyr Leu Gln Lys Pro Gly Gln Ser
            35                  40                  45
Pro Gln Leu Leu Val Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser Leu Val Pro Trp Ala Phe Gly Gly Gly Thr Lys Val Glu Ile Lys
                100                 105                 110

<210> SEQ ID NO 43
<211> LENGTH: 112
```

```
<212> TYPE: PRT
<213> ORGANISM: Artificial sequence
<220> FEATURE:
<223> OTHER INFORMATION: Synthetic amino acid sequence

<400> SEQUENCE: 43

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Trp Ala Phe Gly Gly Thr Lys Val Glu Ile Lys
            100                 105                 110

<210> SEQ ID NO 44
<211> LENGTH: 171
<212> TYPE: PRT
<213> ORGANISM: Artificial sequence
<220> FEATURE:
<223> OTHER INFORMATION: Synthetic amino acid sequence

<400> SEQUENCE: 44

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Pro Ala Pro Lys Thr Pro Pro Ser Ser Gly Glu
        115                 120                 125

Pro Pro Lys Ser Gly Asp Arg Ser Gly Tyr Ser Ser Pro Gly Ser Pro
    130                 135                 140

Gly Thr Pro Gly Ser Arg Ser Arg Thr Pro Ser Leu Pro Thr Pro Pro
145                 150                 155                 160

Thr Arg Glu Pro Lys Lys Val Ala Val Val Arg
                165                 170

<210> SEQ ID NO 45
<211> LENGTH: 175
<212> TYPE: PRT
<213> ORGANISM: Artificial sequence
<220> FEATURE:
<223> OTHER INFORMATION: Synthetic amino acid sequence
```

-continued

<400> SEQUENCE: 45

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Ala Pro Lys Thr Pro Ser Ser Gly Glu
            115                 120                 125

Pro Pro Lys Ser Gly Asp Arg Ser Gly Tyr Ser Ser Pro Gly Ser Pro
    130                 135                 140

Gly Thr Pro Gly Ser Arg Ser Arg Thr Pro Ser Leu Pro Thr Pro Pro
145                 150                 155                 160

Thr Arg Glu Pro Lys Lys Val Ala Val Val Arg Thr Pro Pro Lys
                165                 170                 175

<210> SEQ ID NO 46
<211> LENGTH: 150
<212> TYPE: PRT
<213> ORGANISM: Artificial sequence
<220> FEATURE:
<223> OTHER INFORMATION: Synthetic amino acid sequence

<400> SEQUENCE: 46

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Ala Pro Lys Thr Pro Ser Ser Gly Glu
            115                 120                 125

Pro Pro Lys Ser Gly Asp Arg Ser Gly Tyr Ser Ser Pro Gly Ser Pro
    130                 135                 140

Gly Thr Pro Gly Ser Arg
145                 150

<210> SEQ ID NO 47
<211> LENGTH: 121
<212> TYPE: PRT

```
<213> ORGANISM: Artificial sequence
<220> FEATURE:
<223> OTHER INFORMATION: Synthetic amino acid sequence

<400> SEQUENCE: 47

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Pro Ala Pro Lys
        115                 120

<210> SEQ ID NO 48
<211> LENGTH: 67
<212> TYPE: PRT
<213> ORGANISM: Artificial sequence
<220> FEATURE:
<223> OTHER INFORMATION: Synthetic amino acid sequence

<400> SEQUENCE: 48

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg
65

<210> SEQ ID NO 49
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 49

Asp His Ala Gly Thr Tyr Gly Leu Gly Asp Arg Lys
1               5                   10

<210> SEQ ID NO 50
<211> LENGTH: 30
<212> TYPE: PRT
<213> ORGANISM: Artificial sequence
<220> FEATURE:
<223> OTHER INFORMATION: Synthetic amino acid sequence

<400> SEQUENCE: 50

Ala Gly Thr Tyr Gly Leu Gly Asp Arg Lys Asp Gln Gly Gly Tyr Thr
```

```
                1               5                   10                  15
Met His Gln Asp Gln Glu Gly Asp Thr Asp Ala Gly Leu Lys
                20                  25                  30

<210> SEQ ID NO 51
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 51

Ala Gly Thr Tyr Gly Leu Gly Asp Arg Lys
1               5                   10

<210> SEQ ID NO 52
<211> LENGTH: 10
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (4)..(4)
<223> OTHER INFORMATION: The amino acid at this position is
      phosphorylated

<400> SEQUENCE: 52

Ala Gly Thr Tyr Gly Leu Gly Asp Arg Lys
1               5                   10

<210> SEQ ID NO 53
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 53

Met Ala Glu Pro Arg Gln Glu Phe Glu Val Met Glu Asp His Ala Gly
1               5                   10                  15

Thr Tyr

<210> SEQ ID NO 54
<211> LENGTH: 23
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (3)..(3)
<223> OTHER INFORMATION: X at this position is L or V

<400> SEQUENCE: 54

Asp Val Xaa Met Thr Gln Ser Pro Leu Ser Leu Pro Val Thr Leu Gly
1               5                   10                  15

Gln Pro Ala Ser Ile Ser Cys
                20

<210> SEQ ID NO 55
<211> LENGTH: 15
<212> TYPE: PRT
<213> ORGANISM: Artificial sequence
<220> FEATURE:
<223> OTHER INFORMATION: Synthetic amino acid sequence
<220> FEATURE:
```

```
<221> NAME/KEY: MISC_FEATURE
<222> LOCATION: (14)..(14)
<223> OTHER INFORMATION: X at this position is V or I

<400> SEQUENCE: 55

Trp Tyr Leu Gln Lys Pro Gly Gln Ser Pro Gln Leu Leu Xaa Tyr
1               5                   10                  15

<210> SEQ ID NO 56
<211> LENGTH: 32
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (29)..(29)
<223> OTHER INFORMATION: X at this position is T or V

<400> SEQUENCE: 56

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Xaa Tyr Tyr Cys
            20                  25                  30

<210> SEQ ID NO 57
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 57

Phe Gly Gly Gly Thr Lys Val Glu Ile Lys
1               5                   10

<210> SEQ ID NO 58
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 58

Gly Ser Gly Gly Ser
1               5

<210> SEQ ID NO 59
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 59

Gly Gly Gly Ser
1

<210> SEQ ID NO 60
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 60

Gly Gly Ser Gly
```

```
<210> SEQ ID NO 61
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 61

Gly Gly Ser Gly Gly
1               5

<210> SEQ ID NO 62
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 62

Gly Ser Gly Ser Gly
1               5

<210> SEQ ID NO 63
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 63

Gly Ser Gly Gly Gly
1               5

<210> SEQ ID NO 64
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 64

Gly Gly Gly Ser Gly
1               5

<210> SEQ ID NO 65
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 65

Gly Ser Ser Ser Gly
1               5

<210> SEQ ID NO 66
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 66

His His His His His
1               5
```

<210> SEQ ID NO 67
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 67

His His His His His His
1               5

<210> SEQ ID NO 68
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 68

Glu Gln Lys Leu Ile Ser Glu Glu Asp Leu
1               5                   10

<210> SEQ ID NO 69
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 69

Asp Tyr Lys Asp Asp Asp Asp Lys
1               5

<210> SEQ ID NO 70
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 70

Trp Ser His Pro Gln Phe Glu Lys
1               5

<210> SEQ ID NO 71
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 71

Tyr Pro Tyr Asp Val Pro Asp Tyr Ala
1               5

<210> SEQ ID NO 72
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 72

Arg Tyr Ile Arg Ser
1               5

```
<210> SEQ ID NO 73
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 73

Phe His His Thr
1

<210> SEQ ID NO 74
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 74

Trp Glu Ala Ala Ala Arg Glu Ala Cys Cys Arg Glu Cys Cys Ala Arg
1               5                   10                  15

Ala

<210> SEQ ID NO 75
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 75

Thr Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 76

Thr Phe Phe Tyr Gly Gly Ser Arg Gly Lys Arg Asn Asn Phe Lys Thr
1               5                   10                  15

Glu Glu Tyr

<210> SEQ ID NO 77
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 77

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 78
<211> LENGTH: 20
<212> TYPE: PRT
<213> ORGANISM: Artificial sequence
```

<220> FEATURE:
<223> OTHER INFORMATION: Synthetic amino acid sequence

<400> SEQUENCE: 78

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 79
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 79

Thr Phe Val Tyr Gly Gly Cys Arg Ala Lys Arg Asn Asn Phe Lys Ser
1               5                   10                  15

<210> SEQ ID NO 80
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 80

Ala Glu Pro Arg Gln Glu Phe Glu Val Met Glu Asp His Ala Gly Thr
1               5                   10                  15

Tyr

<210> SEQ ID NO 81
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 81

Glu Val Met Glu Asp His Ala Gly Thr Tyr Gly Leu Gly Asp Arg Lys
1               5                   10                  15

<210> SEQ ID NO 82
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 82

Ala Gly Thr Tyr Gly Leu Gly Asp
1               5

<210> SEQ ID NO 83
<211> LENGTH: 30
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (3)..(3)
<223> OTHER INFORMATION: X at this position is an H or Q

<400> SEQUENCE: 83

-continued

```
Glu Val Xaa Leu Val Glu Ser Gly Gly Ala Leu Val Lys Pro Gly Gly
1               5                   10                  15

Ser Leu Arg Leu Ser Cys Ala Ala Ser Gly Phe Ser Phe Ser
            20                  25                  30

<210> SEQ ID NO 84
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 84

Trp Val Arg Gln Ala Pro Gly Lys Gly Leu Glu Trp Val Ala
1               5                   10

<210> SEQ ID NO 85
<211> LENGTH: 32
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (18)..(18)
<223> OTHER INFORMATION: X at this position is an S or N
<220> FEATURE:
<221> NAME/KEY: MISC_FEATURE
<222> LOCATION: (20)..(20)
<223> OTHER INFORMATION: X at this position is an S or L
<220> FEATURE:
<221> NAME/KEY: MISC_FEATURE
<222> LOCATION: (21)..(21)
<223> OTHER INFORMATION: X at this position is a K or R
<220> FEATURE:
<221> NAME/KEY: MISC_FEATURE
<222> LOCATION: (22)..(22)
<223> OTHER INFORMATION: X at this position is a S or A
<220> FEATURE:
<221> NAME/KEY: MISC_FEATURE
<222> LOCATION: (31)..(31)
<223> OTHER INFORMATION: X at this position is a S or A

<400> SEQUENCE: 85

Arg Phe Thr Ile Ser Arg Asp Asn Ala Lys Asn Thr Leu Tyr Leu Gln
1               5                   10                  15

Met Xaa Ser Xaa Xaa Xaa Glu Asp Thr Ala Met Tyr Tyr Cys Xaa Ile
            20                  25                  30

<210> SEQ ID NO 86
<211> LENGTH: 11
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (6)..(6)
<223> OTHER INFORMATION: X at this position is an S or T

<400> SEQUENCE: 86

Trp Gly Gln Gly Thr Xaa Val Thr Val Ser Ser
1               5                   10
```

METHODS OF TREATING A TAUOPATHY

CROSS-REFERENCE

This application is a U.S. national stage filing of International Application No. PCT/US2013/055203, filed Aug. 15, 2013, which claims the benefit of U.S. Provisional Patent Application No. 61/683,902, filed Aug. 16, 2012; 61/754,085, filed Jan. 18, 2013; 61/781,823, filed Mar. 14, 2013; 61/813,797, filed Apr. 19, 2013; and 61/833,355, filed Jun. 10, 2013, each of which applications is incorporated herein by reference in its entirety.

INCORPORATION BY REFERENCE OF SEQUENCE LISTING PROVIDED AS A TEXT FILE

A Sequence Listing is provided herewith as a text file, "IPRN-745WO SeqList_ST25.txt" created on Aug. 15, 2013 and having a size of 69 KB. The contents of the text file are incorporated by reference herein in their entirety.

INTRODUCTION

The microtubule associated protein tau is abundant in the central nervous system and is produced primarily by neurons. The primary function of tau is to stabilize microtubules. Six tau isoforms exist in the adult human brain; tau isoforms are the products of alternative splicing of a single gene.

Tauopathies are a class of neurodegenerative diseases resulting from the pathological aggregation of tau protein in so-called neurofibrillary tangles (NFT) in the brain. Some examples of tauopathies include frontotemporal dementia (FTD), Alzheimer's disease, progressive supranuclear palsy, corticobasal degeneration, and frontotemporal lobar degeneration.

There is a need in the art for methods of treating tauopathies, and for reagents suitable for use in such methods.

SUMMARY

The present disclosure provides methods of treating a tauopathy, involving administering an anti-Tau antibody. The present disclosure also provides anti-Tau antibodies, and formulations comprising same, for use in the methods.

Features

The present disclosure provides an isolated humanized monoclonal antibody that specifically binds an epitope within amino acids 15-24 of a Tau polypeptide. In some cases, the epitope does not comprise a phosphorylated amino acid. In some cases, the epitope does not comprise a nitrated amino acid. In some instances, the epitope comprises a phosphorylated amino acid, a nitrated amino acid, or both a phosphorylated amino acid and a nitrated amino acid.

The present disclosure provides an isolated antibody comprising a humanized light chain framework region; and a humanized heavy chain framework region, wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some cases, the light chain region and the heavy chain region are present in separate polypeptides. In some cases, the light chain region and the heavy chain region are present in a single polypeptide. In some cases, the heavy chain region is of the isotype IgG1, IgG2, IgG3, or IgG4. In some cases, the heavy chain region is of the isotype IgG4. In some of these embodiments, the hinge region comprises an S241P substitution. See, e.g., Angal et al. (1993) *Mol. Immunol.* 30:105. In some cases, the antibody is a Fv, scFv, Fab, F(ab')2, or Fab'. In some cases, the antibody comprises a covalently linked non-peptide synthetic polymer, e.g., a poly(ethylene glycol) polymer. In some cases, the antibody is fused, directly or via a linker, to a carrier molecule, a peptide or a protein that promotes the crossing of the blood-brain barrier. In some cases, the epitope is within amino acids 15-24 of a Tau polypeptide. In some cases, the humanized light chain framework region comprises 1, 2, 3, 4, 5, 6, 7, 8, 9, or 10 of the amino acid substitutions depicted in Table 3. In some instances, the humanized heavy chain framework region comprises 1, 2, 3, 4, 5, 6, 7, 8, 9, 10, 11, or 12 of the amino acid substitutions depicted in Table 2.

The present disclosure provides an isolated antibody, wherein the antibody is a Fv, scFv, Fab, F(ab')2, or Fab', and wherein the antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some cases, the isolated antibody comprises a humanized light chain framework region. In some cases, the humanized light chain framework region comprises 1, 2, 3, 4, 5, 6, 7, 8, 9, or 10 of the amino acid substitutions depicted in Table 3. In some cases, the isolated antibody comprises a humanized heavy chain framework region. In some cases, the humanized heavy chain framework region comprises 1, 2, 3, 4, 5, 6, 7, 8, 9, 10, 11, or 12 of the amino acid substitutions depicted in Table 2.

The present disclosure provides an isolated antibody, wherein the isolated antibody comprises a human light chain constant region and a human heavy chain constant region, and wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12.

The present disclosure provides a pharmaceutical formulation comprising: a) an anti-Tau antibody of the present disclosure; and b) a pharmaceutically acceptable excipient.

The present disclosure provides a pharmaceutical formulation comprising: a) an antibody that specifically binds an epitope within an N-terminal portion of Tau, wherein the antibody comprises: (i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; (iv) a $V_H$ CDR1 comprising an amino acid sequence of SEQ ID NO:4 or SEQ ID NO:10; (v) a $V_H$ CDR2 comprising an amino acid sequence of SEQ ID NO:5 or SEQ ID NO:11; and (vi) a $V_H$ CDR3 comprising an amino acid sequence of SEQ ID NO:6 or SEQ ID NO:12; and b) a pharmaceutically acceptable excipient suitable for administration to a human, wherein the formulation is free of endotoxins. In some cases, the antibody comprises a humanized light chain framework region. In some cases, the humanized light chain framework region comprises 1, 2, 3, 4, 5, 6, 7, 8, 9, or 10 of the amino acid substitutions depicted in Table 3. In some cases, the antibody comprises a humanized heavy chain framework region. In some cases, the humanized heavy chain framework region comprises 1, 2, 3, 4, 5, 6, 7, 8, 9, 10, 11, or 12 of the amino acid substitutions depicted in Table 2. In some cases, the antibody is encapsulated in a liposome. In some cases, the antibody is formulated with an agent that facilitates crossing the blood-brain barrier. In some cases, the antibody is fused, directly or via a linker, to a carrier molecule, a peptide or a protein that promotes the crossing of the blood-brain barrier. In some cases, the antibody is a Fv, scFv, Fab, F(ab')2, or Fab'.

The present disclosure provides a recombinant expression vector comprising a nucleotide sequence encoding an anti-Tau antibody of the present disclosure, wherein the nucleotide sequence is operably linked to a transcriptional control element that is active in a eukaryotic cell. The present disclosure provides an in vitro host cell genetically modified with a recombinant expression vector of the present disclosure.

The present disclosure provides a sterile container comprising a pharmaceutical formulation of the present disclosure. In some cases, the container is a syringe.

The present disclosure provides a method of treating a tauopathy in an individual, the method comprising administering to the individual an anti-Tau antibody of the present disclosure, or a pharmaceutical composition of the present disclosure.

The present disclosure provides a method of treating a tauopathy in an individual, the method comprising administering to the individual a pharmaceutical composition comprising: a) an antibody that competes for binding to an epitope in an N-terminal region of a Tau polypeptide with an antibody that comprises: i) light chain complementarity-determining regions (CDRs) of an antibody depicted in FIG. 1B; and heavy chain CDRs of an antibody depicted in FIG. 1A; or ii) light chain CDRs of an antibody depicted in FIG. 2B; and heavy chain CDRs of an antibody depicted in FIG. 2A; and b) a pharmaceutically acceptable excipient suitable for administration to a human. In some cases, the antibody comprises: (i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; (iv) a $V_H$ CDR1 comprising an amino acid sequence of SEQ ID NO:4 or SEQ ID NO:10; (v) a $V_H$ CDR2 comprising an amino acid sequence of SEQ ID NO:5 or SEQ ID NO:11; and (vi) a $V_H$ CDR3 comprising an amino acid sequence of SEQ ID NO:6 or SEQ ID NO:12. In some cases, the antibody comprises a humanized light chain framework region. In some cases, the antibody comprises a humanized heavy chain framework region. In some cases, the antibody is encapsulated in a liposome. In some cases, the antibody is formulated with an agent that facilitates crossing the blood-brain barrier. In some cases, the antibody is fused, directly or via a linker, to a carrier molecule, a peptide or a protein that promotes the crossing of the blood-brain barrier. In some cases, the antibody is a Fv, scFv, Fab, F(ab')2, or Fab'. In some cases, the administering is intravenous. In some cases, the administering is intrathecal.

In some cases, administration of a subject anti-Tau antibody results in a change in one or more of: a) the amount of free extracellular tau in brain tissue; b) the amount of free extracellular tau in interstitial fluid (ISF); c) the amount of free extracellular tau in cerebrospinal fluid (CSF); d) the neuron-to-neuron spread of tau; e) the amount of intraneuron tau aggregates; f) the degree of microglial and/or astrocyte activation; g) the amount of phosphorylated or hyperphosphorylated tau; h) the amount of total Tau or free tau in ISF or CSF; i) the amount of intracellular N-terminal tau fragments; j) neuronal hyperactivity; k) the amount of Aβ40 and/or Aβ42 in CSF; l) the Aβ plaque burden; m) secretion of Aβ40 and/or Aβ42 from a neuron; n) amyloid precursor protein (APP) promoter activity; o) APP mRNA and/or protein level; p) the activity of beta-secretase and/or gamma secretase; q) the activation state of an Aβ induced signaling pathway; r) the amount of intracellular total tau or free tau; s) the amount of anti-tau antibody-bound tau in ISF or CSF; and t) the amount of intracellular anti-Tau antibody-bound tau.

In some cases, a method of the present disclosure for treating a tauopathy in an individual further comprises administering at least one additional agent that treats the tauopathy.

The present disclosure provides a method of monitoring progression of a tauopathy in a individual, the method comprising: a) determining a first level of a Tau polypeptide in a biological sample obtained from the individual at a first time point; b) determining a second level of a Tau polypeptide in a biological sample obtained from the individual at a second time point; and c) comparing the second level of Tau with the first level of Tau, wherein said determining comprises: i) contacting the biological sample with an antibody of any one of claims 1, 5, 16, and 21; and ii) quantitating binding of the antibody to Tau polypeptide present in the sample. In some cases, the biological sample is cerebrospinal fluid, blood, plasma, serum, urine, or saliva. In some cases, the quantitated Tau polypeptide is total Tau polypeptide. In some cases, the quantitated Tau polypeptide is an N-terminal fragment of a full-length Tau polypeptide. In some cases, the first time point is a time point before initiation of a treatment regimen, and the second time point is a time point after initiation of a treatment regimen.

The present disclosure provides a method of detecting a Tau polypeptide in a living individual in vivo, the method comprising: a) administering to the individual an antibody of any one of claims 1, 5, 16, and 21; and b) detecting binding of the antibody to tau polypeptide in a brain tissue in the individual using an imaging method. In some cases, the antibody comprises a contrast agent suitable for use in the imaging method. In some cases, the imaging method is magnetic resonance imaging or positron emission tomography.

The present disclosure provides an in vitro method of detecting a Tau polypeptide in a biological sample obtained from an individual, the method comprising: a) contacting the biological sample with an antibody competes for binding to an epitope within the N-terminal region of Tau with an antibody that comprises: i) light chain complementarity-determining regions (CDRs) of an antibody depicted in FIG. 1B; and heavy chain CDRs of an antibody depicted in FIG. 1A; or ii) light chain CDRs of an antibody depicted in FIG. 2B; and heavy chain CDRs of an antibody depicted in FIG. 2A; and b) detecting binding of the antibody to Tau polypeptide present in the sample. In some cases, the biological sample is blood, serum, plasma, urine, saliva, or cerebrospinal fluid. In some cases, the individual is suspected of having a tauopathy, has been diagnosed as having a tauopathy, or has a genetic predisposition to developing a tauopathy. In some cases, the method is quantitative. In some cases, the Tau polypeptide detected is total Tau polypeptide. In some cases, the Tau polypeptide detected is an N-terminal fragment of a full-length Tau polypeptide.

BRIEF DESCRIPTION OF THE DRAWINGS

FIGS. 1A and 1B provide amino acid sequences of IPN001 VH (FIG. 1A) and VL (FIG. 1B). Complementarity-determining regions (CDRs) are in bold text and underlined.

FIGS. 2A and 2B provide amino acid sequences of IPN002 VH (FIG. 2A) and VL (FIG. 2B). Complementarity-determining regions (CDRs) are in bold text and underlined.

FIGS. 6A-D provide amino acid sequences of full-length human Tau.

FIG. 9 depicts an amino acid sequence of humanized IPN002 VH variant 1; and a nucleotide sequence encoding the amino acid sequence.

FIG. 10 depicts an amino acid sequence of humanized IPN002 VH variant 2; and a nucleotide sequence encoding the amino acid sequence.

FIG. 11 depicts an amino acid sequence of humanized IPN002 VH variant 3; and a nucleotide sequence encoding the amino acid sequence.

FIG. 12 depicts an amino acid sequence of humanized IPN002 VH variant 4; and a nucleotide sequence encoding the amino acid sequence.

FIG. 13 depicts an amino acid sequence of humanized IPN002 Vκ variant 1; and a nucleotide sequence encoding the amino acid sequence.

FIG. 14 depicts an amino acid sequence of humanized IPN002 Vκ variant 2; and a nucleotide sequence encoding the amino acid sequence.

FIG. 15 depicts an amino acid sequence of humanized IPN002 Vκ variant 3; and a nucleotide sequence encoding the amino acid sequence.

FIG. 16 depicts an amino acid sequence of humanized IPN002 Vκ variant 4; and a nucleotide sequence encoding the amino acid sequence.

FIG. 17 provides Table 4, which shows binding properties of humanized IPN-002 variants to eTau proteins.

FIG. 18 provides Table 5, which shows binding properties of humanized IPN-002 variants to Tau-383.

FIG. 19A depicts binding of humanized IPN-002 variants to tau present in iPSC-CN conditioned media; iPSC-CN lysates; AD brain lysates; and P301L tau mouse brain cortex lysates; and cynomologus monkey brain lysates. FIG. 19B depicts inhibition of eTau-induced neuronal hyperactivity by humanized IPN002 variants.

FIG. 20 depicts amino acid sequences of eTau fragments, in alignment with a fetal tau amino acid sequence.

FIG. 30 depicts competition of non-biotinylated forms of synthetic tau peptides with biotinylated forms of synthetic tau peptides for binding to a humanized variant of IPN002.

FIG. 41 depicts an assay for detecting various tau polypeptides in CSF.

DEFINITIONS

Figure 3:
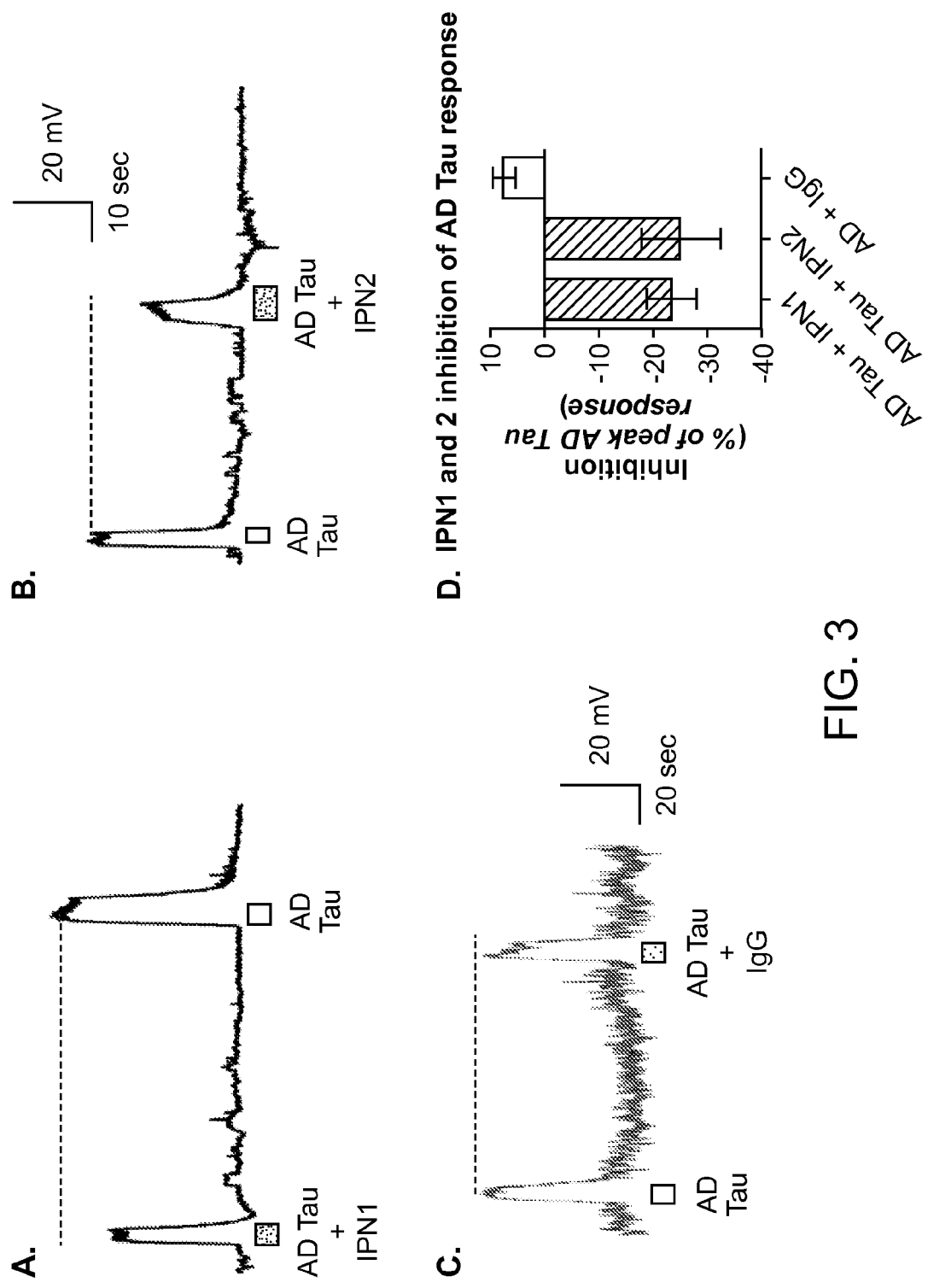
FIGS. 3A-D depicts the effect of anti-Tau antibody IPN002 on Tau-mediated membrane depolarization in cortical neurons.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, bi-specific antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816, 397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519, 596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-Tau antibody binds specifically to an epitope within a Tau polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., *J. Biol. Chem.* 252:6609-6616 (1977); Kabat et al., U.S. Dept. of Health and Human Services, "Sequences of proteins of immunological interest" (1991); by Chothia et al., *J. Mol. Biol.* 196:901-917 (1987); and MacCallum et al., *J. Mol. Biol.* 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of an anti-Tau antibody that, when administered to a mammal or other subject for treating a disease, is sufficient to effect such treatment for the disease. The "therapeutically effective amount" will vary depending on the anti-Tau antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, blood fractions such as plasma and serum, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a humanized anti-Tau antibody" includes a plurality of such antibodies and reference to "the tauopathy" includes reference to one or more tauopathies and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of treating a tauopathy, involving administering an anti-Tau antibody. The present disclosure also provides anti-Tau antibodies, and formulations comprising same, for use in the methods.

The present disclosure further provides in vitro and in vivo detection methods using an anti-Tau antibody described herein.

Methods of Treating a Tauopathy

The present disclosure provides methods of treating a tauopathy. The methods generally involve administering an effective amount of an anti-Tau antibody of the present disclosure to an individual in need thereof. In some cases, administration of a subject anti-tau antibody reduces the level of a pathological tau polypeptide in a cell, a tissue, or a fluid of an individual, and treats the tauopathy.

For example, in some embodiments, a subject method can comprise administering to an individual in need thereof an effective amount of an isolated humanized monoclonal antibody that specifically binds an epitope within amino acids 15-24 of a Tau polypeptide. In some embodiments, the antibody is present in a pharmaceutical formulation with a pharmaceutically acceptable excipient, e.g., a pharmaceutically acceptable excipient that is suitable for administration to a human.

For example, in some embodiments, a subject method can comprise administering to an individual in need thereof an effective amount of an isolated antibody comprising a humanized light chain framework region; and a humanized heavy chain framework region, wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some embodiments, the antibody is present in a pharmaceutical formulation with a pharmaceutically acceptable excipient, e.g., a pharmaceutically acceptable excipient that is suitable for administration to a human.

For example, in some embodiments, a subject method can comprise administering to an individual in need thereof an effective amount of an isolated antibody, wherein the antibody is a Fv, scFv, Fab, F(ab')2, or Fab', and wherein the antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some embodiments, the antibody is present in a pharmaceutical formulation with a pharmaceutically acceptable excipient, e.g., a pharmaceutically acceptable excipient that is suitable for administration to a human.

For example, in some embodiments, a subject method can comprise administering to an individual in need thereof an effective amount of an isolated antibody, wherein the isolated antibody comprises a human light chain constant region and a human heavy chain constant region, and wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some embodiments, the antibody is present in a pharmaceutical formulation with a pharmaceutically acceptable excipient, e.g., a pharmaceutically acceptable excipient that is suitable for administration to a human.

An anti-Tau antibody of the present disclosure binds extracellular tau. "Extracellular tau" ("eTau"), as used herein, encompasses any Tau polypeptide that can be detected in cerebrospinal fluid (CSF) or interstitial fluid (ISF). In some embodiments, eTau is a polypeptide having a length of 175 amino acids and comprising amino acids 2-176 of full-length tau; for example, in some embodiments eTau is a polypeptide comprising the amino acid sequence set forth in SEQ ID NO:45. In some embodiments, eTau is a polypeptide having a length of 171 amino acids and comprising amino acids 2-172 (SEQ ID NO:44) of full-length tau; for example, in some embodiments eTau is a polypeptide comprising the amino acid sequence set forth in SEQ ID NO:44. In some embodiments, eTau is an eTau-2 polypeptide comprising the amino acid sequence set forth in SEQ ID NO:46. In some embodiments, eTau is an eTau-3 polypeptide comprising the amino acid sequence set forth in SEQ ID NO:47. In some embodiments, eTau is an eTau-4 polypeptide comprising the amino acid sequence set forth in SEQ ID NO:48.

In some cases, an eTau polypeptide has a length of from about 50 amino acids to about 175 amino acids, e.g., from about 50 amino acids (aa) to about 75 aa, from about 75 aa to about 100 aa, from about 100 aa to about 125 aa, from about 125 aa to about 150 aa, or from about 150 aa to about 175 aa; and can comprise from 50 to about 75, from about 75 to about 100, from about 100 to about 125, from about 125 to about 150, or from about 150 to about 175, contiguous amino acids of amino acids 2-176 of full-length tau. Exemplary eTau polypeptides are depicted in FIG. 20.

As described in more detail below, an anti-Tau antibody of the present disclosure specifically binds Tau, where the epitope bound by the antibody is a linear epitope, and comprises amino acid residues within an amino-terminal (N-terminal) portion of Tau, e.g., within amino acids 1-25 of Tau, within amino acids 1-18 of Tau, within amino acids 9 to 18 of Tau, within amino acids 13-24 of Tau, within amino acids 15-44 of Tau, or within amino acids 15-24 of Tau. Amino acid sequences of human Tau isoforms are depicted in FIGS. 6A-D. Amino acids 1-18 of Tau are: MAEPRQEFEVMEDHAGTY; SEQ ID NO:53). See, e.g., Garcia-Sierra et al. (2003) *J. Alzheimer's Disease* 5:65; and Horowitz et al. (2004) *J. Neurosci.* 24:7895. Amino acids 15-24 of Tau are: AGTYGLGDRK (SEQ ID NO:51).

In some embodiments, an anti-Tau antibody of the present disclosure specifically binds Tau, where the epitope bound by the antibody is a linear epitope, and comprises amino acid residues within amino acids 1-25 of Tau, within amino acids 13-24 of Tau, or within amino acids 15-24 of Tau. In some cases, a humanized anti-Tau antibody of the present disclosure specifically binds a linear epitope comprising amino acid residues within amino acids 1-25 of Tau, within amino acids 13-24 of Tau, or within amino acids 15-24 of Tau, where the epitope does not include a phosphorylated amino acid. In some cases, a humanized anti-Tau antibody of the present disclosure specifically binds a linear epitope comprising amino acid residues within amino acids 1-25 of Tau, within amino acids 13-24 of Tau, or within amino acids 15-24 of Tau, where the epitope includes a phosphorylated amino acid. In some cases, a humanized anti-Tau antibody of the present disclosure specifically binds a linear epitope comprising amino acid residues within amino acids 1-25 of Tau, within amino acids 13-24 of Tau, or within amino acids 15-24 of Tau, where the epitope does not include a nitrated amino acid. In some cases, a humanized anti-Tau antibody of the present disclosure specifically binds a linear epitope comprising amino acid residues within amino acids 1-25 of Tau, within amino acids 13-24 of Tau, or within amino acids 15-24 of Tau, where the epitope includes a nitrated amino acid. In some cases, a humanized anti-Tau antibody of the present disclosure specifically binds a linear epitope comprising amino acid residues within amino acids 1-25 of Tau, within amino acids 13-24 of Tau, or within amino acids 15-24 of Tau, where the epitope includes a nitrated amino acid, and does not include a phosphorylated amino acid. In some cases, a humanized anti-Tau antibody of the present disclosure specifically binds a linear epitope comprising amino acid residues within amino acids 1-25 of Tau, within amino acids 13-24 of Tau, or within amino acids 15-24 of Tau, where the epitope includes a phosphorylated amino acid and does not include a nitrated amino acid. In some cases, a humanized anti-Tau antibody of the present disclosure specifically binds a linear epitope comprising amino acid residues within amino acids 1-25 of Tau, within amino acids 13-24 of Tau, or within amino acids 15-24 of Tau, where the epitope includes a nitrated amino acid and a phosphorylated amino acid.

For example, in some embodiments, an anti-Tau antibody of the present disclosure specifically binds a linear epitope comprising amino acid residues within amino acids AGTYGLGDRK (SEQ ID NO:51) of Tau. In some embodiments, a humanized anti-Tau antibody of the present disclosure specifically binds a linear epitope comprising amino acid residues within amino acids AGTYGLGDRK (SEQ ID NO:51) of Tau.

In some cases, a humanized anti-Tau antibody of the present disclosure specifically binds a linear epitope comprising amino acid residues within amino acids AGTYGLGDRK (SEQ ID NO:51) of Tau, where the epitope does not include a phosphorylated amino acid. In some cases, a humanized anti-Tau antibody of the present disclosure specifically binds a linear epitope comprising amino acid residues within amino acids AGTYGLGDRK (SEQ ID NO:51) of Tau, where the epitope includes a phosphorylated amino acid. In some cases, a humanized anti-Tau antibody of the present disclosure specifically binds a linear epitope comprising amino acid residues within amino acids AGTYGLGDRK (SEQ ID NO:51) of Tau, where the epitope does not include a nitrated amino acid. In some cases, a humanized anti-Tau antibody of the present disclosure specifically binds a linear epitope comprising amino acid residues within amino acids AGTYGLGDRK (SEQ ID NO:51) of Tau, where the epitope includes a nitrated amino acid. In some cases, a humanized anti-Tau antibody of the present disclosure specifically binds a linear epitope comprising amino acid residues within amino acids AGTYGLGDRK (SEQ ID NO:51) of Tau, where the epitope includes a nitrated amino acid, and does not include a phosphorylated amino acid. In some cases, a humanized anti-Tau antibody of the present disclosure specifically binds a linear epitope comprising amino acid residues within amino acids AGTYGLGDRK (SEQ ID NO:51) of Tau, where the epitope includes a phosphorylated amino acid and does not include a nitrated amino acid. In some cases, a humanized anti-Tau antibody of the present disclosure specifically binds a linear epitope comprising amino acid residues within amino acids AGTYGLGDRK (SEQ ID NO:51) of Tau, where the epitope includes a nitrated amino acid and a phosphorylated amino acid.

In some cases, a method of the present disclosure for treating a tauopathy comprises administering to an individual in need thereof a pharmaceutical composition comprising: a) an anti-Tau antibody comprising: i) one, two, or three light chain complementarity-determining regions (CDRs) of an antibody depicted in FIG. 1; and one, two, or three heavy chain CDRs of an antibody depicted in FIG. 1; or ii) one, two, or three light chain CDRs of an antibody depicted in FIG. 2; and one, two, or three heavy chain CDRs of an antibody depicted in FIG. 2; and b) a pharmaceutically acceptable excipient suitable for administration to a human.

In some cases, a method of the present disclosure for treating a tauopathy comprises administering to an individual in need thereof a pharmaceutical composition comprising: a) an antibody that specifically binds an epitope within a human Tau polypeptide, where the antibody competes for binding to the epitope with an antibody that comprises: i) light chain complementarity-determining regions (CDRs) of an antibody depicted in FIG. 1B; and heavy chain CDRs of an antibody depicted in FIG. 1A; or ii) light chain CDRs of an antibody depicted in FIG. 2B; and heavy chain CDRs of an antibody depicted in FIG. 2A; and b) a pharmaceutically acceptable excipient suitable for administration to a human.

In some cases, a method of the present disclosure for treating a tauopathy comprises administering to an individual in need thereof a pharmaceutical composition comprising: a) an antibody that competes for binding with humanized IPN002 (hu-IPN002) to an epitope in Tau that is recognized by hu-IPN002 (e.g., a linear epitope within an N-terminal portion of Tau, e.g., within amino acids 1-25 of Tau, within amino acids 1-18 of Tau, within amino acids 9 to 18 of Tau, within amino acids 15-44 of Tau, within amino acids 13-24 of Tau, or within amino acids 15-24 of Tau); and b) a pharmaceutically acceptable excipient suitable for administration to a human.

IPN001 (also referred to herein as "IPN1" or "IPN-1") and IPN002 (also referred to herein as "IPN2" or "IPN-2") specifically bind Tau. The epitope bound by IPN001 is a linear epitope, and comprises amino acid residues within an amino-terminal (N-terminal) portion of Tau, e.g., within amino acids 1-25 of Tau.

In some instances, an anti-Tau antibody of the present disclosure that is suitable for use in a method of treating a tauopathy comprises: a) a light chain variable region comprising: i) one, two, or three $V_L$ CDRs of an IPN001 antibody; and ii) a humanized light chain framework region; and b) a heavy chain variable region comprising: i) one, two, or three $V_H$ CDRs of an IPN001 antibody; and ii) a humanized heavy chain framework region; where the $V_H$ and $V_L$ CDRs are as defined by Kabat (see, e.g., Table 1, above; and Kabat et al., U.S. Dept. of Health and Human Services, "Sequences of proteins of immunological interest" (1991)).

In some instances, an anti-Tau antibody of the present disclosure that is suitable for use in a method of treating a tauopathy comprises: a) a light chain region comprising: i) one, two, or three V$_L$ CDRs of an IPN001 antibody; and ii) a humanized light chain framework region; and b) a heavy chain region comprising: i) one, two, or three V$_H$ CDRs of an IPN001 antibody; and ii) a humanized heavy chain framework region; where the V$_H$ and V$_L$ CDRs are as defined by Chothia (see, e.g., Table 1, above; and Chothia et al., J. Mol. Biol. 196:901-917 (1987)).

In other instances, an anti-Tau antibody of the present disclosure that is suitable for use in a method of treating a tauopathy comprises: a) a light chain region comprising: i) one, two, or three V$_L$ CDRs of an IPN002 antibody; and ii) a humanized light chain framework region; and b) a heavy chain region comprising: i) one, two, or three V$_H$ CDRs of an IPN002 antibody; and ii) a humanized heavy chain framework region; where the V$_H$ and V$_L$ CDRs are as defined by Kabat (see, e.g., Table 1, above; and Kabat et al., U.S. Dept. of Health and Human Services, "Sequences of proteins of immunological interest" (1991)).

In other instances, an anti-Tau antibody of the present disclosure (e.g., a subject antibody that specifically binds an epitope in a Tau polypeptide, where the epitope is within an amino-terminal (N-terminal) portion of Tau, e.g., within amino acids 1-25 of Tau, within amino acids 1-18 of Tau, within amino acids 9 to 18 of Tau, within amino acids 15-44 of Tau, within amino acids 13-24 of Tau, or within amino acids 15-24 of Tau) comprises: a) a light chain region comprising: i) one, two, or three V$_L$ CDRs of an IPN002 antibody; and ii) a humanized light chain framework region; and b) a heavy chain region comprising: i) one, two, or three V$_H$ CDRs of an IPN002 antibody; and ii) a humanized heavy chain framework region; where the V$_H$ and V$_L$ CDRs are as defined by Chothia (see, e.g., Table 1, above; and Chothia et al., J. Mol. Biol. 196:901-917 (1987)).

In some cases, a method of the present disclosure for treating a tauopathy comprises administering to an individual in need thereof an effective amount of a pharmaceutical composition comprising: a) an antibody that specifically binds a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)), where the antibody comprises: (i) a V$_L$ CDR1 comprising an amino acid sequence of SEQ ID NO:1 or SEQ ID NO:7; (ii) a V$_L$ CDR2 comprising an amino acid sequence of SEQ ID NO:2 or SEQ ID NO:8; (iii) a V$_L$ CDR3 comprising an amino acid sequence of SEQ ID NO:3 or SEQ ID NO:9; (iv) a V$_H$ CDR1 comprising an amino acid sequence of SEQ ID NO:4 or SEQ ID NO:10; (v) a V$_H$ CDR2 comprising an amino acid sequence of SEQ ID NO:5 or SEQ ID NO:11; and (vi) a V$_H$ CDR3 comprising an amino acid sequence of SEQ ID NO:6 or SEQ ID NO:12; and b) a pharmaceutically acceptable excipient suitable for administration to a human.

V$_H$ and V$_L$ amino acid sequences of IPN001 are depicted in FIGS. 1A and 1B. CDRs (as defined by Kabat) are in bold text and underlined. V$_H$ and V$_L$ amino acid sequences of IPN002 are depicted in FIGS. 2A and 2B. CDRs (as defined by Kabat) are in bold text and underlined.

SEQ ID NOs:1-12 are as follows:

```
                              (SEQ ID NO: 1)
RSSQTILHSNGNTYLE;

(SEQ ID NO: 2)
KVSKRFS;

(SEQ ID NO: 3)
FQGSLVPWA;

(SEQ ID NO: 4)
SYGMS;

(SEQ ID NO: 5)
TISSSGSRTYFPDSVKG;

(SEQ ID NO: 6)
TWDGAMDY;

(SEQ ID NO: 7)
KSSQSIVHSNGNTYLE;

(SEQ ID NO: 8)
KVSNRFS;

(SEQ ID NO: 9)
FQGSLVPWA;

(SEQ ID NO: 10)
KYGMS;

(SEQ ID NO: 11)
TISSSGSRTYYPDSVKG;

(SEQ ID NO: 12)
SWDGAMDY.
```

In some cases, the antibody comprises a humanized light chain framework region and/or a humanized heavy chain framework region. Humanized anti-Tau antibodies are described in detail below.

A tauopathy is a disorder characterized by an abnormal level of tau in a cell, a tissue, or a fluid in an individual. In some cases, a tauopathy is characterized by the presence in a cell, a tissue, or a fluid of elevated (higher than normal) levels of tau or tau polypeptides and/or pathological forms of tau. For example, in some cases, a tauopathy is characterized by the presence in brain tissue and/or cerebrospinal fluid of elevated levels of tau or tau polypeptides and/or pathological forms of tau. A "higher than normal" level of tau in a cell, a tissue, or a fluid indicates that the level of tau in the tissue or fluid is higher than a normal, control level, e.g., higher than a normal, control level for an individual or population of individuals of the same age group. See, e.g., Blomberg et al. (2001) "Cerebrospinal fluid tau levels increase with age in healthy individuals" Dement. Geriatr. Cogn. Disord. 12:127. In some cases, an individual having a tauopathy exhibits one or more additional symptoms of a tauopathy (e.g., cognitive decline).

In other cases, a tauopathy is characterized by the presence in a cell, a tissue, or a fluid of lower than normal levels of tau. A "lower than normal" level of tau in a tissue or a fluid indicates that the level of tau in the cell, tissue, or fluid is lower than a normal, control level, e.g., lower than a normal, control level for an individual or population of individuals of the same age group.

Alzheimer's disease and certain forms of Frontotemporal dementia (Pick's disease, sporadic Frontotemporal dementia and Frontotemporal dementia with Parkinsonism linked to chromosome 17) are the most common forms of tauopathy. The present disclosure provides a treatment method as described above, wherein the tauopathy is Alzheimer's, Pick's disease, sporadic Frontotemporal dementia and Frontotemporal dementia with Parkinsonism linked to chromosome 17. Other tauopathies include, but are not limited to, Progressive supranuclear palsy (PSP), Corticobasal degeneration (CBD) and Subacute sclerosing panencephalitis.

A neurodegenerative tauopathy includes Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia (FTD), frontotemporal dementia with parkinsonism linked to chromosome 17, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

The present disclosure also provides methods of treating a synucleinopathy, e.g., Parkinson's disease (PD); dementia with Lewy Bodies (DLB); multiple system atrophy (MSA); etc. For example, PD with dementia (PDD) can be treated with a subject method.

In one embodiment, an anti-tau antibody of the present disclosure prevents or delays the onset of at least one symptom of a neurodegenerative tauopathy in a subject. In one embodiment, a subject anti-tau antibody reduces or eliminates at least one symptom of a neurodegenerative tauopathy in a subject. The symptom may be the formation of one or more of: pathological tau deposits; extracellular soluble Tau and/or Tau fragments; hyperphosphorylated tau deposits; insoluble tau deposits; neurofibrillary tangles; neurofibrillary fibers; pre-tangle phospho-tau aggregates; intraneuronal neurofibrillary tangles; neuronal hyperactivity; and extraneuronal neurofibrillary tangles in the brain or spinal cord of a subject. The symptom may be a neurological symptom, for example, impaired cognitive function, memory impairment, loss of motor function, etc. In some cases, an anti-tau antibody of the present disclosure can improve cognitive function. In some cases, an anti-tau antibody of the present disclosure can reduce the rate of decline in cognitive function. In some cases, an anti-tau antibody of the present disclosure can improve motor function. In some cases, an anti-tau antibody of the present disclosure can reduce the rate of decline in motor function.

The symptom can also be the level of a Tau polypeptide in the CSF of the individual. For example, in some embodiments, a subject anti-tau antibody, when administered in one or more doses as monotherapy or in combination therapy to an individual having a tauopathy, reduces the level of a Tau polypeptide in the CSF of the individual by at least about 10%, at least about 15%, at least about 20%, at least about 25%, at least about 30%, at least about 40%, at least about 50%, or more than 50%, compared to the level of the Tau polypeptide in the CSF of the individual before treatment with the anti-tau antibody.

Administration of a subject anti-tau antibody to an individual can result in one or more of: reduction in the amount of free extracellular Tau in brain tissue; reduction in the cell-to-cell spread (e.g., neuron-to-neuron spread) of Tau (e.g., Tau fragments); reduction in the amount of tau aggregates (e.g., intracellular (e.g., intraneuronal) tau aggregates); reduction in the amount of neurofibrillary tangles in brain tissue; reduction in the level of microglial activation and/or astrocyte activation; reduction in the amount of phosphorylated tau; reduction in the amount of hyperphosphorylated tau; reduction in total Tau (e.g., total intracellular Tau; and/or total extracellular Tau); reduction in free Tau (e.g., Tau that is not bound to a subject anti-Tau antibody); reduction in neuronal hyperactivity; and reduction in the amount of N-terminal Tau fragments. "Total Tau" can include the sum total of full-length Tau of any isoform; and any N-terminal Tau fragments that are present and that display the epitope recognized by a subject anti-Tau antibody. Amino acid sequences of human full-length Tau are presented in FIGS. 6A-D. Reduction in phosphorylated Tau can be determined using any known method, e.g., an immunological method using an anti-phospho-Tau antibody.

Administration of a subject anti-tau antibody to an individual can result in a change in one or more of: a) the amount of free extracellular tau in brain tissue; b) the amount of free extracellular tau in interstitial fluid (ISF); c) the amount of free extracellular tau in cerebrospinal fluid (CSF); d) the neuron-to-neuron spread of tau; e) the amount of intraneuron tau aggregates; f) the degree of microglial and/or astrocyte activation; g) the amount of phosphorylated or hyperphosphorylated tau; h) the amount of total Tau or free tau in ISF or CSF; i) the amount of intracellular N-terminal tau fragments; j) neuronal hyperactivity; k) the amount of Aβ40 and/or Aβ42 in CSF; l) the Aβ plaque burden; m) secretion of Aβ40 and/or Aβ42 from a neuron; n) amyloid precursor protein (APP) promoter activity; o) APP mRNA and/or protein level; p) the activity of beta-secretase and/or gamma secretase; q) the activation state of an Aβ induced signaling pathway; r) the amount of intracellular total tau or free tau; s) the amount of anti-tau antibody-bound tau in ISF or CSF; and t) the amount of intracellular anti-Tau antibody-bound tau.

Administration of a subject anti-tau antibody to an individual can in some cases improve cognitive function in the individual, or at least reduce the rate of decline of cognitive function in the individual.

In some cases, administration of a subject anti-tau antibody to an individual reduces the amount of free extracellular tau polypeptide (e.g., the amount of free extracellular tau polypeptide in a brain tissue) by at least about 10%, at least about 20%, at least about 25%, at least about 50%, or more than 50%, compared to the amount of free extracellular tau polypeptide in the individual before administration with the anti-tau antibody.

In some cases, administration of a subject anti-tau antibody to an individual reduces the cell-to-cell (e.g., neuron-to-neuron) spread of a tau polypeptide (e.g., a pathological tau polypeptide) by at least about 10%, at least about 20%, at least about 25%, at least about 50%, or more than 50%, compared to the cell-to-cell spread before administration with a subject anti-tau antibody.

In some cases, administration of a subject anti-tau antibody to an individual reduces the amount of tau aggregates (e.g., intracellular (e.g., intraneuronal) tau aggregates) by at least about 10%, at least about 20%, at least about 25%, at least about 50%, or more than 50%, compared to the amount of tau aggregates before administration with the anti-tau antibody.

In some cases, administration of a subject anti-tau antibody to an individual reduces neurotoxicity in an individual; and/or reduces neuroinflammation in an individual; and/or reduces activation of astrocytes and microglia; and/or reduces induction of pathological electrophysiological effects; and/or reduces the amount of tau in exosomes.

In some cases, administration of a subject anti-tau antibody to an individual reduces neuronal hyperactivity by at least about 10%, at least about 20%, at least about 25%, at least about 50%, or more than 50%, compared to the level of degree of neuronal hyperactivity before administration with the anti-tau antibody. In some cases, administration of a subject anti-tau antibody to an individual reduces neuronal hyperactivity by at least about 10%, at least about 20%, at least about 25%, at least about 50%, or more than 50%, as determined by whole cell patch clamp recording of a neuron; e.g., whole cell patch clamp recording of an induced pluripotent stem cell-derived cortical neuron (iPSC-CN) or of a human cortical neuron cultures (HCC).

Administration of the suitable compositions may be effected by different ways, e.g., by intravenous, intraperitoneal, subcutaneous, intracranial, intrathecal, intraarterial (e.g., via the carotid artery), intramuscular, intranasal, topical or intradermal administration or spinal or brain delivery. Aerosol formulations such as nasal spray formulations include purified aqueous or other solutions of the active agent with preservative agents and isotonic agents. Such formulations are adjusted to a pH and isotonic state compatible with the nasal mucous membranes.

In some cases, a subject anti-tau antibody is modified, or formulated, in such a manner as to provide the ability of the antibody to cross the blood-brain barrier. Such an antibody or antibody composition can be administered to an individual having a tauopathy by various enteral and parenteral routes of administration including oral, intravenous, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the present disclosure may comprise further agents such as dopamine or psychopharmacologic drugs, depending on the intended use of the pharmaceutical composition.

The dosage regimen will be determined by the attending physician or other medical personnel, based on various clinical factors. As is well known in the medical arts, dosages for any one patient depends upon various factors, including the patient's size, body surface area, age, the particular compound to be administered, sex, time and route of administration, general health, and other drugs being administered concurrently. A dose of a subject anti-tau antibody can be, for example, in the range of 0.001 μg to 1000 μg; however, doses below or above this exemplary range are envisioned, especially considering the aforementioned factors. Generally, the dosage can range, e.g., from about 0.0001 to 100 mg/kg, or from about 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment.

Combination Therapy

An anti-tau antibody of the present disclosure can be administered to an individual in need thereof alone (e.g., as monotherapy); or in combination therapy with one or more additional therapeutic agents.

For the treatment of AD, suitable additional therapeutic agents include, but are not limited to, acetylcholinesterase inhibitors, including, but not limited to, Aricept (donepezil), Exelon (rivastigmine), metrifonate, and tacrine (Cognex); an anti-Aβ antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art.

Another suitable additional therapeutic agent in the treatment of AD is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Individuals to be Treated

Individuals suitable for treatment with a subject anti-tau antibody include individuals who have been diagnosed as having a tauopathy; individuals at greater risk than the general population for developing a tauopathy (e.g., individuals having a genetic predisposition to developing a tauopathy); individuals with PDD; and the like. In some cases, the individual is an adult human. In some cases, the adult human is 30 years of age or older; 40 years of age or older, 50 years of age or older, 60 years of age or older, 70 years of age or older, or 80 years of age or older. For example, the adult human can be from 40 years old to 50 years old, from 50 years old to 60 years old, from 60 years old to 70 years old, or older than 70 years.

Methods of Reducing Aβ40 and Aβ42 Levels

The present disclosure provides a method of reducing the level of $A\beta_{40}$ and/or $A\beta_{42}$ in a neuronal cell and/or extracellular fluid in an individual. The method generally involves administering to the individual: a) an effective amount of a humanized antibody that binds an N-terminal region of a tau polypeptide; or b) a pharmaceutical composition comprising the humanized antibody.

A humanized antibody that binds an N-terminal region of a tau polypeptide, and that is suitable for use in a subject method of reducing Aβ40 and Aβ42 in a neuronal cell and/or extracellular fluid, is a humanized antibody that binds an epitope of Tau that is within amino acids 2-176 of Tau, e.g., within amino acids 2-15, amino acids 15-24, amino acids 24-50, amino acids 2-25, amino acids 15 to 50, amino acids 50 to 75, amino acids 40 to 60, amino acids 75 to 100, amino acids 60 to 80, amino acids 100 to 125, amino acids 80-115, amino acids 125 to 150, amino acids 115 to 140, amino acids 150 to 176, or amino acids 140 to 160, of Tau. Exemplary Tau polypeptides are depicted in FIG. 20; an antibody that reduces the level of $A\beta_{40}$ and/or $A\beta_{42}$ in a neuronal cell and/or extracellular fluid in an individual can be a humanized antibody that specifically binds an epitope in a Tau polypeptide depicted in FIG. 20.

In some cases, an antibody that reduces the level of $A\beta_{40}$ and/or $A\beta_{42}$ in a neuronal cell and/or extracellular fluid in an individual, and that is suitable for use in a subject method, is a humanized anti-Tau antibody of the present disclosure. In some cases, the antibody is a humanized antibody that binds an epitope within amino acids 15-24 of Tau.

Anti-Tau Antibodies

The present disclosure provides isolated anti-Tau antibodies, and pharmaceutical formulations comprising same.

The present disclosure provides an isolated antibody that specifically binds an epitope within an N-terminal region of a Tau polypeptide (e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51). In some instances, the antibody is humanized, e.g., one or more framework regions of the heavy chain variable region and/or the light chain variable region includes sequences derived from a human immunoglobulin framework.

The present disclosure provides an isolated humanized monoclonal antibody that specifically binds an epitope within amino acids 15-24 of a Tau polypeptide. In some cases, the epitope does not comprise a phosphorylated amino acid. In some case, the epitope does not comprise a nitrated amino acid. In some cases, the epitope comprises a phosphorylated amino acid, a nitrated amino acid, or both a phosphorylated amino acid and a nitrated amino acid.

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIACORE) and/or solid-phase enzyme-linked immunosorbent assay (ELISA) analysis. In many cases, a subject humanized anti-Tau antibody does not substantially elicit a HAMA response in a human subject. In some cases, a subject humanized anti-Tau antibody has reduced immunogenic potential, as determined by an EpiScreen™ assay performed using $CD8^+$-depleted peripheral blood mononuclear cells. In some cases, a subject humanized anti-Tau antibody exhibits a Stimulation Index of less than 2.0.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, e.g., those sharing at least 60%, 70%, 80%, 90%, or more than 90%, sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

The present disclosure provides an isolated antibody comprising a humanized light chain framework region; and a humanized heavy chain framework region, wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some cases, the light chain region and the heavy chain region are present in separate polypeptides. In other cases, the light chain region and the heavy chain region are present in a single polypeptide. The isolated antibody can include a heavy chain that comprises a constant region of the isotype IgG1, IgG2, IgG3, or IgG4. In other cases, the antibody is a Fv, scFv, Fab, F(ab')2, or Fab'. The antibody can comprise a covalently linked non-peptide synthetic polymer, e.g., where the synthetic polymer is a poly(ethylene glycol) polymer. In some cases, the isolated antibody is fused, directly or via a linker, to a carrier molecule, a peptide or a protein that promotes the crossing of the blood-brain barrier. In some cases, the epitope bound by the isolated antibody is within amino acids 15-24 of a Tau polypeptide. The isolated antibody humanized light chain framework region can comprise 1, 2, 3, 4, 5, 6, 7, 8, 9, or 10 of the amino acid substitutions depicted in Table 3. The isolated antibody humanized heavy chain framework region comprises 1, 2, 3, 4, 5, 6, 7, 8, 9, 10, 11, or 12 of the amino acid substitutions depicted in Table 2.

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)) comprises: a) a light chain region comprising: i) one, two, or three complementarity determining regions (CDRs) of an IPN001 antibody, where the CDRs are as defined by Kabat (see, e.g., Table 1, above; and Kabat et al., U.S. Dept. of Health and Human Services, "Sequences of proteins of immunological interest" (1991)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)) comprises: a) a light chain region comprising: i) one, two, or three $V_L$ CDRs of an IPN001 antibody; and ii) a humanized light chain framework region; and b) a heavy chain region comprising: i) one, two, or three $V_H$ CDRs of an IPN001 antibody; and ii) a humanized heavy chain framework region; where the $V_H$ and $V_L$ CDRs are as defined by Kabat (see, e.g., Table 1, above; and Kabat et al., U.S. Dept. of Health and Human Services, "Sequences of proteins of immunological interest" (1991)). In some of these embodiments, the anti-Tau antibody includes a humanized $V_H$ and/or $V_L$ framework region.

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)) comprises: a) a light chain region comprising: i) one, two, or three $V_L$ CDRs of an IPN001 antibody; and ii) a humanized light chain framework region; and b) a heavy chain region comprising: i) one, two, or three $V_H$ CDRs of an IPN001 antibody; and ii) a humanized heavy chain framework region; where the $V_H$ and $V_L$ CDRs are as defined by Chothia (see, e.g., Table 1, above; and Chothia et al., J. Mol. Biol. 196:901-917 (1987)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)) comprises: a) a light chain region comprising: i) one, two, or three $V_L$ CDRs of an IPN002 antibody; and ii) a humanized light chain framework region; and b) a heavy chain region comprising: i) one, two, or three $V_H$ CDRs of an IPN002 antibody; and ii) a humanized heavy chain framework region; where the $V_H$ and $V_L$ CDRs are as defined by Kabat (see, e.g., Table 1, above; and Kabat et al., U.S. Dept. of Health and Human Services, "Sequences of proteins of immunological interest" (1991)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)) comprises: a) a light chain region comprising: i) one, two, or three $V_L$ CDRs of an IPN002 antibody; and ii) a humanized light chain framework region; and b) a heavy chain region comprising: i) one, two, or three $V_H$ CDRs of an IPN002 antibody; and ii) a humanized heavy chain framework region; where the $V_H$ and $V_L$ CDRs are as defined by Chothia (see, e.g., Table 1, above; and Chothia et al., J. Mol. Biol. 196:901-917 (1987)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)) comprises: a) a light chain region comprising: i) one, two, or three CDRs selected from SEQ ID NO:1, SEQ ID NO:2, and SEQ ID NO:3; and ii) a humanized light chain framework region; and b) a heavy chain region comprising: i) one, two, or three CDRs selected from SEQ ID NO:4, SEQ ID NO:5, and SEQ ID NO:6; and ii) a humanized heavy chain framework region.

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, within amino acids 9 to 18 of Tau (where amino acids 1-18 of Tau are: MAEPRQEFEVMEDHAGTY; SEQ ID NO:53), within amino acids 15-44 of Tau, within amino acids 13-24 of Tau, or within amino acids 15-24 of Tau (where amino acids 15-24 of Tau are: AGTYGLGDRK (SEQ ID NO:51)) comprises: a) a light chain region comprising: i) one, two, or three CDRs selected from SEQ ID NO:7, SEQ ID NO:8, and SEQ ID NO:9; and ii) a humanized light chain framework region; and b) a heavy chain region comprising: i) one, two, or three CDRs selected from SEQ ID NO:10, SEQ ID NO:11, and SEQ ID NO:12; and ii) a humanized heavy chain framework region.

In some instances, the antibody comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; and (iv) a humanized light chain framework region; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; (iii) a $V_H$ CDR3 comprising an amino acid sequence of SEQ ID NO:6 or SEQ ID NO:12; and iv) a humanized heavy chain framework region.

In some embodiments, a subject anti-Tau antibody comprises a heavy chain variable region comprising one, two, or three of the heavy chain CDRs having an amino acid sequence selected from one or more of SEQ ID NOs:4, 5, and 6; and one, two, three, or four FR regions that are humanized. For example, in some embodiments, a subject antibody comprises a heavy chain variable region that comprises, in order from N-terminus to C-terminus: a humanized heavy chain FR1; a CDR1 comprising the amino acid sequence set forth in SEQ ID NO:4; a humanized heavy chain FR2; a CDR2 comprising the amino acid sequence set forth in SEQ ID NO:5; a humanized heavy chain FR3; a CDR3 comprising the amino acid sequence set forth in SEQ ID NO:6; and a humanized heavy chain FR4.

In some embodiments, a subject anti-Tau antibody comprises a light chain variable region comprising one, two, or three of the light chain CDRs having a polypeptide sequence selected from one or more of SEQ ID NOs:1, 2, and 3; and one, two, three, or four FR regions that are humanized. For example, in some embodiments, a subject antibody comprises a light chain variable region that comprises, in order from N-terminus to C-terminus: a humanized light chain FR1; a CDR1 comprising the amino acid sequence set forth in SEQ ID NO:1; a humanized light chain FR2; a CDR2 comprising the amino acid sequence set forth in SEQ ID NO:2; a humanized light chain FR3; a CDR3 comprising the amino acid sequence set forth in SEQ ID NO:3; and a humanized light chain FR4.

In some embodiments, a subject anti-Tau antibody comprises a heavy chain variable region comprising one, two, or three of the heavy chain CDRs having an amino acid sequence selected from one or more of SEQ ID NOs:10, 11, and 12; and one, two, three, or four FR regions that are humanized. For example, in some embodiments, a subject antibody comprises a heavy chain variable region that comprises, in order from N-terminus to C-terminus: a humanized heavy chain FR1; a CDR1 comprising the amino acid sequence set forth in SEQ ID NO:10; a humanized heavy chain FR2; a CDR2 comprising the amino acid sequence set forth in SEQ ID NO:11; a humanized heavy chain FR3; a CDR3 comprising the amino acid sequence set forth in SEQ ID NO:12; and a humanized heavy chain FR4.

In some embodiments, a subject anti-Tau antibody comprises a light chain variable region comprising one, two, or three of the light chain CDRs having a polypeptide sequence selected from one or more of SEQ ID NOs:7, 8, and 9; and one, two, three, or four FR regions that are humanized. For example, in some embodiments, a subject antibody comprises a light chain variable region that comprises, in order from N-terminus to C-terminus: a humanized light chain FR1; a CDR1 comprising the amino acid sequence set forth in SEQ ID NO:7; a humanized light chain FR2; a CDR2 comprising the amino acid sequence set forth in SEQ ID NO:8; a humanized light chain FR3; a CDR3 comprising the amino acid sequence set forth in SEQ ID NO:9; and a humanized light chain FR4.

$V_H$ and $V_L$ amino acid sequences of IPN001 are depicted in FIGS. 1A and 1B. CDRs (as defined by Kabat) are in bold text and underlined. $V_H$ and $V_L$ amino acid sequences of IPN002 are depicted in FIGS. 2A and 2B. CDRs (as defined by Kabat) are in bold text and underlined.

SEQ ID NOs:1-12 are as follows:

```
                                    (SEQ ID NO: 1)
      RSSQTILHSNGNTYLE;

(SEQ ID NO: 2)
      KVSKRFS;

(SEQ ID NO: 3)
      FQGSLVPWA;

(SEQ ID NO: 4)
      SYGMS;

(SEQ ID NO: 5)
      TISSSGSRTYFPDSVKG;

(SEQ ID NO: 6)
      TWDGAMDY;

(SEQ ID NO: 7)
      KSSQSIVHSNGNTYLE;
```

-continued

KVSNRFS; (SEQ ID NO: 8)

FQGSLVPWA; (SEQ ID NO: 9)

KYGMS; (SEQ ID NO: 10)

TISSSGSRTYYPDSVKG; (SEQ ID NO: 11)

SWDGAMDY. (SEQ ID NO: 12)

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 1B and set forth in SEQ ID NO:13.

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 1A and set forth in SEQ ID NO:14.

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 2B and set forth in SEQ ID NO:15.

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 2A and set forth in SEQ ID NO:16.

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 9 (VH variant 1).

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 10 (VH variant 2).

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 11 (VH variant 3).

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 12 (VH variant 4).

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 13 (Vk variant 1).

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 14 (Vk variant 2).

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 15 (Vk variant 3).

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 16 (Vk variant 4).

A subject anti-Tau antibody can comprise a heavy chain variable region comprising 1, 2, 3, 4, 5, 6, 7, 8, 9, 10, 11, or 12 of the framework (FR) amino acid substitutions, relative to the IPN002 parental antibody FR amino acid sequences, depicted in Table 2.

TABLE 2

| Amino Acid Position | IPN002 (Parental antibody) | VH Variant 1 | VH Variant 2 | VH Variant 3 | VH Variant 4 |
|---|---|---|---|---|---|
| FR1 | | | | | |
| 3 | H | H | H | Q | Q |
| 19 | K | R | R | R | R |
| FR2 | | | | | |
| 40 | T | A | A | A | A |
| 42 | D | G | G | G | G |
| 44 | R | G | G | G | G |
| FR3 | | | | | |
| 66 | Q | R | R | R | R |
| 83 | S | S | N | N | N |
| 85 | L | S | L | L | L |
| 86 | K | K | R | R | R |
| 87 | S | S | A | A | A |
| 93 | S | S | S | S | A |
| FR4 | | | | | |
| 108 | S | S | T | T | T |

For example, a subject anti-Tau antibody can comprise a heavy chain variable region comprising an H→W substitution at amino acid position 3 in VH FR1 and/or a K→R substitution at amino acid position 19 in VH FR1.

As another example, a subject anti-Tau antibody can comprise a heavy chain variable region comprising a T→A substitution at amino acid position 40 in VH FR2 and/or a D→G substitution at amino acid position 42 in VH FR2 and/or an R→G substitution at position 44 in VH FR2.

As another example, a subject anti-Tau antibody can comprise a heavy chain variable region comprising a Q→R substitution at amino acid position 66 in VH FR3 and/or an S→N substitution at amino acid position 83 in VH FR3 and/or an L→S substitution at amino acid position 85 in VH FR3 and/or a K→R substitution at amino acid position 86 in FR3 and/or an S→A substitution at amino acid position 87 in VH FR3 and/or an S→A substitution at amino acid position 93 in VH FR3.

As another example, a subject anti-Tau antibody can comprise a heavy chain variable region comprising an S→T substitution at amino acid position 108 in VH FR4.

In some cases, a subject isolated anti-Tau antibody can comprise, in order from N-terminus to C-terminus a VH region comprising: EVX$_1$LVESGGALVKPGGSLRLSCAASGFSFS (SEQ ID NO:83); VH CDR1 as shown in FIG. 2A; WVRQAPGKGLEWVA (SEQ ID NO:84); VH CDR2 as shown in FIG. 2A; RFTISRDNAKNTLYLQMX$_2$SX$_3$X$_4$X$_5$EDTAMYYCX$_6$I (SEQ ID NO:85); VH CDR3 as shown in FIG. 2A;

WGQGTX$_7$VTVSS (SEQ ID NO:86), where X$_1$ is H or Q; X$_2$ is S or N; X$_3$ is S or L; X$_4$ is K or R; X$_5$ is S or A; X$_6$ is S or A; and X$_7$ is S or T.

A subject anti-Tau antibody can comprise a light chain variable region comprising 1, 2, 3, 4, 5, 6, 7, 8, 9, or 10 of the framework (FR) amino acid substitutions, relative to the IPN002 parental antibody FR amino acid sequences, depicted in Table 3.

TABLE 3

| | | Vk Variants | | | |
|---|---|---|---|---|---|
| Amino Acid Position | IPN002 (Parental antibody) | Vk Variant 1 | Vk Variant 2 | Vk Variant 3 | Vk Variant 4 |
| FR1 | | | | | |
| 3 | L | L | V | V | V |
| 7 | T | S | S | S | S |
| 14 | S | T | T | T | T |
| 17 | D | Q | Q | Q | Q |
| 18 | Q | P | P | P | P |
| FR2 | | | | | |
| 45 | K | Q | Q | Q | Q |
| 48 | V | V | V | V | I |
| FR3 | | | | | |
| 83 | L | V | V | V | V |
| 85 | T | T | T | V | V |
| FR4 | | | | | |
| 104 | L | V | V | V | V |

For example, a subject anti-Tau antibody can comprise a light chain variable region comprising an L→N substitution at amino acid position 3 in VL FR1 and/or a T→S substitution at amino acid position 7 in VL FR1 and/or an S→T substitution at amino acid position 14 in VL FR1 and/or a D→Q substitution at amino acid position 17 in VL FR1 and/or a Q→P substitution at amino acid position 18 in VL FR1.

As another example, a subject anti-Tau antibody can comprise a light chain variable region comprising a K→Q substitution at amino acid position 45 of VL FR2 and/or a V→I substitution at amino acid position 48 of VL FR2.

As another example, a subject anti-Tau antibody can comprise a light chain variable region comprising an L→N substitution at amino acid position 83 of VL FR3 and/or a T→N substitution at amino acid position 85 of VL FR3.

As another example, a subject anti-Tau antibody can comprise a light chain variable region comprising an L→N substitution at amino acid position 104 of VL FR4.

In some cases, a subject isolated anti-Tau antibody can comprise, in order from N-terminus to C-terminus a VL region comprising: DVX$_1$MTQSPLSLPVTLGQPASISC (SEQ ID NO:54); VL CDR1 as shown in FIG. 2B; WYLQKPGQSPQLLX$_2$Y (SEQ ID NO:55); VL CDR2 as shown in FIG. 2B; GVPDRFSGSGSGTDFTLKISRVEAEDVGX$_3$YYC (SEQ ID NO:56); VL CDR3 as shown in FIG. 2B; FGGGTKVEIK (SEQ ID NO:57); where X$_1$ is L or V; X$_2$ is V or I; and X$_3$ is T or V.

In some cases, an anti-Tau antibody of the present disclosure comprises:

a) a VH variant 1 comprising the amino acid sequence depicted in FIG. 9; and a Vk variant 1 comprising the amino acid sequence depicted in FIG. 13;

b) a VH variant 1 comprising the amino acid sequence depicted in FIG. 9; and a Vk variant 2 comprising the amino acid sequence depicted in FIG. 14;

c) a VH variant 1 comprising the amino acid sequence depicted in FIG. 9; and a Vk variant 3 comprising the amino acid sequence depicted in FIG. 15;

d) a VH variant 1 comprising the amino acid sequence depicted in FIG. 9; and a Vk variant 4 comprising the amino acid sequence depicted in FIG. 16;

e) a VH variant 2 comprising the amino acid sequence depicted in FIG. 10; and a Vk variant 1 comprising the amino acid sequence depicted in FIG. 13;

f) a VH variant 2 comprising the amino acid sequence depicted in FIG. 10; and a Vk variant 2 comprising the amino acid sequence depicted in FIG. 14;

g) a VH variant 2 comprising the amino acid sequence depicted in FIG. 10; and a Vk variant 3 comprising the amino acid sequence depicted in FIG. 15;

h) a VH variant 2 comprising the amino acid sequence depicted in FIG. 10; and a Vk variant 4 comprising the amino acid sequence depicted in FIG. 16;

i) a VH variant 3 comprising the amino acid sequence depicted in FIG. 11; and a Vk variant 1 comprising the amino acid sequence depicted in FIG. 13;

j) a VH variant 3 comprising the amino acid sequence depicted in FIG. 11; and a Vk variant 2 comprising the amino acid sequence depicted in FIG. 14;

k) a VH variant 3 comprising the amino acid sequence depicted in FIG. 11; and a Vk variant 3 comprising the amino acid sequence depicted in FIG. 15;

l) a VH variant 3 comprising the amino acid sequence depicted in FIG. 11; and a Vk variant 4 comprising the amino acid sequence depicted in FIG. 16;

m) a VH variant 4 comprising the amino acid sequence depicted in FIG. 12; and a Vk variant 1 comprising the amino acid sequence depicted in FIG. 13;

n) a VH variant 4 comprising the amino acid sequence depicted in FIG. 12; and a Vk variant 2 comprising the amino acid sequence depicted in FIG. 14;

o) a VH variant 4 comprising the amino acid sequence depicted in FIG. 12; and a Vk variant 3 comprising the amino acid sequence depicted in FIG. 15; or p) a VH variant 4 comprising the amino acid sequence depicted in FIG. 12; and a Vk variant 4 comprising the amino acid sequence depicted in FIG. 16.

In some embodiments, a subject antibody comprises anti-Tau heavy chain CDRs and anti-Tau light chain CDRs in a single polypeptide chain, e.g., in some embodiments, a subject antibody is a scFv. In some embodiments, a subject antibody comprises, in order from N-terminus to C-terminus: a first amino acid sequence of from about 5 amino acids to about 25 amino acids in length; a CDR1 comprising the amino acid sequence set forth in SEQ ID NO:1; a second amino acid sequence of from about 5 amino acids to about 25 amino acids in length; a CDR2 comprising the amino acid sequence set forth in SEQ ID NO:2; a third amino acid sequence of from about 5 amino acids to about 25 amino acids in length; a CDR3 comprising the amino acid sequence set forth in SEQ ID NO:3; a fourth amino acid sequence of from about 5 amino acids to about 25 amino acids in length; a CDR1 comprising the amino acid sequence set forth in SEQ ID NO:4; a fifth amino acid sequence of from about 5 amino acids to about 25 amino acids in length; a CDR2 comprising the amino acid sequence set forth in SEQ ID NO:5; a sixth amino acid sequence of from about 5 amino acids to about 25 amino acids in length; a CDR3 comprising the amino acid sequence set forth in SEQ ID NO:6; and a seventh amino acid sequence of from about 5 amino acids to about 25 amino acids in length.

In some embodiments, a subject antibody comprises, in order from N-terminus to C-terminus: a light chain FR1 region; a CDR1 comprising the amino acid sequence set forth in SEQ ID NO:1; a light chain FR2 region; a CDR2 comprising the amino acid sequence set forth in SEQ ID NO:2; a light chain FR3 region; a CDR3 comprising the amino acid sequence set forth in SEQ ID NO:3; optionally a light chain FR4 region; a linker region; optionally a heavy chain FR1 region; a CDR1 comprising the amino acid sequence set forth in SEQ ID:4; a heavy chain FR2 region; a CDR2 comprising the amino acid sequence set forth in SEQ ID NO:5; a heavy chain FR3 region; a CDR3 comprising the amino acid sequence set forth in SEQ ID NO:6; and a heavy chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a heavy chain FR1 region; a CDR1 comprising the amino acid sequence set forth in SEQ ID:4; a heavy chain FR2 region; a CDR2 comprising the amino acid sequence set forth in SEQ ID NO:5; a heavy chain FR3 region; a CDR3 comprising the amino acid sequence set forth in SEQ ID NO:6; optionally a heavy chain FR4 region; a linker; optionally a light chain FR1 region; a CDR1 comprising the amino acid sequence set forth in SEQ ID NO:1; a light chain FR2 region; a CDR2 comprising the amino acid sequence set forth in SEQ ID NO:2; a light chain FR3 region; a CDR3 comprising the amino acid sequence set forth in SEQ ID NO:3; and a light chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a light chain FR1 region; a CDR1 comprising the amino acid sequence set forth in SEQ ID NO:7; a light chain FR2 region; a CDR2 comprising the amino acid sequence set forth in SEQ ID NO:8; a light chain FR3 region; a CDR3 comprising the amino acid sequence set forth in SEQ ID NO:9; optionally a light chain FR4 region; a linker region; optionally a heavy chain FR1 region; a CDR1 comprising the amino acid sequence set forth in SEQ ID:10; a heavy chain FR2 region; a CDR2 comprising the amino acid sequence set forth in SEQ ID NO:11; a heavy chain FR3 region; a CDR3 comprising the amino acid sequence set forth in SEQ ID NO:12; and a heavy chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a heavy chain FR1 region; a CDR1 comprising the amino acid sequence set forth in SEQ ID:10; a heavy chain FR2 region; a CDR2 comprising the amino acid sequence set forth in SEQ ID NO:11; a heavy chain FR3 region; a CDR3 comprising the amino acid sequence set forth in SEQ ID NO:12; optionally a heavy chain FR4 region; a linker; optionally a light chain FR1 region; a CDR1 comprising the amino acid sequence set forth in SEQ ID NO:7; a light chain FR2 region; a CDR2 comprising the amino acid sequence set forth in SEQ ID NO:8; a light chain FR3 region; a CDR3 comprising the amino acid sequence set forth in SEQ ID NO:9; and a light chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO:58) and $GGGS_n$ (SEQ ID NO:59), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGSG (SEQ ID NO:60), GGSGG (SEQ ID NO:61), GSGSG (SEQ ID NO:62), GSGGG (SEQ ID NO:63), GGGSG (SEQ ID NO:64), GSSSG (SEQ ID NO:65), and the like. The ordinarily skilled artisan will recognize that design of a peptide conjugated to any elements described above can include linkers that are all or partially flexible, such that the linker can include a flexible linker as well as one or more portions that confer less flexible structure.

In some cases, a subject isolated antibody is an antibody fragment, an Fv, scFv, Fab, F(ab')2, or Fab'. Thus, the present disclosure provides an isolated antibody, wherein the antibody is a Fv, scFv, Fab, F(ab')2, or Fab', and wherein the antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some of these embodiments, the isolated antibody comprises one, two, three, or four humanized VL framework regions, as described above. In some of these embodiments, the isolated antibody comprises one, two, three, or four humanized VH framework regions, as described above.

In some embodiments, an anti-Tau antibody of the present disclosure is a scFv antibody. In some embodiments, an anti-Tau antibody of the present disclosure comprises scFv multimers. For example, in some embodiments, a subject antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids (aa) in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

In some cases, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. In some cases, the heavy chain region is of the isotype IgG4. In some of these embodiments, the hinge region comprises an S241P substitution. See, e.g., Angal et al. (1993) Mol. Immunol. 30:105. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, the present disclosure provides an isolated antibody, wherein the isolated antibody comprises a human light chain constant region and a human heavy chain constant region, and wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12. In some of these embodiments, the isolated antibody comprises one, two, three, or four humanized VL framework regions, as described above. In some of these embodiments, the isolated antibody comprises one, two, three, or four humanized VH framework regions, as described above.

A subject antibody can comprise a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to the antibody, where the antibody comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) copolymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula R(O—CH$_2$—CH$_2$)$_n$ O—R, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., a subject antibody can comprise a covalently linked carbohydrate or polysaccharide moiety. Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866, 132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123I}I$ (iodine), $^{18}F$ (fluorine), $^{99}Tc$ (technetium), $^{111}In$ (indium), and $^{67}Ga$ (gallium), and contrast agent such as gadolinium (Gd), dysprosium, and iron. Radioactive Gd isotopes ($^{153}Gd$) also are available and suitable for imaging procedures in non-human mammals. A subject antibody can be labeled using standard techniques. For example, a subject antibody can be iodinated using chloramine T or 1,3,4,6-tetrachloro-3α,6α-diphenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10): 752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., YPYDVPDYA; SEQ ID NO:71), FLAG (e.g., DYKDDDDK; SEQ ID NO:69), c-myc (e.g., EQKLISEEDL; SEQ ID NO:68), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:66), HisX6 (HHHHHH) (SEQ ID NO:67), C-myc (EQKLISEEDL) (SEQ ID NO:68), Flag (DYKDDDDK) (SEQ ID NO:69), StrepTag (WSHPQFEK) (SEQ ID NO:70), hemagglutinin, e.g., HA Tag (YPYDVPDYA; SEQ ID NO:71), glutathinone-S-transferase (GST), thioredoxin, cellulose binding domain, RYIRS (SEQ ID NO:72), Phe-His-His-Thr (SEQ ID NO:73), chitin binding domain, S-peptide, T7 peptide, SH2 domain, C-end RNA tag, WEAAAREACCRECCARA (SEQ ID NO:74), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

A subject antibody will in some embodiments be fused to a polypeptide that binds to an endogenous blood brain barrier (BBB) receptor. Linking a subject antibody to a polypeptide that binds to an endogenous BBB receptor facilitates crossing the BBB, e.g., in a subject treatment method (see below) involving administration of a subject antibody to an individual in need thereof. Suitable polypeptides that bind to an endogenous BBB receptor include antibodies, e.g., monoclonal antibodies, or antigen-binding fragments thereof, that specifically bind to an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

As an example, a subject anti-Tau antibody can be a bi-specific antibody comprising a first antigen-binding portion that specifically binds an epitope in a Tau polypeptide (e.g., a linear epitope within an amino-terminal (N-terminal) portion of Tau, e.g., within amino acids 1-25 of Tau, within amino acids 1-18 of Tau, or within amino acids 9 to 18 of Tau); and a second antigen-binding portion that binds an endogenous BBB receptor. For example, in some instances, a subject anti-Tau antibody is a bi-specific antibody comprising a first antigen-binding portion that specifically binds an epitope in a Tau polypeptide (e.g., a linear epitope within an amino-terminal (N-terminal) portion of Tau, e.g., within amino acids 1-25 of Tau, within amino acids 1-18 of Tau, or within amino acids 9 to 18 of Tau); and a second antigen-binding portion that binds a transferrin receptor.

For example, an anti-Tau antibody of the present disclosure can be fused to a peptide that facilitates crossing the BBB, the peptide having a length of from about 15 amino acids to about 25 amino acids, and comprising an amino acid sequence having at least about 85% amino acid sequence identity to one of the following peptides: Angiopep-1 (TFFYGGCRGKRNNFKTEEY; SEQ ID NO:75); Angiopep-2 (TFFYGGSRGKRNNFKTEEY; SEQ ID NO:76); cys-Angiopep-2 (CTFFYGGSRGKRNNFKTEEY; SEQ ID NO:77); Angiopep-2-cys (TFFYGGSRGKRNNFKTEEYC; SEQ ID NO:78); and an aprotinin fragment (TFVYGGCRAKRNNFKS; SEQ ID NO:79). See, e.g., U.S. Patent Publication Nos. 2011/0288011; and 2009/0016959. A peptide that facilitates crossing the BBB can be fused to the N-terminus of an anti-Tau light chain region, to the C-terminus of an anti-Tau light chain region, to the N-terminus of an anti-Tau heavy chain region, to the C-terminus of an anti-Tau heavy chain region, to the N-terminus of a subject anti-Tau single-chain antibody, to the C-terminus of a subject anti-Tau single-chain antibody, etc.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-diaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or $N(R)_2$ moieties, wherein R is H, ($C_1$-$C_4$) alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

Methods of Producing a Subject Antibody

A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce an anti-tau antibody of the present disclosure (e.g., polynucleotides encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids, Expression Vectors, and Host Cells

The present disclosure provides nucleic acids comprising nucleotide sequences encoding a subject anti-Tau antibody.

A nucleotide sequence encoding subject anti-Tau antibody can comprise a nucleotide sequence encoding a light chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 1B and set forth in SEQ ID NO:17.

A nucleotide sequence encoding subject anti-Tau antibody can comprise a nucleotide sequence encoding a heavy chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 1A and set forth in SEQ ID NO:18.

A nucleotide sequence encoding subject anti-Tau antibody can comprise a nucleotide sequence encoding a light chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 2B and set forth in SEQ ID NO:19.

A nucleotide sequence encoding subject anti-Tau antibody can comprise a nucleotide sequence encoding a heavy chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 2A and set forth in SEQ ID NO:20.

A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject antibody. A subject nucleic acid can comprise a nucleotide sequence encoding heavy- and light-chain CDRs of IPN001. In some embodiments, a subject nucleic acid comprises a nucleotide sequence encoding heavy- and light-chain CDRs of IPN002, where the CDR-encoding sequences are interspersed with FR-encoding nucleotide sequences. In some embodiments, the FR-encoding nucleotide sequences are human FR-encoding nucleotide sequences.

Host Cells

The present disclosure provides isolated genetically modified host cells (e.g., in vitro cells) that are genetically modified with a subject nucleic acid. In some embodiments, a subject isolated genetically modified host cell can produce a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLL3), human embryonic kidney (HEK) cells (ATCC No. CRL1573), HLHepG2 cells, and the like. In some cases, the cells are HEK cells. In some cases, the cells are CHO cells, e.g., CHO-K1 cells (ATCC No. CCL-61), CHO-M cells, CHO-DG44 cells (ATCC No. PTA-3356), and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., and the like. See, e.g., Carrier et al. (1992) *J. Immunol.* 148:1176-1181; U.S. Pat. No. 6,447,784; and Sizemore et al. (1995) *Science* 270:299-302. Typically, the laboratory strain is one that is non-pathogenic. Non-limiting examples of other suitable bacteria include, but are not limited to, *Bacillus subtilis*, and the like. In some embodiments, the host cell is *Escherichia coli*.

Pharmaceutical Formulations

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in an adverse symptom associated with a tauopathy, amelioration of a symptom of a tauopathy, slowing progression of a tauopathy, etc. Generally, the desired result is at least a reduction in a symptom of a tauopathy, as compared to a control. A subject antibody can be delivered in such a manner as to avoid the blood-brain barrier, as described in more detail below. A subject antibody can be formulated and/or modified to enable the antibody to cross the blood-brain barrier.

The present disclosure provides a pharmaceutical formulation comprising: a) an antibody that specifically binds an epitope within an N-terminal portion of Tau, wherein the antibody comprises: (i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; (iv) a $V_H$ CDR1 comprising an amino acid sequence of SEQ ID NO:4 or SEQ ID NO:10; (v) a $V_H$ CDR2 comprising an amino acid sequence of SEQ ID NO:5 or SEQ ID NO:11; and (vi) a $V_H$ CDR3 comprising an amino acid sequence of SEQ ID NO:6 or SEQ ID NO:12; and b) a pharmaceutically acceptable excipient suitable for administration to a human, wherein the formulation is free of endotoxins.

The present disclosure provides a pharmaceutical formulation comprising: a) an isolated humanized monoclonal antibody that specifically binds an epitope within amino acids 15-24 of a Tau polypeptide; and b) a pharmaceutically acceptable excipient, where in some embodiments the pharmaceutically acceptable excipient is suitable for administration to a human.

The present disclosure provides a pharmaceutical formulation comprising: A) an isolated antibody comprising a humanized light chain framework region; and a humanized heavy chain framework region, wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12; and B) a pharmaceutically acceptable excipient, where in some embodiments the pharmaceutically acceptable excipient is suitable for administration to a human.

The present disclosure provides a pharmaceutical formulation comprising: A) an isolated antibody, wherein the antibody is a Fv, scFv, Fab, F(ab')2, or Fab', and wherein the antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12; and B) a pharmaceutically acceptable excipient, where in some embodiments the pharmaceutically acceptable excipient is suitable for administration to a human.

The present disclosure provides a pharmaceutical formulation comprising: A) an isolated antibody, wherein the isolated antibody comprises a human light chain constant region and a human heavy chain constant region, and wherein the isolated antibody competes for binding to an epitope in an N-terminal region of a Tau polypeptide with an antibody that comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; and (iii) a $V_L$ CDR3 comprising an amino acid sequence of SEQ ID NO:3 or SEQ ID NO:9; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; and (iii) a $V_H$ CDR3 comprising an amino acid sequence of SEQ ID NO:6 or SEQ ID NO:12; and B) a pharmaceutically acceptable excipient, where in some embodiments the pharmaceutically acceptable excipient is suitable for administration to a human.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an anti-Tau antibody of the present disclosure, calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(–)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of the present disclosure can be taken to mean any one of a number of extended release dosage forms. The following terms may be considered to be substantially equivalent to controlled release, for the purposes of the present disclosure: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intrathecal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously. In some embodiments, a subject antibody composition is administered intrathecally.

An antibody of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a tauopathy. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Detection Methods

The present disclosure provides in vitro methods of detecting a Tau polypeptide in a biological sample obtained from an individual; and methods of detecting a Tau polypeptide in a living individual in vivo. A subject in vitro detection method can be quantitative. Tau can thus serve as a biomarker for progression of a tauopathy, or response to treatment for a tauopathy.

The Tau polypeptide that is detected/quantitated can be: a) full-length Tau; b) an N-terminal fragment of full-length Tau; c) total Tau, where "total Tau" can include full-length Tau of any isoform; d) free Tau, e.g., Tau that is not bound to a subject anti-tau antibody; and e) any N-terminal Tau fragments that are present in a biological sample and that display the epitope recognized by a subject anti-Tau antibody. Amino acid sequences of human full-length Tau are presented in FIGS. 6A-D.

In some cases, a subject detection method can further comprise determining the level of Aβ40 and/or Aβ42 in a biological sample. Determination of the level of Aβ40 and/or Aβ42 in a biological sample can be carried out using an immunological assay (e.g., an ELISA), e.g., using antibody that binds Aβ40 and/or Aβ42.

Suitable biological samples include, e.g., cerebrospinal fluid, blood, plasma, serum, urine, and saliva.

An in vitro method of the present disclosure of detecting a Tau polypeptide in a biological sample obtained from an individual generally involves: a) contacting the biological sample with an anti-Tau antibody as described herein; and b) detecting binding of the antibody to Tau polypeptide present in the sample. In some cases, the anti-Tau antibody comprises VH and/or VL CDRs of depicted in FIGS. 1A and 1B. In some cases, the anti-Tau antibody comprises VH and/or VL CDRs of FIGS. 2A and 2B.

A detection method of the present disclosure can be used to determine whether an individual has, or is at risk of developing, a tauopathy. A detection method of the present disclosure can be used to determine the stage (severity) of a tauopathy. A detection method of the present disclosure can be used to determine a patient's response to a treatment regimen for treating a tauopathy. A biological sample can be tested using a subject detection method, where the biological sample is obtained from an individual suspected of having a tauopathy, an individual who has been diagnosed as having a tauopathy, an individual who has a genetic predisposition to developing a tauopathy, etc.

The present disclosure provides a method of diagnosing a neurodegenerative tauopathy in an individual. The method generally involves (a) assessing the level of a Tau polypeptide in a biological sample obtained from the individual; and (b) comparing the level of the Tau polypeptide to a reference, a standard, or a normal control value that indicates the level of Tau in normal control subjects. A significant difference between the level of Tau polypeptide in the biological sample and the normal control value indicates that the individual has a neurodegenerative tauopathy.

The present disclosure provides a method of monitoring the progression of, or monitoring response to treatment for, a neurodegenerative tauopathy in an individual. The method generally involves comparing the level of a Tau polypeptide in a biological sample obtained from the individual at a first time point with the level of a Tau polypeptide in a biological sample obtained from the individual at a second time point. A difference in the level of the Tau polypeptide in a biological sample obtained from the individual at a second time point, compared to the level of the Tau polypeptide in a biological sample obtained from the individual at a first time point, can provide an indication as to: i) whether the tauopathy is progressing or whether progression of the disease has halted; and/or ii) how quickly the tauopathy is progressing; and/or iii) whether the individual is exhibiting a beneficial clinical response to treatment with a drug or other treatment regimen for treating the tauopathy.

The present disclosure provides a method of staging a tauopathy. For example, a subject method can provide for staging Alzheimer's disease. For example, the level of a Tau polypeptide in a biological sample (e.g., the CSF or other liquid biological sample) from a living individual can provide an indication as to the Braak stage of AD. Braak and Braak (1995) *Neurobiol. Aging* 16:271. For example, the level of a Tau polypeptide in a biological sample from a living individual can provide an indication as to whether the individual is in transentorhinal stages I-II of AD; limbic stages III-IV of AD; or neocortical stages V-VI of AD.

The level of a Tau polypeptide in a biological sample can be assessed by any suitable method known in the art. Suitable methods include, but are not limited to, a protein ("Western") blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry.

The present disclosure provides a method of monitoring progression of a tauopathy in an individual, where the method generally involves: a) determining a first level of a Tau polypeptide in a biological sample obtained from the individual at a first time point; b) determining a second level of a Tau polypeptide in a biological sample obtained from the individual at a second time point; and c) comparing the second level of Tau with the first level of Tau. The determining steps can comprise: i) contacting the biological sample with a subject anti-Tau antibody; and ii) quantitating binding of the antibody to Tau polypeptide present in the sample.

In some cases, the first time point is a time point before initiation of a treatment regimen, and the second time point is a time point after initiation of a treatment regimen. Thus, the instant disclosure provides a method of monitoring response to treatment with an agent that treats a tauopathy, where the method involves: a) determining a first level of a Tau polypeptide in a biological sample obtained from the individual at a first time point that is before treatment with an agent to treat a tauopathy is initiated; b) determining a second level of a Tau polypeptide in a biological sample obtained from the individual at a second time point that is after initiation of treatment with an agent to treat a tauopathy; and c) comparing the second level of Tau with the first level of Tau.

A subject method of monitoring progression of a tauopathy can also be applied to methods of monitoring progression of a synucleinopathy, e.g., Parkinson's disease (PD); dementia with Lewy Bodies (DLB); multiple system atrophy (MSA); etc. For example, progression of PD with dementia (PDD) can be monitored with a subject method.

In some tauopathies, the level of Tau increases with progression of the disease. In other tauopathies, the level of Tau decreases with progression of the disease. Thus, e.g., the level of Tau increases with progression of AD; and decreases with progression of FTD.

A subject method can involve use of a kit or an assay device comprising a subject anti-Tau antibody. The present disclosure provides kits and assay devices for carrying out a method as described herein. A subject kit includes an anti-tau antibody of the present disclosure.

The anti-tau antibody can be immobilized on an insoluble support (e.g., a test strip, a well of a multi-well plate, a bead (e.g., a magnetic bead), etc.). Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

An anti-tau antibody of the present disclosure can comprise a detectable label. Where the antibody comprises a detectable label, a subject kit can include one or more reagents for developing the detectable label. A labeled antibody can comprise a label such as a chemiluminescent agent, a particulate label, a colorimetric agent, an energy transfer agent, an enzyme, a fluorescent agent, or a radioisotope. Suitable detectable labels include any composition detectable by spectroscopic, photochemical, biochemical, immunochemical, electrical, optical, or chemical means. Suitable detectable labels include, but are not limited to, fluorescent labels (e.g., fluorescein isothiocyanate, texas red, rhodamine, a green fluorescent protein, a red fluorescent protein, a yellow fluorescent protein, and the like); radiolabels (e.g., $^{3}$H, $^{125}$I, $^{35}$S, $^{14}$C, or $^{32}$P); and enzymes (e.g., horse radish peroxidase, alkaline phosphatase, luciferase, and other enzymes that act on a substrate to produce a product that can be detected by fluorometric, colorimetric, or spectrophotometric means).

A subject kit can further include one or more additional components, where suitable additional components include: 1) a positive control; 2) a buffer (e.g., a binding buffer; a wash buffer; etc.); 3) reagents for use in generating a detectable signal; and the like. Other optional components of the kit include: a protease inhibitor; a detectable label; etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

An assay device can include a subject anti-Tau antibody immobilized on a solid substrate. The assay device can be in any of a variety of formats, e.g., a test strip, a dipstick; etc.

In Vivo Imaging

As discussed above, the present disclosure provides methods of detecting a Tau polypeptide in a living individual, e.g., by an in vivo imaging technique. For example, in one embodiment, in vivo imaging of a Tau polypeptide can be accomplished by positron emission tomography (PET), single photon emission tomography (SPECT), near infrared (NIR) optical imaging, or magnetic resonance imaging (MRI). A subject anti-tau antibody is administered to an individual, and the presence and/or level of the tau polypeptide is detected. The anti-tau antibody can comprise a label suitable for use in PET, SPECT, NIR, or MRI. Such labels include a contrast agent or a radioisotope, where the contrast agent or radioisotope is one that is suitable for use in imaging, e.g., imaging procedures carried out on humans, as described above. In some cases, the anti-Tau antibody comprises VH and/or VL CDRs of IPN001. In some cases, the anti-Tau antibody comprises VH and/or VL CDRs of IPN002. The anti-Tau antibody can comprise one or more humanized framework regions, as described above.

Generating a Report

In some instances, a subject detection method comprises detecting a Tau polypeptide in a biological sample obtained from an individual; and, based on the level of detected Tau polypeptide, generating a report and/or directing therapy or management of the individual from whom the biological sample was obtained.

A report can include one or more of: an indication as to whether the individual likely has a tauopathy; an indication of the severity of the tauopathy; an indication as to whether the individual exhibits a beneficial clinical response to treatment for the tauopathy; and the like.

Thus, a report can include information such as a predicted likelihood that the individual has, or will develop, a tauopathy; a recommendation regarding further evaluation; a recommendation regarding therapeutic drug and/or other health management intervention; and the like.

For example, the methods disclosed herein can further include a step of generating or outputting a report providing the results of a subject assessment, which report can be provided in the form of an electronic medium (e.g., an electronic display on a computer monitor), or in the form of a tangible medium (e.g., a report printed on paper or other tangible medium). An assessment as to the likelihood that a person has, or at risk of developing, a tauopathy can be referred to as a "risk report," "a risk score," or "a likelihood score." A person or entity that prepares a report ("report generator") may also perform steps such as sample gathering, sample processing, and the like. Alternatively, an entity other than the report generator can perform steps such as sample gathering, sample processing, and the like. A risk assessment report can be provided to a user. A "user" can be a health professional (e.g., a clinician, a laboratory technician, or a physician).

Directing Health Management

In some instances, a subject detection method comprises detecting a Tau polypeptide in a biological sample obtained from an individual; and, based on the level of detected Tau polypeptide, generating a report and/or directing therapy or management of the individual from whom the biological sample was obtained.

Thus, e.g., depending on the outcome of a subject detection method, a recommendation can be made that the individual undergo therapeutic intervention (treatment) for the tauopathy and/or that the individual be considered for special health management.

Therapeutic intervention can include, e.g., drug therapy for the treatment of Alzheimer's disease. Examples of drug therapy for the treatment of Alzheimer's disease include, but are not limited to, acetylcholinesterase inhibitors, including, but not limited to, Aricept (donepezil), Exelon (rivastigmine), metrifonate, and tacrine (Cognex); an anti-Aβ antibody (e.g., solanezumab); an anti-tau antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept can be administered at 50 mg orally per day for 6 weeks, and, if well tolerated by the individual, at 10 mg per day thereafter.

Determining the Amount of Free and Bound Extracellular Tau

Following administration of an anti-eTau antibody to an individual, it may be of interest to determine the amount of eTau remaining in the CSF or ISF that is not bound to the anti-eTau antibody. The present disclosure provides methods for determining the amount of such free eTau. A schematic representation of a method for determining the amount of eTau remaining in the CSF or ISF that is not bound to the anti-eTau antibody is depicted in FIG. 54A. Following administration of an anti-eTau antibody to an individual, it may also be of interest to determine the amount of eTau in CSF or ISF that is bound to an anti-eTau antibody. A schematic representation of a method for determining the amount of eTau in CSF or ISF that is bound to an anti-eTau antibody is depicted in FIG. 54B.

Determining the Amount of Free Extracellular Tau

The present disclosure provides a method of determining the amount of extracellular Tau (eTau) unbound to an anti-eTau antibody in a sample of CSF or ISF obtained from a subject undergoing therapy with the anti-eTau antibody. The method generally involves: a) contacting an immobilized antibody with a sample of CSF or ISF obtained from the subject, where the immobilized antibody competes for binding to eTau with the anti-eTau antibody administered to the subject, and where the contacting is under conditions suitable for binding of the unbound eTau to the immobilized antibody; and b) determining the amount of eTau bound to the immobilized antibody. The amount of eTau bound to the immobilized antibody is an indication of the amount of eTau unbound to the anti-Tau antibody in the sample. In some cases, the amount of eTau bound to the immobilized antibody is determined using a detectably labeled third antibody that does not compete with the immobilized antibody for binding to the eTau.

As noted above, the assay measures the amount of eTau in a CSF or ISF sample obtained from an individual undergoing therapy with an anti-eTau antibody. In some cases, the anti-eTau antibody is a therapeutic humanized anti-eTau antibody. In some cases, the anti-eTau antibody is a humanized anti-eTau antibody of the present disclosure. In some cases, the anti-eTau antibody is hu-IPN002.

In some cases, a subject method will comprise: a) determining the amount of eTau unbound to an anti-eTau antibody in a sample of CSF or ISF obtained from a subject undergoing therapy with the anti-eTau antibody, as described above; and b) determining the level of total tau in the sample.

In some cases, a subject method will comprise: a) determining the amount of eTau unbound to an anti-eTau antibody in a sample of CSF or ISF obtained from a subject undergoing therapy with the anti-eTau antibody, as described above; and b) comparing the level of unbound Tau in the sample to the level of total tau in a CSF or ISF sample obtained from the individual before treatment with the anti-eTau antibody.

A subject detection method is suitable for determining the level of extracellular tau. "Extracellular tau" ("eTau"), as used herein, encompasses any Tau polypeptide that can be detected in cerebrospinal fluid (CSF) or interstitial fluid (ISF). In some embodiments, eTau is a polypeptide having a length of 175 amino acids and comprising amino acids 2-176 of full-length tau; for example, in some embodiments eTau is a polypeptide comprising the amino acid sequence set forth in SEQ ID NO:45. In some embodiments, eTau is a polypeptide having a length of 171 amino acids and comprising amino acids 2-172 of full-length tau; for example, in some embodiments eTau is a polypeptide comprising the amino acid sequence set forth in SEQ ID NO:44. In some embodiments, eTau is an eTau-2 polypeptide comprising the amino acid sequence set forth in SEQ ID NO:46. In some embodiments, eTau is an eTau-3 polypeptide comprising the amino acid sequence set forth in SEQ ID NO:47. In some embodiments, eTau is an eTau-4 polypeptide comprising the amino acid sequence set forth in SEQ ID NO:48.

In some cases, an eTau polypeptide has a length of from about 50 amino acids to about 175 amino acids, e.g., from about 50 amino acids (aa) to about 75 aa, from about 75 aa to about 100 aa, from about 100 aa to about 125 aa, from about 125 aa to about 150 aa, or from about 150 aa to about 175 aa; and can comprise from 50 to about 75, from about 75 to about 100, from about 100 to about 125, from about 125 to about 150, or from about 150 to about 175, contiguous amino acids of amino acids 2-176 of full-length tau. Exemplary eTau polypeptides are depicted in FIG. 20.

Determining the Amount of Extracellular Tau Bound to an Anti-eTau Antibody

The present disclosure provides a method of determining the amount of eTau bound to a therapeutic anti-eTau antibody in a sample of CSF or ISF obtained from a subject undergoing therapy with the therapeutic anti-eTau antibody. The method generally involves: a) contacting an immobilized antibody with a sample of CSF or ISF obtained from the subject, where the immobilized antibody does not compete for binding to eTau with the anti-eTau antibody administered to the subject, said contacting being under conditions suitable for binding of the therapeutic antibody-bound eTau to the immobilized antibody; and b) determining the amount of therapeutic anti-eTau/eTau complex bound to the immobilized antibody, wherein the amount of therapeutic anti-eTau antibody/eTau complex bound to the immobilized antibody is an indication of the amount of therapeutic antibody-bound eTau present in the sample. The amount of therapeutic anti-eTau antibody/eTau complex bound to the immobilized antibody is determined by detecting the anti-eTau antibody present in the anti-eTau antibody/eTau complex. The amount of therapeutic anti-eTau antibody/eTau complex bound to the immobilized antibody is determined by detecting the anti-eTau antibody present in the anti-eTau antibody/eTau complex provides an indication of the amount of Tau bound to the therapeutic antibody in the CSF or ISF sample.

As noted above, the assay measures the amount of therapeutic antibody-bound eTau in a CSF or ISF sample obtained from an individual undergoing therapy with the anti-eTau antibody. In some cases, the anti-eTau antibody is a therapeutic humanized anti-eTau antibody. In some cases, the anti-eTau antibody is a humanized anti-eTau antibody of the present disclosure. In some cases, the anti-eTau antibody is hu-IPN002.

In some cases, a subject method will comprise: a) determining the amount of eTau bound to an anti-eTau antibody in a sample of CSF or ISF obtained from a subject undergoing therapy with the anti-eTau antibody, as described above; and b) determining the level of total tau in the sample. In some cases, a subject method will comprise: a) determining the amount of eTau bound to an anti-eTau antibody in a sample of CSF or ISF obtained from a subject undergoing therapy with the anti-eTau antibody, as described above; and b) determining the amount of eTau in the CSF or ISF sample that is not bound to the therapeutic anti-eTau antibody. In some cases, a subject method will comprise: a) determining the amount of eTau bound to an anti-eTau antibody in a sample of CSF or ISF obtained from a subject undergoing therapy with the anti-eTau antibody, as described above; b) determining the level of total tau in the sample; and c) determining the amount of eTau in the CSF or ISF sample that is not bound to the therapeutic anti-eTau antibody.

In some cases, a subject method will comprise: a) determining the amount of eTau bound to an anti-eTau antibody in a sample of CSF or ISF obtained from a subject undergoing therapy with the anti-eTau antibody, as described above; and b) comparing the level of anti-eTau antibody-bound Tau in the sample to the level of total tau in a CSF or ISF sample obtained from the individual before treatment with the anti-eTau antibody.

In some cases, a subject method will comprise: a) determining the amount of eTau unbound to an anti-eTau antibody in a sample of CSF or ISF obtained from a subject undergoing therapy with the anti-eTau antibody, as described above; b) determining the amount of eTau bound to an anti-eTau antibody in a sample of CSF or ISF obtained from a subject undergoing therapy with the anti-eTau antibody, as described above; and c) comparing the level of unbound Tau and the level of anti-eTau antibody-bound Tau in the sample to the level of total tau in a CSF or ISF sample obtained from the individual before treatment with the anti-eTau antibody.

A subject detection method is suitable for determining the level of extracellular tau bound to a therapeutic antibody. "Extracellular tau" ("eTau"), as used herein, encompasses any Tau polypeptide that can be detected in cerebrospinal fluid (CSF) or interstitial fluid (ISF). In some embodiments, eTau is a polypeptide having a length of 175 amino acids and comprising amino acids 2-176 of full-length tau; for example, in some embodiments eTau is a polypeptide comprising the amino acid sequence set forth in SEQ ID NO:45. In some embodiments, eTau is a polypeptide having a length of 171 amino acids and comprising amino acids 2-172 of full-length tau; for example, in some embodiments eTau is a polypeptide comprising the amino acid sequence set forth in SEQ ID NO:44. In some embodiments, eTau is an eTau-2 polypeptide comprising the amino acid sequence set forth in SEQ ID NO:46. In some embodiments, eTau is an eTau-3 polypeptide comprising the amino acid sequence set forth in SEQ ID NO:47. In some embodiments, eTau is an eTau-4 polypeptide comprising the amino acid sequence set forth in SEQ ID NO:48.

In some cases, an eTau polypeptide has a length of from about 50 amino acids to about 175 amino acids, e.g., from about 50 amino acids (aa) to about 75 aa, from about 75 aa to about 100 aa, from about 100 aa to about 125 aa, from about 125 aa to about 150 aa, or from about 150 aa to about 175 aa; and can comprise from 50 to about 75, from about 75 to about 100, from about 100 to about 125, from about 125 to about 150, or from about 150 to about 175, contiguous amino acids of amino acids 2-176 of full-length tau. Exemplary eTau polypeptides are depicted in FIG. 20.

Generating a Report

In some cases, a subject method will comprise: a) determining the amount of eTau unbound to an anti-eTau antibody in a sample of CSF or ISF obtained from a subject undergoing therapy with the anti-eTau antibody, as described above; and b) generating a report and/or directing therapy or management of the individual from whom the sample was obtained. In some cases, a subject method will comprise: a) determining the amount of eTau unbound to an anti-eTau antibody in a sample of CSF or ISF obtained from a subject undergoing therapy with the anti-eTau antibody, as described above; b) comparing the level of unbound Tau in the sample to the level of total tau in a CSF or ISF sample obtained from the individual before treatment with the anti-eTau antibody; and c) generating a report and/or directing therapy or management of the individual from whom the sample was obtained.

In some cases, a subject method will comprise: a) determining the amount of eTau bound to an anti-eTau antibody in a sample of CSF or ISF obtained from a subject undergoing therapy with the anti-eTau antibody, as described above; and b) generating a report with the results of the determination. The report can further include one or both of the amount of unbound Tau in the sample to the level of total tau in a CSF or ISF sample after treatment with the anti-Tau antibody; and the amount of total Tau in a CSF or ISF sample obtained from the individual before treatment with the anti-eTau antibody.

A report can include, e.g., an indication as to whether the individual exhibits a beneficial clinical response to treatment for the tauopathy; an indication as to whether the dosage of the anti-eTau antibody should be maintained, increased, or decreased; and the like.

Thus, a report can include information such as a recommendation regarding further evaluation; a recommendation regarding therapeutic drug and/or other health management intervention; a recommendation to increase the dosage of anti-eTau antibody; a recommendation to maintain the dosage of anti-eTau antibody; a recommendation to reduce the dosage of anti-eTau antibody; and the like.

For example, the methods disclosed herein can further include a step of generating or outputting a report providing the results of a subject assessment, which report can be provided in the form of an electronic medium (e.g., an electronic display on a computer monitor), or in the form of a tangible medium (e.g., a report printed on paper or other tangible medium). A person or entity that prepares a report ("report generator") may also perform steps such as sample gathering, sample processing, and the like. Alternatively, an entity other than the report generator can perform steps such as sample gathering, sample processing, and the like. A risk assessment report can be provided to a user. A "user" can be a health professional (e.g., a clinician, a laboratory technician, or a physician).

Directing Health Management

In some instances, a subject method comprises a) determining the amount of eTau unbound to an anti-eTau antibody in a sample of CSF or ISF obtained from a subject undergoing therapy with the anti-eTau antibody, as described above; and, based on the determined amount of eTau unbound to an anti-eTau antibody, generating a report and/or directing therapy or management of the individual from whom the biological sample was obtained.

In some cases, a subject method comprises a) determining the amount of eTau unbound to an anti-eTau antibody in a sample of CSF or ISF obtained from a subject undergoing therapy with the anti-eTau antibody, as described above; and, based on the determined amount of eTau unbound to an anti-eTau antibody, maintaining the dosage of anti-eTau antibody that was administered to the subject. In some cases, a subject method comprises a) determining the amount of eTau unbound to an anti-eTau antibody in a sample of CSF or ISF obtained from a subject undergoing therapy with the anti-eTau antibody, as described above; and, based on the determined amount of eTau unbound to an anti-eTau antibody, increasing the dosage of anti-eTau antibody administered to the subject. In some cases, a subject method comprises a) determining the amount of eTau unbound to an anti-eTau antibody in a sample of CSF or ISF obtained from a subject undergoing therapy with the anti-eTau antibody, as described above; and, based on the determined amount of eTau unbound to an anti-eTau antibody, decreasing the dosage of anti-eTau antibody administered to the subject.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Cloning and Sequencing of IPN001 and IPN002 VH and VL Regions

Amino acid sequences of the VH and VL regions of IPN001 (also referred to herein as "IPN1" or "IPN-1") and IPN002 (also referred to herein as "IPN2" or "IPN-2") antibodies were determined. The amino acid sequences of the VH and VL regions of IPN001 are depicted in FIGS. 1A and 1B, respectively. The amino acid sequences of the VH and VL regions of IPN002 are depicted in FIGS. 2A and 2B, respectively. The CDRs are in bold text and are underlined. CDRs were determined using the method of Kabat et al. (see Table 1; and J. Biol. Chem. 252:6609-6616 (1977); and Kabat et al., U.S. Dept. of Health and Human Services, "Sequences of proteins of immunological interest" (1991)).

Example 2

Electrophysiological Analysis of the Effect of Anti-Tau Antibodies

Materials and Methods

Whole cell patch clamp recording from induced pluripotent stem cells (iPSC) derived cortical neurons cultured on a monolayer of normal human astrocytes was carried out using a patch pipette (2-5 MOhm) filled with solution containing (mM): K-methyl-sulfate (140), NaCl (10), $CaCl_2$ (1), Mg-ATP (3); Na-GTP (0.4), EGTA (0.2), HEPES (10), Phosphocreatine with adjusted pH=7.3 and mOsm=300. Neurons were perfused (2 ml/min) with artificial cerebral spinal fluid containing (mM): NaCl (140), KCl (2.5), $MgCl_2$ (2) $CaCl_2$ (2), Hepes (10), D-Glucose (10), sucrose (20). Adjusted pH=7.4 mOsm=310. Recordings were done using pClamp-10.3 data acquisition software (Molecular Devices) and MultiClamp 700B amplifier (Axon Instrument; Foster City Calif.). AD tau and AD Tau pre-incubated with IPN001 or IPN002 (2-hrs at room temperature or 24-hrs at 4 degree C. at 10:1 weight ratio) were applied via MinisQuirt microperfusion system (AutoMate, Berkeley, Calif.). Data analysis was done off-line using Clampfit 10.2 analysis software (Molecular Devices). All recordings were done at room temperature.

Results

The data are depicted in FIGS. 3A-D.

Application of AD-Tau (6 µg/ml) causes cortical neuron membrane depolarization (A, B, and C). Pre-incubation of AD-Tau (6 µg/ml) with IPN001 (60 µg/ml) (A) or IPN002 (60 µg/ml) (B) for >2 hrs reduces AD-Tau mediated membrane depolarization. C. Pre-incubation of AD-Tau (6 µg/ml) with mouse IgG (60 µg/ml) did not reduce AD-Tau mediated membrane depolarization in cortical neurons. D. Data summary showing IPN001 and IPN002 significantly reduced AD-Tau mediated membrane depolarization (Paired t-test * $p<0.037$; ** $p<0.009$, $p<0.003$).

Example 3

Immunoreactivity of IPN001 and IPN002 with Tau in CSF from AD Patients

Cerebrospinal fluid (CSF) was pooled from 10 healthy donors (1 ml each). CSF was also pooled from 10 Alzheimer's disease (AD) patients (1 ml each). Aliquots of CSF pools were saved for ELISA analysis. 10 mls of conditioned media from cortical neurons differentiated for 315 days from a Down's induced pluripotent stem cell (iPSC) iPSC line (8941.1) was used as a control for the CSF affinity isolations and an aliquot was also saved for ELISA analysis. To determine if CSF contains IPN002-reactive Tau, each of the CSF pooled samples and conditioned media were precleared on an IgG1 coupled resin and the flow-through subsequently applied to an IPN001-coupled resin. The IPN001 resins were washed thoroughly with phosphate buffered saline (PBS) and bound proteins eluted with 50 mM Glycine, 150 mM NaCl, pH 2.3 and neutralized with 1M Tris, pH 8.3 after elution. The eluted proteins were concentrated on YM10 concentrators and added to sample buffer for sodium dodecyl sulfate-polyacrylamide gel electrophoresis (SDS-PAGE) electrophoresis and Western blotting analysis.

Figure 4A:
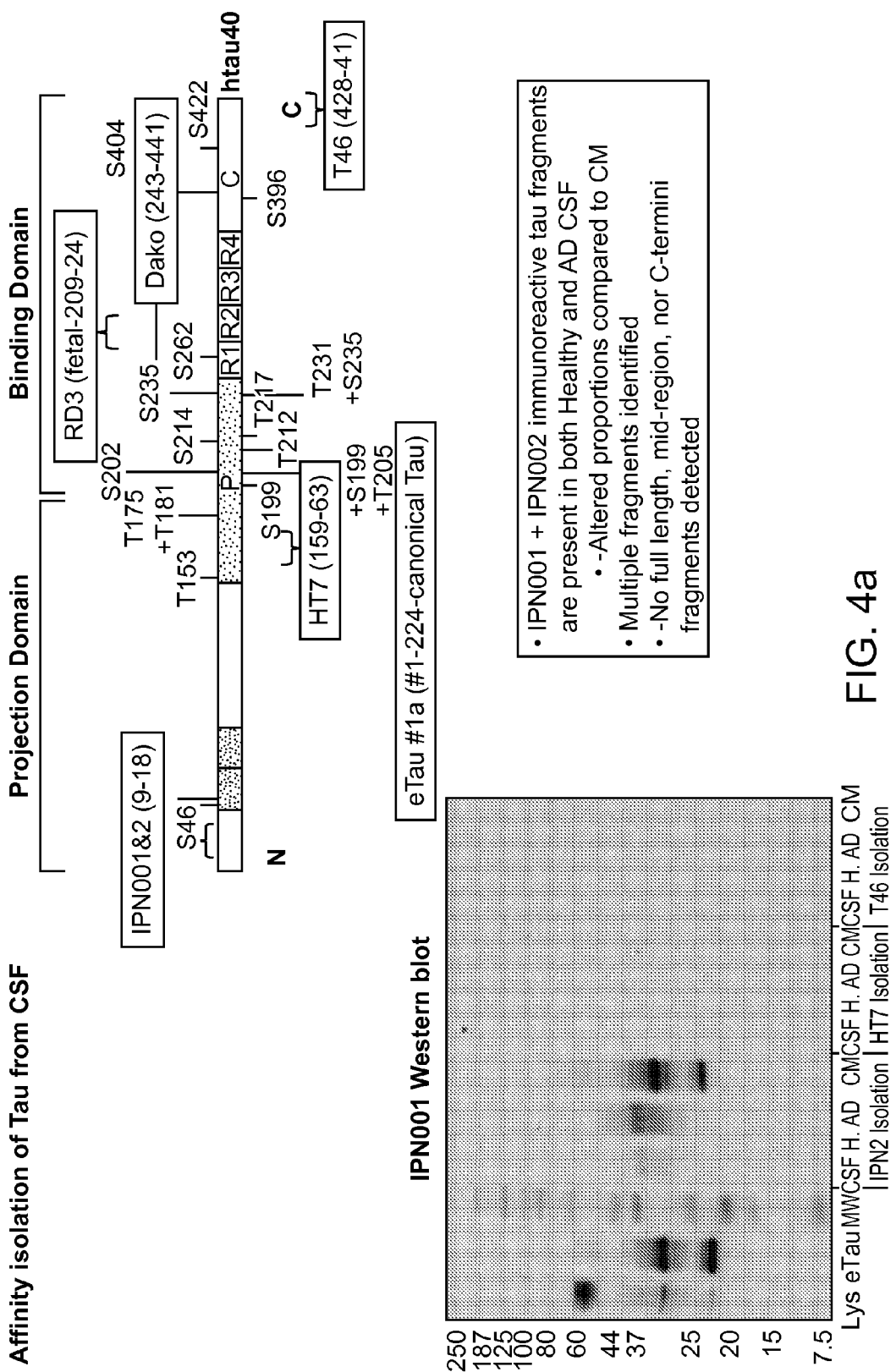
FIGS. 4A-C depict affinity isolation of Tau from cerebrospinal fluid (CSF).
Figure 4A:
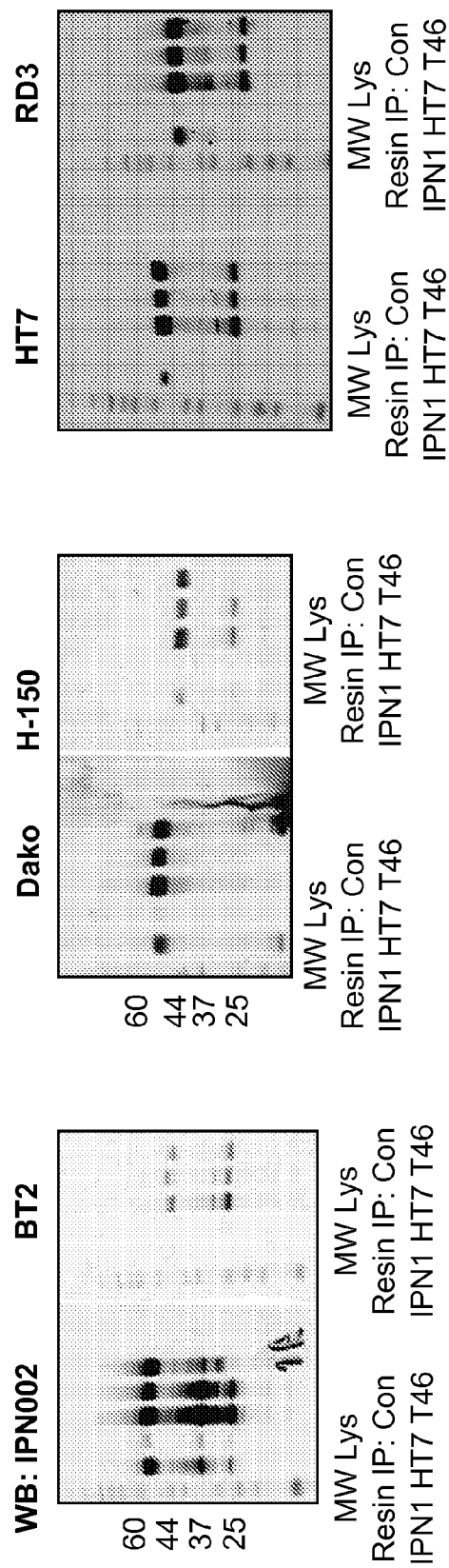
Figure 4B:
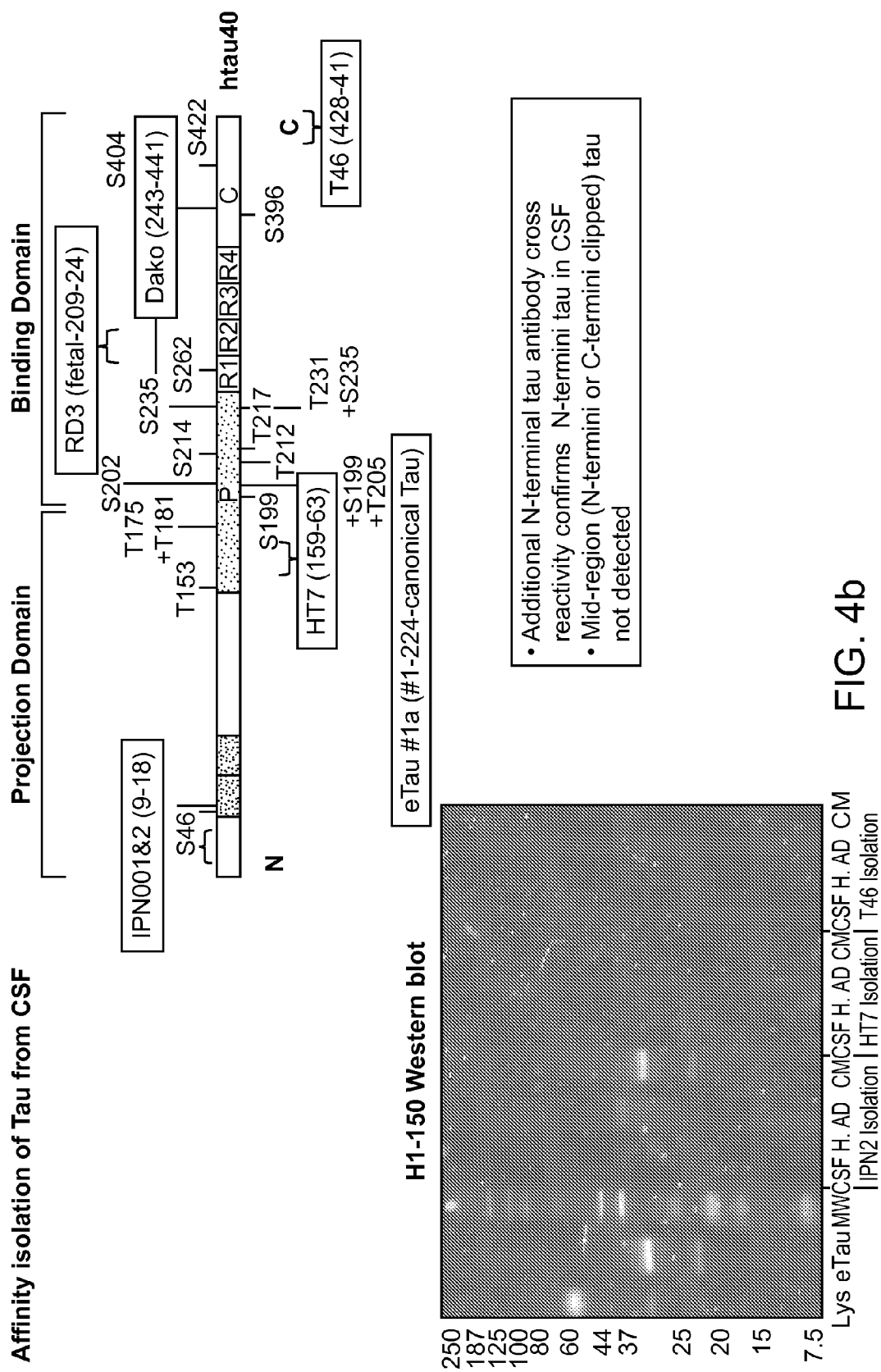
Figure 4B:
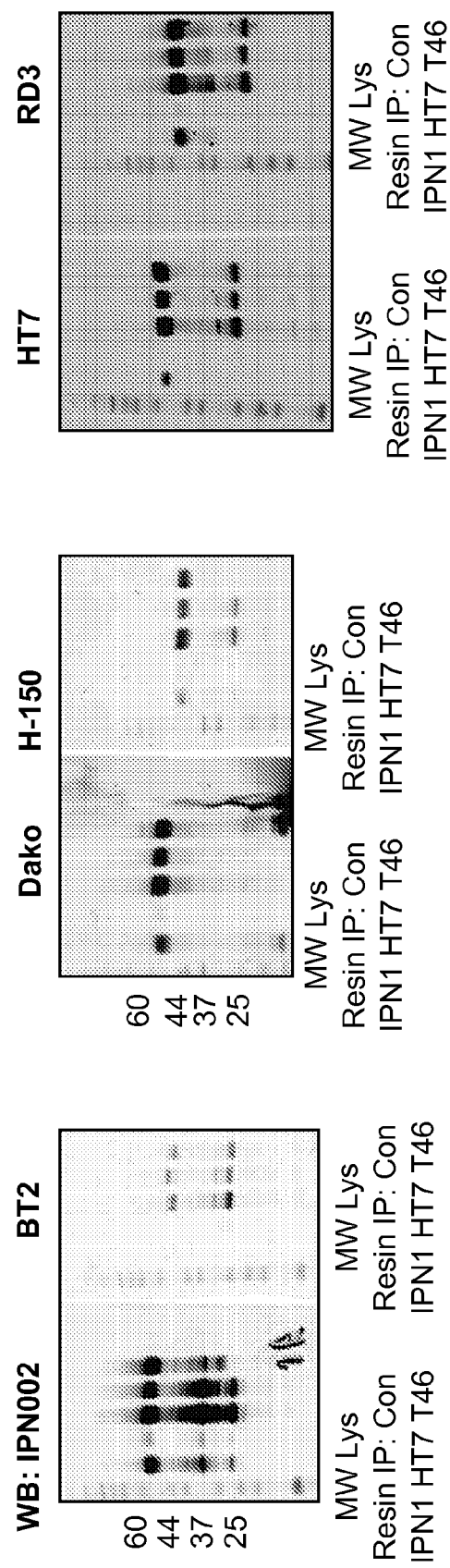
Figure 4C:
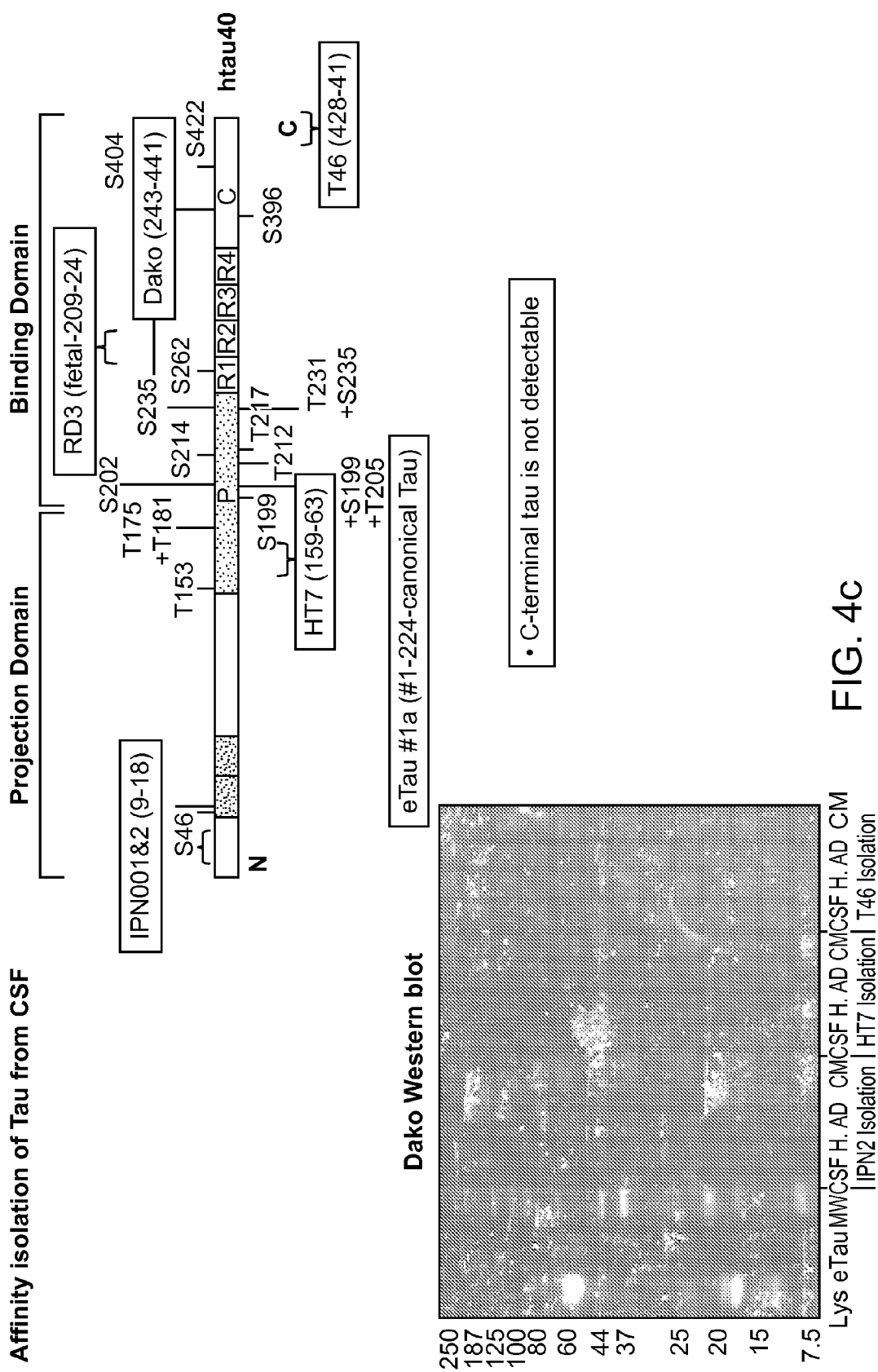
Figure 4C:
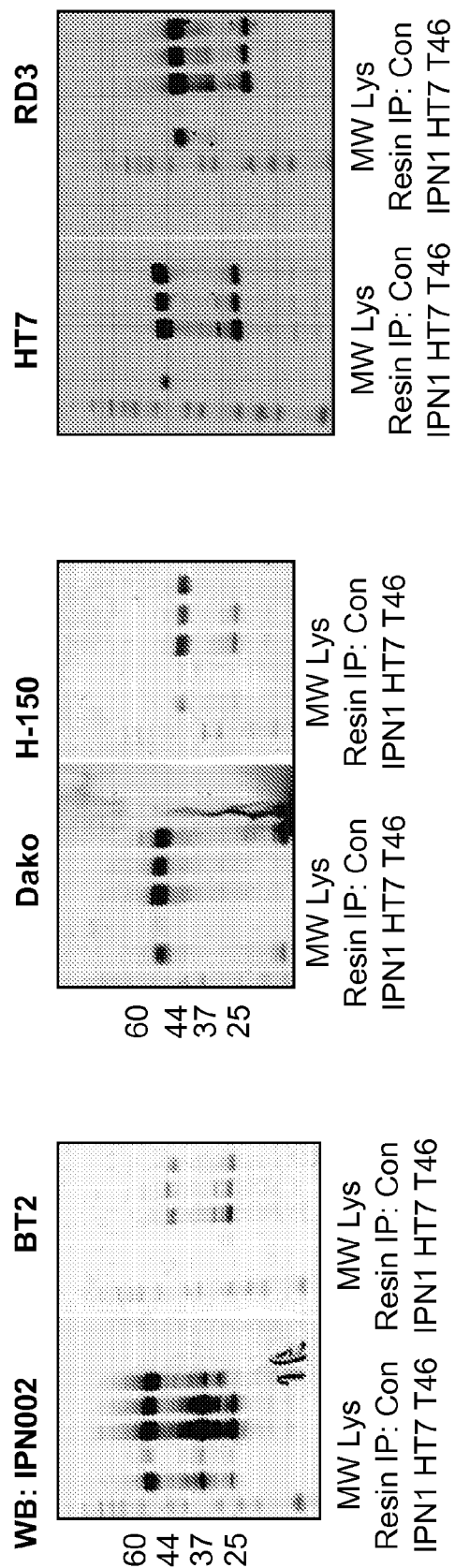

To determine if IPN002 reacts with any form of Tau in the CSF, Western blots of the IPN002 eluted protein were probed with IPN001, Santa Cruz Tau H-150 (aa1-150) and with Dako's Tau #A0024 antibody which reacts with the C-termini (aa#243-441) of Tau. The data are depicted in FIGS. 4A-C.

Western blots showed IPN001 (FIG. 4a) and Tau H-150 (FIG. 4b) immunoreactive bands present in the IPN002 affinity purified protein from both healthy and AD CSF that ranged in molecular weight from ~25 kd to 37 kd. These Tau fragments were similar in their sizes, but not in their relative abundance, to eTau fragments isolated from the Down's line conditioned media. The Dako C-terminal tau antibody (FIG. 4c) did not detect any reactive species from the IPN002 affinity isolation from either CSF or from conditioned media. Full-length Tau was not detected by any of the Tau antibodies from the IPN002 affinity isolation. Because the IPN002 affinity isolated proteins were reactive with IPN001 and IPN002 on Western blot, it was concluded that Tau in CSF is also IPN001 reactive.

The CSF and conditioned media flow-through from the IPN002 affinity resins were then applied sequentially to and eluted from T46 (Tau #428-441) and HT7 (Tau #159-163) to determine if any C-terminal or mid-region tau fragments were present that were not isolated by IPN002. The eluates were probed with the Dako C-terminal antibody (FIG. 4c) but no immunoreactivity was detected. These data suggest that IPN001 and IPN002 immunoreactive tau is more abundant than full length, mid-region only or C-terminal tau fragments.

Figure 5:
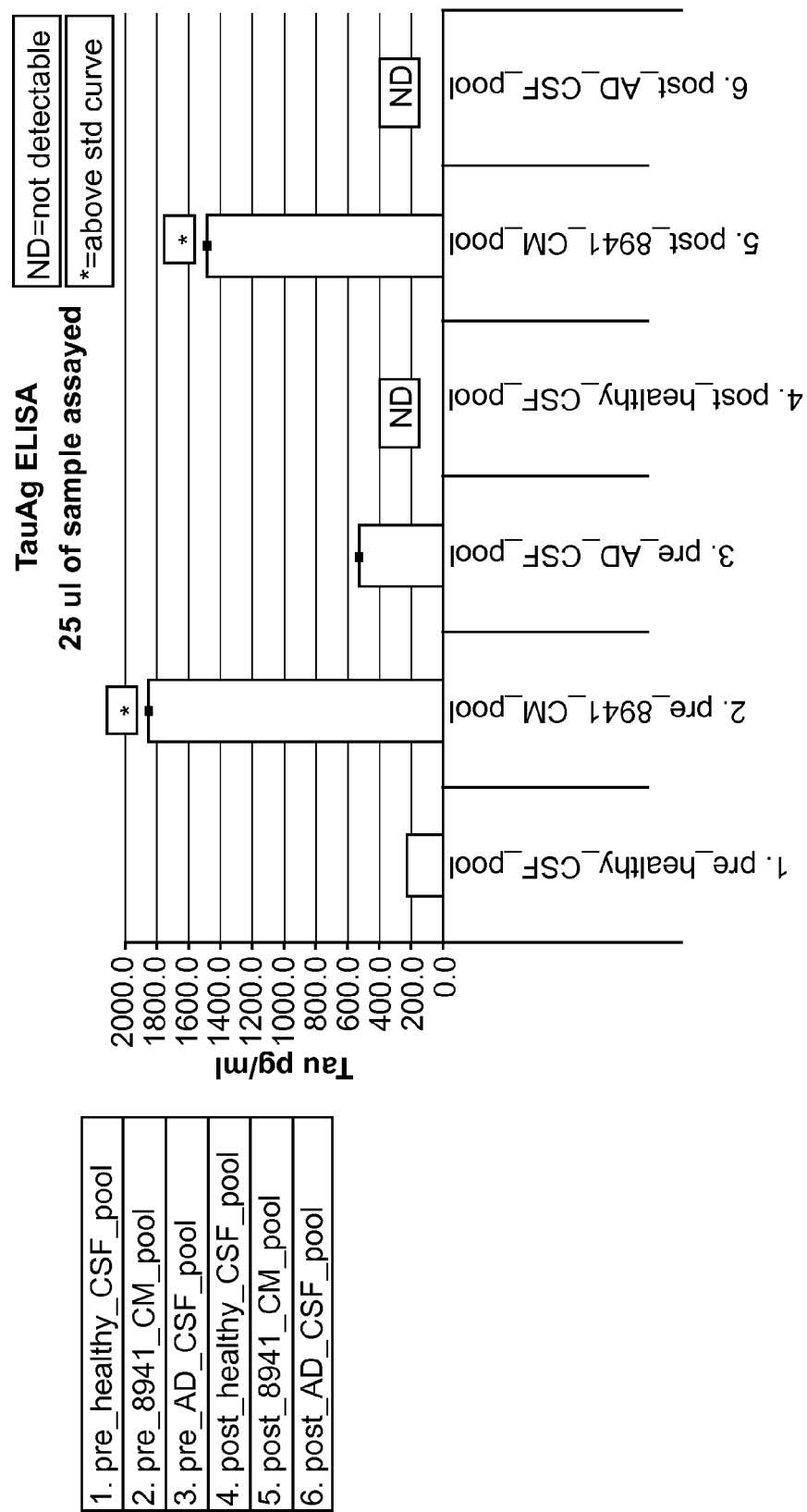
FIG. 5 depicts quantification of CSF and conditioned medium (CM) samples pre- and post-Tau affinity isolation.

Aliquots of the flow-through from each of the CSFs and conditioned media were saved for pre-versus post-isolation comparison to determine if all detectable tau was removed during the isolation, using a commercially available kit commonly used to determine Tau levels in CSF. The data are shown in FIG. 5. This analysis demonstrated that all the detectable tau was removed from the post-CSF samples during the affinity isolation process.

These data provide strong evidence that both IPN001 and IPN002 react with the major tau species present in CSF from both healthy and AD patients.

Example 4

Detection of eTau in Patient Samples

Materials and Methods

Conditioned Media Collection from iPSC-Derived Cortical Neurons iPSC (induced pluripotent stem cells) were generated from healthy age matched controls and Alzheimer's patients using the Yamanaka method (Takahashi et al. (2007) *Cell* 131(5), 861) as described in Dimos et al. (2008) *Science* 321:1218. iPSC were differentiated to cortical neurons largely in line with published protocols using the dual SMAD monolayer method (Chambers et al. (2009) *Nat. Biotechnol.* 27:275) followed by cortical neuron differentiation similar to that described in Shi et al. (2012) *Nat. Neurosci.* 15:477). iPSC-derived cortical neurons (iPSC-CN), cultured for 108 days, were washed, fresh media added, and conditioned media collected after three days unless otherwise noted. Multiple differentiations from the lines were conducted to ensure reproducibility of the eTau levels. Conditioned media was spun at 15,000 rpm for 15 minutes prior to processing for Western blot or tau ELISA. For the brefeldin A experiment, iPSC-CN cultures were washed with PBS prior to addition of fresh media with and without 1 µM brefeldin A and media conditioned for one hour prior to collection.

Conditioned Media Collection from Human Primary Cortical Neurons

Human cortical neuron cultures (HCC) were prepared as described in Wright et al. (2007) *Neurobiol. Aging* 28:226. Briefly, human fetal cerebral cortical tissue was obtained by Advanced Bioscience Resources (Alameda, Calif.) and complied with federal guidelines for fetal research and with the Uniformed Anatomical Gift Act. The tissue was rinsed in Hank's buffered saline solution (Cellgro) and triturated in the presence of 1 µg/ml DNase (EMD) and passed through a 100 µm cell strainer. After centrifugation the pellet was resuspended in 0.05% trypsin/EDTA (Invitrogen) for 20 min at 37° C. Trypsin was inactivated by adding an equal volume of media containing 10% fetal bovine serum (FBS) and sample gently triturated again in presence of DNase. After centrifugation, cells were resuspended in plating media (Neurobasal containing B27, Invitrogen) and counted. Cells were plated in plates or on coverslips coated with poly-d-lysine with laminin Three week old HCC were washed, fresh media added and media collected after three days of conditioning. Conditioned media was spun at 15,000 rpm for 15 minutes prior to processing for Western blot.

P301L Mouse ISF and Human CSF Collections

Mice were anesthetized using isoflurane (2%, 800 mL/min $O_2$). Bupivacain/epinephrine was used for local analgesia and fynadine or carprophen for peri-/post-operative analgesia. The animals were placed in a stereotaxic frame (Kopf instruments, USA). Push-pull microdialysis probes (phosphatidyl ethanolamine (PEE) membrane, Brainlink, the Netherlands) were inserted into the hippocampus (3 mm exposed surface). Microdialysis sampling was performed 24 and 48 hours after surgery. On the days of the sampling, the probes of the animals were connected with fluorinated ethylene propylene (FEP) tubing to a microperfusion pump (Harvard PHD 2000 Syringe pump, Holliston, Mass. or similar). Microdialysis probes were perfused with artificial CSF (aCSF) containing 147 mM NaCl, 3.0 mM KCl, 1.2 mM $CaCl_2$ and 1.2 mM $MgCl_2$, and 0.15% bovine serum albumin (BSA) at a flow rate of 0.75 µL/min. Microdialysis samples were collected for 60 minute periods.

After the stabilization period, basal samples were collected. On the second day of sampling, the above procedure was repeated (Brains Online) The interstitial fluid (ISF) was spun at 15,000 rpm for 15 minutes and cleared supernatants used for eTau Western blots.

10 mls of CSF (Precision Med) from a pool of 10 healthy (Precision Med), 10 AD patients (Precision Med) and 10 PSP patients were collected, spun at 15,000 rpm for 15 minutes, supernatants precleared on IgG affinity resin followed by tau isolation on an IPN002 anti-tau affinity resin, washed, eluted with 50 mM glycine, pH 2.3 with 150 mM NaCl into a tube containing 1M TBS, pH 8.3 to neutralize the pH, concentrated on YM10 filters and prepared for tau Western blots. iPSC-CN conditioned media from a fAD PSEN1 patient was similarly isolated as a positive control to compare banding patterns.

Western Blots

Conditioned media were diluted in Laemmli buffer (Sigma). Cultured neurons were rinsed with PBS before incubation in 0.05% trypsin in DMEM (Invitrogen), rinsed and lysed in Laemmli buffer. All samples were boiled, separated on tris-glycine polyacrylamide gels (Invitrogen) and transferred to nitrocellulose using iBlot (Invitrogen). Membranes were incubated in blocking buffer (LiCor), probed with 0.5 µg/ml IPN001 antibody to tau and antibody to β-actin (1:2000; Abcam) in blocking buffer containing 0.1% Tween-20, and anti-mouse 680 and anti-rabbit 800 secondary antibodies (LiCor). Blots were scanned with the Odyssey SA infrared imaging system and analyzed using Odyssey SA software (LiCor).

Tau ELISA

Media were collected after a three day conditioning period from iPSC-derived cortical neuron cultures and assayed using an Alphascreen homogeneous assay to measure tau. 10 µg/ml anti-tau AlphaLISA acceptor beads and 1 nM biotinylated-anti-tau antibody were mixed with conditioned media overnight at room temperature. 40 µg/ml streptavidin-donor beads (Perkin Elmer) were added for 30 minutes at room temperature and the plate read on Envision plate reader.

eTau Purification

Conditioned media collected from iPSC-CN from AD patients was spun at 15,000 rpm for 15 minutes, supernatants collected and precleared on an IgG affinity resin. The precleared supernatant was passed through an IPN002 anti-tau antibody resin, washed and eTau eluted with 50 mM sodium citrate, pH 2.3 with 150 mM NaCl into a tube containing 1M TBS, pH 8.3 to neutralize the pH. The eluate was concentrated and buffer exchanged to PBS.

Immunofluorescence

MCC were rinsed with PBS, fixed in 4% paraformaldehyde, blocked with 10% normal donkey serum (Jackson ImmunoResearch) in PBS, permeabilized (unless otherwise specified) with 0.2% Triton-x-100 in PBS for 15 minutes, and stained using IPN001 antibody to tau with donkey-anti-mouse-A488 secondary antibody (Molecular Probes) and DAPI (Invitrogen). Images were acquired using the Leica DMI 600 B microscope at 40× using the LAS AF software (Leica). Confocal images were acquired using the Nikon Eclipse Ti confocal microscope (Nikon).

Results

Figure 7:
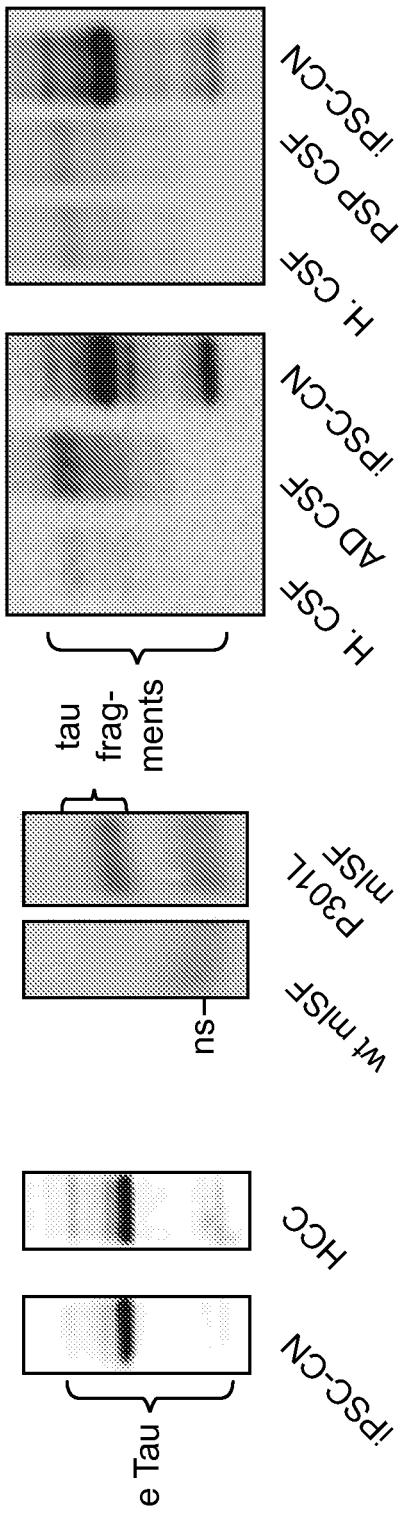
FIG. 7 depicts detection of Tau fragments in conditioned medium, in interstitial fluid (ISF) from P301L tau mice, and in CSF from PSP and AD patients

Assays were conducted to detect eTau fragments in various fluids. The results are depicted in FIG. 7. As shown in FIG. 7, left panel, endogenous tau is secreted from cortical neurons derived from human induced pluripotent stem cells (human iPSC-cortical neurons; iPSC-CN), where the secreted Tau is referred to as extracellular Tau or "eTau." As shown in FIG. 7, second panel from left, eTau is also present in conditioned media from human primary neurons (human cortical cells; "HCC"), confirming that eTau is not an artifact of iPSC-differentiation. These eTau fragments were also detected in neuronal lysates, suggesting that tau is cleaved inside neurons prior to eTau secretion.

As shown in FIG. 7, middle panel, similar tau fragments were detected in interstitial fluid (ISF) from P301L tau mice, where full length tau was not detected in either system. P301L mice are transgenic for a form of human tau having a P301L mutation; P301L mice are models for human tauopathy. See, e.g., Götz et al. (2001) *J. Biol. Chem.* 276:529; and Lewis et al. (2000) *Nature Genetics* 25:402.

As shown in FIG. 7, right panels, eTau levels are increased in CSF from AD patients, and in multiple lines from familial AD (fAD) patients compared to lines from healthy patients. As shown in FIG. 7, right panels, eTau was also detected in CSF from PSP patients.

Example 5 eTau Induces Neuronal Hyperactivity

Methods

Whole cell patch clamp recording from iPSC-CN cultured on monolayer of normal human astrocytes using micropipette (2-5 MOhm) were filled with solution containing (mM): K-methyl-sulfate (140), NaCl (10), CaCl$_2$ (1), Mg-ATP (3); Na-GTP (0.4), EGTA (0.2), HEPES (10), Phosphocreatine (10) with adjusted pH=7.3, and mOsm=305. Neurons were perfused (2 ml/min) with artificial cerebral spinal fluid containing (mM): NaCl (140), KCl (2.5), MgCl$_2$ (2) CaCl$_2$ (2), Hepes (10), D-Glucose (10), sucrose (20), adjusted pH=7.4 mOsm=310. Recordings were made using pClamp-10.3 data acquisition software (Molecular Devices) and MultiClamp 700B amplifier (Axon Instrument; Foster City Calif.). Puff application of eTau, or eTau with inhibitors, tetrodotoxin (TTX) (Tocris), MK801 (Sigma), NBQX (Tocris), or anti-tau antibody, IPN001, was performed using MiniSquirt micro-perfusion system (AutoMate, Berkeley, Calif.). Off-line data analysis used Clampfit 10.2 analysis software (Molecular Devices). Recordings were conducted at 34-37° C.

Results

To determine whether eTau can alter neuronal function, purified eTau fragment eTau was applied to iPSC-CN or HCC. The results are shown in FIGS. 8A-C.

Figure 8:
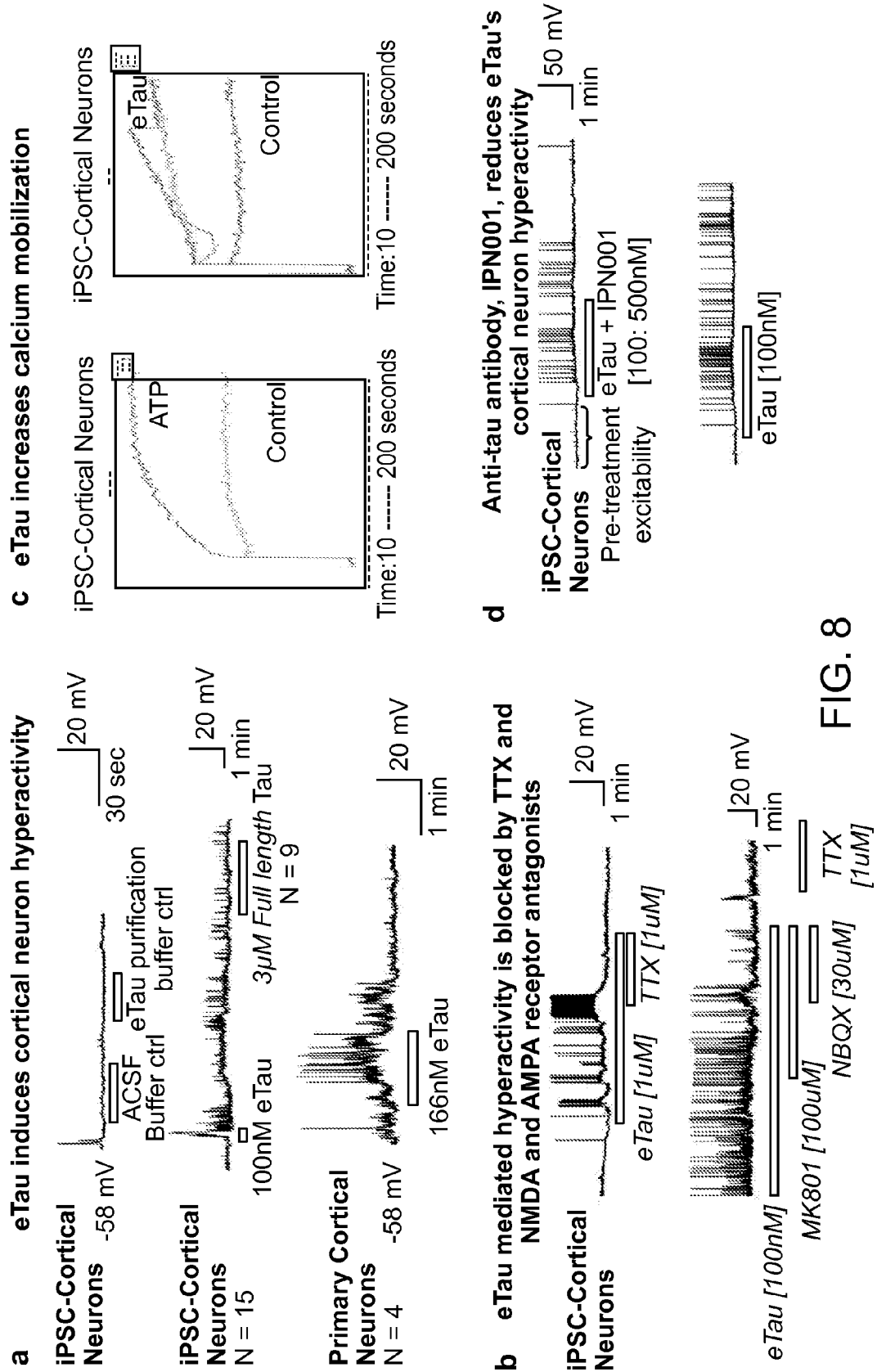
FIGS. 8A-D depict induction of cortical neuron hyperactivity by an extracellular tau (eTau) fragment (FIGS. 8A-C); and reduction of eTau-induced neuronal hyperactivity by anti-Tau antibody IPN001.

As shown in FIG. 8A, addition of a purified eTau fragment mixture onto these neurons promoted hyperactivity. As shown in FIG. 8B, hyperactivity induced by the eTau mixture was inhibited by tetrodotoxin (TTX) and by the NMDA and AMPA glutamate receptor antagonists, MK801 and NBQX, respectively. TTX blocks action potentials in nerves by binding to the voltage-gated, fast sodium channels in nerve cell membranes. These data suggest that eTau-induced neuronal hyperactivity is dependent on action potential-mediated release of glutamate. In contrast, as shown in the middle panel of FIG. 8A, application of full length tau produced no detectable changes in neuronal activity even at substantially higher concentrations, showing that eTau-induced hyperactivity is dependent on tau fragments. These eTau-induced hyperactivity results strongly suggest that calcium mobilization could be occurring in the neurons. To determine whether calcium mobilization occurs in the neurons, the effect of eTau on calcium mobilization was tested. As shown in FIG. 8C, eTau-1a robustly mobilized calcium. This type of neuronal hyperactivity, if sustained in a chronic setting such as in AD, could result in neuronal dysfunction through altered synaptic firing and aberrant neuronal stimulation. eTau-1a includes amino acids 2-166 of fetal tau, i.e., amino acids 2-166 of SEQ ID NO:27.

Example 6

Anti-Tau Antibody Reduces eTau-Mediated Neuronal Hyperactivity

Electrophysiological analyses were carried out as described in Example 5. The effect of IPN001 and IPN002 on e-Tau-mediated neuronal hyperactivity was assessed.

Figure 19:
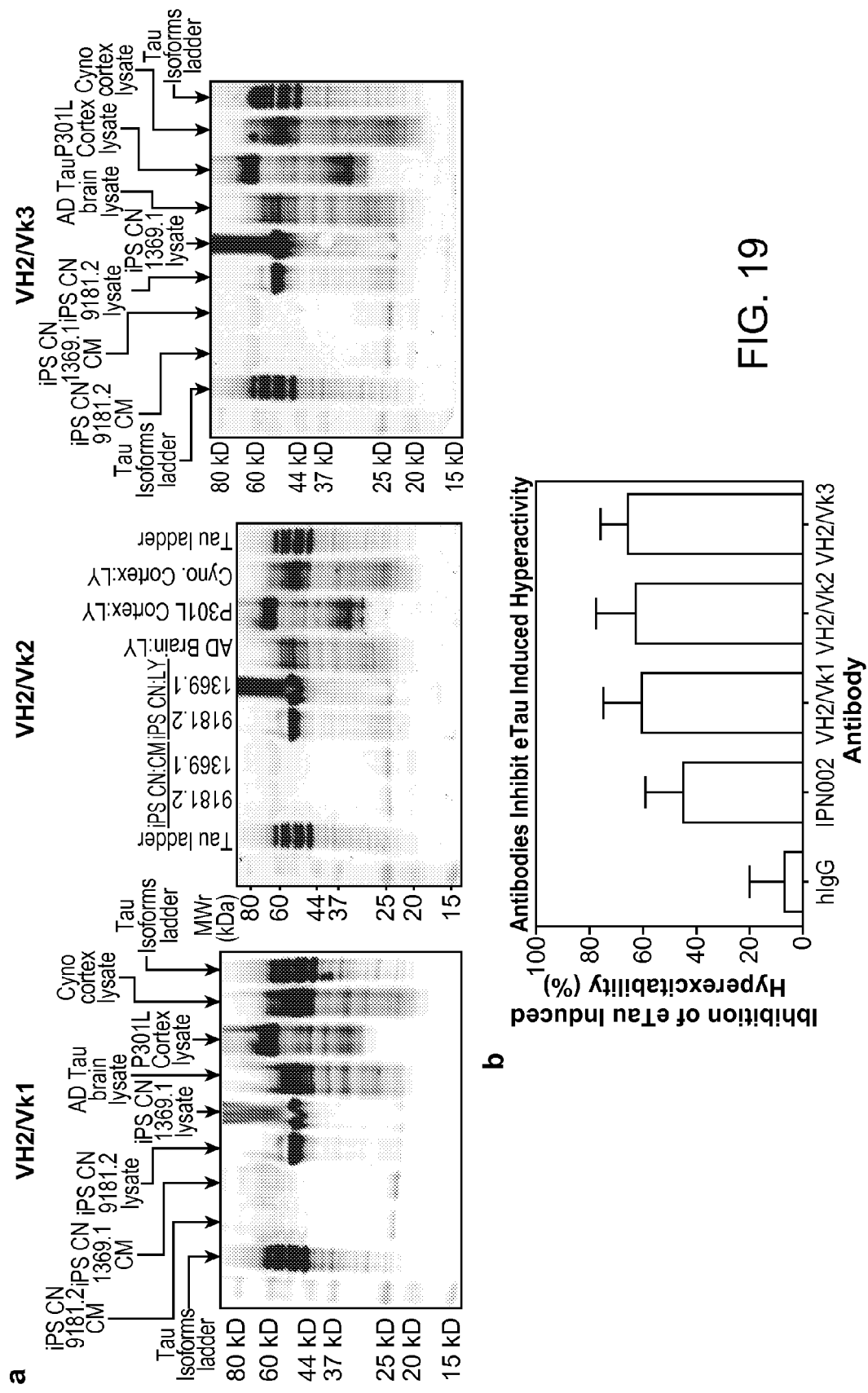
FIGS. 19A and 19B depict properties of humanized IPN002 variants.

As shown in FIG. 8D, IPN001 reduces eTau-mediated neuronal hyperactivity. As shown in FIG. 19B, IPN002 reduces eTau-mediated neuronal hyperactivity.

Example 7

Humanized Anti-Tau Antibodies

Humanized variants of IPN002 were generated. Amino acid sequences of the heavy chain VH domains of humanized variants 1-4, and nucleotide sequences encoding the heavy chain VH domain of the humanized variants, are shown in FIGS. 9-12. Amino acid sequences of the light chain VL domain of humanized variants 1-4, and nucleotide sequences encoding the light chain VL domain of the humanized variants, are shown in FIGS. 13-16. Amino acid differences relative to the amino acid sequence of IPN002 are summarized in Tables 4 and 5.

TABLE 4

VH Variants

| Amino Acid Position | IPN002 (Parental antibody) | VH Variant 1 | VH Variant 2 | VH Variant 3 | VH Variant 4 |
| --- | --- | --- | --- | --- | --- |
| 3 | H | H | H | Q | Q |
| 19 | K | R | R | R | R |
| 40 | T | A | A | A | A |
| 42 | D | G | G | G | G |
| 44 | R | G | G | G | G |
| 66 | Q | R | R | R | R |
| 83 | S | S | N | N | N |
| 85 | L | S | L | L | L |
| 86 | K | K | R | R | R |
| 87 | S | S | A | A | A |
| 93 | S | S | S | S | A |
| 108 | S | S | T | T | T |

TABLE 5

Vk Variants

| Amino Acid Position | IPN002 (Parental antibody) | Vk Variant 1 | Vk Variant 2 | Vk Variant 3 | Vk Variant 4 |
| --- | --- | --- | --- | --- | --- |
| 3 | L | L | V | V | V |
| 7 | T | S | S | S | S |
| 14 | S | T | T | T | T |
| 17 | D | Q | Q | Q | Q |
| 18 | Q | P | P | P | P |
| 45 | K | Q | Q | Q | Q |
| 48 | V | V | V | V | I |
| 83 | L | V | V | V | V |
| 85 | T | T | T | V | V |
| 104 | L | V | V | V | V |

Single letter amino acid codes are as follows:
G—Glycine (Gly)
P—Proline (Pro)
A—Alanine (Ala)
V—Valine (Val)
L—Leucine (Leu)
I—Isoleucine (Ile)
M—Methionine (Met)
C—Cysteine (Cys)
F—Phenylalanine (Phe)
Y—Tyrosine (Tyr)
W—Tryptophan (Trp)
H—Histidine (His)
K—Lysine (Lys)
R—Arginine (Arg)
Q—Glutamine (Gln)
N—Asparagine (Asn)
E—Glutamic Acid (Glu)
D—Aspartic Acid (Asp)
S—Serine (Ser)
T—Threonine (Thr)

Example 8

Characterization of Humanized IPN002 Variants

The relative tau binding affinities for binding to each of the recombinant tau (383 amino acid recombinant tau) as well as to eTau 1a, eTau1b, eTau2, eTau3 and eTau4 for each of the 16 antibody combinations of VH#1-4 with Vk#1-4 are shown in Table 4, which is presented in FIG. 17. The relative binding affinities for each tau and eTau species range from 121 pM to 1030 pM for each of the VH/Vk antibody combinations. eTau1a includes amino acids 2-166 of fetal tau, i.e., amino acids 2-166 of SEQ ID NO:27; and eTau 1b includes amino acids 2-196 and 217-228 of fetal tau, i.e., amino acids 2-196 and 217-228 of SEQ ID NO:27. Amino acid sequences of eTau3 and eTau 4 are depicted in FIG. 20.

To obtain absolute affinities as well as $K_{on}$ and $K_{dis}$ for these VH/Vk human antibodies, Octet analysis was conducted using tau (383 amino acid recombinant tau). The $K_D$'s ranged from 42.6 pM to 2120 pM. For all VH/Vk variants, the $K_{on}$ values were high, and $K_{dis}$ values were low for Tau and for each eTau species. The data are provided in Table 5, which is presented in FIG. 18.

A subset of the above-described humanized IPN002 variants was tested in additional analysis. As shown in FIG. 19A, three variants, VH2/Vk1, VH2/Vk2, and VH2/Vk3, were used in a Western blot assay with a variety for samples containing tau. The tau-containing samples included iPSC-CN conditioned media; iPSC-CN lysates; AD brain lysates; and P301L tau mouse brain cortex lysates; and cynomologus monkey brain lysates. The data show that the above-described humanized IPN002 variants are reactive with tau in a variety of samples.

A subset of the above-described humanized IPN002 variants was tested for the ability to reduce eTau-induced neuronal hyperactivity. As shown in FIG. 19B, parental IPN002, and variants VH2/Vk1, VH2/Vk2, and VH2/Vk3 blocked eTau induced hyperactivity.

Example 9

Testing the Immunogenicity of Humanized IPN002 Variants

Humanized anti-tau antibody was assessed for immunogenic potential. An EpiScreen™ assay was used. See, e.g., Jones et al. (2004) *J. Interferon Cytokine Res.* 24:560; and Jones et al. (2005) *J. Thromb. Haemost.* 3:991. Time course T cell assays were performed using CD8+-depleted peripheral blood mononuclear cells (PBMC); and T cell proliferation was measured by incorporation of [$^3$H]-thymidine at various time points after addition of test antibody samples.

PBMC were isolated from healthy community donor buffy coats (e.g., from blood drawn within 24 hours of testing). T cell responses to a test antibody (e.g., a humanized IPN002 variant) were compared to a clinical standard antibody.

Purified test antibody (humanized IPN002 variant) was added to PBMC cultures in vitro to a final concentration of 50 μg/ml in culture medium, to generate a test sample. A clinical antibody control (positive control), and a culture medium-only control (unstimulated control), were included as control samples. Test samples (PBMC plus test antibody), and control samples, were incubated for 8 days at 37° C. with 5% $CO_2$. On days 5, 6, 7, and 7, the cells in the test and control samples were suspended and transferred to wells of a multi-well culture plate. The test and control samples were pulsed with 0.75 μCi [$^3$H]-thymidine and incubated for a further 18 hours before harvesting onto filter mats. Counts per minute (cpm) for each well were determined using scintillation counting.

For proliferation assays, a threshold of an SI equal to or greater than 2 was used, where samples inducing a proliferative response above this threshold were considered positive. SI (Stimulation Index) is the mean test sample counts divided by the mean of the unstimulated control.

Figure 21:
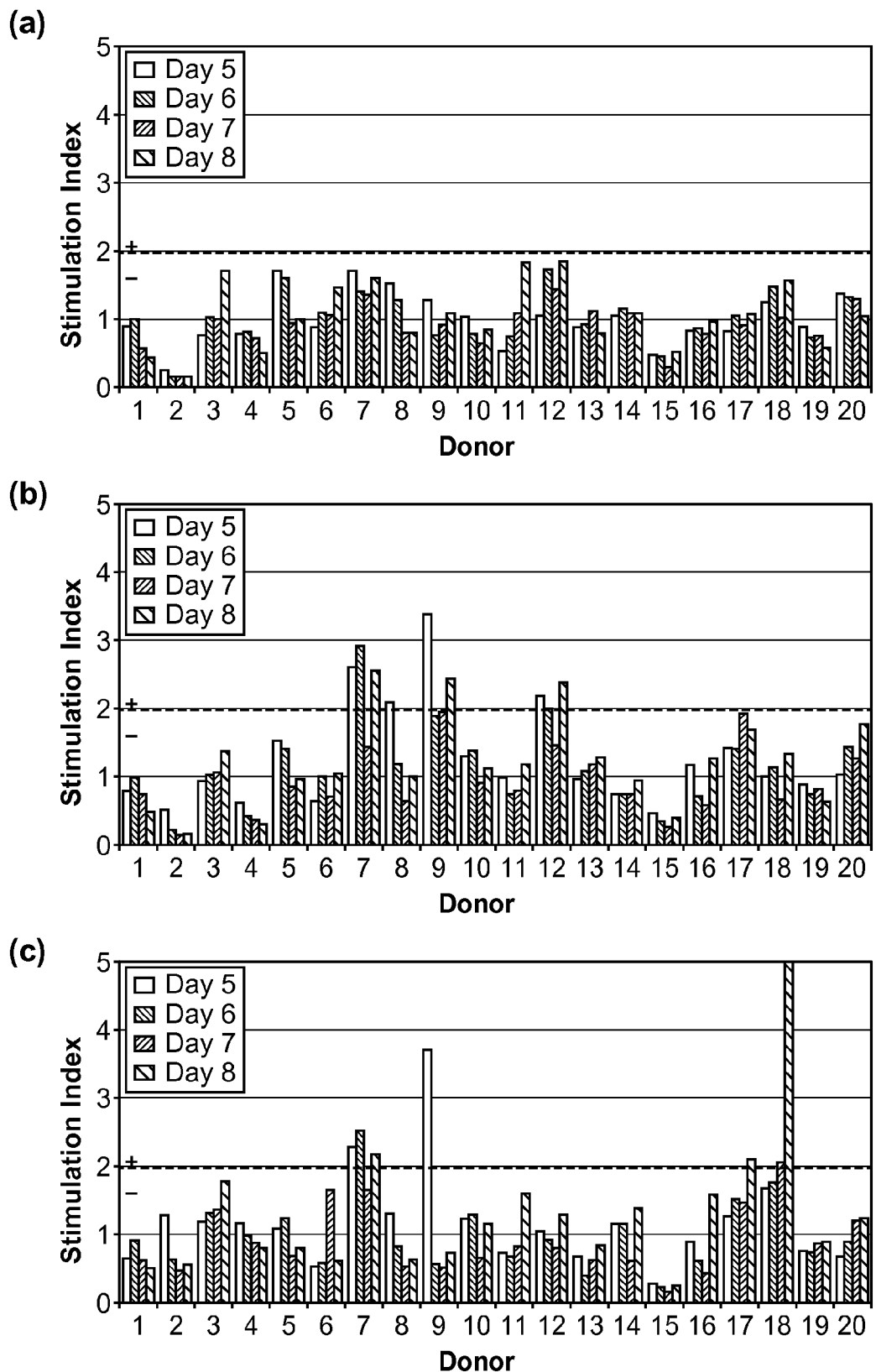
FIGS. 21A-C depict proliferation responses to a humanized anti-Tau antibody (FIG. 21A), a chimeric antibody (FIG. 21B), and humanized A33 (FIG. 21C).

The data are shown in FIGS. 21A-C. Healthy donor T cell proliferation responses to a humanized IPN002 test antibody. PBMC from bulk cultures were sampled an assessed for proliferation on days 5, 6, 7, and 8 after incubation with the test samples. Proliferation responses with an SI≥2.0 (p<0.05), indicated by the dashed horizontal line, that were significant (p<0.05) using an unpaired, two sample student's t test were considered positive.

As shown in FIG. 21A, a test fully humanized IPN002 antibody had low immunogenic potential (below the SI threshold of 2.0). FIG. 21B shows results with a reference chimeric antibody, where the reference chimeric antibody has IPN002 murine heavy and light chain variable regions and human IgG4 constant region; and FIG. 21C shows results with an immunogenic clinical control humanized A33 antibody.

Example 10

IPN002 Reduces the Level of Phosphorylated Tau In Vivo

The effect of IPN002 administration on the level of Tau that is phosphorylated at amino acids 202 and 205 was assessed.

The P301L mouse model was used. P301L mice are transgenic for a form of human tau having a P301L mutation; P301L mice are models for human tauopathy. See, e.g., Götz et al. (2001) *J. Biol. Chem.* 276:529.

P301L mice (3-4 months old) were treated with: 1) control IgG; 2) PHF1 anti-phosphorylated Tau antibody; or 3) IPN002. IgG control and IPN002 antibodies were injected intraperitoneally at a concentration of 10 mg/kg for 4 weeks; then at 20 mg/kg for a further 4 weeks. PHF1 was administered at 10 mg/kg for the entire 8-week course. On day 60 after the beginning of the antibody treatment regimen, the level of phosphorylated Tau was measured in the hippocampus. The data are depicted in FIG. 22.

Figure 22:
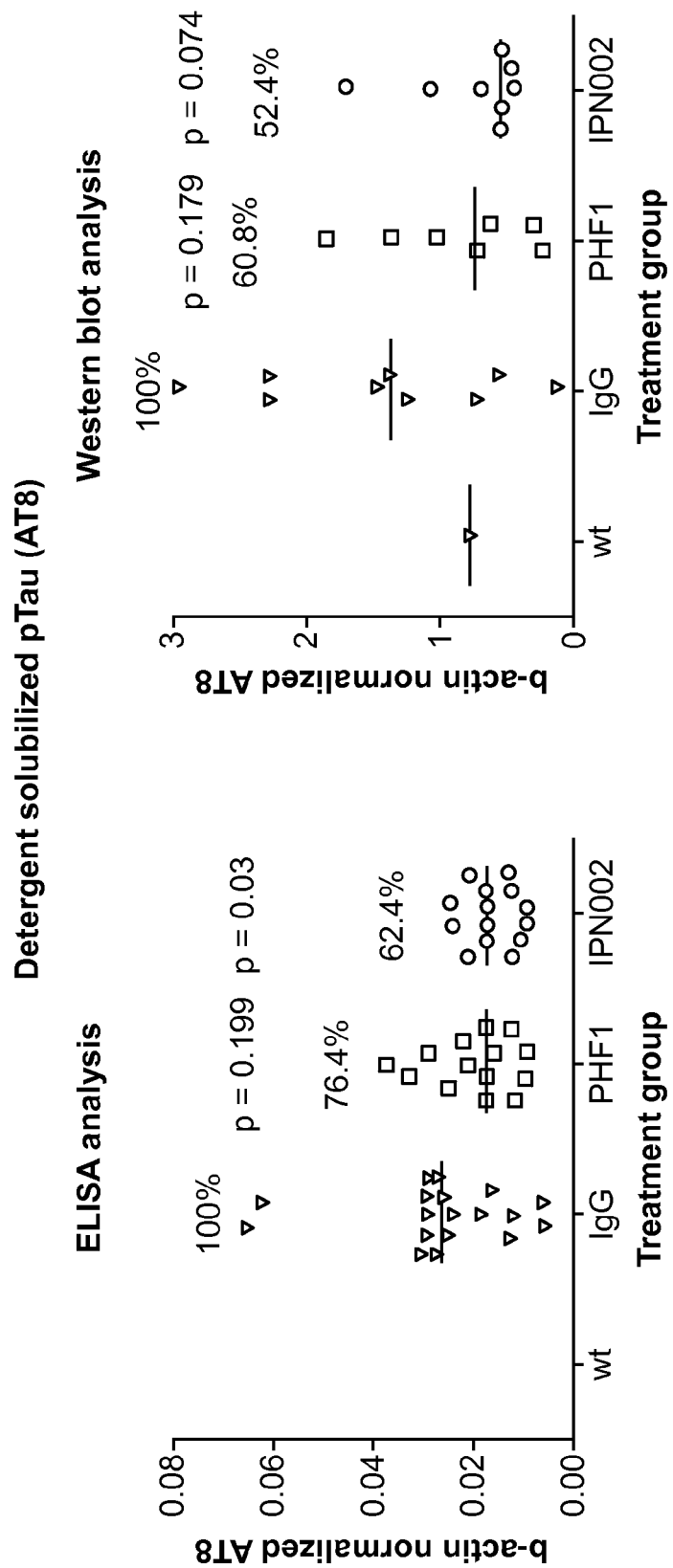
FIG. 22 depicts the effect of IPN002 on phosphorylated Tau levels in vivo.

Tau that is phosphorylated at amino acids 202 and 205 is referred to as "AT8." As shown in FIG. 22, treatment with IPN002 resulted in a statistically significant decrease in insoluble phospho-Tau (AT8) as assessed by ELISA (left panel), and trending toward a decrease as assessed by Western blot analysis (right panel) compared to IgG control treatment. PHF1 treatment showed a trend toward a decrease in insoluble AT8, in support of findings by Chai et al. ((2011) *J. Biol. Chem.* 286:34457) and Boutajangout et al. ((2011) *J. Neurochem.* 118:658).

Example 11

IPN002 Reduces Free Tau Levels in Both ISF and CSF

Figure 23:
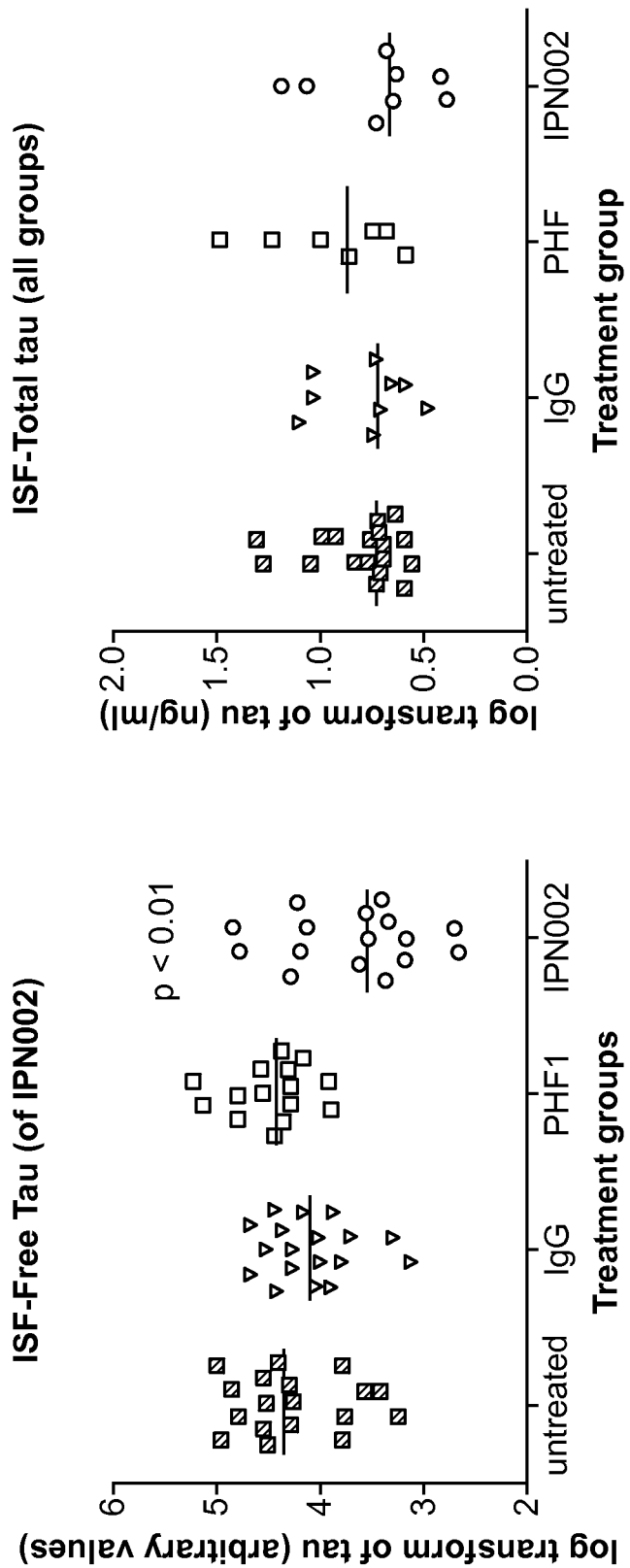
FIG. 23 depicts reduction in free tau levels and in total tau levels in interstitial fluid (ISF) following treatment with IPN002.

The effect of IPN002 administration on levels of free tau in CSF and interstitial fluid (ISF) was determined. P301L mice were treated as described in Example 10. The level of free tau present in ISF that is not bound to IPN002 was determined using IPN001. As shown in FIG. 23, IPN002 treatment reduced free Tau levels (not bound to IPN002) (left panel) in ISF in P301L mice treated with IPN002.

To determine whether IPN002 reduces free Tau levels in CSF to the same extent as it does in ISF, P301L mice were treated as described in Example 10, and the effect of IPN002 treatment on the level of free tau (not bound to IPN002) in the CSF of the treated mice was determined. The results are shown in FIG. 24.

Figure 24:
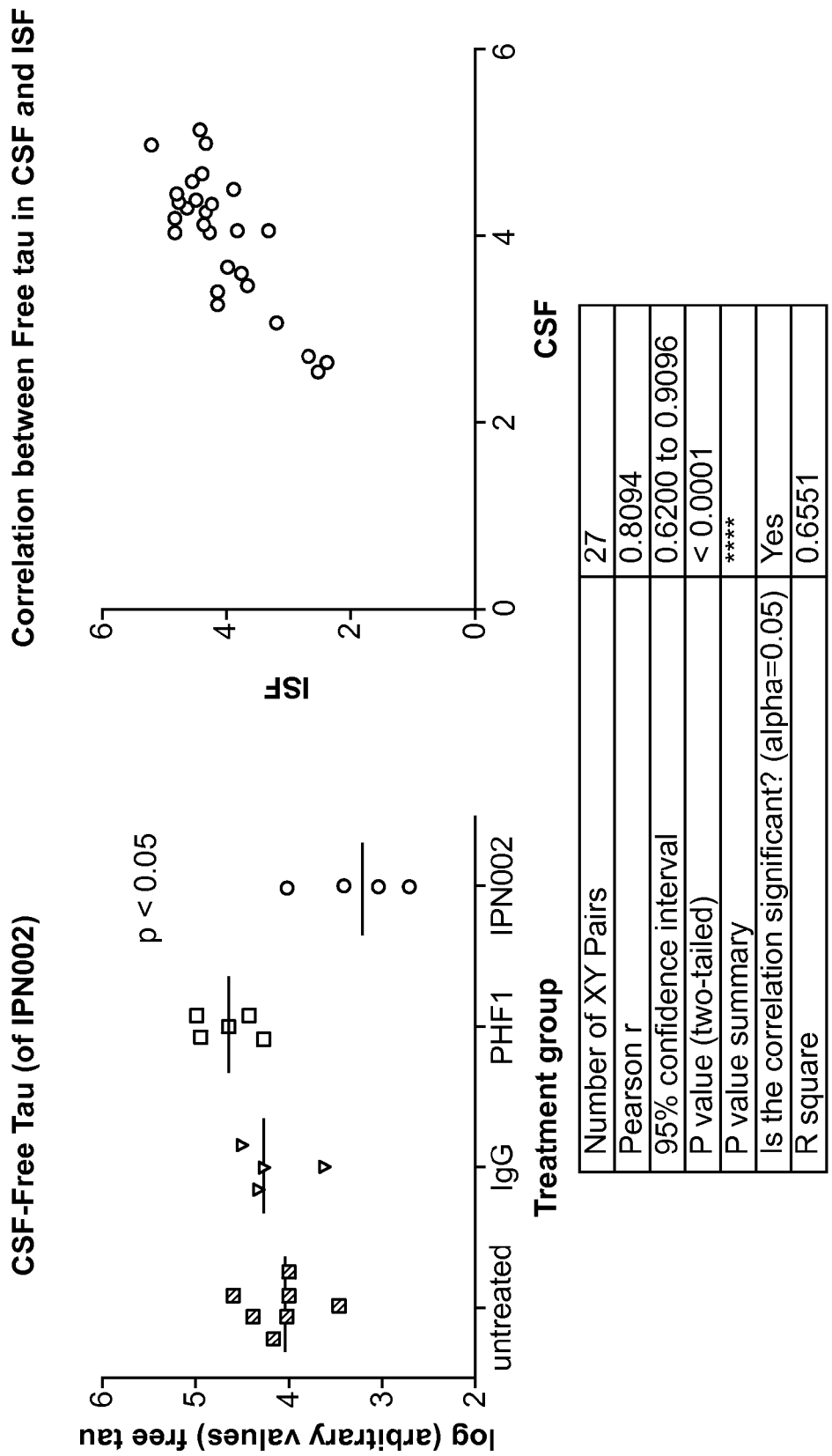
FIG. 24 depicts reduction in free tau levels in cerebrospinal fluid (CSF) following treatment with IPN002.

In the left panel of FIG. 24, the levels of free tau (unbound to IPN002; referred to as "Free tau (of IPN002)") in CSF of untreated, control IgG-treated, PHF1-treated, and IPN002-treated mice, are shown. As shown in the right panel of FIG. 24, free tau levels in CSF is comparable to free tau levels in ISF of IPN002-treated mice, demonstrating that ISF tau analysis correlates well with the more clinically relevant material, CSF.

Example 12

Anti-Tau Antibody Reduces eTau-Mediated Neuronal Hyperactivity

Electrophysiological analyses were carried out as described in Example 5. The effect of IPN002 on e-Tau-induced neuronal hyperactivity was assessed.

Figure 25:
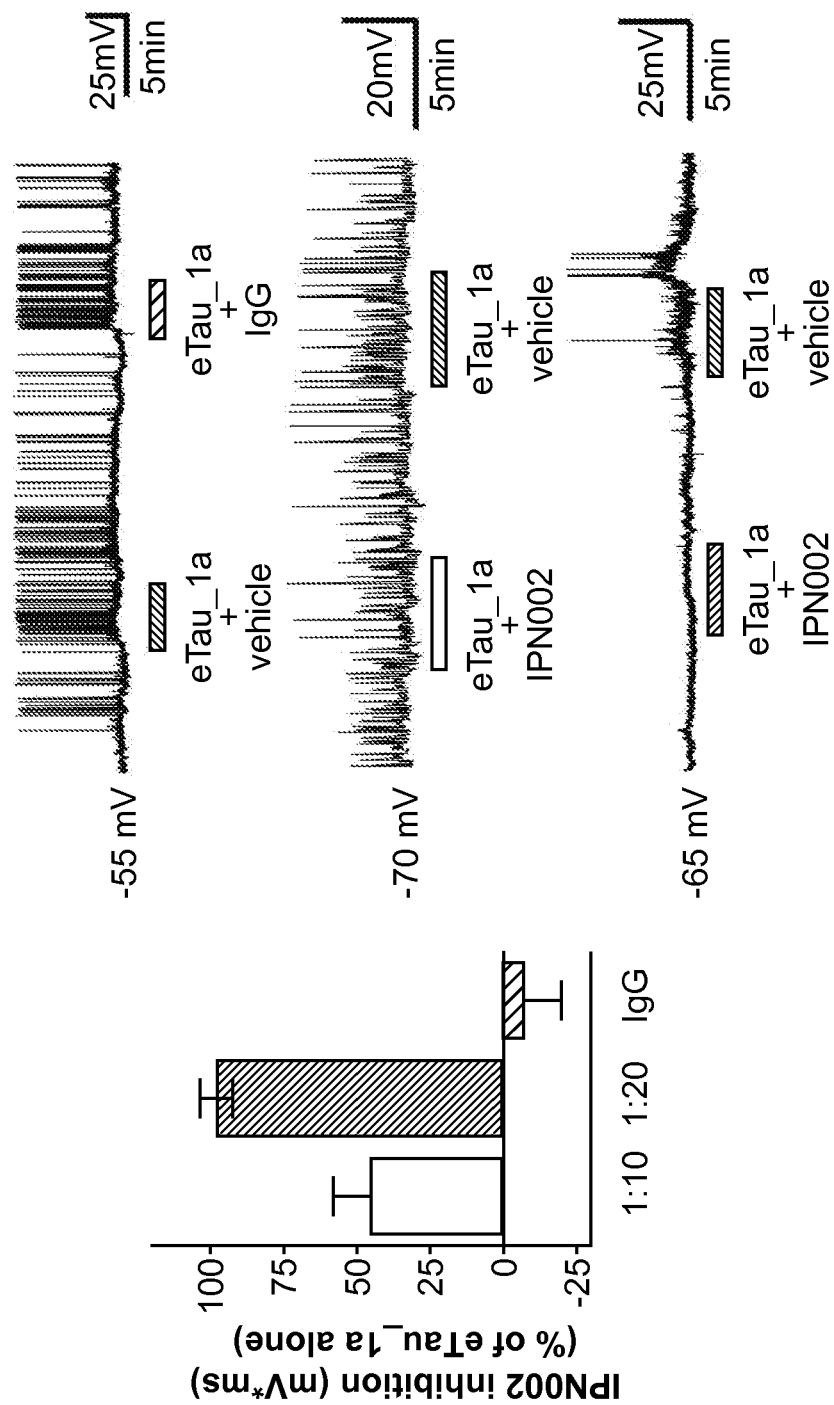
FIG. 25 depicts reduction of eTau-induced neuronal hyperactivity by IPN002.

As shown in FIG. 25, IPN002 reduces eTau-mediated neuronal hyperactivity.

Example 13

Tau Fragments are Present in CSF Obtained from Individuals with Likely Chronic Traumatic Encephalopathy (CTE)

Figure 26:
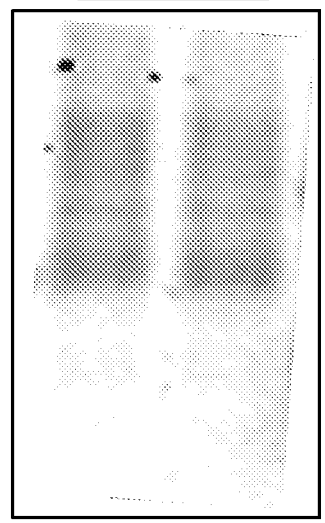
FIG. 26 depicts the presence of Tau fragments in CSF from individuals with likely chronic traumatic encephalopathy.

CSF samples were obtained from former National Football League linemen, who exhibited behavioral/cognitive deficits, and who were considered likely to have CTE. The CSF samples were assayed for the presence of eTau fragments. eTau fragments were affinity isolated from pooled CSF from healthy individuals and individuals with likely CTE. The isolated eTau fragments were separated using polyacrylamide gel electrophoresis; and the separated fragments were transferred to a membrane. The membrane was probed with IPN001. The results, presented in FIG. 26, show that Tau fragments are present in CSF obtained from individuals with likely CTE.

Example 14

Binding of a Humanized Variant of IPN002 to Synthetic Tau Peptides

The binding of a humanized variant of IPN002 ("hu-IPN002") to synthetic biotinylated Tau Peptide 1 and 2 was tested in both solid phase and solution phase assays.

The amino acid sequences of Peptide 1 and Peptide 2 are as follows:

Peptide 1 (Tau amino acids 13-24): DHAGTYGLGDRK (SEQ ID NO:49);

Peptide 2 (Tau amino acids 15-44): AGTYGL-GDRKDQGGYTMHQDQEGDTDAGLK (SEQ ID NO:50).

Antibody or biotinylated peptide was diluted in phosphate-buffered saline. The final concentrations were as follows: 1 µg/ml hu-IPN002; 1 µg/ml rTau383 (full-length recombinant Tau); 5 µg/ml (biotinylated Peptide 1); and 5 µg/ml (biotinylated Peptide 2). 100 µl 0.1% casein in PBS was added to wells of a multi-well plate. 150 µl of the 1 µg/ml solution of hu-IPN002 was added. Serial dilutions were made. 100 µl d biotin-peptides were added to the wells containing serially diluted antibody. The multi-well plate was incubated for one hour at room temperature. After the incubation period, wells were washed 5 times with a solution of 0.05% Tween 20 in PBS; followed by 2 washes with PBS.

Streptavidin-horse radish peroxidase (HRP)-conjugated secondary antibody was added to wells, and the plates were incubated at room temperature for 1 hour. After the incubation period, wells were washed 5 times with a solution of 0.05% Tween 20 in PBS; followed by 2 washes with PBS.

HRP substrate 3,3',5,5'-tetramethylbenzidine (TMB) was added, and incubated for 1-15 minutes. The reaction was stopped by addition of 100 µl 1 N sulfuric acid. Absorbance at 450 nm was read.

Figure 27:
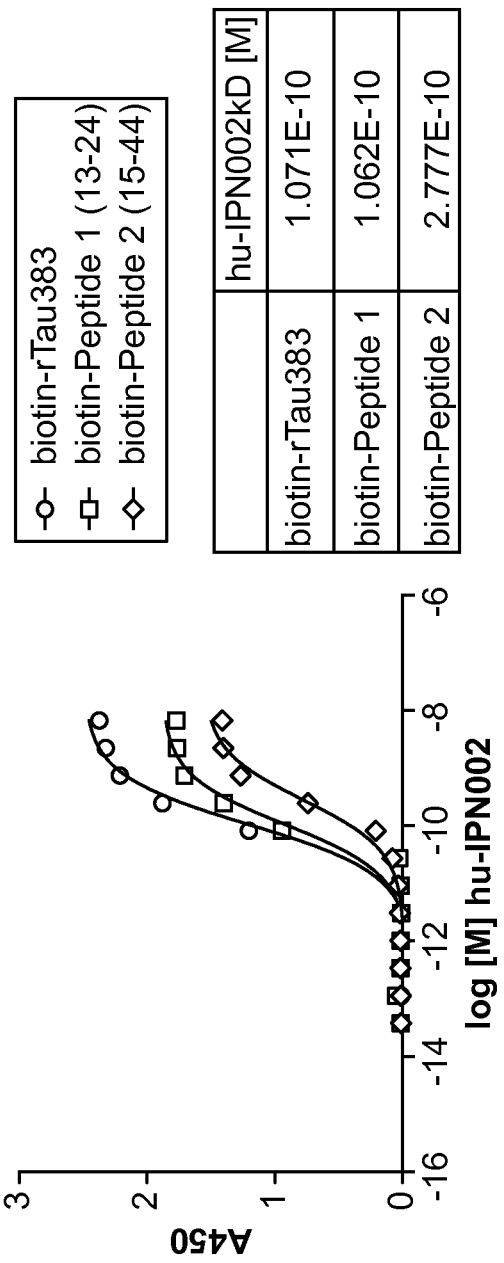
FIG. 27 depicts binding of a humanized variant of IPN002 to synthetic tau peptides using a solid phase assay.
Figure 28:
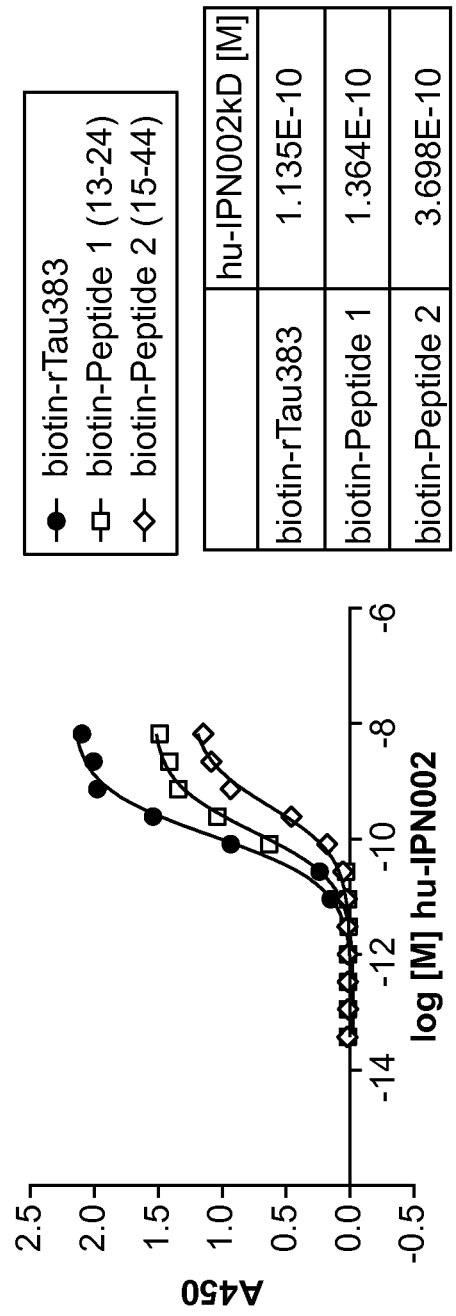
FIG. 28 depicts binding of a humanized variant of IPN002 to synthetic tau peptides using a solution phase assay.

The results are shown in FIGS. 27 and 28, and are summarized in Table 6.

TABLE 6

| | Hu-IPN002 kD [M] w/ biotin-rTau383 | Hu-IPN002 kD [M] w/ biotin-Peptide 1 | Hu-IPN002 kD [M] w/ biotin-Peptide 2 |
| --- | --- | --- | --- |
| solid phase | 1.071E−10 | 1.062E−10 | 2.777E−10 |
| solution phase | 1.135E−10 | 1.364E−10 | 3.698E−10 |

Figure 29:
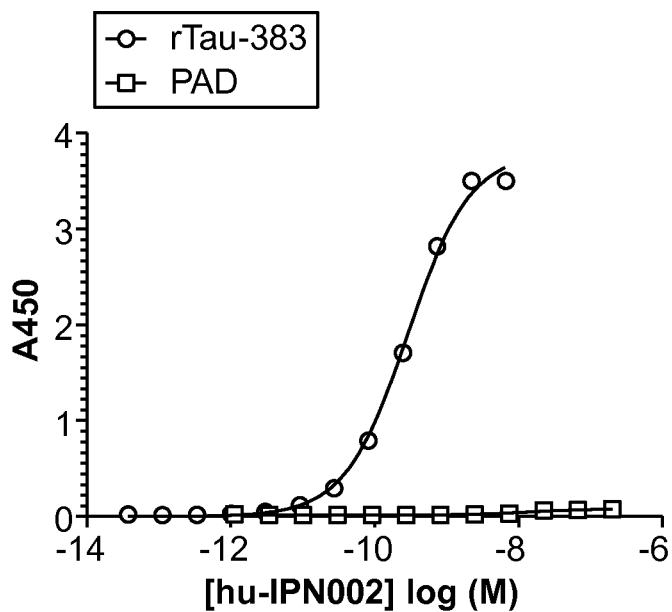
FIG. 29 depicts binding of a humanized variant of IPN002 to recombinant Tau and to a PAD peptide.

FIG. 29 depicts binding of hu-IPN002 to full-length recombinant Tau (rTau-383) and phosphatase-activating domain (PAD) peptide (tau amino acids 2-28; AEPRQEFE-VMEDHAGTY; SEQ ID NO:80). As shown in FIG. 29, hu-IPN002 does not bind to PAD peptide.

FIG. 30 shows that non-biotinylated Tau Peptide 1 (Tau amino acids 13-24) and non-biotinylated Peptide 2 (Tau amino acids 15-44) compete with biotinylated forms of Tau Peptide 1 and Tau Peptide 2 for binding to hu-IPN002. These data show that the binding of Tau Peptide 1 and Tau Peptide 2 to hu-IPN002 is specific and not due to the addition of the biotin.

Example 15

In Vivo Effect of IPN002 on Pathology

In this study, the effect of a therapeutic intervention on the reduced mobility and Tau pathology in a transgenic mouse model of tauopathy (hTau.P301L-Tg) was investigated. In these mice, a clinical mutant of human Tau (P301L) is expressed under control of the murine Thy1 promoter (neuron-specific expression). Behavior (beam walk) was measured at 7, 8, 8.5 and 9 months of age as well as the day before study termination. End-points of the study included: (1) survival; (2) behavior: beam walk performance and clasping score; (3) biochemistry: pan-Tau in total homogenate, soluble and insoluble brain stem fractions; and (4) biomarkers: AT8 in total homogenate and insoluble brainstem fractions.

Materials and Methods

P301L mice (3-4 months old) were treated with: 1) control IgG; 2) PHF1 anti-phosphorylated Tau antibody; or 3) IPN002. IgG control and IPN002 antibodies were injected intraperitoneally at a concentration of 20 mg/kg once a week for 6 months. PHF1 was administered at 10 mg/kg for 6 months. PHF1 is a mouse monoclonal antibody that recognizes an epitope that includes phospho-Ser$^{396}$ and phospho-Ser$^{404}$. Santacruz et al. (2005) *Science* 309:476.

Body Weights and Clasping Behavior

Body weights were determined weekly during treatment and at sacrifice. Body weight and clasping score were recorded weekly as of study start up to the age of 7 months. From the age of 7 months onwards, mice were monitored twice a week for mobility in home cage, weight loss and first signs of clasping of the hind and fore limbs. Once clasping signs were present, body weight was determined daily and clasping behavior was scored until moment of 'premature sacrifice'. To score clasping behavior, mice were kept approximately 1.5 cm above their tail base for about ten seconds. Clasping was scored for each limb separately using a 4-point rating scale. Preliminary sacrificed mice were ascribed a maximum score. Forelimb scores were primarily used as supporting evidence for sacrifice decisions. The latter were made on the combined observations of clasping, weight loss and mobility in the home cage and according to predefined criteria. Left and right hind limb scores unified in one clasping score were used for evaluation of clasping evolution throughout treatment and assessment of group differences at study termination. Mice that died prematurely from epilepsy are excluded from the analysis. Statistical analysis were performed using 2-way ANOVA with repeated measures followed by Bonferroni post-hoc testing, and using Student's T-test on the group averages of the last clasping scores before sacrifice, respectively.

Beam Walk

The beam walk test was performed with the baseline group and at 7, 8, 8.5, and 9 months of age, as well as the day before study termination, with the treatment groups, to determine motor dysfunction and motor learning. The ability of a given mouse to balance on the beam and the time that is needed to walk over a distance of 1 meter is a measure of their balance, coordination, physical condition and motor-planning A copper beam with a circular diameter of 12 mm was placed under an angle of 30°. The start area of the beam was illuminated with a desk lamp, while an indoor escape platform was placed at the end. For the initial training trials, a wider beam was used to train mice to balance and walk to the platform. After the training trials, the latency of the mice was timed over a distance of 1 m. In addition, by gait observations, the first symptoms of motor dysfunction (foot slips and belly dragging) were determined. Statistical analysis of latency scores were performed using 2-way ANOVA followed by Bonferroni post-hoc testing.

Results

Clasping Behavior and Beam Walk

Figure 31:
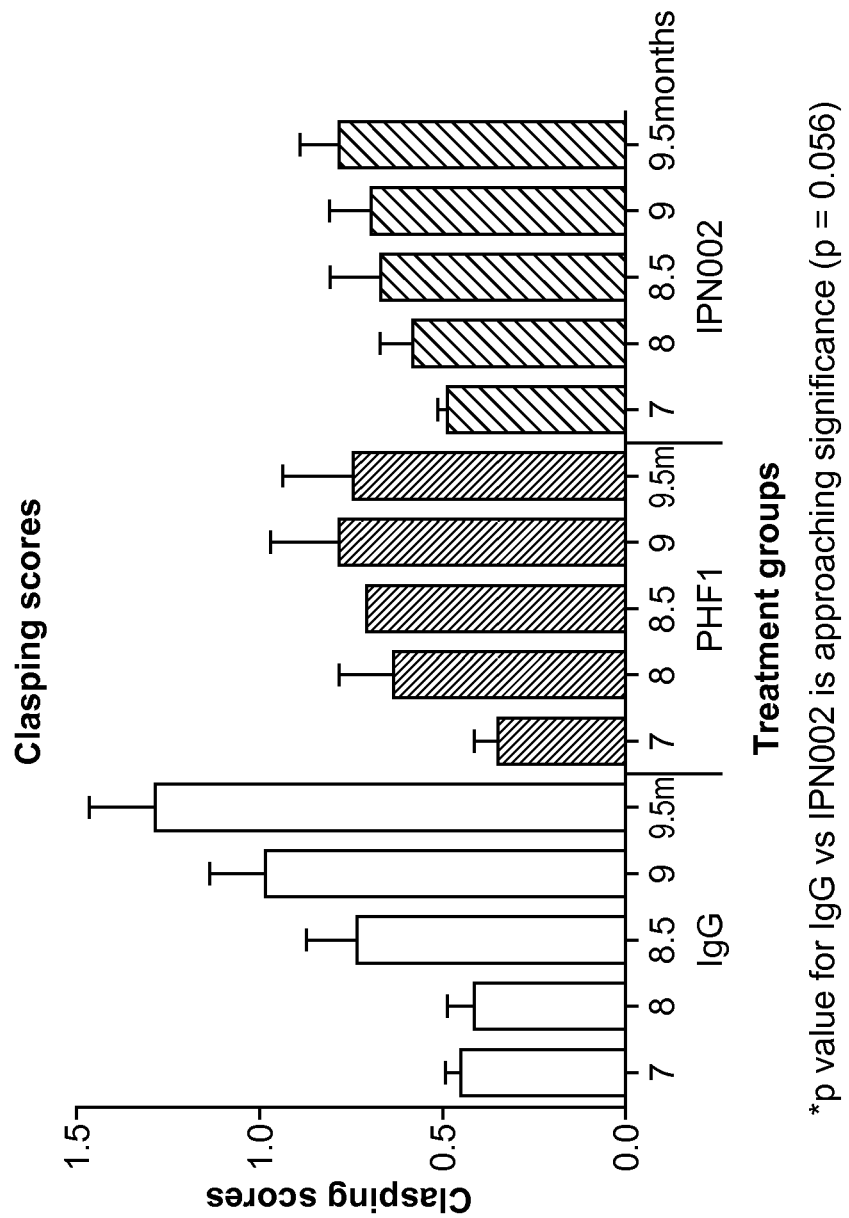
FIG. 31 depicts the effect of administration of control IgG, PHF1, or IPN002 on clasping scores in the P310L mouse model.
Figure 32:
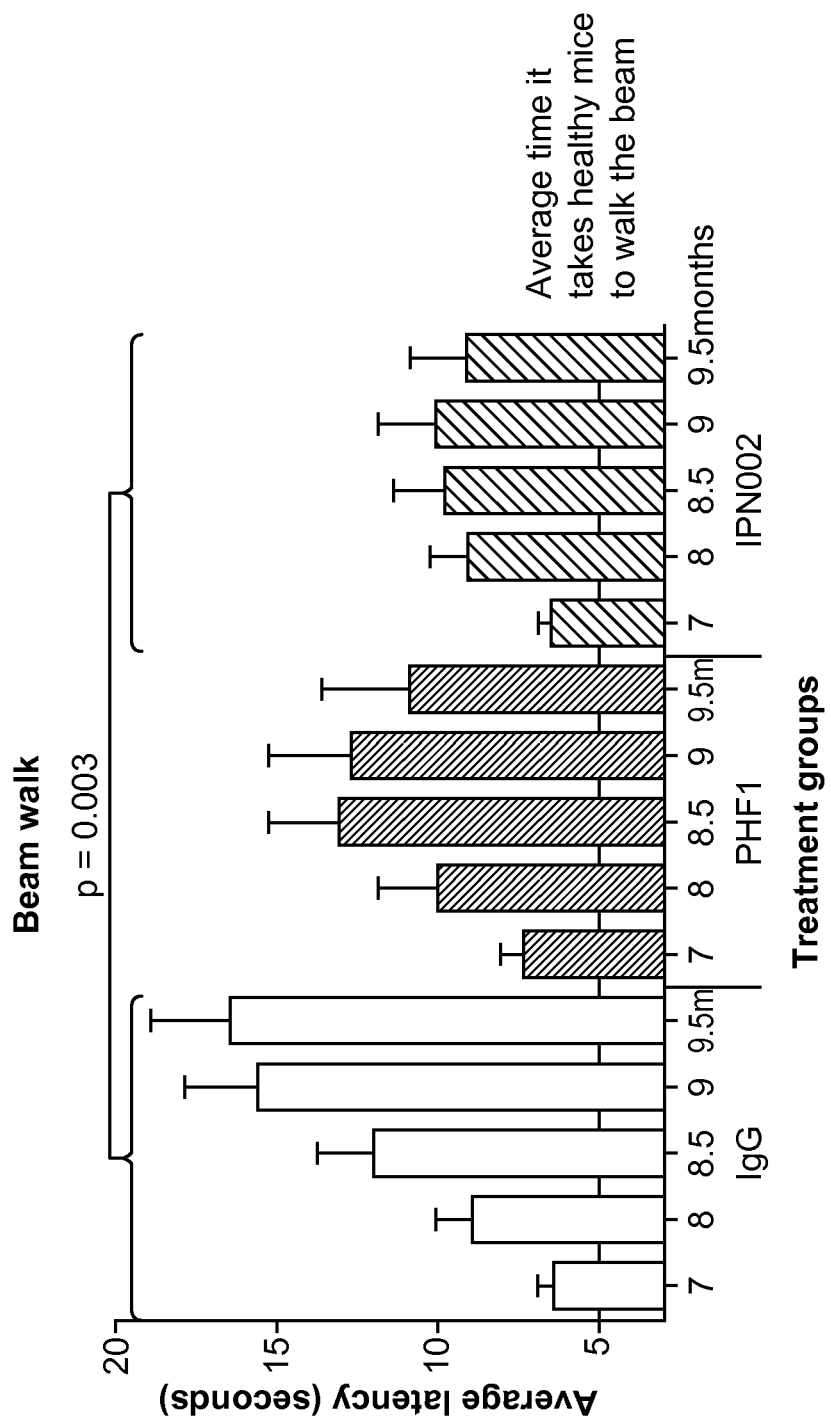
FIG. 32 depicts the effect of administration of control IgG, PHF1, or IPN002 on average latency in the beam walk test in the P310L mouse model.

The effect of IPN002 on clasping behavior is depicted in FIG. 31. As shown in FIG. 31, IPN002 treatment reduced the clasping score, compared to control IgG. The effect of IPN002 on motor function, as assessed by the beam walk, is depicted in FIG. 32. As shown in FIG. 32, IPN002 treatment significantly reduced the average latency (and thus improved motor function), compared to control IgG. Thus, IPN002 treatment significantly reduces the motor deficit in P301L tau transgenic mice. Using the same statistical method, the results with PHF1 treatment did not reach significance.

Tau Levels

Figure 33:
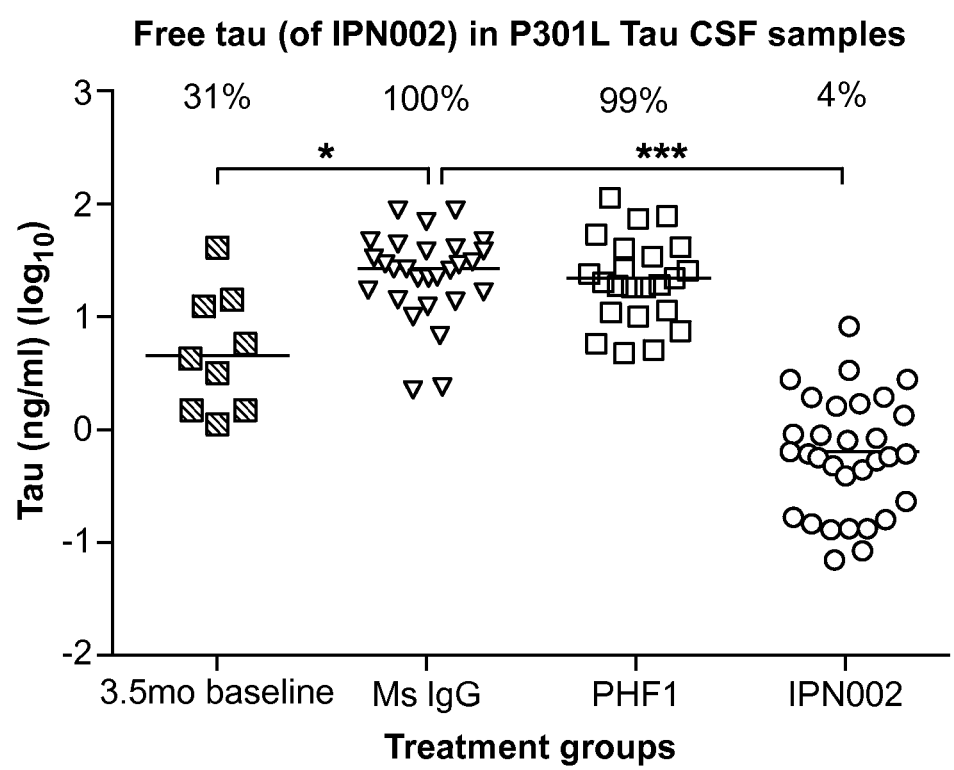
FIG. 33 depicts the effect of administration of control IgG, PHF1, or IPN002 on the level of free tau (tau not bound to anti-tau antibody) in CSF samples in the P310L mouse model.

The level of free tau (tau unbound to IPN002) in the CSF of P301L mice following treatment with control IgG, PHF1, or IPN002 was assessed. The level of free tau present in CSF that is not bound to IPN002 was determined using IPN001. The data are shown in FIG. 33. As shown in FIG. 33, IPN002 treatment reduced free tau (unbound to IPN002) levels by 96%, compared to the levels in mice treated with control IgG.

Example 16

Effect of IPN002 on eTau-Induced Neuronal Hyperexcitability

Materials and Methods

Whole cell patch clamp recording was conducted on human primary cortical cultures. Neurons were perfused (2 ml/min) with artificial cerebral spinal fluid containing (mM): NaCl (140), KCl (2.5), MgCl$_2$ (2) CaCl$_2$ (2), Hepes (10), D-Glucose (10), sucrose (20), adjusted pH=7.4 mOsm=310. Recordings were made using pClamp-10.3 data acquisition software (Molecular Devices) and MultiClamp 700B amplifier (Axon Instrument; Foster City Calif.). Puff application of: 1) eTau 1a (amino acids 2-166); 2) phosphorylated tau or eTau with inhibitors; 3) control IgG; or 4) anti-tau antibodies, PHF1, IPN001, or Dako (polyclonal anti-C-terminal tau) was performed using MiniSquirt micro-perfusion system (AutoMate, Berkeley, Calif.). Off-line data analysis used Clampfit 10.2 analysis software (Molecular Devices). Recordings were conducted at 34-37° C.

Results

Figure 34:
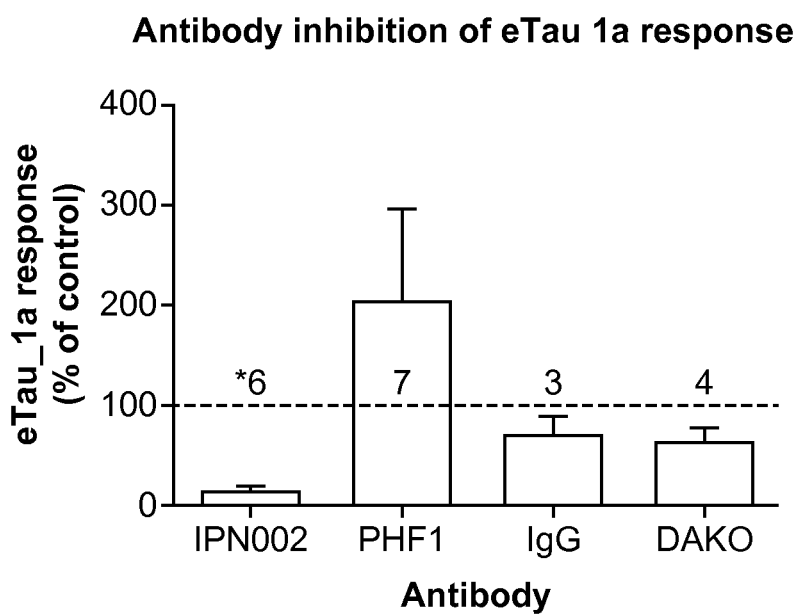
FIG. 34 depicts antibody inhibition of eTau1a-induced neuronal hyperexcitability.
Figure 35:
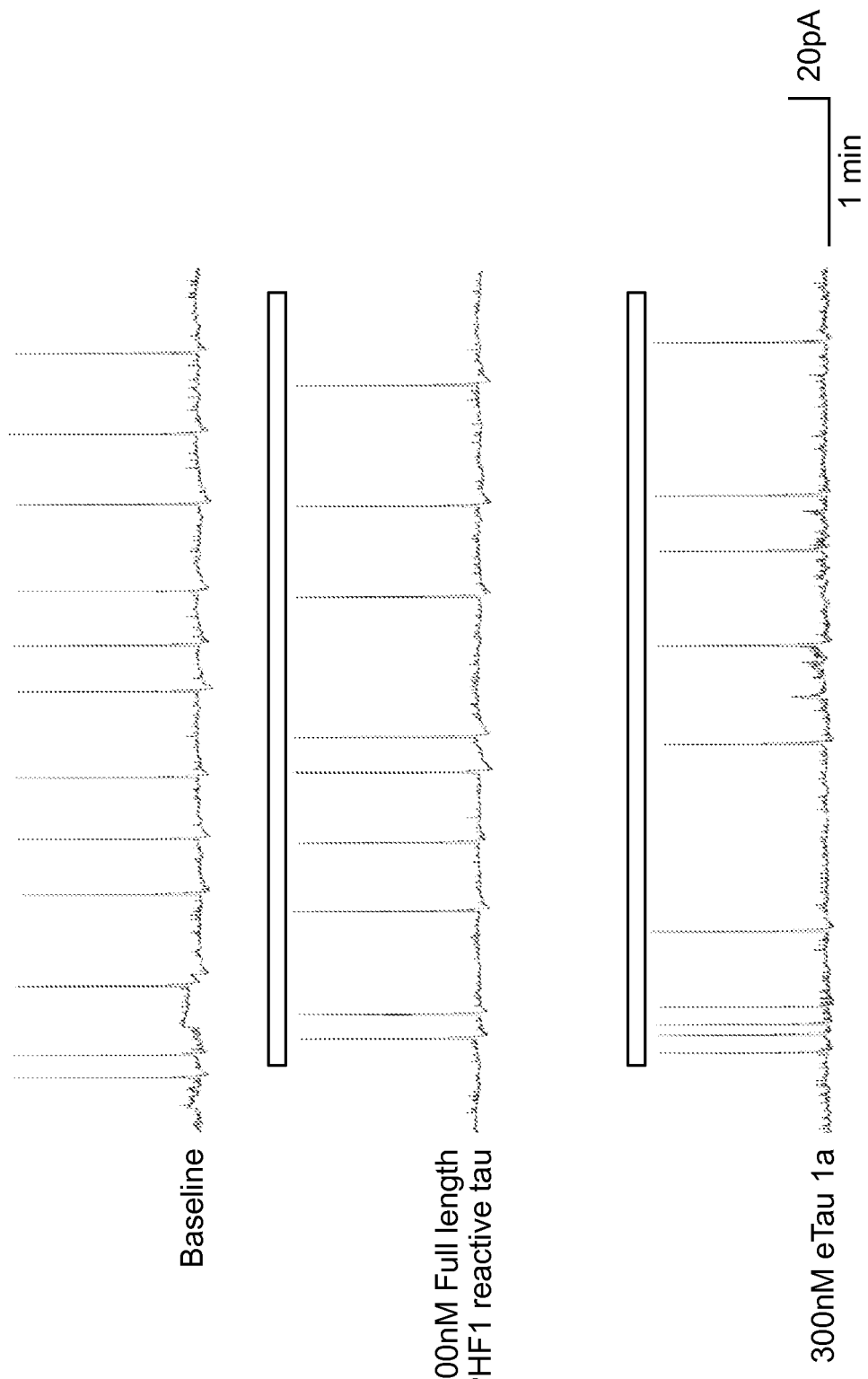
FIG. 35 depicts the effect of full-length, PHF1-reactive tau, or eTau1a, on neuronal hyperexcitability in cortical neurons in vitro.

The data are shown in FIGS. 34 and 35. As shown in FIG. 34, IPN002 reduced eTau1a-induced neuronal hyperactivity. Neither control IgG nor "Dako" (anti-C-terminal polyclonal Ab) effected a significant reduction in neuronal hyperactivity. PHF1 did not reduce eTau1a-induced neuronal hyperactivity.

Figure 36:
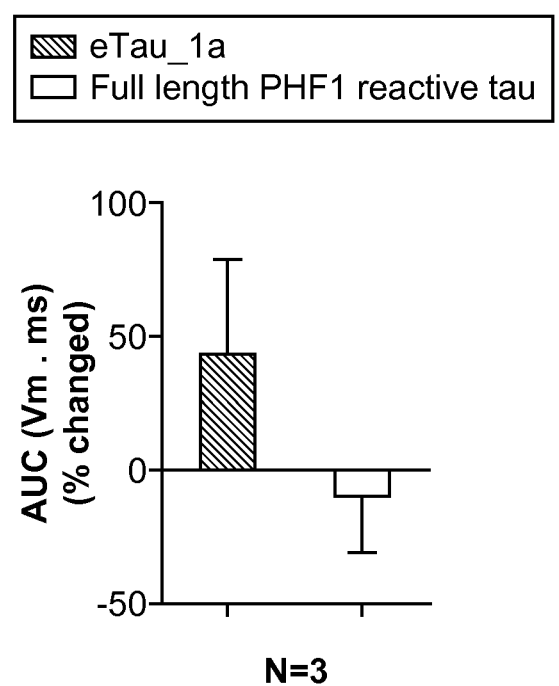
FIG. 36 depicts graphically the effect of full-length, PHF1-reactive tau, or eTau1a, on neuronal hyperexcitability in cortical neurons in vitro.

The effect of eTau1a on neuronal hyperactivity was compared to the effect of full-length, PHF1-reactive, phosphorylated Tau (phospho-Tau) on neuronal hyperactivity. As shown in FIG. 35, middle panel, full-length, PHF1-reactive, phospho-Tau did not induce neuronal hyperactivity in 2 of the 3 cells tested; the third cell tested showed only a small degree of neuronal hyperactivity, compared to baseline (top panel). In contrast, eTau1a induced neuronal hyperactivity in all 3 cells tested (bottom panel). These data are depicted graphically in FIG. 36.

Example 17

Effect of IPN002 on Aβ Levels

Materials and Methods

Aβ Secretion from iPSC-Derived Cortical Neurons iPSC-derived cortical neurons (iPSC-CN) were cultured in vitro. The iPSCs were generated from healthy individuals; individuals with familial AD with a mutation in a presenilin protein (PSEN1); an individual with familial AD with a mutation in a presenilin protein (PSEN2); and an individual with sporadic AD (sAD). After approximately ~55-60 day in culture, iPSC-CN were sorted based on L1-CAM (CD171) expression to enrich for mature cortical neurons; the sorted cells were grown in co-culture with normal human astrocytes for 30 days. After co-culturing for 30 days, iPSC-CN were treated for an additional 25 days with various concentrations of beta-site amyloid precursor protein cleaving enzyme (BACE) inhibitor, control IgG, or IPN002, with 2×/week media changes. Conditioned media was collected and tested in Millipore High Sensitivity Human Amyloid-beta 40 and Amyloid-beta 42 ELISAs, to detect Aβ$_{1-40}$ ("Aβ40") and Aβ$_{1-42}$ ("A42"). Aβ40 and Aβ42 are cleavage products of amyloid precursor protein; senile plaques contain both Aβ42 and Aβ40.

Aβ Secretion from Primary Human Cortical Neurons

Human fetal cerebral cortical tissue was obtained by Advanced Bioscience Resources (Alameda, Calif.) and complied with federal guidelines for fetal research and with the Uniform Anatomical Gift Act. The tissue was rinsed in Hank's buffered saline solution (Cellgro) and triturated in the presence of 1 mg/ml DNase (EMD) and passed through a 100 mm cell strainer. After centrifugation, the pellet was resuspended in 0.05% trypsin/EDTA (Invitrogen) for 20 min at 37° C. Trypsin was inactivated by adding an equal volume of media containing 10% fetal bovine serum (FBS) and sample gently triturated again in presence of DNase. After centrifugation, cells were resuspended in plating media (Neurobasal containing B27, Invitrogen) and counted. Cells were plated, cultured for 5 weeks and fresh media added containing antibodies at the stated concentrations for 10 days with media changes every 3-4 days with conditioned media collected after 10 days of treatment. Conditioned media was spun at 15,000 rpm for 15 minutes prior to processing for Aβ40 and Aβ42 ELISA analysis, as described above.

Results

Figure 37:
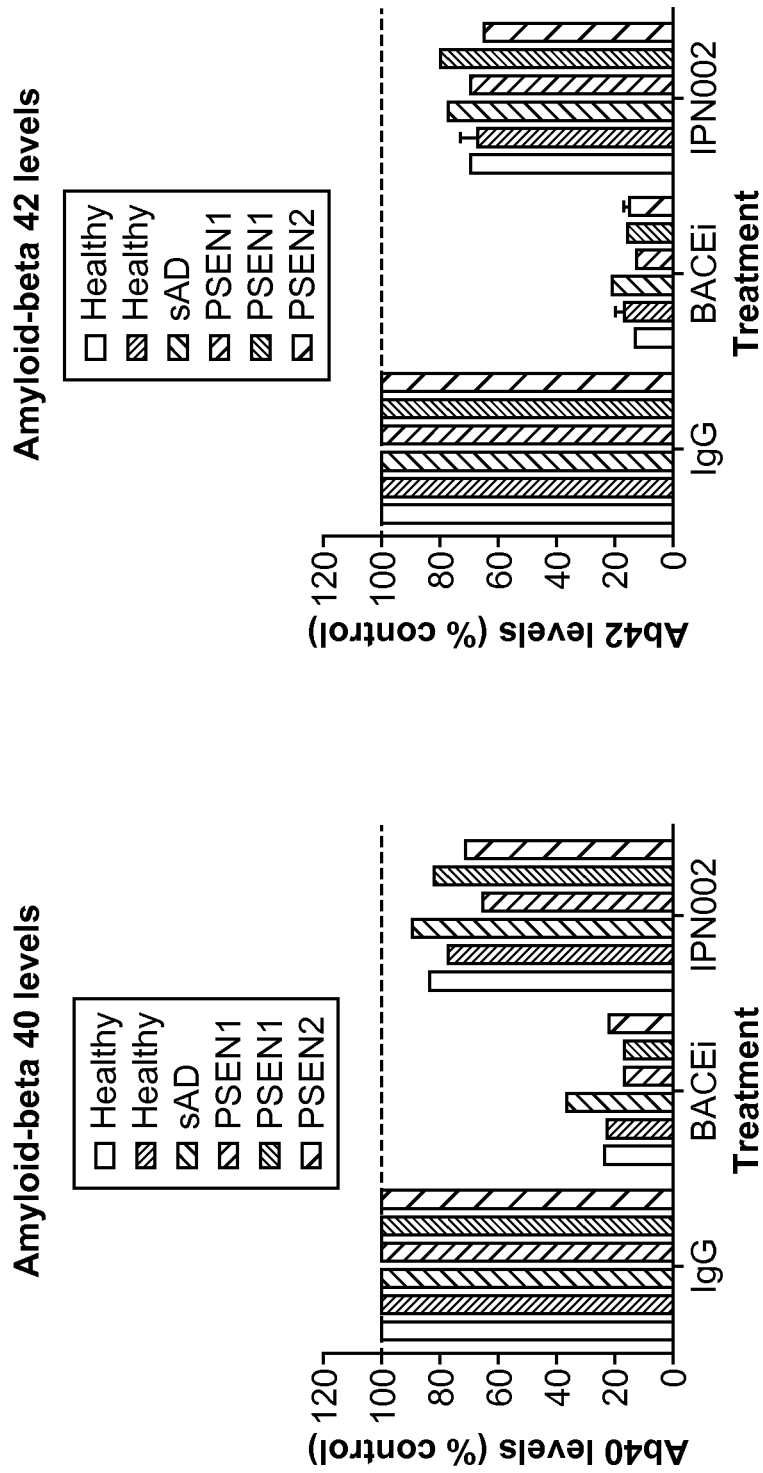
FIG. 37 depicts the effect of control IgG, BACE inhibitor, or IPN002 on levels of Aβ40 (left panel) or Aβ42 (right panel) secreted from cortical neurons.
Figure 38:
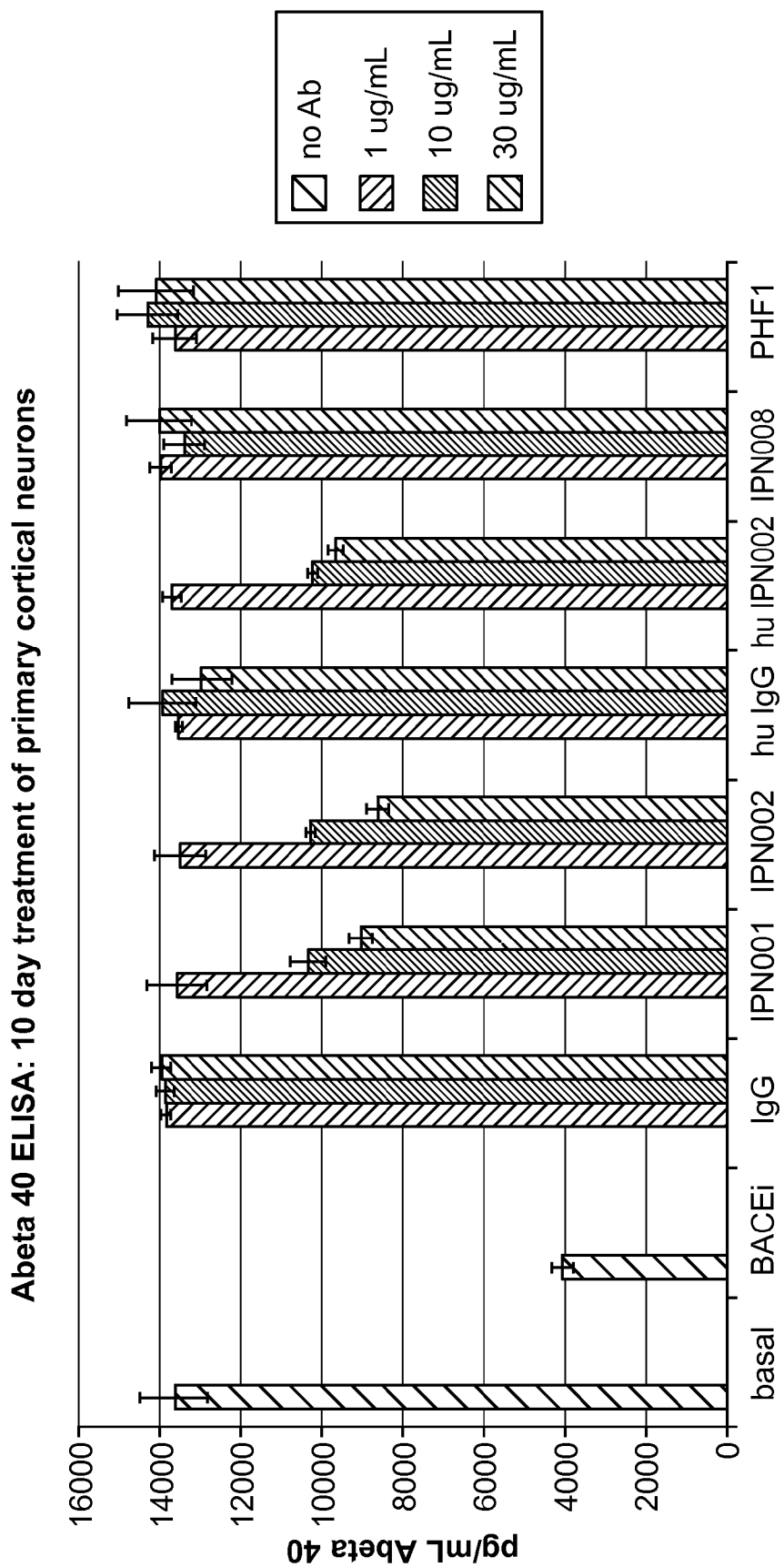
FIG. 38 depicts the effect of control IgG, BACE inhibitor, or anti-Tau antibodies on levels of Aβ40 secreted from primary cortical neurons.
Figure 39:
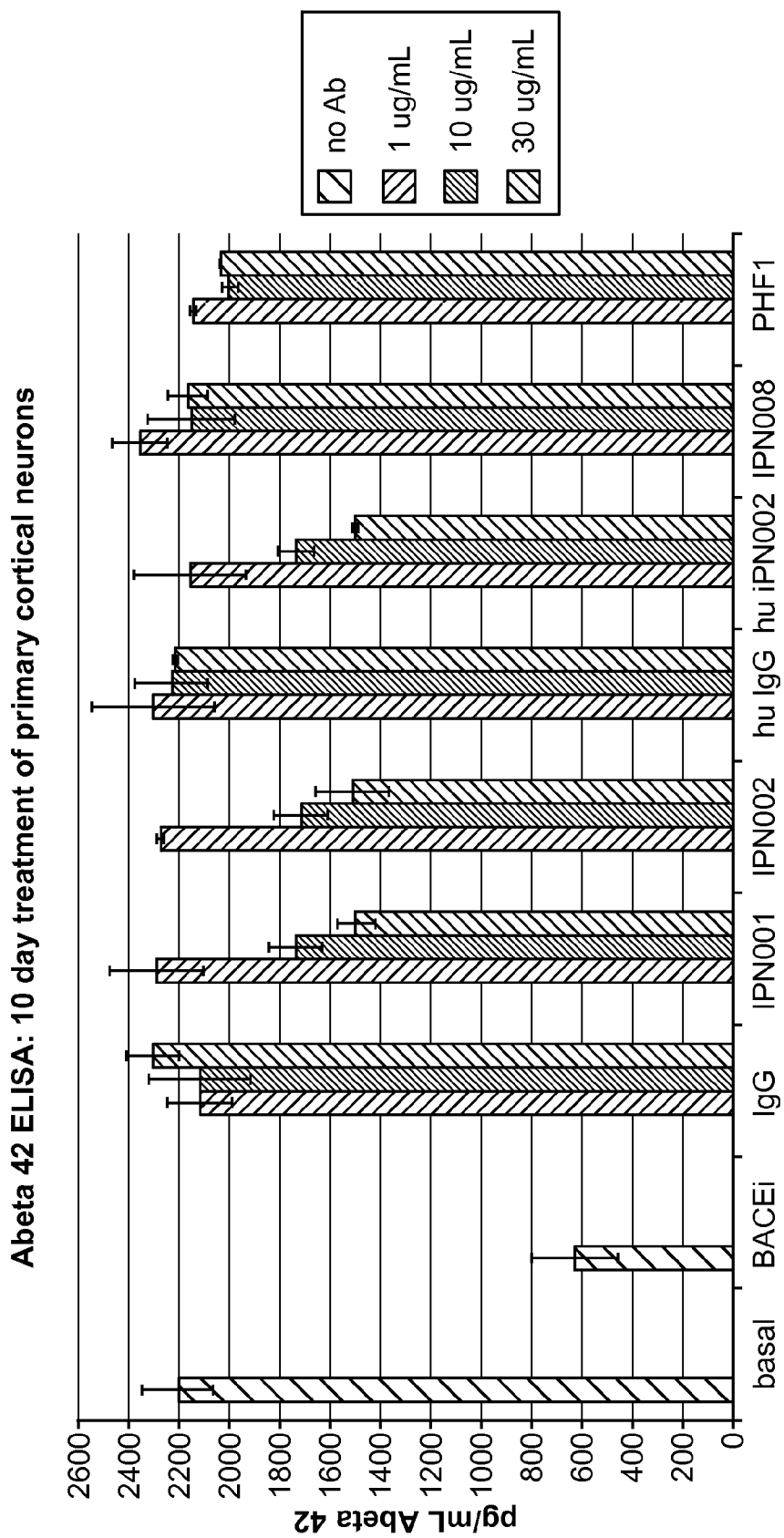
FIG. 39 depicts the effect of control IgG, BACE inhibitor, or anti-Tau antibodies on levels of Aβ42 secreted from primary cortical neurons.

The results are shown in FIGS. 37-39.

As shown in FIG. 37, treatment of iPSC-CN with IPN002 reduced the levels of Aβ40 and Aβ42 secreted by all iPSC-CN, whereas control IgG did not reduce Aβ40 or Aβ42 secretion.

FIG. 38 shows dose-dependent effects of various antibodies on the amount of Aβ40 secreted by primary human cortical neurons. As shown in FIG. 38, incubation of primary human cortical neurons with 10 μg/ml or 30 μg/ml IPN001, IPN002, or hu-IPN002 (humanized variant of IPN002) reduced the amount of Aβ40 secreted. Neither control IgG nor PHF1 had any significant effect on the amount of Aβ40 secreted.

FIG. 39 shows dose-dependent effects of various antibodies on the amount of A1342 secreted by primary human cortical neurons. As shown in FIG. 39, incubation of primary human cortical neurons with 10 μg/ml or 30 μg/ml IPN001, IPN002, or hu-IPN002 reduced the amount of Aβ42 secreted. Neither control IgG nor PHF1 had any significant effect on the amount of Aβ42 secreted.

Example 18

Epitope Mapping of a Humanized Variant of IPN002

Materials and Methods

Antibody or biotinylated peptide was diluted in phosphate-buffered saline (PBS). The final concentrations were as follows: 1 µg/ml humanized variant of IPN002 (hu-IPN002); 1 µg/ml rTau383 (full-length recombinant Tau); 5 µg/ml biotinylated Peptides. 100 µl 0.1% casein in PBS was added to wells of a multi-well plate. 150 µl of the 1 µg/ml solution of hu-IPN002 was added. Serial dilutions of hu-IPN002 were made, and were coated onto wells of a multi-well plate. 100 µl biotin-peptides or biotin-full-length Tau were added to the wells containing serially diluted antibody. The multi-well plate was incubated for one hour at room temperature. After the incubation period, wells were washed 5 times with a solution of 0.05% Tween 20 in PBS; followed by 2 washes with PBS.

Streptavidin-horse radish peroxidase (HRP)-conjugated secondary antibody was added to wells, and the plates were incubated at room temperature for 1 hour. After the incubation period, wells were washed 5 times with a solution of 0.05% Tween 20 in PBS; followed by 2 washes with PBS.

HRP substrate 3,3',5,5'-tetramethylbenzidine (TMB) was added, and incubated for 1-15 minutes. The reaction was stopped by addition of 100 µl 1 N sulfuric acid. Absorbance at 450 nm was read.

Results

Figure 40:
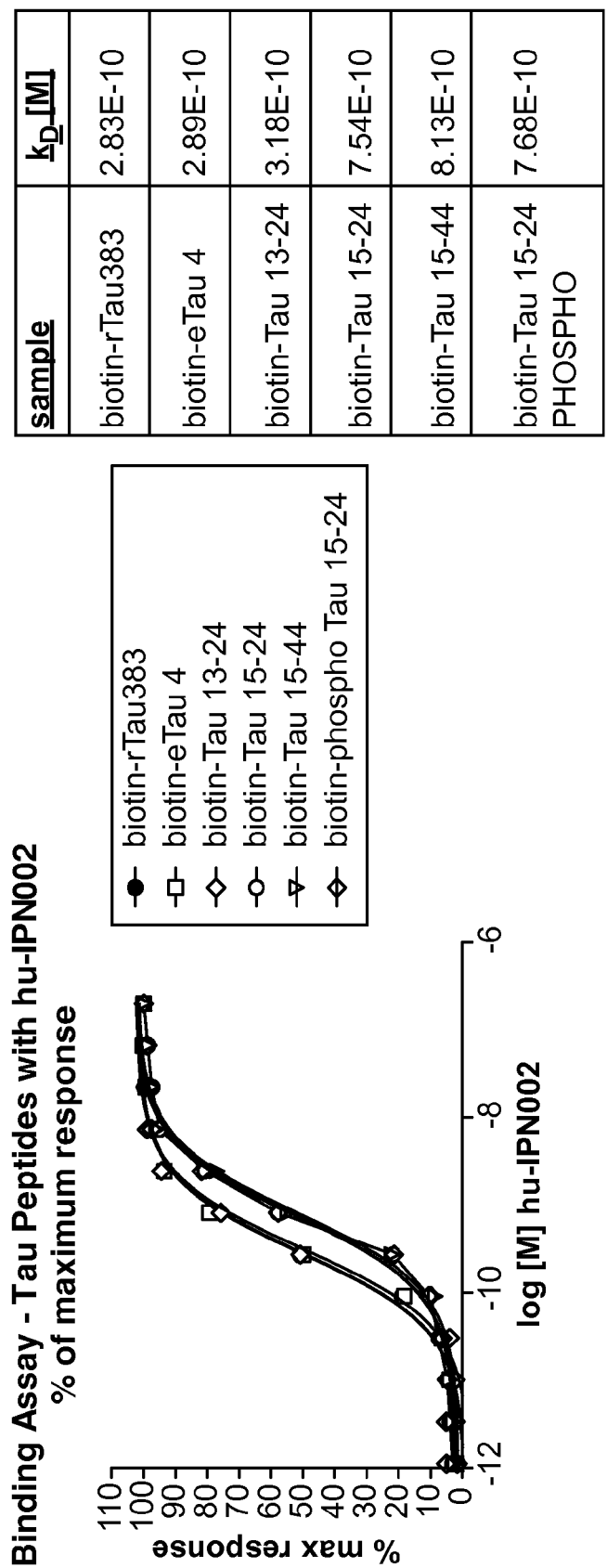
FIG. 40 depicts results of epitope mapping of a humanized variant of IPN002 (hu-IPN002).

The data are shown in FIG. 40. The data presented in FIG. 40 show that biotin-Tau 13-24, biotin-Tau 15-24, biotin-Tau15-44, and biotin-phospho Tau 15-24 (with a phosphorylated Tyr corresponding to amino acid 18 of full-length Tau), and full-length Tau (rTau383) all bound efficiently to hu-IPN002. Thus, hu-IPN002 binds an epitope within Tau amino acids 15-24, regardless of the phosphorylation status of Tyr-18.

Example 19

Antibody Binding to Tau in CSF

Binding of IPN002, PHF1, an antibody specific for a linear phosphorylated epitope, and control antibody, to tau present in CSF was assessed.

A binding assay to identify antibodies that bind tau present in CSF was developed. The assay is depicted schematically in FIG. 41. Control IgG, polyclonal antibody specific for a linear phosphorylated epitope ("polyAb-C-terminal tau"), PHF1, or IPN002 was coated on wells of a multi-well plate. Antibody was diluted in phosphate-buffered saline (PBS). The final concentrations were as follows: 5 µg/ml IPN002, IgG, PHF1, or polyAb-C-terminal tau. 100 µl 0.1% casein in PBS was added to wells of a multi-well plate. 100 µl 1 human CSF was added and incubated for 1 hour at RT. 100 µl 1 biotin-BT2+biotin-HT7 were added to the wells. BT2 is a mouse monoclonal antibody that binds an epitope within amino acids 194-198 of human tau. HT7 is a mouse monoclonal antibody that binds an epitope within amino acids 159-163 of human tau. The multi-well plate was incubated for one hour at room temperature. After the incubation period, wells were washed 5 times with a solution of 0.05% Tween 20 in PBS; followed by 2 washes with PBS.

Streptavidin-horse radish peroxidase (HRP)-conjugated secondary antibody was added to wells, and the plates were incubated at room temperature for 1 hour. After the incubation period, wells were washed 5 times with a solution of 0.05% Tween 20 in PBS; followed by 2 washes with PBS. HRP substrate 3,3',5,5'-tetramethylbenzidine (TMB) was added, and incubated for 1-15 minutes. The reaction was stopped by addition of 100 µl 1 N sulfuric acid. Absorbance at 450 nm was read.

The assay was quantitated using known amounts of full-length phospho-tau or known amounts of eTau1a (amino acids 2-166 of tau). As shown in FIG. 41, lower panel, the assay was carried out using full-length tau (lower left panel) or eTau-1a (lower right panel), in concentrations of 0 ng/ml, 0.16 ng/ml, 0.8 ng/ml, 4 ng/ml, 20 ng/ml, and 100 ng/ml. As shown in FIG. 41, lower left panel, IPN002, polyAb-C-terminal tau, and PHF1 bind full-length tau. As shown in FIG. 41, lower right panel, only IPN002 binds eTau1a.

Figure 42:
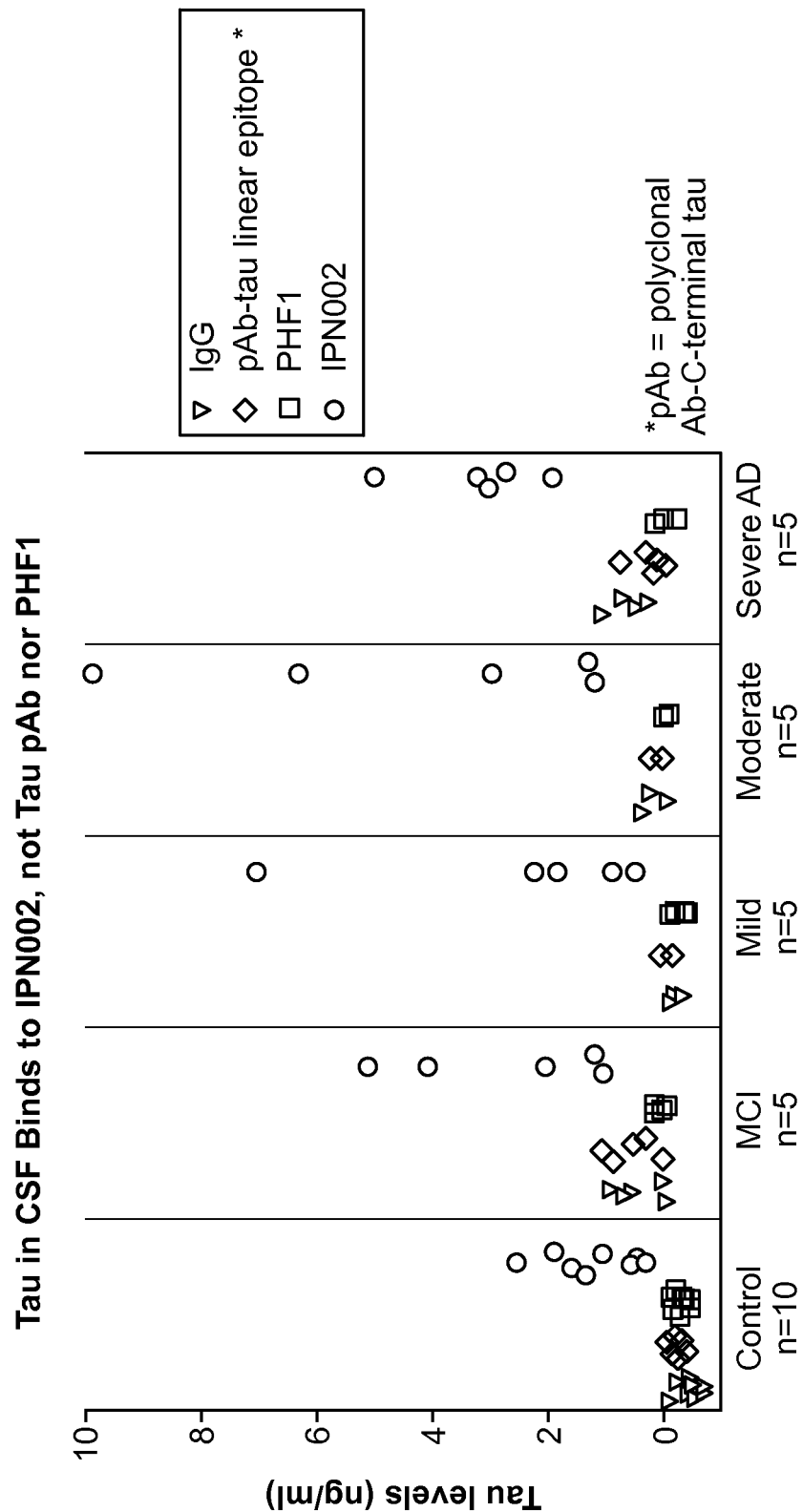
FIG. 42 depicts binding of Tau in CSF by IPN002, PHF1, or a polyclonal antibody that binds a linear epitope in the C-terminal portion of Tau (pAb-tau linear epitope).

The above-described assay was carried out to test binding of polyAb-C-terminal tau, PHF1, and IPN002 to tau present in human CSF from: 1) control (healthy) patients; 2) MCI patients; 3) patients with mild AD ("mild"); 4) patients with moderate AD ("moderate"); and patients with severe AD. The results are shown in FIG. 42. As shown in FIG. 42, tau present in CSF is bound by IPN002, but not by pAb-tau linear epitope or by PHF1. The data show that: 1) N-terminal Tau fragments are present in CSF; 2) full-length tau was detected in CSF; and 3) no C-terminal tau fragments that include BT2 and HT7 epitopes were detected in CSF.

Example 20

In Vivo Effects of IPN002

Results were obtained from a six month tau antibody efficacy study in P301L tau transgenic mice. It was found that IPN002 globally reduces disease progression, as exemplified by dramatically lowered free tau levels in the CSF, reduced levels of a protein marker of astrogliosis, improvement in tau pathology across multiple brain regions and phosphotau epitopes, and improved behavioral/functional read outs. IPN002 performed as well or better than the anti-tau antibody PHF1. Finally, in vivo confirmation was obtained for a novel secreted tau mechanism-of-action: positive feedback regulation of amyloid-beta levels. This study clearly distinguished the ability of the eTau antibody, IPN002, compared to PHF1, to modulate amyloid beta levels.

Materials and Methods

Animal Studies

The P301L transgenic mouse model was used. The P301L transgenic mouse includes a murine Thy1 promoter (neuron-specific expression) expression driven 4R2N human tau mutated at P301L as a transgene. The P301L transgenic model displays an age-dependent hyperphosphorylation of tau (AT8 and AT100) in spinal cord, brainstem, midbrain and cortex. The hyperphosphorylated tau shows conformational changes which lead to tau aggregation and mice develop neurofibrillary tangles from the age of 6 months, although with a high variability of onset. Concomitant to the pathology, these mice progressively develop motoric deficits such as hind limb clasping, decreased mobility on beam walk and require premature sacrifice at the age range between 8-11 months. Terwel et al. (2005) *Proc. Natl. Acad. Sci. USA* 280:3963.

100 randomized mice were dosed i.p. weekly with antibody from 3.5 months of age for 6 months through 9.5 months of age. 20 mg/kg (mpk) IPN002 treatment was compared to a negative control antibody, 20 mpk IgG1, and to an anti-tau antibody, 10 mpk PHF1. PHF1 is a mouse monoclonal antibody that recognizes an epitope that includes phospho-Ser$^{396}$ and phospho-Ser$^{404}$. Santacruz et al. (2005) *Science* 309:476. Living mice were examined for clasping deficits and on beam walk performance. Mice that rapidly progressed to end-stage disease were prematurely sacrificed (prior to 9.5 months of age) using predetermined criteria. Serum, CSF, hippocampus, cortex, mid-brain and hind brain were obtained; and hemibrains were sagittally sectioned for histopathology. Antibody levels were measured in serum and CSF; total tau and free tau (tau not bound to IPN002; "free of IPN002" tau) were measured in CSF; biochemical/histological analyses on human and mouse tau were conducted; and mouse amyloid-beta, inflammatory and synaptic protein markers and gene expression changes in inflammatory, synaptic and neuronal activity markers were analyzed. All analyses were conducted in a blinded manner.

The numbers of mice dedicated to this study were 25-33 mice per study arm and 10 for baseline. All mice reserved for this study were given a random number by computer and allocated randomly to a treatment. The mouse groups are shown in Table 7.

TABLE 7

| Group | N | Strain | Treatment |
|---|---|---|---|
| 1 | 10 | hTau.P301L-Tg | None (baseline group) |
| 2 | 32 | hTau.P301L-Tg | 20 mpk mIgG1 in vehicle |
| 3 | 25 | hTau.P301L-Tg | 10 mpk PHF1 in vehicle |
| 4 | 33 | hTau.P301L-Tg | 20 mpk IPN002 in vehicle |

Clasping Behavior.

To score clasping behavior, mice were kept by the base of their tail for ten seconds. Hind limb clasping is scored using a 3-point rating scale: 0. Hind limbs stretched and toes spread. 1. One hind limb partially retracted >50% of the time. 2. Both hind limbs partially retracted >50% of the time. 3. Both hind limbs retracted completely during >50% of the time. Forelimb clasping is scored according to 0. Forelimbs stretched forward and distant from body. 1. One forelimb partially retracted >50% of the time. 2. Both forelimbs partially retracted >50% of the time. 3. Both forelimbs completely retracted, immobile, muscle loss, mouse is "praying". The mice showing severe clasping phenotype were early sacrificed.

Beam Walk.

The beam walk was performed at 7 months, 8 months, 8.5 months, 9 months, and 8.5 months of age to determine motor dysfunction and motor learning. The ability of a mouse to balance on the beam and the time needed to walk 1 meter is a measure of its balance, coordination, physical condition, and motor-planning A copper beam with a circular diameter of 12 mm was placed at an angle of 30°. The start area was illuminated and an indoor escape platform was placed at the far end. After the training trials, the latency of the mice was timed. In addition, foot slips and belly dragging were counted.

The baseline group was sacrificed prior to study initiation. Mice in the study arms that displayed severe clasping, reduced body weight and/or became moribund were prematurely sacrificed (early sacrifice). The remaining mice were sacrificed after 6 months of treatment (late sacrifice).

TABLE 9

| | |
|---|---|
| Anaesthesia | A mixture of ketamine, xylazine 2%, atropine and saline/isoflurane. |
| Perfusion | The thoracic cavity was accessed for perfusion via trans-cardial perfusion with ice-cold saline for 3 minutes via the left ventricle. The right atrium was cut as an outflow route. |
| Left hemisphere | Dissected into hippocampus, cortex, midbrain, cerebellum and brainstem and rest, frozen in liquid nitrogen. |
| Right hemisphere | Post-fixed overnight in PBS with 4% paraformaldehyde and stored in PBS with 0.1% sodium azide at 4° C. |
| CSF | Collected via incision in the neck muscles between the skull and the first cervical vertebrae. The cisterna magna was punctured with a 26 gauge needle and 10-20 ul CSF collected, centrifuged at 10,000 × g at 4° C. and stored at −80° C. |
| Blood/plasma | Collected via heart puncture into EDTA-tubes, centrifuged at 2000 × g at 4° C. for 15 minutes and stored at −70° C. |
| Body weight | Measured at sacrifice |

All animal experiments were conducted in accordance with bioethical guidelines that are fully compliant to internationally accepted principles for the care and use of laboratory animals. Table 8 provides the treatment parameters.

TABLE 8

| | |
|---|---|
| Administration route | i.p. |
| Dosing volume, concentration | 10 ml/kg; 1 mg/ml; 10 mpk/day |
| Frequency of treatment | Once per week |
| Duration of treatment | Up to 6 months dependent on survival |
| Allocation to treatment group | Randomized |

Body weights were determined weekly during treatment and at sacrifice. Clasping scores were recorded weekly from 7 months of age onward. From 7 months of age onward, mice were monitored twice a week for mobility in cage, weight loss and first signs of clasping of the hind limbs.

Free PHF1 in plasma was measured by adding appropriately diluted plasma to tau-coated plates and detecting using an ELISA with HRP-anti-mouse IgG antibody and TMB. The sensitivity of the Free PHF1 assay was insufficient to measure free PHF1 levels in the CSF.

Free IPN002, in plasma and in CSF, was measured by adding appropriately diluted plasma or CSF to tau-coated plates and detecting using an ELISA with HRP-anti-mouse IgG antibody and TMB.

Total tau in CSF was measured using a sandwich ELISA using both coating anti-tau antibody and detecting anti-tau antibodies that were demonstrated to not compete with either IPN002 or PHF1.

Free tau (of IPN002) in CSF was measured using a homogenous ELISA using two anti-tau antibodies to capture the tau in CSF. One of these antibodies competes with IPN002 and therefore will not interact with the tau that is previously bound to IPN002 in the CSF.

Hippocampus and cortex was fractionated by homogenizing in 10 weight volumes of cold TBS/Roche protease/phosphatase inhibitor cocktail. The homogenate was generated by spinning debris out at 10,000×g for 15 minutes. BCA protein content was conducted on homogenates; all homogenates were diluted to 1 mg/ml and corresponding fractions diluted equivalently. A portion of the homogenate was spun 1 hour at 100,000×g at 4° C. to generate a soluble fraction (S1) and insoluble pellet. The insoluble pellets were resuspended in 1% Sarkosyl/Roche protease/phosphatase inhibitor cocktail and spun again for 1 hour at 100,000×g. The Sarkosyl solubilized supernatants were labeled (P1); the Sarkosyl insoluble pellet was resuspended and was labeled (P2). The hindbrains were similarly fractionated, except high salt (0.85M NaCl) followed by 1% Sarkosyl was used to solubilize the P1 pellets.

The human tau homogenous ELISA specifically reports on human tau and was used to determine human tau levels in the homogenate, 51, P1 and P2 fractions in hippocampus, cortex and hindbrain.

The human AT8 homogenous ELISA specifically reports on human p202/205 tau and was used to determine human AT8 levels in the homogenate, 51, P1 and P2 fractions in hippocampus, cortex and hindbrain.

HT7, IPN001, Dako polyclonal-tau, AT8, AT100, anti-p262, anti-p396 and AD2, GFAP, Iba1, synapsin SDS-PAGE Western blots were conducted on hippocampus, cortex and/or hindbrain fractions (Homogenate, 51, P1 and/or P2). One or more lysate controls were run on each gel to ensure proper normalization between gels. All analyzed bands were normalized to β-actin in the corresponding homogenate sample. Antibodies and their targets are shown in Table 10.

TABLE 10

| Antibody | Target |
| --- | --- |
| IPN001 | Tau and eTau |
| HT7 | Human tau |
| Dako polyclonal tau | Human and mouse tau |
| AT8 | Human and mouse p202/205 (phosphorylated at Ser202 and Thr205) tau |
| AT100 | Human and mouse p212 (phosphorylated at Ser212) tau |
| Anti-p262 | Human p262 (phosphorylated at Ser262) tau |
| AD2 | Human and mouse p396 (phosphorylated at Ser396) tau |
| p396 | Human and mouse p396 (phosphorylated at Ser396) tau |
| glial fibrillary acidic protein (GFAP) | Mouse GFAP on astrocytes |
| ionized calcium binding adaptor molecule 1 (Iba1) | Mouse Iba1 on microglia |
| Synapsin | Mouse synapsin (synaptic protein) |

For histopathology, 6/32 randomized, sagittally sectioned hemibrains were stained for AT8 and AT100; signals were developed with DAB. Both the Subthalamic nucleus annex zona incerta (bregma 2.08-1.12) and the Interposed nucleus of the cerebellum (anterior and posterior part) annex lateral cerebellar nucleus (IntA/P/LAT; bregma 2.28-1.32) were quantified (blinded).

Mouse amyloid-beta ELISAs (both Aβ40 and A1342) were conducted for specific detection of Aβ40 and Aβ42 in mouse brain homogenates. The mouse Aβ42 ELISA was not sensitive enough to reliably detect levels in mouse brain homogenates. The mouse Aβ40 ELISA detected mouse Aβ40 levels well within the linear range of the assay. The mouse Aβ40 ELISA was used to determine Aβ40 levels in all cohort homogenates and soluble (S1) fractions.

Taqman analysis was conducted on markers of inflammation, synaptic markers and markers of neuronal activity. Table 11 lists the markers.

TABLE 11

| Gene | Function |
| --- | --- |
| APP | Amyloid precursor protein: mutated/causal in some fAD patients |
| Human Tau | MTB protein; aggregates in AD |
| Arc | Neuronal activity |
| Synapsin | Synaptic protein |
| Synaptophysin | Synaptic protein |
| Calbindin | Synaptic protein |
| Neuropeptide Y | Neuronal activity |
| Cox2 | Inflammation |
| GFAP | Inflammation-astrocyte |
| Iba1 | Inflammation-microglia |
| IL-1b | Inflammation |
| P67phox | Inflammation |
| Pg91phox | Inflammation |
| PBR1 | Inflammation |
| TNFa | Inflammation |

Statistics

Clasping and Beam walk Longitudinal statistical analysis was conducted by an independent statistician. In brief, the slope of the curve of decline was determined for each mouse both for clasping deficit and beam walk and these coefficients used to determine if significant differences existed between groups. Multiple methods were used to determine the slope of the curves and significance. For clasping these included Longitudinal Complete Case Analysis, Joint Model Adjusting for Missing Data and Bayesian Ordered Longitudinal Analysis. For Beam walk these included Longitudinal Complete Case Analysis, Joint Model Adjusting for Missing Data, Longitudinal Analysis using 30 Second Values, Bayesian Longitudinal Analysis with Missing Values and Alive but Non-cross Analysis.

Statistical analysis to determine significance for biochemistry, histology and gene expression was conducted on whole cohort, early sacrifice and late sacrifice cohorts using one-way ANOVA followed by Dunnett's post-hoc analysis. The t-test was also conducted for disease progression (3.5 month baseline vs 9.5 month IgG treated arms) as a comparator to significance derived from one-way ANOVA analysis. When PHF1 or IPN002 appeared to be greatly trending toward changes but not reflecting this by one-way ANOVA analysis, t-test comparing IgG to PHF1 or IPN002 was conducted solely to determine if trending patterns were emerging for that endpoint without reaching one-way ANOVA significance.

To determine which of the 116 endpoints best correlate with each other, a matrix correlation was conducted; and the highest correlators were rank ordered based on a combination of their $r^2$ values and p values.

Results

Antibody Levels and Target Engagement

Plasma and CSF were obtained prior to sacrifice. The levels of Free IPN002 and Free PHF1 in plasma, and Free IPN002 in the CSF, were determined. The Free PHF1 assay was not sensitive enough to measure Free PHF1 levels in the CSF. Sufficient CSF was also obtained to determine levels of both Total Tau and Free Tau (free of IPN002).

Plasma Free IPN002 and Free PHF1 Levels

P301L Tau transgenic mice were treated with 20 mpk IgG, 20 mpk IPN002 or 10 mpk PHF1. These dosages were chosen based on results from the Target Engagement #1 study. Summary data are shown in Table 12.

TABLE 12

| | Target Engagement Study #1 | | Efficacy Study | |
|---|---|---|---|---|
| Antibody | Dose administered | Average Free Antibody levels (Plasma) | Dose administered | Average Free Antibody levels (Plasma) |
| IPN002 | 10 mpk for 4 wks-> 20 mpk for 4 wks | 0.65 μM | 20 mpk for 26 weeks | 0.9 −/+ 0.26 μM |
| PHF1 | 10 mpk for 8 wks | 0.65 μM | 10 mpk for 26 weeks | 0.55 −/+ 0.05 μM |

It was found in Target Engagement #1 that 10 mpk IPN002 for 4 weeks followed by 20 mpk IPN002 for an additional 4 weeks resulted, on average, in 0.65 μM Free IPN002 in the plasma. The same concentration, 0.65 μM Free PHF1, was obtained with constant 10 mpk PHF1 throughout the 8 weeks. In the current study, as shown in Table 12, the average plasma concentrations were 0.55 μM Free PHF1 and 0.9 μM IPN002. Thus, the average levels for Free IPN002 were higher than Free PHF1 in plasma.

CSF Free IPN002 Levels

On average, 0.9 nM Free IPN002 was present in the CSF of IPN002-treated P301L tau mice, as shown in Table 13. This translates to 0.1% Free IPN002 in CSF:plasma; i.e., the concentration of IPN002 in the CSF was 0.1% of the concentration of IPN002 in plasma (0.9 nM in CSF; 0.9 μM in plasma). 0.1% antibody in CSF is consistent with percentages determined for other antibodies in accessing the brain and draining into CSF subsequent to peripheral administration. The Free IPN002 assay, however, only reports on IPN002 that is not bound to tau. Tau is bound to IPN002 in the CSF; thus, the 0.1% value underrepresents total IPN002 in the CSF. Calculations adding Free IPN002 levels to IPN002 levels bound to tau suggested that the total IPN002 levels in CSF are ~0.2% of plasma levels. As noted in the Methods, the Free PHF1 assay is not sufficiently sensitive to measure CSF levels of Free PHF1.

TABLE 13

| | Efficacy Study | |
|---|---|---|
| Antibody | Average Free Antibody (Plasma) | Average Free Antibody (CSF) |
| Free IPN002 | 0.9 −/+ 0.26 μM | 0.9 −/+ 0.28 μM |

Total Tau in CSF

Figure 43:
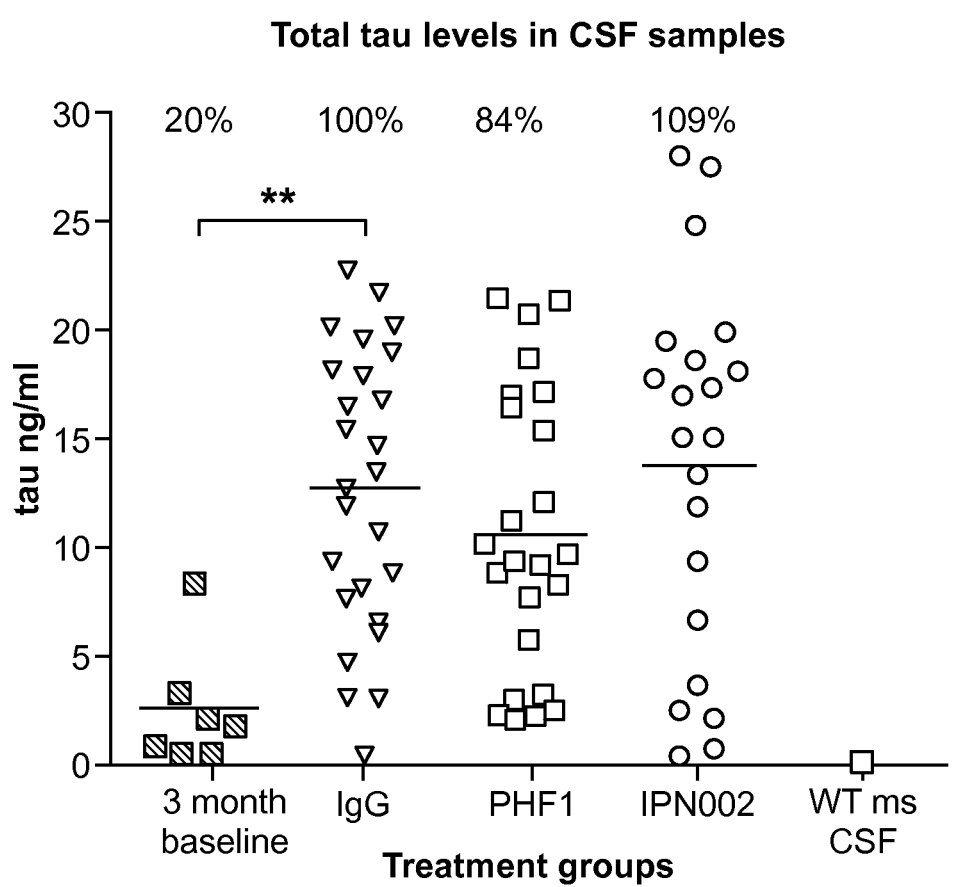
FIG. 43 depicts the effect of treatment of P301L mice with control IgG, PHF1, or IPN002 on the total tau levels in CSF.
Figure 44A:
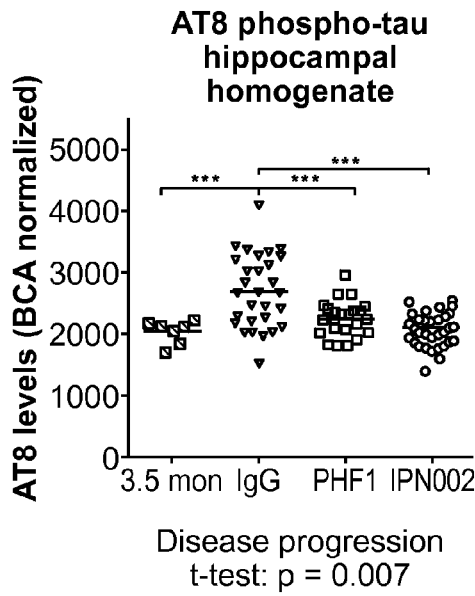
FIGS. 44A-H depict the effect of treatment of P301L mice with control IgG, PHF1, or IPN002 on AT8 phospho Tau in various brain regions and tissues.
Figure 44B:
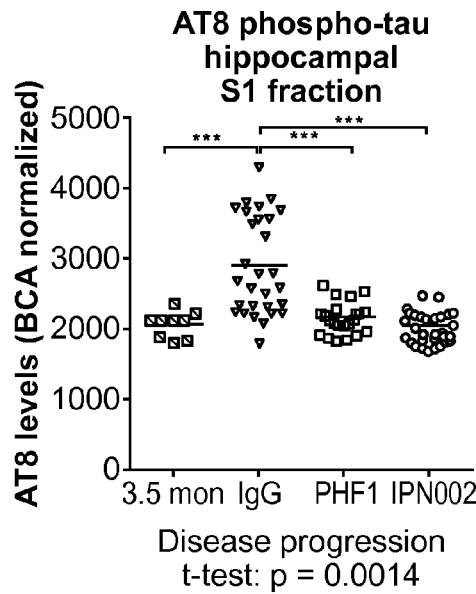
Figure 44C:
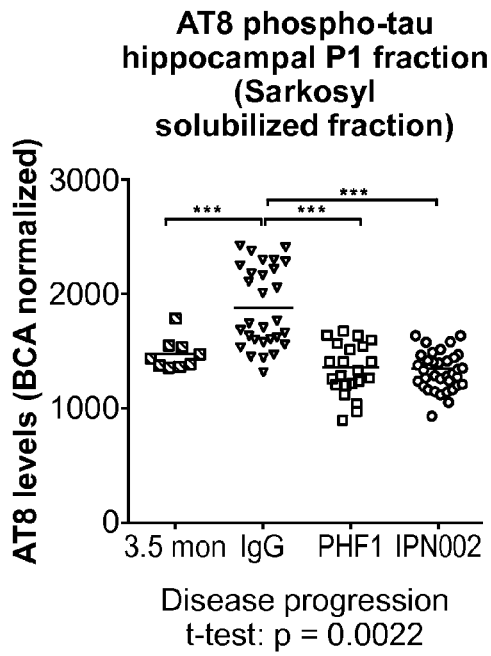
Figure 44D:
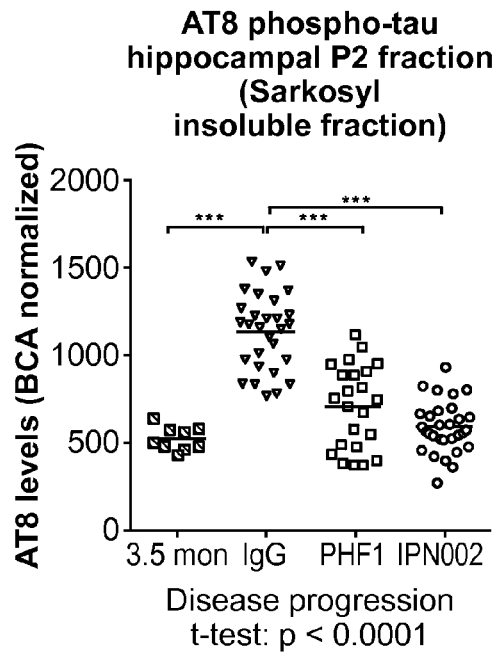
Figure 44E:
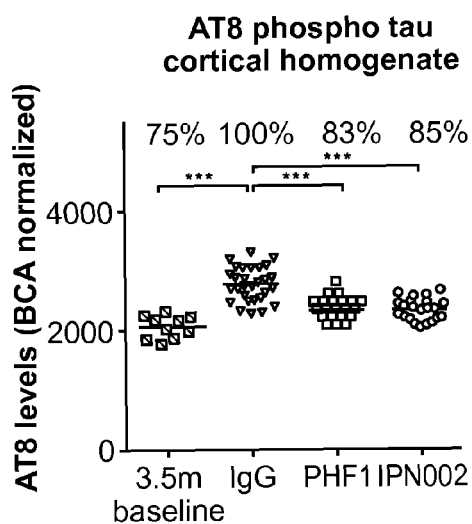
Figure 44F:
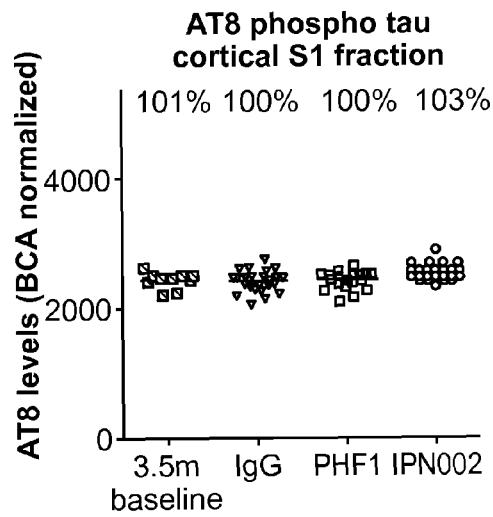
Figure 44G:
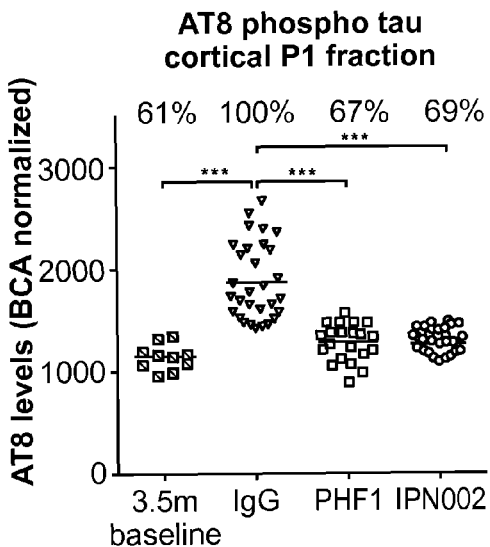
Figure 44H:
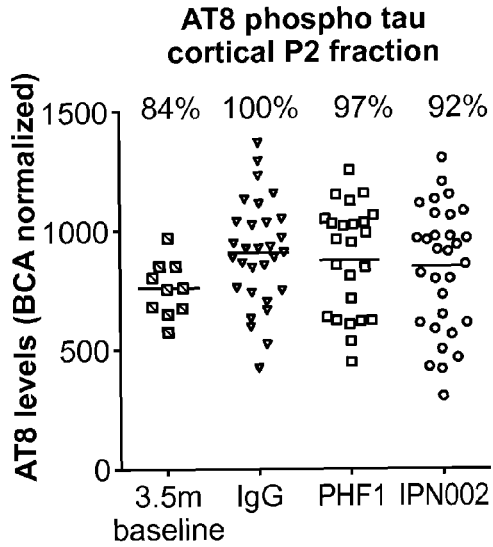

The levels of Total Tau in the CSF were measured to determine if either PHF1 or IPN002 altered these levels. As shown in FIG. 43, the levels of total tau in CSF were not significantly altered by PHF1 or IPN002 treatment. This result was expected from the data obtained in the Target Engagement Study.

FIG. 43: Total tau levels in the P301L tau transgenic mice CSF were measured using a tau antibody sandwich ELISA assay. As shown in FIG. 43, tau levels in the CSF significantly increased with age (compare 3 month baseline to mouse IgG). Neither PHF1 nor IPN002 altered total tau levels.

Free Tau (of IPN002) in CSF

The Free Tau (of IPN002) in CSF assay, as described in Methods, is an ELISA in which one of the two tau antibodies competes with IPN002; therefore, the assay will not detect tau that is bound to IPN002. This assay indicates whether IPN002 has entered the brain and CSF and has engaged its target (i.e., has bound to tau). If IPN002 has engaged its target, the signal in the assay will be lowered. This assay is specific to free tau of IPN002, and therefore does not detect Free Tau (of PHF1). As shown in FIG. 33, Free Tau (of IPN002) levels increase with disease progression consistent with the data shown above. PHF1 does not affect Free Tau levels. In contrast, IPN002 treatment resulted in a 96% reduction in levels of the Free Tau (of IPN002) signal. These data show that IPN002 has fully engaged its target, CSF tau.

Tau and PhosphoTau Biochemistry and Histology

As described in Methods, hippocampus, cortex, and hindbrain were fractionated into homogenate, soluble (Sarkosyl solubilized), and insoluble (Sarkosyl insoluble) fractions. The fractions were analyzed for both human and mouse tau, and for multiple phosphotau epitopes (AT8, AT100, p262, p396 and AD2) that are hyperphosphorylated in Alzheimer's disease brains. As shown in FIGS. 44 A-H, IPN002 treatment reduced AT8 levels in the hippocampal homogenate (FIG. 44A), hippocampal S1 fraction (FIG. 44B), hippocampal P1 fraction (FIG. 44C), hippocampal P2 fraction (FIG. 44D), cortical homogenate (FIG. 44E), and cortical P1 fraction (FIG. 44G), compared to treatment with mouse IgG control antibody. The data in FIG. 44A-H show that IPN002 treatment reduced AT8 levels to a similar or greater degree than PHF1 treatment. The data depicted in FIGS. 44A-H were normalized to BCA.

Figure 45A:
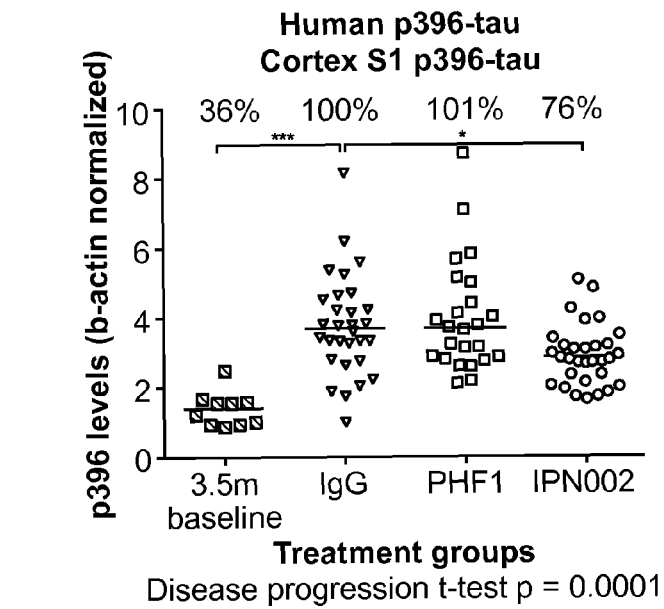
FIGS. 45A-E depict the effect of treatment of P301L mice with control IgG, PHF1, or IPN002 on the levels of phosphorylated Tau in various brain regions and tissues.
Figure 45B:
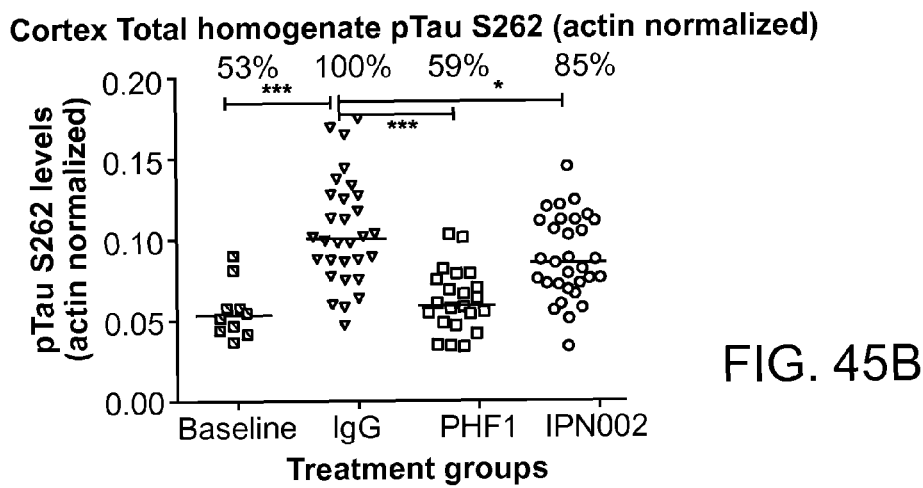
Figure 45C:
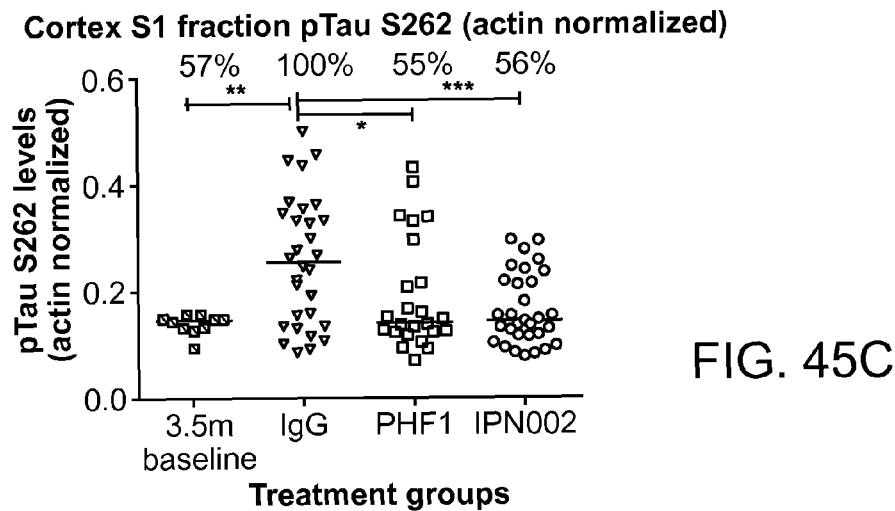
Figure 45D:
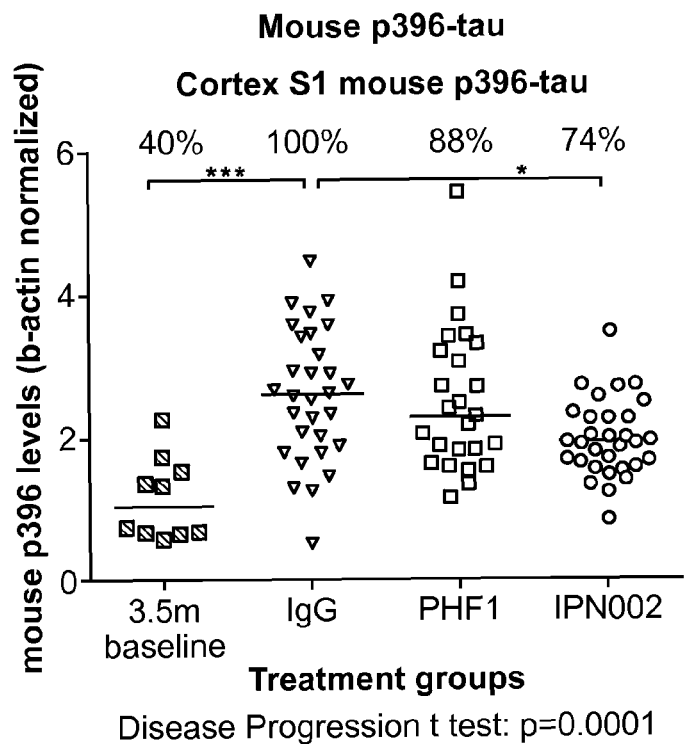
Figure 45E:
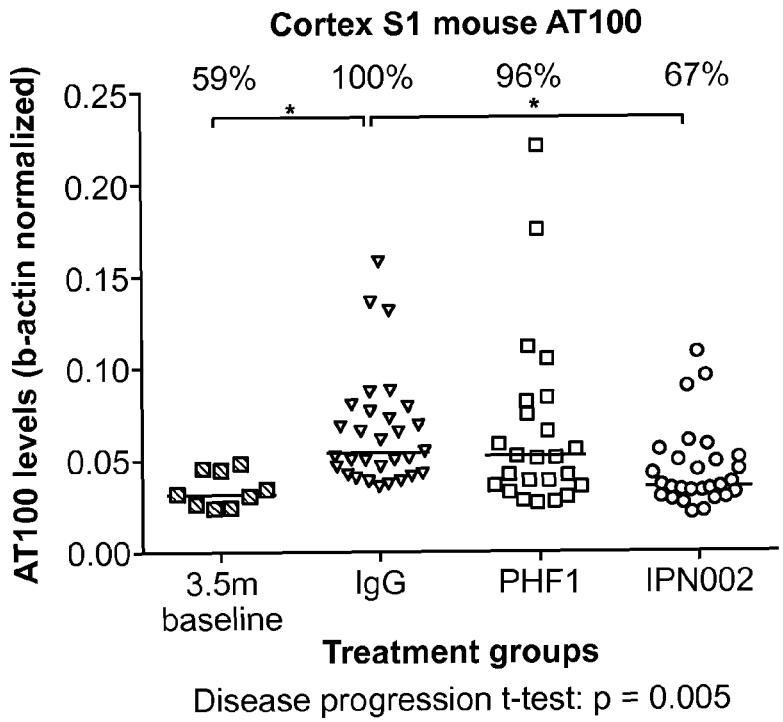

As shown in FIG. 45A, IPN002 treatment reduced the level of human p396-tau in the cortex S1 fraction, compared to treatment with mouse IgG control antibody. As shown in FIGS. 45B and 45C, IPN002 treatment reduced the level of phospho-tau 5262 in the cortex homogenate (FIG. 45B), and in the cortex S1 fraction (FIG. 45C), compared to treatment with mouse IgG control antibody. As shown in FIGS. 45D and 45E, treatment with IPN002 reduced the level of mouse p396-tau in the cortex S1 fraction (FIG. 45D), and reduced the level of mouse AT100 in the cortex S1 fraction (FIG. 45E), compared to treatment with mouse IgG control antibody.

Figure 46:
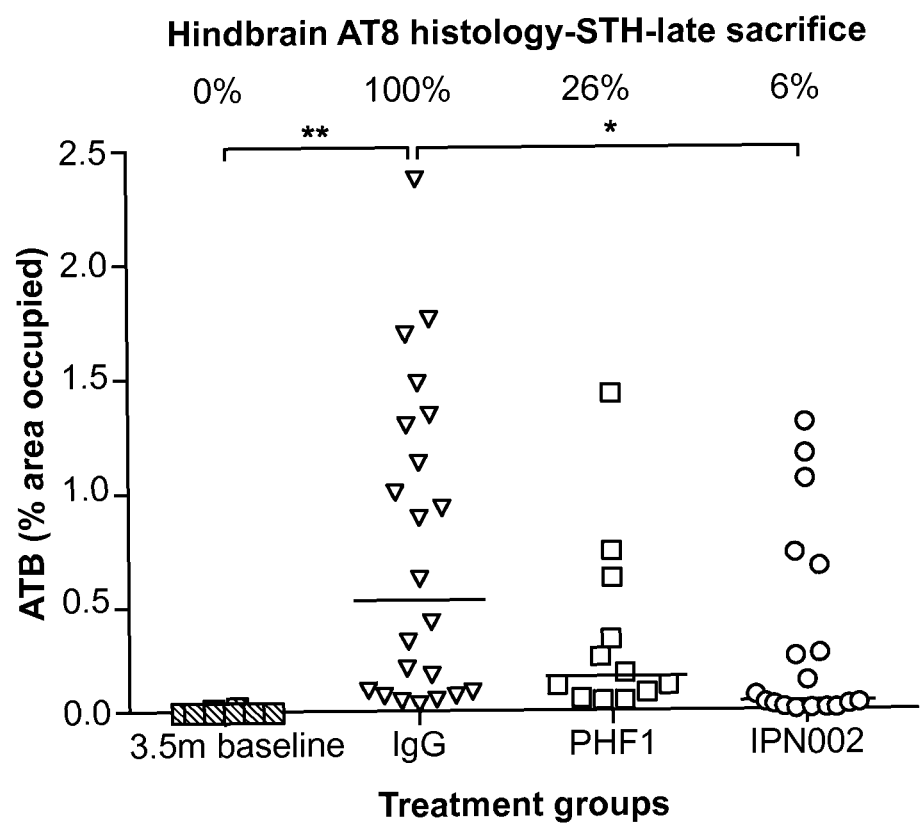
FIG. 46 depicts the effect of treatment of P301L mice with control IgG, PHF1, or IPN002 on the level of AT8 phospho Tau histology in the hindbrain.
Figure 47:
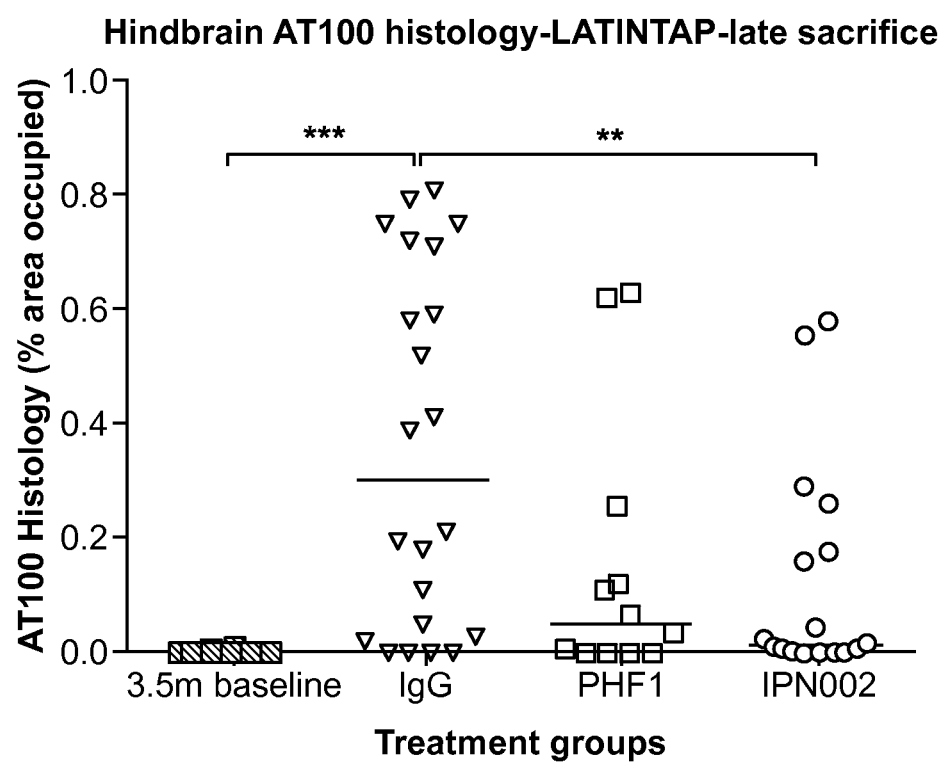
FIG. 47 depicts the effect of treatment of P301L mice with control IgG, PHF1, or IPN002 on the level of AT100 phospho Tau histology in the hindbrain.

Tau histopathology (AT8 and AT100) was analyzed in two distinct nuclei within the hindbrain, the Subthalamic nucleus annex zona incerta (STH) and the Interposed nucleus of the cerebellum (anterior and posterior part) annex lateral cerebellar nucleus (IntA/P/LAT). As shown in FIG. 46, IPN002, in the late sacrifice mice, significantly improved AT8 disease pathology. PHF1 trended toward a decrease, but did not significantly improve, tau histopathology. As shown in FIG. 47, IPN002 treatment improved AT100 and MC1 disease pathology, compared to treatment with control IgG.

Inflammation

Both astrogliosis and microgliosis develop in models of AD and tauopathies. The role that activated astrocytes or microglia play in disease, however, is not entirely clear. If astrocytes or microglia are activated in the P301L tau transgenic model, such activation would result from mutated tau overexpression. It is hypothesized that secreted tau induces AD pathology. If secreted tau induces AD pathology, then it might also induce glial activation. As such, it was determined whether the proteins that are increased in astrogliosis (GFAP) or microgliosis (Iba1) are increased in the P301L transgenic mouse model.

Figure 48A:
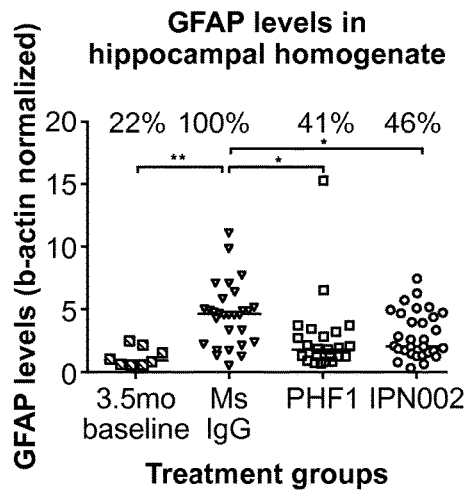
FIGS. 48A and 48B depict the effect of treatment of P301L mice with control IgG, PHF1, or IPN002 on the level of GFAP protein in hippocampal homogenate and in cortex homogenate.
Figure 48B:
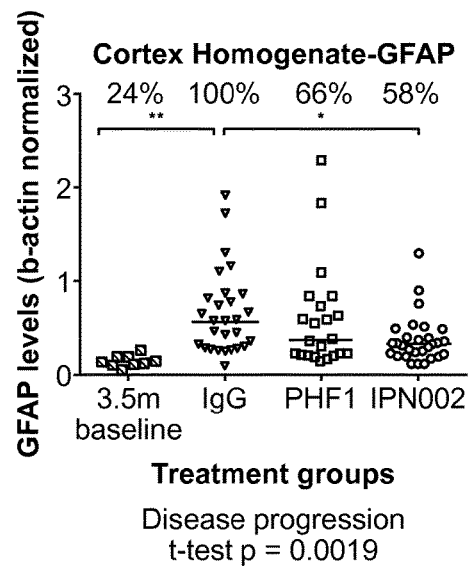

As shown in FIGS. 48A and 48B, GFAP protein levels are increased with disease progression in both the hippocampus and cortex. These data indicate either that astrocytes are activated in the hippocampus and cortex or that they have infiltrated these brain regions. IPN002 treatment significantly reduced GFAP protein levels in both the hippocampus and cortex, showing that IPN002 treatment reduced the disease-related increase in astrogliosis. PHF1 significantly reduced GFAP in the hippocampus but not in the cortex.

Figure 49A:
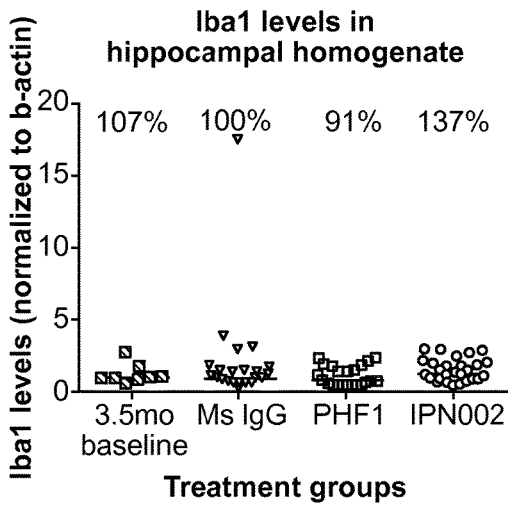
FIGS. 49A and 49B depict the effect of treatment of P301L mice with control IgG, PHF1, or IPN002 on the level of Iba1 protein in hippocampal homogenate and in cortex homogenate.
Figure 49B:
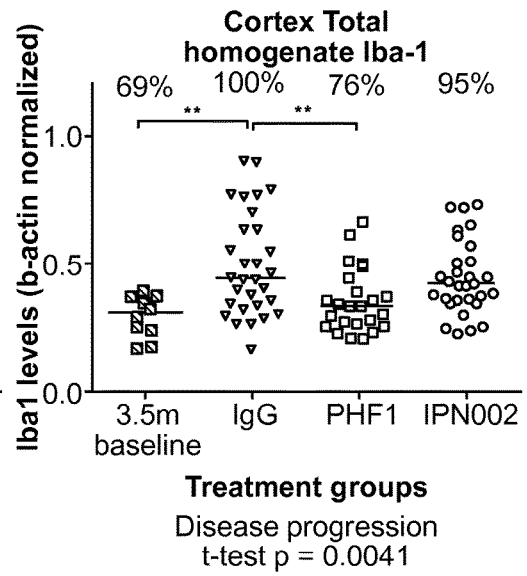

Iba1 protein levels, a marker for microglia, were measured in both hippocampus and cortex. As shown in FIGS. 49A and 49B, Iba1 is not increased with disease progression in the hippocampus but is increased in the cortex. IPN002 treatment had no effect on disease progression of Iba1 protein levels. In contrast, PHF1 treatment did significantly reduce Iba1 protein levels. The data suggest different mechanisms of action for IPN002 and PHF1.

Modulation of Amyloid-Beta Level

Figures 50A, 50B:
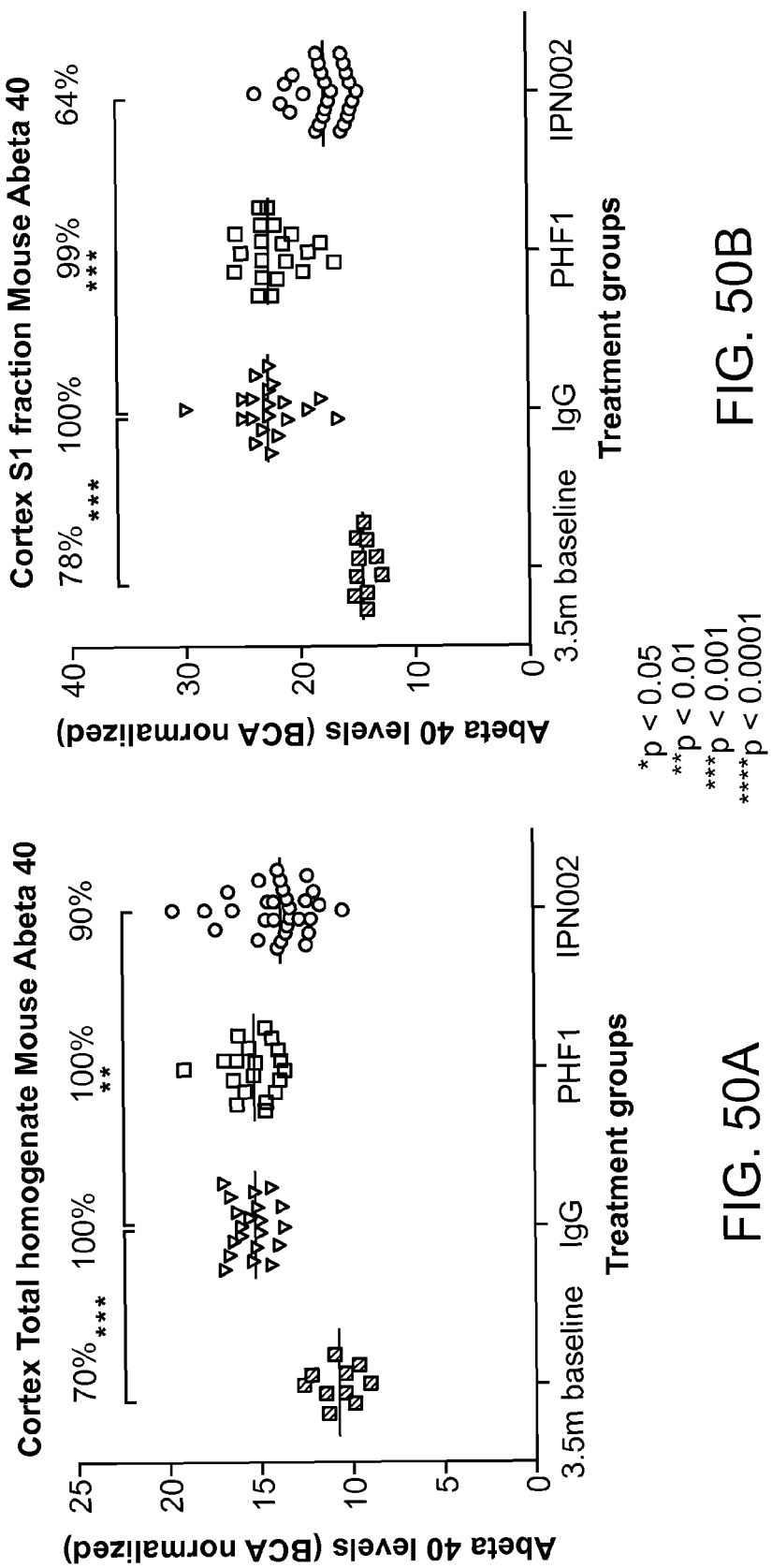
FIGS. 50A and 50B depict the effect of treatment of P301L mice with control IgG, PHF1, or IPN002 on the level of Aβ40 in cortex homogenate and cortex S1 fraction.

As shown in Example 17, treatment of iPSC-CN with IPN002 reduced the levels of Aβ40 and Aβ42 secreted by all iPSC-CN, whereas control IgG did not reduce Aβ40 or A1342 secretion. It was then determined whether IPN002 also modulates Aβ levels in vivo. In the P301L mouse model, there is no over overexpression of human APP; therefore, mouse Aβ levels were measured. The sensitivity of the mouse Aβ42 ELISA was not sufficient to measure A1342 levels in these homogenates. The mouse Aβ40 ELISA, however, was sufficiently sensitive and was therefore used to determine mouse Aβ40 levels in the homogenates and supernatant fractions. Mouse Aβ40 levels increase with disease progression. The observed increase in Aβ40 levels could be tau dependent and/or age dependent. As shown in FIGS. 50A and 50B, IPN002 treatment lowered Ab40 levels in both the homogenate (FIG. 50A) and soluble fraction (FIG. 50B).

The data in FIGS. 50A and 50B show that tau overexpression (perhaps in conjunction with aging) drives a disease progression associated increase in Aβ40 levels. The data suggest that secreted tau is the causal factor in driving the increase in Aβ levels, which IPN002 in turn inhibits by blocking eTau function. PHF1, in contrast, a non-eTau binding antibody, has no effect on Aβ levels.

Motor Function

The effect of IPN002 treatment on motor function, as assessed by the clasping and the beam walk tests, was determined. The data are shown in FIGS. 31, 32, 51, and 52.

As shown in FIG. 31, IPN002 treatment improved clasping scores, compared to treatment with mouse IgG control.

Figure 51:
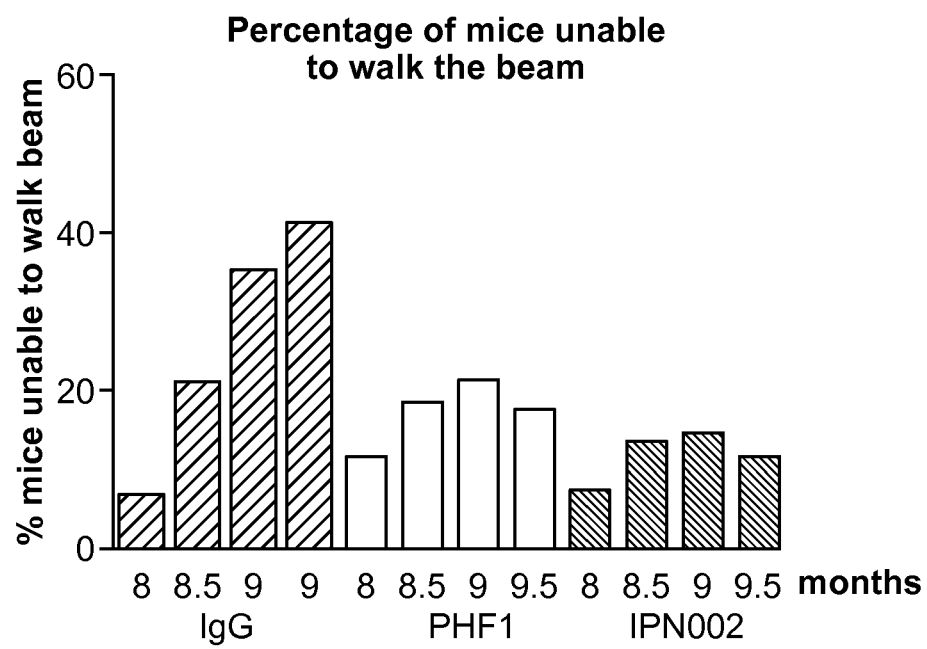
FIG. 51 depicts the effect of treatment of P301L mice with control IgG, PHF1, or IPN002 on the percent of mice able to perform in the beam walk test.

As shown in FIGS. 32 and 51, IPN002 treatment improved average latency in the beam walk test (FIG. 32), and reduced the percent of mice unable to walk the beam (FIG. 51), compared to treatment with mouse IgG control.

Example 21

Epitope Mapping

Peptide binding and competition assays were carried out as described in Example 18, above.

The following peptides were used:

IPIG-1: EVMEDHAGTYGLGDRK (SEQ ID NO:81; amino acids 9-24 of tau);

IPIG-2: DHAGTYGLGDRK (SEQ ID NO:49; amino acids 13-24 of tau);

IPIG-3: AGTYGLGD (SEQ ID NO:82; amino acids 15-22 of tau);

IPIG-4: AGTYGLGDRKDQGGYTM-HQDQEGDTDAGLK (SEQ ID NO:50; amino acids 15-44 of tau);

PAD peptide: AEPRQEFEVMEDHAGTY (SEQ ID NO:80; amino acids 2-18 of tau).

Figure 53:
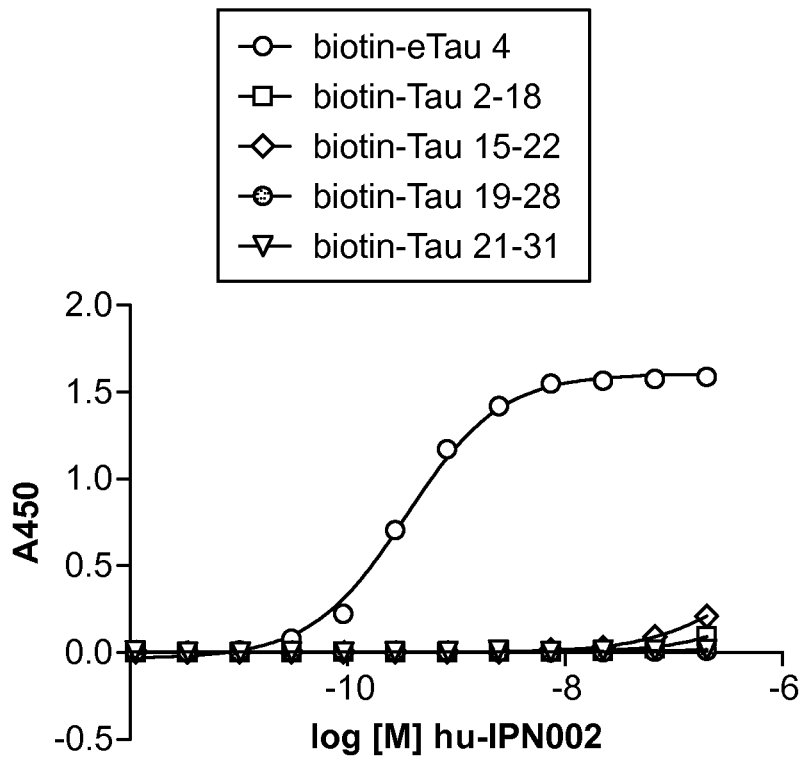
FIG. 53 depicts binding of various biotinylated Tau peptides to hu-IPN002.
Figure 54:
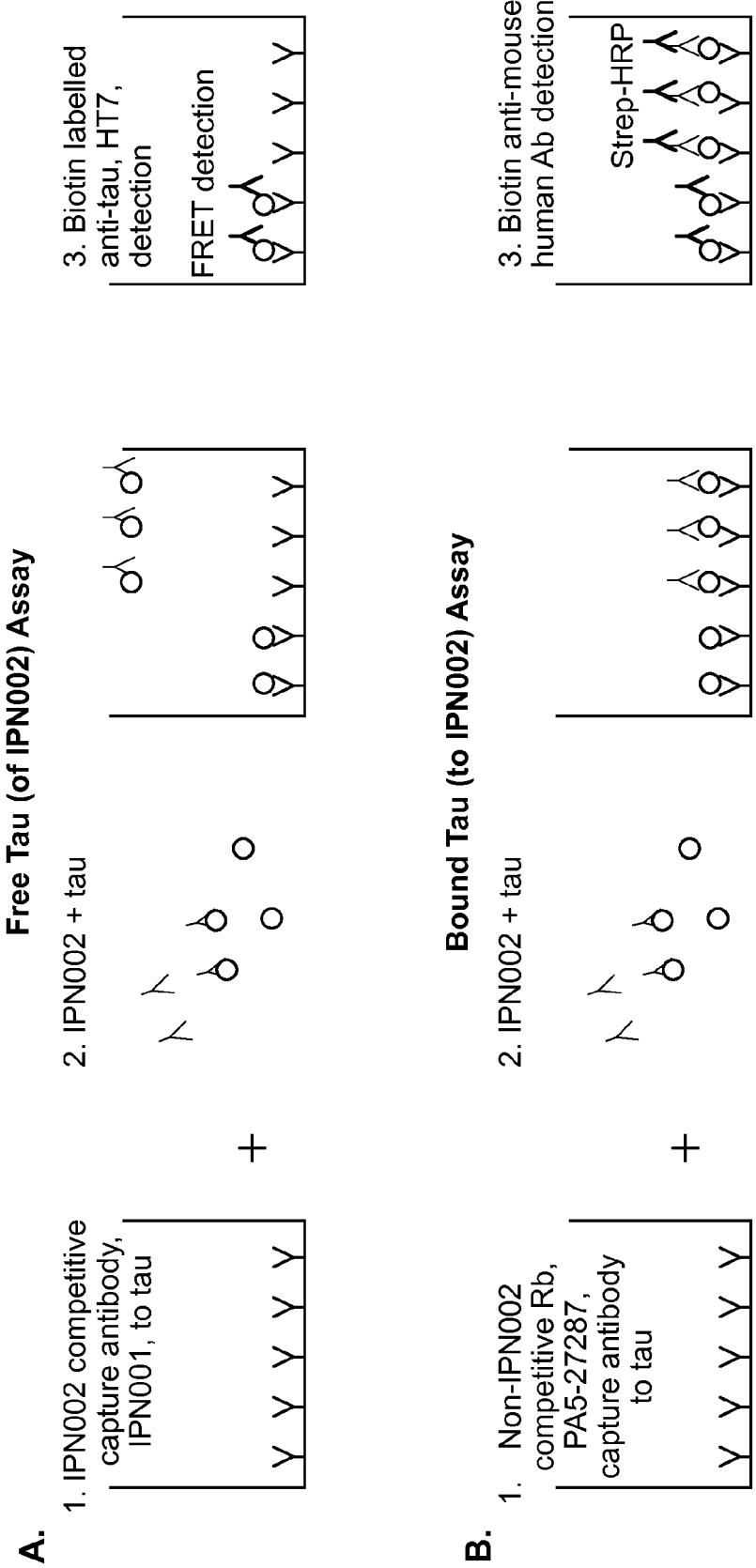
FIGS. 54A and 54B are schematic depictions of assays for Tau not bound to IPN002 (Free Tau) (FIG. 54A); and Tau bound to IPN002 (Bound Tau) (FIG. 54B).

The results are shown in FIGS. 53-55.

FIG. 30 shows that unbiotinylated tau peptides compete with biotinylated forms of tau. The upper panel shows competition of biotinylated Tau 13-24 peptide (IPIG-2; SEQ ID NO:49) with unbiotinylated Tau 13-24 for binding to hu-IPN002.

Figure 52:
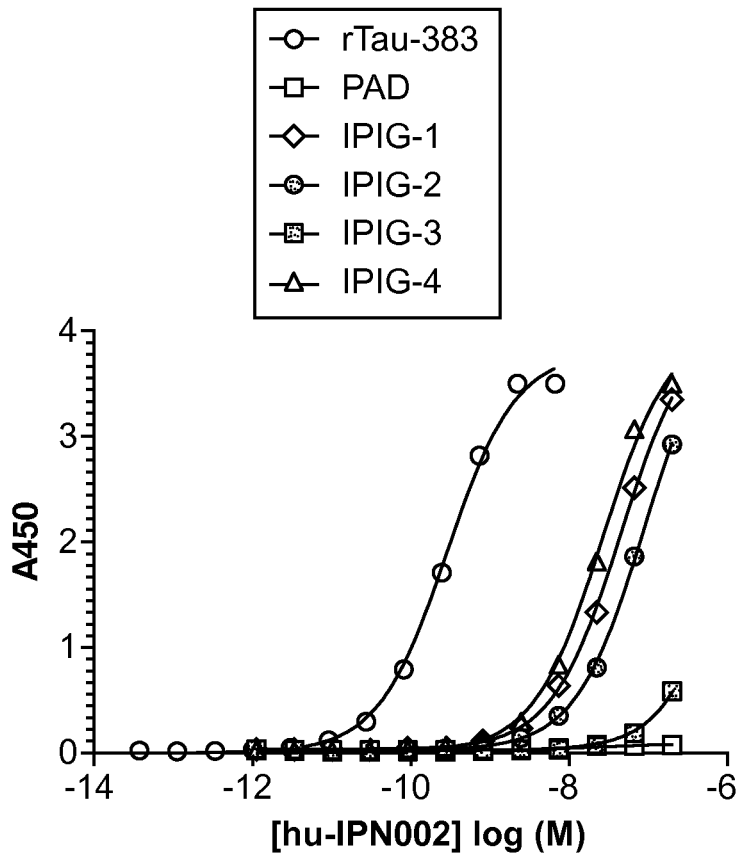
FIG. 52 depicts binding of hu-IPN002 to various Tau peptides.

FIG. 52 shows that full-length tau, IPIG-1, IPIG-2, and IPIG-4 were bound by hu-IPN002. IPIG-3, which lacks resides 23 and 24, was not bound by hu-IPN002, nor was PAD. Thus, residues 23 and 24 appear to be required for hu-IPN002 binding.

FIG. 53 shows that eTau-4 peptide binds hu-IPN002; however, PAD (tau 2-18), Tau 15-22, Tau 19-28, and Tau 21-31 peptides did not bind hu-IPN002.

The data indicate that residues 15-24 appear to be necessary for hu-IPN002 binding.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a tauopathy in an individual, the method comprising administering to the individual a humanized antibody that specifically binds an epitope within an N-terminal portion of a human Tau polypeptide, wherein the humanized antibody comprises:

a) a light chain region comprising:
  (i) a VL CDR1 comprising an amino acid sequence of SEQ ID NO:7;
  (ii) a VL CDR2 comprising an amino acid sequence of SEQ ID NO:8;

(iii) a VL CDR3 comprising an amino acid sequence of SEQ ID NO:9; and
(iv) a humanized light chain framework region; and
b) a heavy chain region comprising:
(i) a VH CDR1 comprising an amino acid sequence of SEQ ID NO:10;
(ii) a VH CDR2 comprising an amino acid sequence of SEQ ID NO:11;
(iii) a VH CDR3 comprising an amino acid sequence of SEQ ID NO:12; and
(iv) a humanized heavy chain framework region.

2. The method of claim 1, wherein the humanized antibody is a Fv, scFv, Fab, F(ab')2, or Fab'.

3. The method of claim 1, wherein the humanized antibody comprises a heavy chain region of the isotype IgG1, IgG2, IgG3, or IgG4.

4. The method of claim 1, wherein said administering is intravenous.

5. The method of claim 1, wherein said administering is intrathecal.

6. The method of claim 1, wherein said administering is subcutaneous.

7. The method of claim 1, wherein the tauopathy is Alzheimer's disease.

8. The method of claim 1, wherein the tauopathy is progressive supranuclear palsy.

9. A method of treating a tauopathy in an individual, the method comprising administering to the individual a humanized antibody that specifically binds an epitope within an N-terminal portion of a human Tau polypeptide, wherein the humanized antibody comprises a heavy chain variable region comprising the amino acid sequence set forth in SEQ ID NO:37 and a light chain variable region comprising the amino acid sequence set forth in SEQ ID NO:41.

10. The method of claim 9, wherein the humanized antibody is a Fv, scFv, Fab, F(ab')2, or Fab'.

11. The method of claim 9, wherein the humanized antibody comprises a heavy chain region of the isotype IgG1, IgG2, IgG3, or IgG4.

12. The method of claim 9, wherein said administering is intravenous.

13. The method of claim 9, wherein said administering is intrathecal.

14. The method of claim 9, wherein said administering is subcutaneous.

15. The method of claim 9, wherein the tauopathy is Alzheimer's disease.

16. The method of claim 9, wherein the tauopathy is progressive supranuclear palsy.

* * * * *

UNITED STATES PATENT AND TRADEMARK OFFICE
CERTIFICATE OF CORRECTION

PATENT NO. : 9,567,395 B2  
APPLICATION NO. : 14/421073  
DATED : February 14, 2017  
INVENTOR(S) : Irene Griswold-Prenner et al.

Page 1 of 1

It is certified that error appears in the above-identified patent and that said Letters Patent is hereby corrected as shown below:

In the Specification

At Column 1, Line number 8, please delete "No." and insert with -- Nos. --, therefor.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*